US006962696B1

(12) United States Patent
Bermudes et al.

(10) Patent No.: US 6,962,696 B1
(45) Date of Patent: Nov. 8, 2005

(54) COMPOSITIONS AND METHODS FOR TUMOR-TARGETED DELIVERY OF EFFECTOR MOLECULES

(75) Inventors: David G. Bermudes, Wallingford, CT (US); Ivan C. King, New Haven, CT (US); Caroline A. Clairmont, Cheshire, CT (US); Stanley L. Lin, Madison, CT (US); Michael Belcourt, Wallingford, CT (US)

(73) Assignee: Vion Pharmaceuticals Inc., New Haven, CT (US)

( * ) Notice: Subject to any disclaimer, the term of this patent is extended or adjusted under 35 U.S.C. 154(b) by 662 days.

(21) Appl. No.: 09/645,415

(22) Filed: Aug. 24, 2000

Related U.S. Application Data

(60) Provisional application No. 60/157,500, filed on Oct. 4, 1999, provisional application No. 60/157,581, filed on Oct. 4, 1999, and provisional application No. 60/157,637, filed on Oct. 4, 1999.

(51) Int. Cl.[7] .................. A01N 63/00; C12N 15/63; C12N 1/20; G01N 33/569
(52) U.S. Cl. ............... 424/93.4; 435/320.1; 435/252.8; 435/7.35
(58) Field of Search .......................... 435/252.8, 7.35, 435/245, 234, 325, 320.1, 295; 424/93.1, 93.2, 93.4; 514/44

(56) References Cited

U.S. PATENT DOCUMENTS

| | | | |
|---|---|---|---|
| 4,436,727 A | 3/1984 | Ribi | |
| 5,021,234 A | 6/1991 | Ehrenfeld | |
| 5,344,762 A | 9/1994 | Karapetian | |
| 5,705,151 A | 1/1998 | Dow et al. | |
| 5,824,538 A | 10/1998 | Branstrom | |
| 5,877,159 A | 3/1999 | Powell et al. | |
| 5,997,881 A | 12/1999 | Powell et al. | |
| 6,080,849 A | 6/2000 | Bermudes et al. | |
| 6,150,170 A | 11/2000 | Powell et al. | |
| 6,190,657 B1 * | 2/2001 | Pawelek et al. | 424/93.1 |
| 6,251,406 B1 | 6/2001 | Haefliger et al. | |
| 6,410,012 B1 * | 6/2002 | Sizemore et al. | 424/93.2 |
| 6,537,558 B2 * | 3/2003 | Kaniga et al. | 424/234.1 |
| 2001/0006642 A1 | 7/2001 | Steidler et al. | |
| 2001/0029043 A1 | 10/2001 | Haefliger et al. | |

FOREIGN PATENT DOCUMENTS

| | | |
|---|---|---|
| WO | WO 9106317 | 5/1991 |
| WO | WO 9211361 | 7/1992 |
| WO | WO 9502048 | 1/1995 |
| WO | WO 9611277 | 4/1996 |
| WO | WO 9634631 | 11/1996 |
| WO | WO 9640238 | 12/1996 |
| WO | WO 9718225 | 5/1997 |
| WO | WO 9718837 | 5/1997 |
| WO | WO 9719688 | 6/1997 |
| WO | WO 9725061 | 7/1997 |
| WO | WO 9833923 | 8/1998 |
| WO | WO 9853854 | 12/1998 |
| WO | WO 9913003 | 3/1999 |
| WO | WO 9952563 | 10/1999 |
| WO | WO 00/09733 | 2/2000 |

OTHER PUBLICATIONS

Boehm et al. Nature 390:404–407, 1997.*
Hakkaart et al. Mol Gen Genet 183:326–332, 1981.*
Pascual et al. Behring Inst. Mitt, 1997, 98: 143–152.*
Dietrich et al. Nature Biotechnology, 1998, 16: 181–185.*
Grillot–Courvalin. Nature Biotechnology, 1998, 16: 862–866.*
Tiball et al Vaccine 19:4175–4184, 20001.*
Curtiss R. J. Clin. Invest. 110(8):1061–1066, 2002.*
Dietrich et al. Antisense & Nucleic Acid Drug Development 10:391–399, 2000.*
Adler, 1973, "A Method for Measuring Chemotaxis and Use of the Method to Determine Optimum Conditions for Chemotaxis by *Escherichia coli*", J. Gen. Microbiol. 74:77–91.
Allzadeh et al., 1994, "Apoptosis as a Mechanism of Cytolysis of Tumor Cells by a Pathogenic Free–Living Amoeba", Infect. Immun. 62:1298–1303.
Anderson et al., 1996, "Development of attenuated *Salmonella* strains that express heterologous antigens", Methods in Molecular Medicine: Vaccine Protocols, ed. Robinson A, Farrar G, Wilblin C., Humana Press New Jersey, pp. 47–62.
Bagshawe, 1995, "Antibody–Directed Enzyme Prodrug Therapy: A Review", Drug Dev. Res. 34:220–230.
Barry et al., 1995, "Protection Against Mycoplasma Infection Using Expression–Library Immunization", Nature 377:632–635.
Barth and Morton, 1995, "The Role of Adjuvant Therapy in Melanoma Management", Cancer 75 (Suppl.):726–734.
Bermudes et al., 2000, "Tumor targeted Salmonella. Strain development and expression of the HSV TK effector gene" Gene Therapy, Methods and Protocols, vol. 35, 419–436.

(Continued)

*Primary Examiner*—Ram R. Shukla
(74) *Attorney, Agent, or Firm*—Law Offices of Albert Wai-Kit Chan, LLC

(57) ABSTRACT

The present application discloses the preparation and use of attenuated tumor-targeted bacteria vectors for the delivery of one or more primary effector molecule(s) to the site of a solid tumor. The primary effector molecule(s) of the invention is used in the methods of the invention to treat a solid tumor cancer such as a carcinoma, melanoma, lymphoma, or sarcoma. The invention relates to the surprising discovery that effector molecules, which may be toxic when administered systemically to a host, can be delivered locally to tumors by attenuated tumor-targeted bacteria with reduced toxicity to the host. The application also discloses to the delivery of one or more optional effector molecule(s) (termed secondary effector molecules) which may be delivered by the attenuated tumor-targeted bacteria in conjunction with the primary effector molecule(s).

9 Claims, 42 Drawing Sheets

OTHER PUBLICATIONS

Figure 2:
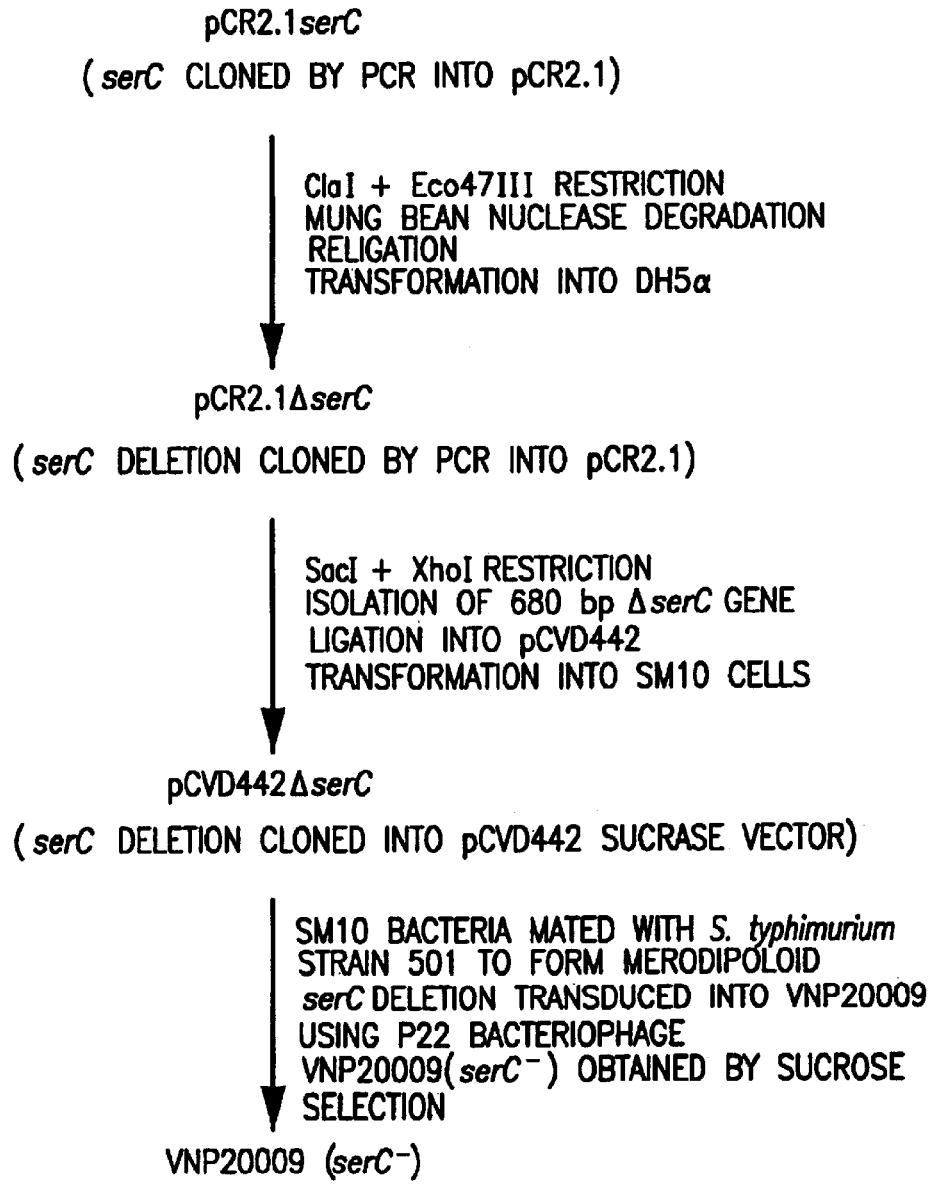

Bermudes et al., 2000, "Tumor–targeted Salmonella.Highly selective delivery vectors", Advances in Exp. Med. And Bio. 465: 57–63.

Bone, 1993, "Gram–Negative Sepsis: A Dilemma of Modern Medicine", Clin. Microbiol. Rev. 6:57–68.

Bonnekoh et al., 1995, "Inhibition of Melanoma Growth by Adenoviral–Mediated HSV Thymidine Kinase Gene Transfer in vivo", J. Invest. Derm. 104:313–317.

Carey et al., "Clostridial Oncolysis in Man", Eur. J. Cancer 3:37–46.

Carrier et al., 1992, "Expression of Human IL–1β in Salmonelle typhimurium; a Model System for the Delivery of Recombinant Therapeutic Proteins in vivo", J. Immunol. 148:1176–1181.

Carswell et al., 1975, "An Endotoxin–Induced Serum Factor that Causes Necrosis of Tumors", Proc. Natl. Acad. Sci. USA 72:3666–3670.

Chabalgoity et al., 1996, "A *Salmonella typhimurium htrA* Live Vaccine Expressing Multiple Copies of a Peptide Comprising Amino Acids 8–23 of Herpes Simplex Virus Glycoprotein D as a Genetic Fusion to Tetanus Toxin Fragment C Protects Mice from Herpes Simplex Virus Infection", Mol. Microbiol. 19:791–801.

Chen et al., 1999, "Liposomes complexed to plasmids encoding angiostatin and endostatin inhibit breast cancer in nude mice", Cancer Res. 59 (14):Abstract.

Christ et al., 1995, "E5531, a Pure Endotoxin Antagonist of High Potency", Science 268:80–83.

Clairmont et al., 2000, "Biodistribution and genetic stability of the novel antitumor agent VNP 20009, a genetically modified strain of *Salmonella typhimurium*", J. Infect. Diseases 181:1996–2002.

Clementz et al., 1997, "Function of the *Escherichia coli msbB* Gene, a Multicopy Suppressor of *htrB* Knockouts, in the Acylation of Lipid A", J. Biol. Chem. 272(16):10354–10360.

Cunningham et al., 1992, "Actin–Binding Protein Requirement for Cortical Stability and Efficient Locomotion", Science 255:325–327.

Elsenstadt, 1987, "Analysis of Mutagenesis", from *Escherichia coli and Salmonella typhimurium, Cellular and Molecular Biology,* Neidhardt et al. (ed.), pp. 1016–1033.

Elsenstein et al., 1995, "Immunotherapy of a Plasmacytoma with Attenuated Salmonella", Med. Oncol. 12:103–108.

Engel et al., 1992, "Murein–metabolizing enzymes from *Escherichia coli:* existence of a second lytic transglycosylase", J. Bacteriol. 174:6394–6403.

Engelbart and Gericke, 1963, "Oncolysis by Clostridia. V. Transplanted Tumors of the Hamster", Cancer Res. 24:239–243.

Falkow, 1991, "Bacterial Entry Into Eukaryotic Cells", Cell 65:1099–1102.

Fields et al., 1989, "A Salmonella locus that controls resistance to microbiocidal proteins from phagocytic cells." Science 243:1059–1062.

Fields et al., 1986, "Mutants of *Salmonella typhimurium* that cannot survive within themacrophage are avirulent". Proc. Natl Acad Sci USA, 83:5189–5193.

Fox et al., 1996, "Anaerobic Bacteria as a Delivery System for Cancer Gene Therapy: In vitro Activation of 5–Fluorocytosine by Genetically Engineered Clostridia", Gene Therapy 3:173–178.

Friberg, 1993, "BCG in the Treatment of Superficial Cancer of the Bladder: A Review", Med. Oncol. Tumor Pharmacother. 10:31–36.

Gatan et al., 1990, "Cloning and characterization of the asd gene of *Salmonella typhimurium*: use in stable maintenance of recombinant plasmids in Salmonella vaccine strains", Gene 94:29–35.

Gericke and Engelbart, 1963, "Oncolysis by Clostridia. II. Experiments on a Tumor Spectrum with a Variety of Clostridia in Combination with Heavy Metal", Cancer Res. 24:217–221.

Hall et al., 1994, "Induced Regression of Bovine Papillomas by Intralesional Immunotherapy", Therapeutic Immunol. 1:319–324.

Han et al., 1967, "Salmonellosis in Disseminated Malignant Diseases", New Eng. J. Med. 276:1045–1052.

Hoiseth and Stocker, 1981, "Aromatic dependent *Salmonella typhimurium* are non virulent and effective as live vaccines", Nature 291:238–239.

Jain, 1994, "Barriers to Drug Delivery in Solid Tumors", Sci. American 271:58–65.

Jones et al., 1992, "Invasion by *Salmonella typhimurium* is Affected by the Direction of Flagellar Rotation", Infect. Immun. 60:2475–2480.

Karow and Georgopoulos, 1992, "Isolation and Characterization of the *Escherichia coli msbB* Gene, a Multicopy Suppresssor of Null Mutations in the High–Temperature Requirement Gene hlrB", J. Bacteriol. 174:702–710.

Kelley et al., 1993, "The firA gene o *E. coli* encodes UDP–3–O–(R–3–hydroxymyristoyl)–glucosamine–acetyltransferase", J. Biol. Chem. 268:19866–19874.

Khan et al., 1998, "A lethal role for lipid A in Salmonella Infections", Mol. Microbiol. 29(2):571–579.

King et al., 1998, "Tumor targeted Salmonella expressing cytosine deaminase converted 5–fluorocytosine to 5–fluorouricil and inhibited tumor growth in vivo", Proc. Of the Amer. Assoc. for Can. Res. 39:512.

King et al., 2000, "Tumor Therapy using Salmonella", Emerging Drugs 5:211–219.

Klimpel et al., 1990, "Bacteria–Infected Fibroblasts have Enhanced Susceptibility to the Cytotoxic Action of Tumor Necrosis Factor", J. Immunol. 145:711–717.

Lee et al., 1992, "Identification of a *Salmonella typhimurium* Invasion Locus by Selection for Hyperinvasive Mutants", Proc. Nat. Acad. Sci. USA 89:1847–1851.

Lemmon et al., 1994, "Anaerobic Bacteria as a Gene Delivery System to Rumors", Proc. Am. Assn. Cancer Res. 35:374 (Abstract 2231).

Lemmon et al., 1997, "Anaerobic Bacteria as a Gene Delivery System that is Controlled by the Tumor Microenvironment", Gene Therapy, 4:791–796.

Lindgren et al., 1996, "Macrophage killing is an essential virulence mechanism of *Salmonella typhimurium*", PNAS, 93(9) 4197–4201.

Loppnow et al., 1990, "Cytokine Induction by Lipopolysaccharide (LPS) Corresponds to Lethal Toxicity and is Inhibited by Nontoxid *Rhodobacter capsulatus* LPS", Infect. Immun. 58:3743–3750.

Low et al., 1999, "VNP20009, a genetically modified *Salmonella Typhimurium* for treatment of solid tumors", Proc. Amer. Assoc. For Can. Res. 40:87.

Low et al., 1999, "Lipid A mutant Salmonella with suppressed virulence and TNFa induction retain tumor–targeting in vivo", Nature Biotechnology, 17:37–41.

Lytvyn et al., 1992, "Comparison of the Thymidine Kinase Genes from Three Entomopoxiviruses", J. Gen. Virol. 73:3235–3240.

Macnab, 1992, "Genetics and Biogenesis of Bacterial Flagella", Ann. Rev. Genet. 26:131–158.

Mahan et al., 1993, "Selection of Bacterial Virulence Genes that are Specifically Induced in Host Tissues", Science 259:686–688.

Marr et al., 1997, "Tumor immunothereapy using an adenoviral vector expressing a membrane–bound mutant of murine TNF alpha", Gene Therapy 4(11):Abstract.

McLaughlin et al., 1979, "Synergistic Activity of Components of Mycobacteria and Mutant *Salmonella* in Causing Regression of Line–10 Tumors in Guinea Pigs", Cancer Res. 39:1766–1771.

Miller et al., 1992, "An Unusual *pagC*::Tn*phoA* Mutation Leads to an Invasion– and Virulence–Defective Phenotype in Salmonellae", Infect. Immun. 60:3763–3770.

Miller et al., 1989, "A Two–Component Regulatory System (*phoP phoQ*) Controls *Salmonella typhimurium* Virulence", Proc. Natl. Acad. Sci. USA 86:5054–5058.

Minton et al., 1995, "Chemotherapeutic Tumor Targeting Using Clostridial Spores", FEMS Micro. Rev. 17:357–364.

Möse and Möse, 1963, "Oncolysis by Clostridia. I. Activity of *Clostridium butyricum* (M–55) and Other Nonpathogenic Clostridia Against the Ehrlich Carcinoma", Cancer Res. 24:212–216.

Mullen et al., 1992, "Transfer of the Bacterial Gene for Cytosine Deaminase to Mammalian Cells Confers Lethal Sensitivity to 5–Fluorocytosine: a Negative Selection System", Proc. Natl. Acad. Sci USA 89:33–37.

Nauts et al., 1953, "A Review of the Influence of Bacterial Infection and of Bacterial Products (Coley's Toxins) on Malignant Tumors in Man", Acta Medica Scandinavica 145 (Suppl. 276):1–105.

O'Callaghan et al., 1988, "Characterization of aromatic and purine dependent *Salmonella typhimurium*: Attenuation, persistence, and ability induce protective immunity in BALB/c mice", Infect. And Immun, 56:419–423.

Pan et al., 1995, "A Recombinant *Listeria monocytogenes* Vaccine Expressing a Model Tumor Antigen Protects Mice Against Lethal Tumor Cell Challenge and Causes Regression of Established Tumors", Nature Medicine 1:471–477.

Parker et al., 1947, "Effect of Histolyticus Infection and Toxin on Transplantable Mouse Tumors", Proc. Soc. Exp. Biol. Med. 16124:461–467.

Pawelek et al., 1995, "Macrophage Characteristics of Metastatic Melanoma", J. Invest. Dermatol. 104:605 (Abstract 304).

Pawelek et al., 1997, "Tumor–targeted *Salmonella* as a Novel Anti–cancer Vector", Cancer Res., 57:4537–4544.

Pidhemey et al., 1993, "In vitro and in vivo Tumoricidal Properties of a Pathogenic Free–Living Amoeba", Cancer Letters 72:91–98.

Platt et al., 2000, "Anti tumor effects of gentically engineered Salmonella in combinationwithradiation", Eur. J. Cancer, 36: 2397–2402.

Pugsley, 1988, "Protein Secretion Across the Outer Membrane of Gram–Negative Bacteria"In: *Protein Transfer and Organelle Biogenesis,* D and Robbins (eds.), Academic Press, Inc., Harcourt Brace Jovanovich, Publishers, San Diego, pp. 607–652.

Raue and Cashel, 1975, "Regulation of RNA Synthesis in *Escherichia coli*", Biochimica et Biophysica Acta 383:290–304.

Reinhard et al., 1950, "Chemotherapy of Malignant Neoplastic Diseases", JAMA 142:383–390.

Saltzman et al., 1998, "Attenuated *Salmonella typhimurium* Containing Interleukin–2 Decreases MC–38 Hepatic Metastases; a Novel Anti–Tumor Agent", Cancer Biotherapy and Radiopharmaceuticals 11:145–153.

Schafer et al., 1992, "Induction of a Cellular Immune Response to a Foreign Antigen by a Recombinant *Listeria monocytogenes* Vaccine", J. Immunol. 149:53–59.

Schlechte and Elbe, 1988, "Recombinant Plasmid DNA Variation of *Clostridium oncolyticum*—Model Experiments of Cancerostatic Gene Transfer", Zbl. Bakt. Hyg. A 268:347–356.

Schlechte et al., 1982, "Chemotherapy for Tumours Using Clostridial Oncolysis, Antibiotics and Cyclophosphamide: Model Trial on the UVT 15264 Tumor", Arch. Geschwuisforsch. 52:41–48.

Shaw et al., 1991, "The Human Dioxin–Inducible NAD(P)H: Quinone Oxidoreductase cDNA–Encoded Protein Expressed in COS–1 Cells is Identical to Diaphorase 4", Eur. J. Biochem. 195:171–176.

Sizemore et al., 1995, "Attenuated *Shigella* as a DNA Delivery Vehicle for DNA–Mediated Immunization", Science 270:299–302.

Sizemore et al., 1997, "Interaction– of *salmonella typhi* strains with cultured human monocyte–derived macrophages", Infect. Immunity 65:309–312.

Slauch et al., 1994, "In vivo Expression Technology for Selection of Bacterial Genes Specifically Induced in Host Tissues", Meth. Enzymol. 235:481–492.

Somerville et al., 1996, "A Novel *Escherichia coli* Lipid A Mutant that Produces an Antiinfllammatory Lipopolysaccharide", J. Clin. Invest. 97:359–365.

Sosnowski et al., 1994, "Complications of Bacillus Calmette–Guerin (BCG) Immunotherapy in Superficial Bladder Cancer", Comp. Ther. 20:695–701.

Sternberg and Maurer, 1991, "Bacteriophage mediated generalized transduction in *Escherichia coli* and *Salmonella typhimurium*", Methods in Enzymology, 204:18–43.

Su et al., 1992, "Extracellular Export of Shiga Toxin B–Subunit/Haemolysin A (C–terminus) Fusion Protein Expressed in *Salmonella typhimurium aroA*–Mutant and Stimulation of B–Subunit Specific Antibody Responses in Mice", Microbial Pathogenesis 13:465–476.

Sunshine et al., 1997, "Mutation of the *htrB* Gene in Virulent *Salmonella typhimurium* Strain by Intergeneric Transduction: Strain Construction and Phenotypic Characterization", J. Bacteriol., 179(17):5521–5533.

Sznol et al., 2000, "Use of preferentially replicating bacteria for treatment of cancer", J. Clinical Invest., 105:1027–1030.

Takayma et al., 1989, "Diphosphoryl Lipid A from *Rhodopseudomonas sphaeroides* ATCC 17023 Blocks Induction of Cachectin in Macrophages by Lipopolysaccharide", Infect. Immun. 57:1336–1338.

Thiele et al., 1963, "Oncolysis by Clostridia. IV. Effect of Nonpathogenic Clostridial Spores in Normal and Pathological Tissues", Cancer Res. 24:234–238.

Thiele et al., 1963, "Oncolysis by Clostridia. III. Effects of Clostridia and Chemotherapeutic Agents on Rodent Tumors", Cancer Res. 24:222–232.

Tuomanen, 1993, "Subversion of Leukocyte Adhesion Systems by Respiratory Pathogens", Am. Soc. Microbiol. 59:292–296.

Vaara et al., 1999, "Outer membrane permeability barrier in *Escherichia coli* mutants that are defective in the late acyltransferases of lipid A biosynthesis", J. Bacteriol. 43(6):1459–1462.

Vinopal, 1987, "Selectable Phenotypes", from *Escherichia coli and Salmonella typhimurium, Cellular and Molecular Biology*, Neldhardt et al. (ed.), pp. 990–1015.

Wolfe et al., 1917, "Salmonellosis in Patients with Neoplastic Disease", Arch. Intern. Med. 128:547–554.

Zheng et al., 1997, "Attenuated *Salmonella typhimurium* inhibited umor metastasis in vivo" Proc Amer Assoc. Can Res. 38:9.

Somerville et al., 1999, "*Escherichia coli* msbB Gene as a Virulence Factor and a Therapeutic Target", Infect. And Immunity 67(12):6583–6590.

Lee et al., 2000, "Comparative evaluation of theacute toxic effects in monkeys, pigs, and mice of a geneically engineered Salmonella strain (VNP20009) being developed as an anti–tumor agent", Int. J. of Toxicology, 19:19–25.

Luo et al., 1999, "Genetically modified *Salmonella typhimurium* inhibited growth of primary tumors and metastases", Abstract #3146, Proc. Amer. Assoc. For Cancer Res. 40:476.

Tacket et al., 1992, "Comparison of the safety and immunogenicity of aroC and aroD and cya crp *Salmonella typhi* strains in adult volunteers", Infect. Immun., 60:536–541.

Hohmann et al., 1996, "Evaluation of a phoP/phoQ–deleted, aroA–deleted live oral *Salmonella typhi* vaccine strain in human volunteers", Vaccine 14:19–24.

Tacket et al., 1997, "Safety of live oral *Salmonella typhi* vaccine strains with deletions in htrA and aroCaroD and Immune response in humans", Infect. Immun, 65(2):452–456.

Tacket et al., 2000, "Phase 2 clinical trial of attentuated Salmonella enterica serovar typhi oral live vector vaccine CVD 908–htrA in US volunteers", Infect. Immun. 68(3):1196–1201.

Anderson WF, 2001, "Recombinant DNA Advisory Committee Meeting on Issues of Concern to IBCs", Human Gene Therapy 12(12):1594–1596.

Darji et al., 1997, "Oral Somatic Transgene Vaccine Using Attenuated *S. typhimurium*", Cell 91:765–775.

MacEwen et al., "Genetically Modified Salmonella for Canine Cancer: a Phase I Study", Abstract 82.

Mier et al., 2001, "Phase I trial of a Live, Attenuated *Salmonella Typhimurium* (VNP20009) Administered by Direct Intra–Tumoral (IT) Injection", Proc Am. Soc. Clin. Oncol. 20:29 Abstract.

Paglia et al., "Gene Transfer in Dendritic Cells, Induced by Oral DNA Vaccination With *S. Typhimurium*, Results in Protective Immunity against a Murine Fibrosarcoma", Blood 92:3172–3176.

Tacket Co, 1997, "Safety of live oral *Salmonella typhi* vaccine strains with deletions in htrA and aroC aroD and Immune response in humans", Infect Immun. 65(2):452–6.

Toso et al, 2002, "Phase 1 Study of the Intravenous Administration of Attenuated *Salmonella typhimurium* to Patients with Metastatic Melanoma", J. of Clin. Oncol. 20:142–152.

Urishima et al., 2000, "An Oral Cd 40 ligand gene therapy against lymphoma using attenuated *Salmonella typhimurium*", Blood 95:1258–1263.

Chatfield et al., 1992, "Use of the nirB promoter to direct the stable expression of heterologous antigens in Salmonela oral vaccine strains: development of a single–dose oral tetanus vaccine", Biotechnology (N Y). 10(8):888–92.

Chatfield et al, 1992, "Construction of a genetically defined *Salmonella typhi* Ty2 aroA, aroC mutant for the engineering of a candidate oral typhoid–tetanus vaccine", Vaccine. 10(1):53–60.

Curtiss et al, 1989, "Selective delivery of antigens by recombinant bacteria", Curr Top Microbiol Immunol. 146:35–49.

Gill et al., 1996, "A malignant pleural effusion infected with *Salmonella enteritidis*", Thorax 51(1):104–5.

Gonzalez et al., 1994, "*Salmonella typhi* vaccine strain CVD 908 expressing the circumsporozoite protein of Plasmodium falciparum: strain construction and safety and immunogenicity in humans", J Infect Dis. 169(4):927–31.

Hohmann et al, 1996, "phoP/phoQ–deleted *Salmonella thphi* (ty800) is a safe and immunogenic single–dose typhoid fever vaccine in volunteers", J Infect Dis. 173(6):1408–14.

Levine et al., 1987, "Safety, infectivity, immunogenicity, and in vivo stability of two attenuated auxotrophic mutant strains of *Salmonella typhi*, 541Ty and 543TY, as live oral vaccines in humans", J. Clin Ivest. 79(3):888–902.

Saltzman et al., 1997, "Patterns of hepatic and splenic colonization by an attenuated strain of *Salmonella typhimurium* containing the gene for human interleukin–2: a novel anti–tumor agent", Cancer Biother Radiophamr 12:37–45.

Tacket et al., 1997, "Volunteer studies investigating the safety and efficacy of live oral El Tor Vibrio cholerae 01 vaccine strain CVD 111", Am J Trop Med Hyg. 56(5):533–7.

Wolfe et al., 1971, "Salmonellosis in patients with neoplastic disease. A review of 100 episodes at Memorial Cancer Center over a 13–year period", Arch Intern Med. 128(4):546–54.

Zheng et al., 2000, "Tumor amplified protein expression therapy: Salmonella as a tumor–selective protein delivery vector", Oncol Res. 12(3):127–35.

Paglia et al., 2000, "In vivo correction of genetic defects of monocyte/macrophages using attenuated Salmonella as oral vectors for targeted gene delivery", Gene Therapy 7:1725–1730.

* cited by examiner

```
ATG GTA CGT AGC TCC TCT CGC ACT CCG TCC GAT AAG CCG GTT GCT
 M   V   R   S   S   S   R   T   P   S   D   K   P   V   A

CAT GTA GTT GCT AAC CCT CAG GCA GAA GGT CAG CTG CAG TGG CTG
 H   V   V   A   N   P   Q   A   E   G   Q   L   Q   W   L

AAC CGT CGC GCT AAC GCC CTG CTG GCA AAC GGC GTT GAG CTC CGT
 N   R   R   A   N   A   L   L   A   N   G   V   E   L   R

GAT AAC CAG CTC GTG GTA CCT TCT GAA GGT CTG TAC CTG ATC TAT
 D   N   Q   L   V   V   P   S   E   G   L   Y   L   I   Y

TCT CAA GTA CTG TTC AAG GGT CAG GGC TGC CCG TCG ACT CAT GTT
 S   Q   V   L   F   K   G   Q   G   C   P   S   T   H   V

CTG CTG ACT CAC ACC ATC AGC CGT ATT GCT GTA TCT TAC CAG ACC
 L   L   T   H   T   I   S   R   I   A   V   S   Y   Q   T

AAA GTT AAC CTG CTG AGC GCT ATC AAG TCT CCG TGC CAG CGT GAA
 K   V   N   L   L   S   A   I   K   S   P   C   Q   R   E

ACT CCC GAG GGT GCA GAA GCG AAA CCA TGG TAT GAA CCG ATC TAC
 T   P   E   G   A   E   A   K   P   W   Y   E   P   I   Y

CTG GGT GGC GTA TTT CAA CTG GAG AAA GGT GAC CGT CTG TCC GCA
 L   G   G   V   F   Q   L   E   K   G   D   R   L   S   A

GAA ATC AAC CGT CCT GAC TAT CTA GAT TTC GCT GAA TCT GGC CAG
 E   I   N   R   P   D   Y   L   D   F   A   E   S   G   Q

GTG TAC TTC GGT ATT ATC GCA CTG TAA
 V   Y   F   G   I   I   A   L   *
```

FIG. 1

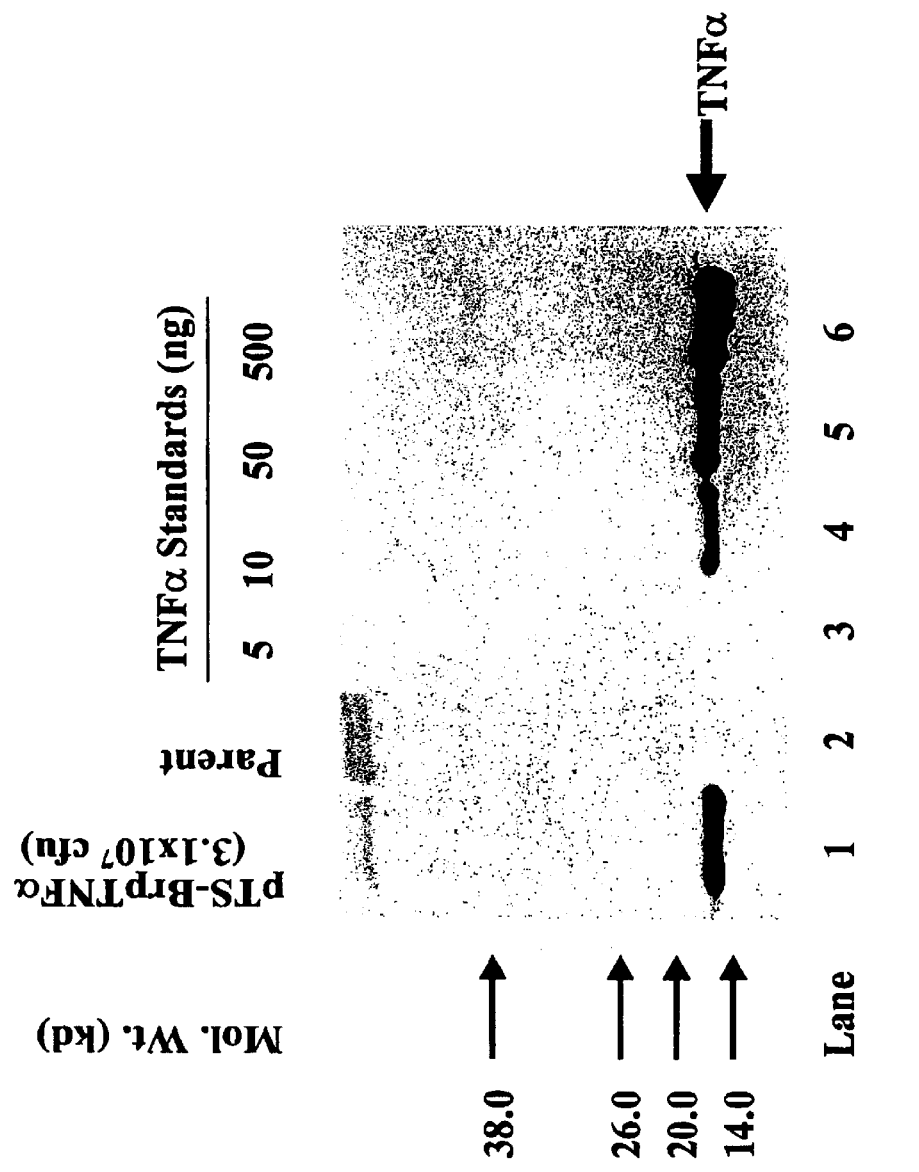
FIG.3 Quantitation of TNFα expression by pTS-BrpTNFα Clone 2.

```
ATG AAA AAG ACA GCT ATC GCG ATT GCA GTG GCA CTG GCT GGT TTC
 M   K   K   T   A   I   A   I   A   V   A   L   A   G   F

GCT ACC GTA GCG CAG GCC CAT ATG GTA CGT AGC TCC TCT CGC ACT
 A   T   V   A   Q   A   H   M   V   R   S   S   S   R   T

CCG TCC GAT AAG CCG GTT GCT CAT GTA GTT GCT AAC CCT CAG GCA
 P   S   D   K   P   V   A   H   V   V   A   N   P   Q   A

GAA GGT CAG CTG CAG TGG CTG AAC CGT CGC GCT AAC GCC CTG CTG
 E   G   Q   L   Q   W   L   N   R   R   A   N   A   L   L

GCA AAC GGC GTT GAG CTC CGT GAT AAC CAG CTC GTG GTA CCT TCT
 A   N   G   V   E   L   R   D   N   Q   L   V   V   P   S

GAA GGT CTG TAC CTG ATC TAT TCT CAA GTA CTG TTC AAG GGT CAG
 E   G   L   Y   L   I   Y   S   Q   V   L   F   K   G   Q

GGC TGC CCG TCG ACT CAT GTT CTG CTG ACT CAC ACC ATC AGC CGT
 G   C   P   S   T   H   V   L   L   T   H   T   I   S   R

ATT GCT GTA TCT TAC CAG ACC AAA GTT AAC CTG CTG AGC GCT ATC
 I   A   V   S   Y   Q   T   K   V   N   L   L   S   A   I

AAG TCT CCG TGC CAG CGT GAA ACT CCC GAG GGT GCA GAA GCG AAA
 K   S   P   C   Q   R   E   T   P   E   G   A   E   A   K

CCA TGG TAT GAA CCG ATC TAC CTG GGT GGC GTA TTT CAA CTG GAG
 P   W   Y   E   P   I   Y   L   G   G   V   F   Q   L   E

AAA GGT GAC CGT CTG TCC GCA GAA ATC AAC CGT CCT GAC TAT CTA
 K   G   D   R   L   S   A   E   I   N   R   P   D   Y   L

GAT TTC GCT GAA TCT GGC CAG GTG TAC TTC GGT ATT ATC GCA CTG
 D   F   A   E   S   G   Q   V   Y   F   G   I   I   A   L

TAA
 *
```

FIG.4

Expression and processing of a *trc* promoter-driven *ompA*-TRAIL fusion gene product in JM109 bacteria.

```
ATG AAA AAG ACA GCT ATC GCG ATT GCA GTG GCA CTG GCT GGT TTC
 M   K   K   T   A   I   A   I   A   V   A   L   A   G   F

GCT ACC GTA GCG CAG GCC CAT ATG GCT AAC GAG CTG AAG CAG ATG
 A   T   V   A   Q   A   H   M   A   N   E   L   K   Q   M

CAG GAC AAG TAC TCC AAA AGT GGC ATT GCT TGT TTC TTA AAA GAA
 Q   D   K   Y   S   K   S   G   I   A   C   F   L   K   E

GAT GAC AGT TAT TGG GAC CCC AAT GAC GAA GAG AGT ATG AAC AGC
 D   D   S   Y   W   D   P   N   D   E   E   S   M   N   S

CCC TGC TGG CAA GTC AAG TGG CAA CTC CGT CAG CTC GTT AGA AAG
 P   C   W   Q   V   K   W   Q   L   R   Q   L   V   R   K

ATG ATT TTG AGA ACC TCT GAG GAA ACC ATT TCT ACA GTT CAA GAA
 M   I   L   R   T   S   E   E   T   I   S   T   V   Q   E

AAG CAA CAA AAT ATT TCT CCC CTA GTG AGA GAA AGA GGT CCT CAG
 K   Q   Q   N   I   S   P   L   V   R   E   R   G   P   Q

AGA GTA GCA GCT CAC ATA ACT GGG ACC AGA GGA AGA AGC AAC ACA
 R   V   A   A   H   I   T   G   T   R   G   R   S   N   T

TTG TCT TCT CCA AAC TCC AAG AAT GAA AAG GCT CTG GGC CGC AAA
 L   S   S   P   N   S   K   N   E   K   A   L   G   R   K

ATA AAC TCC TGG GAA TCA TCA AGG AGT GGG CAT TCA TTC CTG AGC
 I   N   S   W   E   S   S   R   S   G   H   S   F   L   S

AAC TTG CAC TTG AGG AAT GGT GAA CTG GTC ATC CAT GAA AAA GGG
 N   L   H   L   R   N   G   E   L   V   I   H   E   K   G

TTT TAC TAC ATC TAT TCC CAA ACA TAC TTT CGA TTT CAG GAG GAA
 F   Y   Y   I   Y   S   Q   T   Y   F   R   F   Q   E   E

ATA AAA GAA AAC ACA AAG AAC GAC AAA CAA ATG GTC CAA TAT ATT
 I   K   E   N   T   K   N   D   K   Q   M   V   Q   Y   I

TAC AAA TAC ACA AGT TAT CCT GAC CCT ATA TTG TTG ATG AAA AGT
 Y   K   Y   T   S   Y   P   D   P   I   L   L   M   K   S

GCT AGA AAT AGT TGT TGG TCT AAA GAT GCA GAA TAT GGA CTC TAT
 A   R   N   S   C   W   S   K   D   A   E   Y   G   L   Y

TCC ATC TAT CAA GGG GGA ATA TTT GAG CTT AAG GAA AAT GAC AGA
 S   I   Y   Q   G   G   I   F   E   L   K   E   N   D   R

ATT TTT GTT TCT GTA ACA AAT GAG CAC TTG ATA GAC ATG GAC CAT
 I   F   V   S   V   T   N   E   H   L   I   D   M   D   H

GAA GCC AGT TTT TTC GGG GCC TTT TTA GTT GGC TAA
 E   A   S   F   F   G   A   F   L   V   G   *
```

FIG.6

```
ATG AAA AAG ACG GCT CTG GCG CTT CTG CTC TTG CTG TTA GCG CTG
 M   K   K   T   A   L   A   L   L   L   L   L   L   A   L

ACT AGT GTA GCG CAG GCC GCT CCT ACT AGC TCG AGC ACT AAG AAA
 T   S   V   A   Q   A   A   P   T   S   S   S   T   K   K

ACT CAA CTG CAA TTG GAG CAT CTG CTG CTG GAT CTG CAG ATG ATT
 T   Q   L   Q   L   E   H   L   L   L   D   L   Q   M   I

CTG AAT GGC ATC AAT AAC TAC AAG AAC CCT AAG CTG ACT CGC ATG
 L   N   G   I   N   N   Y   K   N   P   K   L   T   R   M

CTG ACT TTC AAA TTC TAC ATG CCG AAA AAG GCT ACC GAG CTC AAA
 L   T   F   K   F   Y   M   P   K   K   A   T   E   L   K

CAT CTC CAG TGC CTG GAA GAG GAA CTG AAG CCG CTG GAG GAA GTA
 H   L   Q   C   L   E   E   E   L   K   P   L   E   E   V

CTT AAC CTG GCA CAG TCT AAG AAC TTC CAC CTG CGT CCG CGT GAC
 L   N   L   A   Q   S   K   N   F   H   L   R   P   R   D

CTG ATC TCC AAC ATC AAT GTA ATC GTT CTT GAG CTG AAG GGA TCC
 L   I   S   N   I   N   V   I   V   L   E   L   K   G   S

GAA ACC ACC TTC ATG TGC GAA TAC GCT GAC GAA ACC GCC ACC ATT
 E   T   T   F   M   C   E   Y   A   D   E   T   A   T   I

GTG GAG TTC CTG AAC CGT TGG ATC ACC TTT GCC CAA TCG ATC ATT
 V   E   F   L   N   R   W   I   T   F   A   Q   S   I   I

AGC ACG TTA ACT TAA
 S   T   L   T   *
```

FIG.8

```
ATG AAA CAG TCG ACT CTG GCG CTT CTG CTC TTG CTG TTA GCG CTG
 M   K   Q   S   T   L   A   L   L   L   L   L   L   A   L

ACT AGT GTG GCC AAA GCG GCT CCT ACT AGC TCG AGC ACT AAG AAA
 T   S   V   A   K   A   A   P   T   S   S   S   T   K   K

ACT CAA CTG CAA TTG GAG CAT CTG CTG CTG GAT CTG CAG ATG ATT
 T   Q   L   Q   L   E   H   L   L   L   D   L   Q   M   I

CTG AAT GGC ATC AAT AAC TAC AAG AAC CCT AAG CTG ACT CGC ATG
 L   N   G   I   N   N   Y   K   N   P   K   L   T   R   M

CTG ACT TTC AAA TTC TAC ATG CCG AAA AAG GCT ACC GAG CTC AAA
 L   T   F   K   F   Y   M   P   K   K   A   T   E   L   K

CAT CTC CAG TGC CTG GAA GAG GAA CTG AAG CCG CTG GAG GAA GTA
 H   L   Q   C   L   E   E   E   L   K   P   L   E   E   V

CTT AAC CTG GCA CAG TCT AAG AAC TTC CAC CTG CGT CCG CGT GAC
 L   N   L   A   Q   S   K   N   F   H   L   R   P   R   D

CTG ATC TCC AAC ATC AAT GTA ATC GTT CTT GAG CTG AAG GGA TCC
 L   I   S   N   I   N   V   I   V   L   E   L   K   G   S

GAA ACC ACC TTC ATG TGC GAA TAC GCT GAC GAA ACC GCC ACC ATT
 E   T   T   F   M   C   E   Y   A   D   E   T   A   T   I

GTG GAG TTC CTG AAC CGT TGG ATC ACC TTT GCC CAA TCG ATC ATT
 V   E   F   L   N   R   W   I   T   F   A   Q   S   I   I

AGC ACG TTA ACT TAA
 S   T   L   T   *
```

FIG. 10

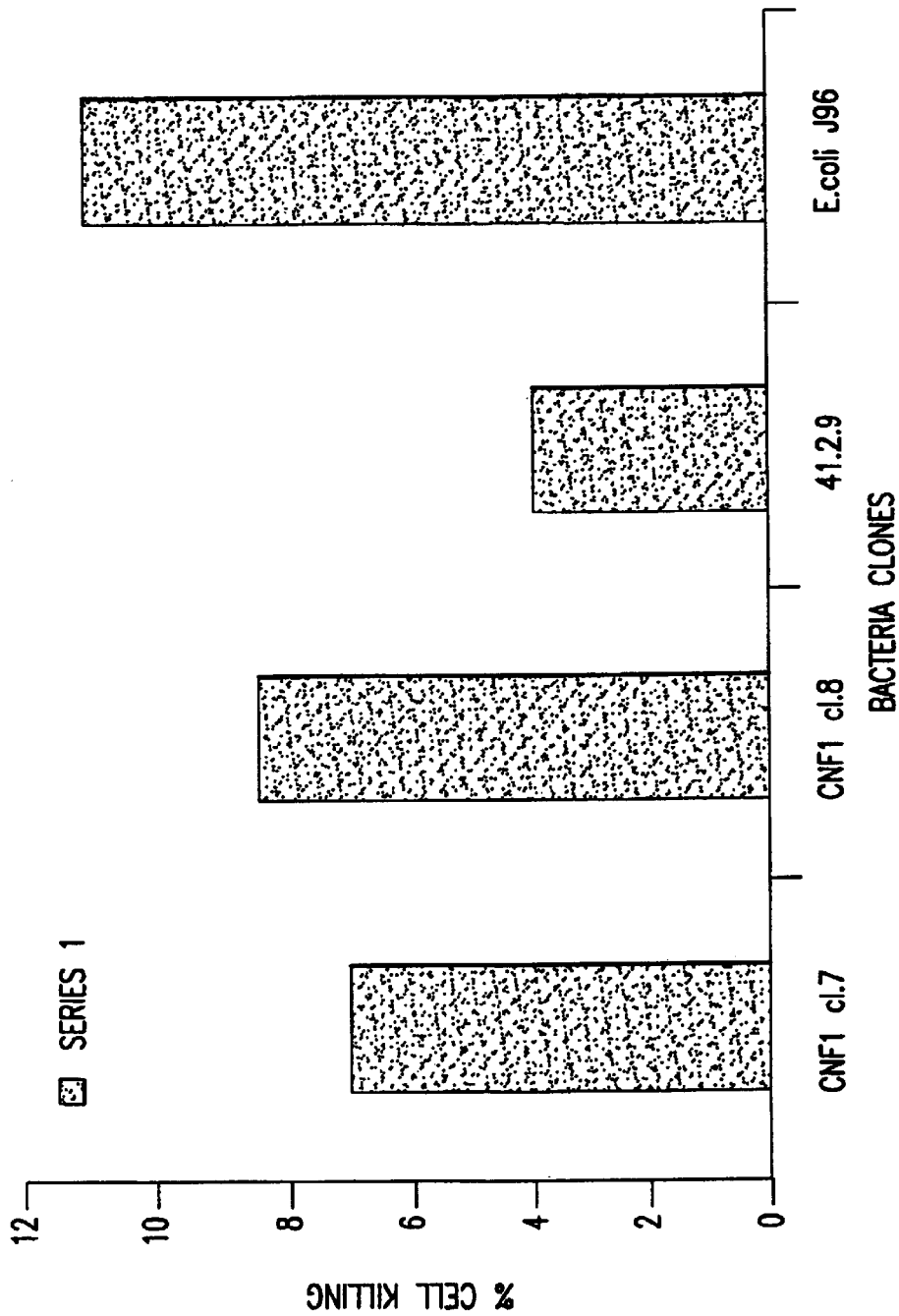

HeLa untreated (20x Obj.)

HeLa CNF1 in DH5 cl.15 (20x Obj.)

```
GATATCATTC TGGCCTCTGA CGTTGTGATG GTCGCACGTG GCGATCTGGG CGTTGAAATC GGCGATCCGG   70
AGCTGGTTGG TATCCAGAAA GCGCTGATTC GCCGTGCGCG TCAGCTAAAC CGCGCAGTCA TCACCGCAAC  140
GCAAATGATG GAGTCGATGA TCACCAACCC GATGCCGACC CGTGCGGAAG TGATGGACGT GGCGAACGCC  210
GTCCTGGATG GCACGGATGC GGTTATGCTG TCTGCCGAAA CCGCAGCCGG TCAGTATCCT TCTGAAACCG  280
TTGCCGCAAT GGCGCGCGTC TGCCTGGGCG CAGAAAAAAT CCCCAGCATC AATGTGTCTA AACACCGTCT  350
CGACGTGCAG TTCGACAACG TTGAAGAAGC CATTGCCATG TCTGCGATGT ATGCGGCAAA CCATCTGAAA  420
GGCGTTACCG CGATCATCAC CATGACGGAA TCCGGTCGTA CCGCGCTAAT GACTTCCCGT ATCAGCTCCG  490
GCCTGCCGAT TTTCGCCATG TCGCGCCATG AACGCACGCT GAACCTGACC GCGCTCTATC GCGGAGTAAC  560
GCCGGTGCAT TTTGATAGCG CGGCTGATGG CGTTGTCGCG GCACATGAAG CTGTTAATCT GCTGCGCGAT  630
AAAGGGTATC TGGTTTCCGG CGACCTGGTT ATCGTGACCC AGGGCGATGT CATGAGCACC GTCGGTTCAA  700
CCAATACCAC GCGGCCGCCC CCTTAATTAA CCCCGCATGC GGGGGGCCAT ATAGGCCGGG GATTTAAATG  770
CAAACGTCCG CCGAAACGCC GACGCACTGT GTTCCAGATA TAGTCAAAAA CCGGATTACC CTGATTATGA  840
AACATCGCCG CCATTTTTTG CCCCTGAGAG GCCATCAGCA TGGCTGGAAT GTCGACGCCC CAGCCATGCG  910
GTACGAGAAA AATGACTTTT TCGTCGTTAC GACGCATCTC CTCGATAATC TCCAGACCTT CCCAGTCAAC  980
ACGCTGTTGA ATTTTTTTCG GACCGCGCAT CGCCAACTCA GCCATCATCG CCATTGCCTG TGGCGCGGTG 1050
GCGAACATCT CATCGACAAT CGCTTCGCGC TCAGCTTCGC TACGCTGCGG AAAGCACAAC GACAGATTAA 1120
TTAGCGCCCG GCGACGAGAA CTCTTCCCCA GCCGTCCGGC AAAACGCCCC AGCGTCGCCA GCAAAGGGTC 1190
GCGGAATGAT GCCGGTGTTA ATGCGATCCC CGCCATTGCC GCCGCGCCCA ACCAGGCGCC CCAATACTGT 1260
GGATAGCGAA AGGATTTTTC GAATTCAGGG ATATACTCAC TATTATTTTT TTTGGTTTCC ATGCTTTTCC 1330
AGGGTCTGCT GACGCGAAAA GGAATTGTGA ATAGTGTAGC GACGTCTGCG TCTCACACAA AACAAAAAAG 1400
CCGGCACACA TCGCGTACCG GCTCTGTCAG CGCATTTGTT AATCGAAGCG CAGTTGCGGC AGAACCTCTT 1470
TCACCTGTGC CAGGTATTCA CGACGATCTG ACCCCGTCAG ACCTTCCGTG CGCGGCAATT TTGCTGTCAG 1530
AGGGTTAACG GCTTGCTGGT TGATC                                                 1555
```

FIG.31

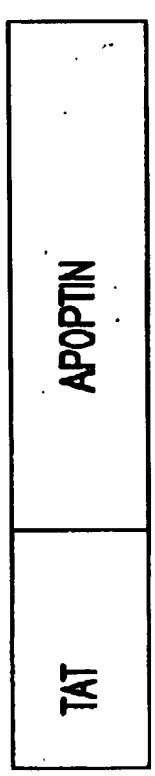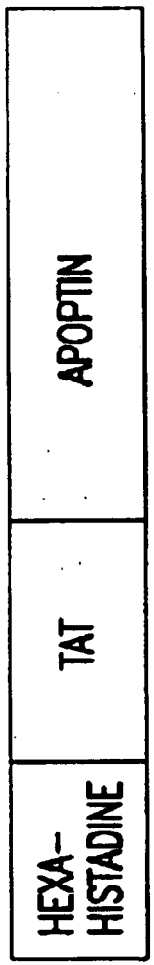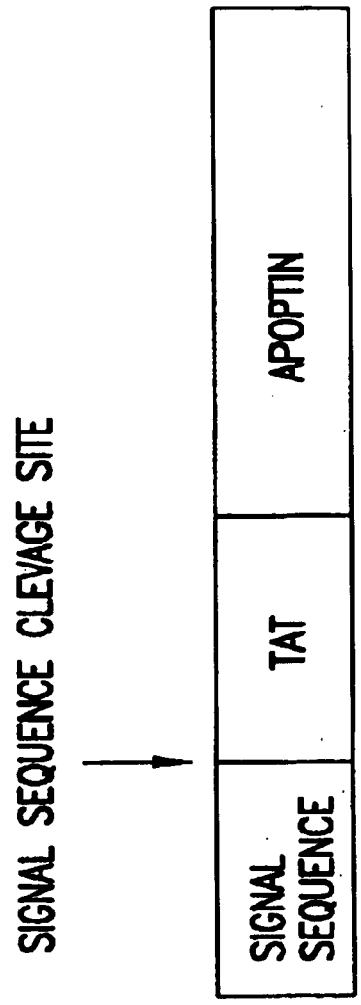
FIG. 36A  FIG. 36B  FIG. 36C
FIG. 36

Protein Sequence of 616-4 F

Length of 616-4 F: 551 bp; Listed from: 1 to: 551;
Translated from: 7 to: 409 (Entire region);
Genetic Code used: Universal; Wed, Aug 16, 2000 1:40 PM

```
Frame 1      M   A   Y   G   R   K   K   R   R   Q   R   R   R   M   N
        NAG ACC ATG GCT TAT GGC AGA AAA AAA AGA AGA CAG AGA AGA AGA ATC AAC
                 9          18          27          36          45

A   L   Q   E   D   T   P   P   G   P   S   T   V   F   R   P   P   T   S
GCG CTG CAG GAA GAT ACC CCG CCG GGC CCG TCC ACC GTG TTT CGC CCG CCG ACC TCC
         60          69          78          87          96         105

S   R   P   L   E   T   P   H   C   R   E   I   R   I   G   I   A   G   I
TCC CGC CCG CTG GAA ACC CCG CAT TGC CGC GAA ATC CGC ATC GGC ATC GCG GGC ATC
        117         126         135         144         153         162

T   I   T   L   S   L   C   G   C   A   N   A   R   A   P   T   L   R   S
ACC ATC ACC CTG TCC CTG TGC GGC TGC GCG AAC GCG CGC GCG CCG ACC CTG CGC TCC
        174         183         192         201         210         219

A   T   A   D   N   S   E   N   T   G   F   K   N   V   P   D   L   R   T
GCG ACC GCG GAT AAC TCC GAA AAC ACC GGC TTT AAA AAC GTC CCG GAT CTG CGC ACC
        231         240         249         258         267         276

D   Q   P   K   P   P   S   K   K   R   S   C   D   P   S   E   Y   R   V
GAT CAG CCG AAA CCG CCG TCC AAA AAA CGC TCC TGC GAT CCG TCC GAA TAT CGC GTC
        288         297         306         315         324         333

S   E   L   K   E   S   L   I   T   T   T   P   S   R   P   R   T   A   R
TCC GAA CTG AAA GAA TCC CTG ATC ACC ACC ACC CCG TCC CGC CCG CGC ACC GCC CGC
        345         354         363         372         381         390

R   C   I   R   L   .
CGC TGC ATC CGC CTC TGA AAG CTT GGC TGT TTT GGC GGA TGA GAG AAG ATT TTC AGC
        402         411         420         429         438         447

CTG ATA CAG ATT AAA TCA GAA CGC AGA AGC GGT CTG ATA AAA CAG AAT TTG CCT GGC
        459         468         477         486         495         504

GGC AGT AGC GCG GTG GTC CCA CCT GAC CCC ATG CCG AAC TCA GA
        516         525         534         543
```

FIG.37

Protein Sequence of TAP6H8 trcF

Length of TAP6H8 trcF: 751 bp; Listed from: 1 to: 444;
Translated from: 7 to: 427 (Entire region);
Genetic Code used: Universal; Mon, Aug 14, 2000 3:19 PM

```
Frame 1           M   A   H   H   H   H   H   H   Y   G   R   K   K   R   R
          NAG ACC ATG GCT CAT CAC CAT CAC CAC CAT TAT GGC CGC AAA AAA CGC CGT
                   9          18          27          36          45

Q   R   R   R   M   N   A   L   Q   E   D   T   P   P   G   P   S   T   V
      CAG CGC CGT CGC ATG AAC GCG CTG CAG GAA GAT ACC CCG CCG GGC CCG TCC ACC GTG
              60          69          78          87          96         105

F   R   P   P   T   S   S   R   P   L   E   T   P   H   C   R   E   I   R
      TTT CGC CCG CCG ACC TCC TCC CGC CCG CTG GAA ACC CCG CAT TGC CGC GAA ATC CGC
             117         126         135         144         153         162

I   G   I   A   G   I   T   I   T   L   S   L   C   G   C   A   N   A   R
      ATC GGC ATC GCG GGC ATC ACC ATC ACC CTG TCC CTG TGC GGC TGC GCG AAC GCG CGC
         174         183         192         201         210         219

A   P   T   L   R   S   A   T   A   D   N   S   E   N   T   G   F   K   N
      GCG CCG ACC CTG CGC TCC GCG ACC GCG GAT AAC TCC GAA AAC ACC GGC TTT AAA AAC
         231         240         249         258         267         276

V   P   D   L   R   T   D   Q   P   K   P   P   S   K   K   R   S   C   D
      GTC CCG GAT CTG CGC ACC GAT CAG CCG AAA CCG CCG TCC AAA AAA CGC TCC TGC GAT
         288         297         306         315         324         333

P   S   E   Y   R   V   S   E   L   K   E   S   L   I   T   T   T   P   S
      CCG TCC GAA TAT CGC GTC TCC GAA CTG AAA GAA TCC CTG ATC ACC ACC ACC CCG TCC
         345         354         363         372         381         390

R   P   R   T   A   R   R   C   I   R   L   *
      CGC CCG CGC ACC GCC CGC CGC TGC ATC CGC CTC TGA AAG CTT GGC TGT TTT
         402         411         420         429         438
```

FIG.38

SEQUENCE LISTING

<160> NUMBER OF SEQ ID NOS: 61

<210> SEQ ID NO 1
<211> LENGTH: 26
<212> TYPE: DNA
<213> ORGANISM: Artificial Sequence
<220> FEATURE:
<223> OTHER INFORMATION: Forward primer

<400> SEQUENCE: 1
gaagatcttc cggaggaggg gaaatg                                           26

<210> SEQ ID NO 2
<211> LENGTH: 44
<212> TYPE: DNA
<213> ORGANISM: Artificial Sequence
<220> FEATURE:
<223> OTHER INFORMATION: Reverse primer

<400> SEQUENCE: 2
cgggatccga gctcgagggc ccgggaaagg atctaagaag atcc                       44

<210> SEQ ID NO 3
<211> LENGTH: 477
<212> TYPE: DNA
<213> ORGANISM: Homo sapiens
<220> FEATURE:
<221> NAME/KEY: CDS
<222> LOCATION: (1)...(474)

<400> SEQUENCE: 3

```
atg gta cgt agc tcc tct cgc act ccg tcc gat aag ccg gtt gct cat       48
Met Val Arg Ser Ser Ser Arg Thr Pro Ser Asp Lys Pro Val Ala His
 1               5                  10                  15 gta gtt gct aac cct cag gca gaa ggt cag ctg cag tgg ctg aac cgt       96
Val Val Ala Asn Pro Gln Ala Glu Gly Gln Leu Gln Trp Leu Asn Arg
                 20                  25                  30 cgc gct aac gcc ctg ctg gca aac ggc gtt gag ctc cgt gat aac cag      144
Arg Ala Asn Ala Leu Leu Ala Asn Gly Val Glu Leu Arg Asp Asn Gln
             35                  40                  45 ctc gtg gta cct tct gaa ggt ctg tac ctg atc tat tct caa gta ctg      192
Leu Val Val Pro Ser Glu Gly Leu Tyr Leu Ile Tyr Ser Gln Val Leu
         50                  55                  60 ttc aag ggt cag ggc tgc ccg tcg act cat gtt ctg ctg act cac acc      240
Phe Lys Gly Gln Gly Cys Pro Ser Thr His Val Leu Leu Thr His Thr
 65                  70                  75                  80 atc agc cgt att gct gta tct tac cag acc aaa gtt aac ctg ctg agc      288
Ile Ser Arg Ile Ala Val Ser Tyr Gln Thr Lys Val Asn Leu Leu Ser
                 85                  90                  95 gct atc aag tct ccg tgc cag cgt gaa act ccc gag ggt gca gaa gcg      336
Ala Ile Lys Ser Pro Cys Gln Arg Glu Thr Pro Glu Gly Ala Glu Ala
                100                 105                 110 aaa cca tgg tat gaa ccg atc tac ctg ggt ggc gta ttt caa ctg gag      384
Lys Pro Trp Tyr Glu Pro Ile Tyr Leu Gly Gly Val Phe Gln Leu Glu
            115                 120                 125 aaa ggt gac cgt ctg tcc gca gaa atc aac cgt cct gac tat cta gat      432
Lys Gly Asp Arg Leu Ser Ala Glu Ile Asn Arg Pro Asp Tyr Leu Asp
        130                 135                 140 ttc gct gaa tct ggc cag gtg tac ttc ggt att atc gca ctg                474
Phe Ala Glu Ser Gly Gln Val Tyr Phe Gly Ile Ile Ala Leu
145                 150                 155
```

-continued taa                                                                477

<210> SEQ ID NO 4
<211> LENGTH: 158
<212> TYPE: PRT
<213> ORGANISM: Homo sapiens

<400> SEQUENCE: 4

Met Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155

<210> SEQ ID NO 5
<211> LENGTH: 28
<212> TYPE: DNA
<213> ORGANISM: Artificial Sequence
<220> FEATURE:
<223> OTHER INFORMATION: Forward primer

<400> SEQUENCE: 5
ccgacgcgtt gacacctgaa aactggag                                      28

<210> SEQ ID NO 6
<211> LENGTH: 29
<212> TYPE: DNA
<213> ORGANISM: Artificial Sequence
<220> FEATURE:
<223> OTHER INFORMATION: Reverse primer

<400> SEQUENCE: 6
ccgacgcgtg aaaggatctc aagaagatc                                     29

<210> SEQ ID NO 7
<211> LENGTH: 543
<212> TYPE: DNA
<213> ORGANISM: Artificial Sequence
<220> FEATURE:
<223> OTHER INFORMATION: Fusion construct
<221> NAME/KEY: CDS
<222> LOCATION: (1)...(540)

<400> SEQUENCE: 7 atg aaa aag aca gct atc gcg att gca gtg gca ctg gct ggt ttc gct    48
Met Lys Lys Thr Ala Ile Ala Ile Ala Val Ala Leu Ala Gly Phe Ala
1               5                   10                  15

```
acc gta gcg cag gcc cat atg gta cgt agc tcc tct cgc act ccg tcc      96
Thr Val Ala Gln Ala His Met Val Arg Ser Ser Ser Arg Thr Pro Ser
             20                  25                  30 gat aag ccg gtt gct cat gta gtt gct aac cct cag gca gaa ggt cag     144
Asp Lys Pro Val Ala His Val Val Ala Asn Pro Gln Ala Glu Gly Gln
         35                  40                  45 ctg cag tgg ctg aac cgt cgc gct aac gcc ctg ctg gca aac ggc gtt     192
Leu Gln Trp Leu Asn Arg Arg Ala Asn Ala Leu Leu Ala Asn Gly Val
     50                  55                  60 gag ctc cgt gat aac cag ctc gtg gta cct tct gaa ggt ctg tac ctg     240
Glu Leu Arg Asp Asn Gln Leu Val Val Pro Ser Glu Gly Leu Tyr Leu
 65                  70                  75                  80 atc tat tct caa gta ctg ttc aag ggt cag ggc tgc ccg tcg act cat     288
Ile Tyr Ser Gln Val Leu Phe Lys Gly Gln Gly Cys Pro Ser Thr His
                 85                  90                  95 gtt ctg ctg act cac acc atc agc cgt att gct gta tct tac cag acc     336
Val Leu Leu Thr His Thr Ile Ser Arg Ile Ala Val Ser Tyr Gln Thr
             100                 105                 110 aaa gtt aac ctg ctg agc gct atc aag tct ccg tgc cag cgt gaa act     384
Lys Val Asn Leu Leu Ser Ala Ile Lys Ser Pro Cys Gln Arg Glu Thr
         115                 120                 125 ccc gag ggt gca gaa gcg aaa cca tgg tat gaa ccg atc tac ctg ggt     432
Pro Glu Gly Ala Glu Ala Lys Pro Trp Tyr Glu Pro Ile Tyr Leu Gly
     130                 135                 140 ggc gta ttt caa ctg gag aaa ggt gac cgt ctg tcc gca gaa atc aac     480
Gly Val Phe Gln Leu Glu Lys Gly Asp Arg Leu Ser Ala Glu Ile Asn
145                 150                 155                 160 cgt cct gac tat cta gat ttc gct gaa tct ggc cag gtg tac ttc ggt     528
Arg Pro Asp Tyr Leu Asp Phe Ala Glu Ser Gly Gln Val Tyr Phe Gly
                 165                 170                 175 att atc gca ctg taa                                                 543
Ile Ile Ala Leu
         180

<210> SEQ ID NO 8
<211> LENGTH: 180
<212> TYPE: PRT
<213> ORGANISM: Artificial Sequence
<220> FEATURE:
<223> OTHER INFORMATION: Fusion construct

<400> SEQUENCE: 8

Met Lys Lys Thr Ala Ile Ala Ile Ala Val Ala Leu Ala Gly Phe Ala
 1               5                  10                  15

Thr Val Ala Gln Ala His Met Val Arg Ser Ser Ser Arg Thr Pro Ser
             20                  25                  30

Asp Lys Pro Val Ala His Val Val Ala Asn Pro Gln Ala Glu Gly Gln
         35                  40                  45

Leu Gln Trp Leu Asn Arg Arg Ala Asn Ala Leu Leu Ala Asn Gly Val
     50                  55                  60

Glu Leu Arg Asp Asn Gln Leu Val Val Pro Ser Glu Gly Leu Tyr Leu
 65                  70                  75                  80

Ile Tyr Ser Gln Val Leu Phe Lys Gly Gln Gly Cys Pro Ser Thr His
                 85                  90                  95

Val Leu Leu Thr His Thr Ile Ser Arg Ile Ala Val Ser Tyr Gln Thr
             100                 105                 110

Lys Val Asn Leu Leu Ser Ala Ile Lys Ser Pro Cys Gln Arg Glu Thr
         115                 120                 125
```

```
Pro Glu Gly Ala Glu Ala Lys Pro Trp Tyr Glu Pro Ile Tyr Leu Gly
    130                 135                 140

Gly Val Phe Gln Leu Glu Lys Gly Asp Arg Leu Ser Ala Glu Ile Asn
145                 150                 155                 160

Arg Pro Asp Tyr Leu Asp Phe Ala Glu Ser Gly Gln Val Tyr Phe Gly
                165                 170                 175

Ile Ile Ala Leu
            180

<210> SEQ ID NO 9
<211> LENGTH: 801
<212> TYPE: DNA
<213> ORGANISM: Artificial Sequence
<220> FEATURE:
<223> OTHER INFORMATION: Fusion construct
<221> NAME/KEY: CDS
<222> LOCATION: (1)...(798)

<400> SEQUENCE: 9 atg aaa aag aca gct atc gcg att gca gtg gca ctg gct ggt ttc gct      48
Met Lys Lys Thr Ala Ile Ala Ile Ala Val Ala Leu Ala Gly Phe Ala
  1               5                  10                  15 acc gta gcg cag gcc cat atg gct aac gag ctg aag cag atg cag gac      96
Thr Val Ala Gln Ala His Met Ala Asn Glu Leu Lys Gln Met Gln Asp
             20                  25                  30 aag tac tcc aaa agt ggc att gct tgt ttc tta aaa gaa gat gac agt     144
Lys Tyr Ser Lys Ser Gly Ile Ala Cys Phe Leu Lys Glu Asp Asp Ser
         35                  40                  45 tat tgg gac ccc aat gac gaa gag agt atg aac agc ccc tgc tgg caa     192
Tyr Trp Asp Pro Asn Asp Glu Glu Ser Met Asn Ser Pro Cys Trp Gln
     50                  55                  60 gtc aag tgg caa ctc cgt cag ctc gtt aga aag atg att ttg aga acc     240
Val Lys Trp Gln Leu Arg Gln Leu Val Arg Lys Met Ile Leu Arg Thr
 65                  70                  75                  80 tct gag gaa acc att tct aca gtt caa gaa aag caa caa aat att tct     288
Ser Glu Glu Thr Ile Ser Thr Val Gln Glu Lys Gln Gln Asn Ile Ser
                 85                  90                  95 ccc cta gtg aga gaa aga ggt cct cag aga gta gca gct cac ata act     336
Pro Leu Val Arg Glu Arg Gly Pro Gln Arg Val Ala Ala His Ile Thr
            100                 105                 110 ggg acc aga gga aga agc aac aca ttg tct tct cca aac tcc aag aat     384
Gly Thr Arg Gly Arg Ser Asn Thr Leu Ser Ser Pro Asn Ser Lys Asn
        115                 120                 125 gaa aag gct ctg ggc cgc aaa ata aac tcc tgg gaa tca tca agg agt     432
Glu Lys Ala Leu Gly Arg Lys Ile Asn Ser Trp Glu Ser Ser Arg Ser
    130                 135                 140 ggg cat tca ttc ctg agc aac ttg cac ttg agg aat ggt gaa ctg gtc     480
Gly His Ser Phe Leu Ser Asn Leu His Leu Arg Asn Gly Glu Leu Val
145                 150                 155                 160 atc cat gaa aaa ggg ttt tac tac atc tat tcc caa aca tac ttt cga     528
Ile His Glu Lys Gly Phe Tyr Tyr Ile Tyr Ser Gln Thr Tyr Phe Arg
                165                 170                 175 ttt cag gag gaa ata aaa gaa aac aca aag aac gac aaa caa atg gtc     576
Phe Gln Glu Glu Ile Lys Glu Asn Thr Lys Asn Asp Lys Gln Met Val
            180                 185                 190 caa tat att tac aaa tac aca agt tat cct gac cct ata ttg ttg atg     624
Gln Tyr Ile Tyr Lys Tyr Thr Ser Tyr Pro Asp Pro Ile Leu Leu Met
        195                 200                 205 aaa agt gct aga aat agt tgt tgg tct aaa gat gca gaa tat gga ctc     672
Lys Ser Ala Arg Asn Ser Cys Trp Ser Lys Asp Ala Glu Tyr Gly Leu
    210                 215                 220
```

```
tat tcc atc tat caa ggg gga ata ttt gag ctt aag gaa aat gac aga    720
Tyr Ser Ile Tyr Gln Gly Gly Ile Phe Glu Leu Lys Glu Asn Asp Arg
225                 230                 235                 240 att ttt gtt tct gta aca aat gag cac ttg ata gac atg gac cat gaa    768
Ile Phe Val Ser Val Thr Asn Glu His Leu Ile Asp Met Asp His Glu
                245                 250                 255 gcc agt ttt ttc ggg gcc ttt tta gtt ggc taa                        801
Ala Ser Phe Phe Gly Ala Phe Leu Val Gly
            260                 265

<210> SEQ ID NO 10
<211> LENGTH: 266
<212> TYPE: PRT
<213> ORGANISM: Artificial Sequence
<220> FEATURE:
<223> OTHER INFORMATION: Fusion construct

<400> SEQUENCE: 10

Met Lys Lys Thr Ala Ile Ala Ile Ala Val Ala Leu Ala Gly Phe Ala
1               5                   10                  15

Thr Val Ala Gln Ala His Met Ala Asn Glu Leu Lys Gln Met Gln Asp
                20                  25                  30

Lys Tyr Ser Lys Ser Gly Ile Ala Cys Phe Leu Lys Glu Asp Asp Ser
            35                  40                  45

Tyr Trp Asp Pro Asn Asp Glu Glu Ser Met Asn Ser Pro Cys Trp Gln
        50                  55                  60

Val Lys Trp Gln Leu Arg Gln Leu Val Arg Lys Met Ile Leu Arg Thr
65                  70                  75                  80

Ser Glu Glu Thr Ile Ser Thr Val Gln Glu Lys Gln Gln Asn Ile Ser
                85                  90                  95

Pro Leu Val Arg Glu Arg Gly Pro Gln Arg Val Ala Ala His Ile Thr
            100                 105                 110

Gly Thr Arg Gly Arg Ser Asn Thr Leu Ser Ser Pro Asn Ser Lys Asn
        115                 120                 125

Glu Lys Ala Leu Gly Arg Lys Ile Asn Ser Trp Glu Ser Ser Arg Ser
    130                 135                 140

Gly His Ser Phe Leu Ser Asn Leu His Leu Arg Asn Gly Glu Leu Val
145                 150                 155                 160

Ile His Glu Lys Gly Phe Tyr Tyr Ile Tyr Ser Gln Thr Tyr Phe Arg
                165                 170                 175

Phe Gln Glu Glu Ile Lys Glu Asn Thr Lys Asn Asp Lys Gln Met Val
            180                 185                 190

Gln Tyr Ile Tyr Lys Tyr Thr Ser Tyr Pro Asp Pro Ile Leu Leu Met
        195                 200                 205

Lys Ser Ala Arg Asn Ser Cys Trp Ser Lys Asp Ala Glu Tyr Gly Leu
    210                 215                 220

Tyr Ser Ile Tyr Gln Gly Gly Ile Phe Glu Leu Lys Glu Asn Asp Arg
225                 230                 235                 240

Ile Phe Val Ser Val Thr Asn Glu His Leu Ile Asp Met Asp His Glu
                245                 250                 255

Ala Ser Phe Phe Gly Ala Phe Leu Val Gly
            260                 265

<210> SEQ ID NO 11
<211> LENGTH: 465
<212> TYPE: DNA
<213> ORGANISM: Artificial Sequence
```

```
<220> FEATURE:
<223> OTHER INFORMATION: Fusion construct
<221> NAME/KEY: CDS
<222> LOCATION: (1)...(462)

<400> SEQUENCE: 11 atg aaa aag acg gct ctg gcg ctt ctg ctc ttg ctg tta gcg ctg act    48
Met Lys Lys Thr Ala Leu Ala Leu Leu Leu Leu Leu Leu Ala Leu Thr
1               5                   10                  15 agt gta gcg cag gcc gct cct act agc tcg agc act aag aaa act caa    96
Ser Val Ala Gln Ala Ala Pro Thr Ser Ser Ser Thr Lys Lys Thr Gln
            20                  25                  30 ctg caa ttg gag cat ctg ctg ctg gat ctg cag atg att ctg aat ggc   144
Leu Gln Leu Glu His Leu Leu Leu Asp Leu Gln Met Ile Leu Asn Gly
        35                  40                  45 atc aat aac tac aag aac cct aag ctg act cgc atg ctg act ttc aaa   192
Ile Asn Asn Tyr Lys Asn Pro Lys Leu Thr Arg Met Leu Thr Phe Lys
50                  55                  60 ttc tac atg ccg aaa aag gct acc gag ctc aaa cat ctc cag tgc ctg   240
Phe Tyr Met Pro Lys Lys Ala Thr Glu Leu Lys His Leu Gln Cys Leu
65                  70                  75                  80 gaa gag gaa ctg aag ccg ctg gag gaa gta ctt aac ctg gca cag tct   288
Glu Glu Glu Leu Lys Pro Leu Glu Glu Val Leu Asn Leu Ala Gln Ser
                85                  90                  95 aag aac ttc cac ctg cgt ccg cgt gac ctg atc tcc aac atc aat gta   336
Lys Asn Phe His Leu Arg Pro Arg Asp Leu Ile Ser Asn Ile Asn Val
            100                 105                 110 atc gtt ctt gag ctg aag gga tcc gaa acc acc ttc atg tgc gaa tac   384
Ile Val Leu Glu Leu Lys Gly Ser Glu Thr Thr Phe Met Cys Glu Tyr
        115                 120                 125 gct gac gaa acc gcc acc att gtg gag ttc ctg aac cgt tgg atc acc   432
Ala Asp Glu Thr Ala Thr Ile Val Glu Phe Leu Asn Arg Trp Ile Thr
    130                 135                 140 ttt gcc caa tcg atc att agc acg tta act taa                       465
Phe Ala Gln Ser Ile Ile Ser Thr Leu Thr
145                 150

<210> SEQ ID NO 12
<211> LENGTH: 154
<212> TYPE: PRT
<213> ORGANISM: Artificial Sequence
<220> FEATURE:
<223> OTHER INFORMATION: Fusion construct

<400> SEQUENCE: 12

Met Lys Lys Thr Ala Leu Ala Leu Leu Leu Leu Leu Leu Ala Leu Thr
1               5                   10                  15

Ser Val Ala Gln Ala Ala Pro Thr Ser Ser Ser Thr Lys Lys Thr Gln
            20                  25                  30

Leu Gln Leu Glu His Leu Leu Leu Asp Leu Gln Met Ile Leu Asn Gly
        35                  40                  45

Ile Asn Asn Tyr Lys Asn Pro Lys Leu Thr Arg Met Leu Thr Phe Lys
50                  55                  60

Phe Tyr Met Pro Lys Lys Ala Thr Glu Leu Lys His Leu Gln Cys Leu
65                  70                  75                  80

Glu Glu Glu Leu Lys Pro Leu Glu Glu Val Leu Asn Leu Ala Gln Ser
                85                  90                  95

Lys Asn Phe His Leu Arg Pro Arg Asp Leu Ile Ser Asn Ile Asn Val
            100                 105                 110

Ile Val Leu Glu Leu Lys Gly Ser Glu Thr Thr Phe Met Cys Glu Tyr
```

```
                 115                 120                 125
Ala Asp Glu Thr Ala Thr Ile Val Glu Phe Leu Asn Arg Trp Ile Thr
    130                 135                 140

Phe Ala Gln Ser Ile Ile Ser Thr Leu Thr
145                 150

<210> SEQ ID NO 13
<211> LENGTH: 465
<212> TYPE: DNA
<213> ORGANISM: Artificial Sequence
<220> FEATURE:
<223> OTHER INFORMATION: Fusion construct
<221> NAME/KEY: CDS
<222> LOCATION: (1)...(462)

<400> SEQUENCE: 13 atg aaa cag tcg act ctg gcg ctt ctg ctc ttg ctg tta gcg ctg act        48
Met Lys Gln Ser Thr Leu Ala Leu Leu Leu Leu Leu Leu Ala Leu Thr
1               5                   10                  15 agt gtg gcc aaa gcg gct cct act agc tcg agc act aag aaa act caa        96
Ser Val Ala Lys Ala Ala Pro Thr Ser Ser Ser Thr Lys Lys Thr Gln
                20                  25                  30 ctg caa ttg gag cat ctg ctg ctg gat ctg cag atg att ctg aat ggc       144
Leu Gln Leu Glu His Leu Leu Leu Asp Leu Gln Met Ile Leu Asn Gly
            35                  40                  45 atc aat aac tac aag aac cct aag ctg act cgc atg ctg act ttc aaa       192
Ile Asn Asn Tyr Lys Asn Pro Lys Leu Thr Arg Met Leu Thr Phe Lys
        50                  55                  60 ttc tac atg ccg aaa aag gct acc gag ctc aaa cat ctc cag tgc ctg       240
Phe Tyr Met Pro Lys Lys Ala Thr Glu Leu Lys His Leu Gln Cys Leu
65                  70                  75                  80 gaa gag gaa ctg aag ccg ctg gag gaa gta ctt aac ctg gca cag tct       288
Glu Glu Glu Leu Lys Pro Leu Glu Glu Val Leu Asn Leu Ala Gln Ser
                85                  90                  95 aag aac ttc cac ctg cgt ccg cgt gac ctg atc tcc aac atc aat gta       336
Lys Asn Phe His Leu Arg Pro Arg Asp Leu Ile Ser Asn Ile Asn Val
            100                 105                 110 atc gtt ctt gag ctg aag gga tcc gaa acc acc ttc atg tgc gaa tac       384
Ile Val Leu Glu Leu Lys Gly Ser Glu Thr Thr Phe Met Cys Glu Tyr
        115                 120                 125 gct gac gaa acc gcc acc att gtg gag ttc ctg aac cgt tgg atc acc       432
Ala Asp Glu Thr Ala Thr Ile Val Glu Phe Leu Asn Arg Trp Ile Thr
130                 135                 140 ttt gcc caa tcg atc att agc acg tta act taa                           465
Phe Ala Gln Ser Ile Ile Ser Thr Leu Thr
145                 150

<210> SEQ ID NO 14
<211> LENGTH: 154
<212> TYPE: PRT
<213> ORGANISM: Artificial Sequence
<220> FEATURE:
<223> OTHER INFORMATION: Fusion construct

<400> SEQUENCE: 14

Met Lys Gln Ser Thr Leu Ala Leu Leu Leu Leu Leu Leu Ala Leu Thr
1               5                   10                  15

Ser Val Ala Lys Ala Ala Pro Thr Ser Ser Ser Thr Lys Lys Thr Gln
                20                  25                  30

Leu Gln Leu Glu His Leu Leu Leu Asp Leu Gln Met Ile Leu Asn Gly
            35                  40                  45
```

```
Ile Asn Asn Tyr Lys Asn Pro Lys Leu Thr Arg Met Leu Thr Phe Lys
 50                  55                  60
Phe Tyr Met Pro Lys Lys Ala Thr Glu Leu Lys His Leu Gln Cys Leu
 65                  70                  75                  80
Glu Glu Glu Leu Lys Pro Leu Glu Glu Val Leu Asn Leu Ala Gln Ser
                 85                  90                  95
Lys Asn Phe His Leu Arg Pro Arg Asp Leu Ile Ser Asn Ile Asn Val
                100                 105                 110
Ile Val Leu Glu Leu Lys Gly Ser Glu Thr Thr Phe Met Cys Glu Tyr
            115                 120                 125
Ala Asp Glu Thr Ala Thr Ile Val Glu Phe Leu Asn Arg Trp Ile Thr
130                 135                 140
Phe Ala Gln Ser Ile Ile Ser Thr Leu Thr
145                 150

<210> SEQ ID NO 15
<211> LENGTH: 26
<212> TYPE: DNA
<213> ORGANISM: Artificial Sequence
<220> FEATURE:
<223> OTHER INFORMATION: Forward primer

<400> SEQUENCE: 15
agtctagaca atcaggcgaa gaacgg                                          26

<210> SEQ ID NO 16
<211> LENGTH: 25
<212> TYPE: DNA
<213> ORGANISM: Artificial Sequence
<220> FEATURE:
<223> OTHER INFORMATION: Reverse primer

<400> SEQUENCE: 16
agccatggag tcaccctcac ttttc                                           25

<210> SEQ ID NO 17
<211> LENGTH: 31
<212> TYPE: DNA
<213> ORGANISM: Artificial Sequence
<220> FEATURE:
<223> OTHER INFORMATION: Forward primer

<400> SEQUENCE: 17
ggatccttaa gacccacttt cacatttaag t                                    31

<210> SEQ ID NO 18
<211> LENGTH: 28
<212> TYPE: DNA
<213> ORGANISM: Artificial Sequence
<220> FEATURE:
<223> OTHER INFORMATION: Reverse primer

<400> SEQUENCE: 18
ggttccatgg ttcactttc tctatcac                                         28

<210> SEQ ID NO 19
<211> LENGTH: 33
<212> TYPE: DNA
<213> ORGANISM: Artificial Sequence
<220> FEATURE:
<223> OTHER INFORMATION: Forward primer

<400> SEQUENCE: 19
```

-continued gtgtccatgg ggcacagcca ccgcgacttc cag          33

<210> SEQ ID NO 20
<211> LENGTH: 34
<212> TYPE: DNA
<213> ORGANISM: Artificial Sequence
<220> FEATURE:
<223> OTHER INFORMATION: Reverse primer

<400> SEQUENCE: 20
acacgagctc ctacttggag gcagtcatga agct          34

<210> SEQ ID NO 21
<211> LENGTH: 72
<212> TYPE: DNA
<213> ORGANISM: Artificial Sequence
<220> FEATURE:
<223> OTHER INFORMATION: Forward primer

<400> SEQUENCE: 21
gtgtccatgg ctcggcgggc aagtgtcggg actgaccatc atcatcatca tcatcacagc          60
caccgcgact tc          72

<210> SEQ ID NO 22
<211> LENGTH: 35
<212> TYPE: DNA
<213> ORGANISM: Artificial Sequence
<220> FEATURE:
<223> OTHER INFORMATION: Reverse primer

<400> SEQUENCE: 22
gtgcggatcc ctacttggag gcagtcatga agctg          35

<210> SEQ ID NO 23
<211> LENGTH: 16
<212> TYPE: PRT
<213> ORGANISM: Homo sapiens

<400> SEQUENCE: 23

Met Ala Arg Arg Ala Ser Val Gly Thr Asp His His His His His His
1               5                   10                  15

<210> SEQ ID NO 24
<211> LENGTH: 22
<212> TYPE: PRT
<213> ORGANISM: Artificial Sequence
<220> FEATURE:
<223> OTHER INFORMATION: Peptide sequence TiP 13.40

<400> SEQUENCE: 24

Ala Tyr Arg Trp Arg Leu Ser His Arg Pro Lys Thr Gly Phe Ile Arg
1               5                   10                  15

Val Val Met Tyr Glu Gly
            20

<210> SEQ ID NO 25
<211> LENGTH: 66
<212> TYPE: DNA
<213> ORGANISM: Artificial Sequence
<220> FEATURE:
<223> OTHER INFORMATION: Nucleotide sequence encoding TiP13.40

<400> SEQUENCE: 25
gcgtaccgct ggcgcctgtc ccatcgcccg aaaaccggct ttatccgcgt ggtgatgtac          60

-continued

```
gaaggc                                                              66

<210> SEQ ID NO 26
<211> LENGTH: 101
<212> TYPE: DNA
<213> ORGANISM: Artificial Sequence
<220> FEATURE:
<223> OTHER INFORMATION: Oligonucleotide

<400> SEQUENCE: 26
gtgtactagt gtggcgcagg cggcgtaccg ctggcgcctg tcccatcgcc cgaaaaccgg    60
ctttatccgc gtggtgatgt acgaaggcta aggatccgcg c                      101

<210> SEQ ID NO 27
<211> LENGTH: 101
<212> TYPE: DNA
<213> ORGANISM: Artificial Sequence
<220> FEATURE:
<223> OTHER INFORMATION: Oligonucleotide

<400> SEQUENCE: 27
gcgcggatcc ttagccttcg tacatcacca cgcggataaa gccggttttc gggcgatggg    60
acaggcgcca gcggtacgcc gcctgcgcca cactagtaca c                      101

<210> SEQ ID NO 28
<211> LENGTH: 101
<212> TYPE: PRT
<213> ORGANISM: Homo sapiens

<400> SEQUENCE: 28

Met Ser Ser Ala Ala Gly Phe Cys Ala Ser Arg Pro Gly Leu Leu Phe
  1               5                  10                  15

Leu Gly Leu Leu Leu Leu Pro Leu Val Val Ala Phe Ala Ser Ala Glu
             20                  25                  30

Ala Glu Glu Asp Gly Asp Leu Gln Cys Leu Cys Val Lys Thr Thr Ser
         35                  40                  45

Gln Val Arg Pro Arg His Ile Thr Ser Leu Glu Val Ile Lys Ala Gly
     50                  55                  60

Pro His Cys Pro Thr Ala Gln Leu Ile Ala Thr Leu Lys Asn Gly Arg
 65                  70                  75                  80

Lys Ile Cys Leu Asp Leu Gln Ala Pro Leu Tyr Lys Lys Ile Ile Lys
                 85                  90                  95

Lys Leu Leu Glu Ser
            100

<210> SEQ ID NO 29
<211> LENGTH: 106
<212> TYPE: DNA
<213> ORGANISM: Artificial Sequence
<220> FEATURE:
<223> OTHER INFORMATION: Oligonucleotide

<400> SEQUENCE: 29
cttcactagt gtggcgcagg cgaacggccg caaaatctgc ctggacctgc aggcgccgct    60
gtacaaaaaa atcatcaaaa aactgctgga aagctaagga tccgcg                 106

<210> SEQ ID NO 30
<211> LENGTH: 106
<212> TYPE: DNA
<213> ORGANISM: Artificial Sequence
<220> FEATURE:
```

<223> OTHER INFORMATION: Oligonucleotide

<400> SEQUENCE: 30

```
cgcggatcct tagctttcca gcagtttttt gatgattttt ttgtacagcg gcgcctgcag      60
gtccaggcag attttgcggc cgttcgcctg cgccacacta gtgaag                    106
```

<210> SEQ ID NO 31
<211> LENGTH: 85
<212> TYPE: PRT
<213> ORGANISM: Homo sapiens

<400> SEQUENCE: 31

```
Ile Tyr Ser Phe Asp Gly Arg Asp Ile Met Thr Asp Pro Ser Trp Pro
 1               5                  10                  15

Gln Lys Val Ile Trp His Gly Ser Ser Pro His Gly Val Arg Leu Val
            20                  25                  30

Asp Asn Tyr Cys Glu Ala Trp Arg Thr Ala Asp Thr Ala Val Thr Gly
        35                  40                  45

Leu Ala Ser Pro Leu Ser Thr Gly Lys Ile Leu Asp Gln Lys Ala Tyr
    50                  55                  60

Ser Cys Ala Asn Arg Leu Ile Val Leu Cys Ile Glu Asn Ser Phe Met
65                  70                  75                  80

Thr Asp Ala Arg Lys
                85
```

<210> SEQ ID NO 32
<211> LENGTH: 44
<212> TYPE: DNA
<213> ORGANISM: Artificial Sequence
<220> FEATURE:
<223> OTHER INFORMATION: Oligonucleotide

<400> SEQUENCE: 32

```
ggcttcacta gtgtggcgca ggcgatatac cctttgatg gtcg                       44
```

<210> SEQ ID NO 33
<211> LENGTH: 37
<212> TYPE: DNA
<213> ORGANISM: Artificial Sequence
<220> FEATURE:
<223> OTHER INFORMATION: Oligonucleotide

<400> SEQUENCE: 33

```
cgcggatcct tacttcctag cgtctgtcat gaaactg                              37
```

<210> SEQ ID NO 34
<211> LENGTH: 7117
<212> TYPE: DNA
<213> ORGANISM: E. coli

<400> SEQUENCE: 34

```
ccgggcact tccgggcat gagtatgtga tatccggggc tgcaccccgg accccgccaa       60
acatcacgg gccacaaaat ttttgtggc ccgctctgcg ttttctaagt gttatccctc      120
tgatttcta aaaattttc cacctgaact tgacagaaaa acgatgacg agtacttttt      180
atctgtaca taaacccagt ggttttatgt acagtattaa tcgtgtaatc aattgtttta    240
cgcttaaaa gagggaattt ttatgagcgg tggcgatgga cgcggccata acacgggcgc   300
catagcaca agtggtaaca ttaatggtgg cccgaccggg cttggtgtag gtggtggtgc   360
tctgatggc tccggatgga gttcggaaaa taacccgtgg ggtggtggtt ccggtagcgg   420
```

```
attcactgg ggtggtggtt ccggtcatgg taatggcggg gggaatggta attccggtgg      480 ggttcggga acaggcggta atctgtcagc agtagctgcg ccagtggcat ttggttttcc      540 gcactttcc actccaggag ctggcggtct ggcggtcagt atttcagcgg gagcattatc      600 gcagctatt gctgatatta tggctgccct gaaaggaccg tttaaatttg gtctttgggg      660 gtggcttta tatggtgtat tgccatcaca aatagcgaaa gatgaccccca atatgatgtc     720 aagattgtg acgtcattac ccgcagatga tattactgaa tcacctgtca gttcattacc      780 ctcgataag gcaacagtaa acgtaaatgt tcgtgttgtt gatgatgtaa aagacgagcg      840 cagaatatt tcggttgttt caggtgttcc gatgagtgtt ccggtggttg atgcaaaacc      900 accgaacgt ccgggtgttt ttacggcatc aattccaggt gcacctgttc tgaatatttc      960 gttaataac agtacgccag cagtacagac attaagccca ggtgttacaa ataatactga     1020 aaggatgtt cgcccggcag gatttactca gggtggtaat accagggatg cagttattcg     1080 ttcccgaag gacagcggtc ataatgccgt atatgtttca gtgagtgatg ttcttagccc     1140 gaccaggta aaacaacgtc aagatgaaga aaatcgccgt cagcaggaat gggatgctac     1200 catccggtt gaagcggctg agcgaaatta tgaacgcgcg cgtgcagagc tgaatcaggc     1260 aatgaagat gttgccagaa atcaggagcg acaggctaaa gctgttcagg tttataattc     1320 cgtaaaagc gaacttgatg cagcgaataa aactcttgct gatgcaatag ctgaaataaa     1380 caatttaat cgatttgccc atgacccaat ggctggcggt cacagaatgt ggcaaatggc     1440 gggcttaaa gcccagcggg cgcagacgga tgtaaataat aagcaggctg catttgatgc     1500 gctgcaaaa gagaagtcag atgctgatgc tgcattgagt tctgctatgg aaagcaggaa     1560 aagaaagaa gataagaaaa ggagtgctga aaataattta acgatgaaa agaataagcc      1620 agaaaaggt tttaaagatt acgggcatga ttatcatcca gctccgaaaa ctgagaatat     1680 aaagggctt ggtgatctta agcctgggat accaaaaaca ccaaagcaga atggtggtgg     1740 aaacgcaag cgctggactg gagataaagg gcgtaagatt tatgagtggg attctcagca     1800 ggtgagctt gagggggtatc gtgccagtga tggtcagcat cttggctcat tgaccctaa      1860 acaggcaat cagttgaaag gtccagatcc gaaacgaaat atcaagaaat atctttgaga     1920 gaagttatg ggacttaaat tggatttaac ttggtttgat aaaagtacag aagattttaa     1980 ggtgaggag tattcaaaag attttggaga tgacggttca gttatggaaa gtctaggtgt     2040
cctttttaag gataatgtta ataacggttg ctttgatgtt atagctgaat gggtacccttt   2100 ctacaacca tactttaatc atcaaattga tattccgat aatgagtatt ttgtttcgtt       2160 gattatcgt gatggtgatt ggtgatcaaa tattatcagg gatgagttga tatacgggct     2220 ctagtgttc atggatgaac gctggagcct ccaaatgtag aaatgttata ttttttattg     2280 gttcttggt tataattgct ccgcaatgat ttaaataagc attatttaaa acattctcag     2340 agaggtgaa ggtggagcta aaaaaagta ttggtgatta cactgaaacc gaattcaaaa      2400 atttattga agacatcatc aattgtgaag gtgatgaaaa aaaacaggat gataacctcg     2460 gtatttat aaatgttact gagcatccta gtggttctga tctgatttat tacccagaag       2520 taataatga tggtagccct gaaggtgtta ttaaagagat taaagaatgg cgagccgcta     2580 cggtaagtc aggatttaaa cagggctgaa atatgaatgc cggttgttta tggatgaatg     2640 ctggcattc tttcacaaca aggagtcgtt atgaaaaaaa taacagggga tattttattg     2700 ttcttgcag tcattattct gtctgcatgt caggcaaact atatccggga tgttcagggc     2760
```

```
ggaccgtat ctccgtcatc aacagctgaa gtgaccggat tagcaacgca gtaacccgaa    2820 tcctctttg acaaaaacaa agcgtgtcag gctgattctg atgcgctttt tttttgaaat    2880 tcacaaaaa ttccatgtgg gagatgggat ctaaaatcct cgtgcagaac tttccatcca    2940 ggggagaaa acttgtcgtt ttgagccgtt cggtgttcag aacgcacgaa accgatcgcg    3000 gcatcgctt tcgtgaatag ttatgcaggc ccctgaaaac gattctgacg cgttttttcg    3060 ttttgcctg gtgttttcct gtcttttttgc gttttttgcg tcagaacgcg tctgagggcg    3120 tttaagggg tgcgtacaac gggagttatg gtaaatggat cggttttttcg ggaaggatcg    3180 caggatttg ccgttgggtg tagtgtaagc gactgaaaaa caaacgcccc gtaaatcgtg    3240 tctcaccgc caagattgat cacgaaatta cagggcgccg ggttccgcgt ttcccgatgg    3300 aaagcgcgg ttagttaaac tgtgtaccga gagaaatcgt atcacatgag cgccgtactt    3360 aacgcttca gggaaaaatt accgcacaaa ccgtactgta cgaacgattt cgcgtacggc    3420 ttcgcattc tgccgaaaaa cattgccatt cttgcccgtt tcatccagca gaaccagcca    3480 atgcactgt actggcttcc ctttgacgtg gaccggacgg gggcatcaat cgactggagc    3540 accggaatt gtccggcccc gaacatcacc gtaaaaaatc cccgtaacgg gcacgcgcat    3600 tgctctacg cgctcgccct tcctgtgaga actgcgccgg atgcatcggc ttcggcgctc    3660 gatacgctg ccgctattga gcgtgcgttg tgtgaaaaac tgggcgcgga tgtgaattac    3720 gcggcctga tctgcaaaaa tccgtgccac cctgaatggc aggaagtgga atggcgcgag    3780 aaccctaca ctctcgacga actggctgat tatctcgatt tgagcgcctc agcgcgccgt    3840 gcgtcgata aaaattacgg gctggggcga aactgctatc tgttcgaaaa gggccgtaaa    3900 gggcttacc gggctattcg tcagggctgg ccggcattct cacaatggct tgatgcggtg    3960 ttcagcgtg tcgaaatgta caacgcatcg ctcccccgttc cgctttcacc tcctgaatgt    4020 gggctattg gcaagagtat tgcgaaatac acgcacagga acttcacgcc ggaaactttc    4080 cacagtatg tggctgatac gcacacgcca gaaattcagg ctacacgcgg tcgcaagggc    4140 gttctaagt ctaagcgcgg cacagtagct acatcagcac gcacgctgaa accttgggag    4200 aattaggga tcagtcgcgc ctggtattac caactgaaaa aacgaggtct cgtagagtag    4260 ccaaataag cctatatcag ataacagcgc cttttttggcg ccttttttgag cagcttggtt    4320 gttgctatt tccctcgttg aatcccgcaa tggcgcggct ttccgcatga ttgaggtggt    4380 gcgctcgcc gcagtctcat gaccgagcgt agcgagcgaa tgagcgagga agcgcaaagg    4440 gtccggtgg tgcatgtggc acttacgcgc cggggcttag tggttctgcg gtttcgccgg    4500 ggtctgggt agcttctcca gctcgttaat cagcggttgt agtcggttca catccacctg    4560 cttgtgact tcctttcgca gaaactggag caggaacgca cgcagttgcg cttcttccgg    4620 ctccgtacc cttgccagca tggctgcccc cacaatgact ttttgcgccg tgtccaggct    4680 cggctcttc gccttcaggc gctgtaatct ggcctcagct tcggcaatct tctgttcgag    4740 gttctgctc atttcgtgac tccgtgcgcg gtgaaaaatc gcattttagc gcgtcactgg    4800 agtttaaaa actaaactgg cataatgcac ggcacatcac gaagtgcgca cttatacaat    4860 tccacttcg tttcgattgt gtgcggtctg cgacgctaaa agaaaacggc aaaaaggcat    4920 acggcagaa atggcgattc atcatctcag catgaaaatc atttcgcgaa aaaacggcta    4980 agtgctgtt gcttctgctg cctaccgttc cggctctgtc atacccgatg accgtaccgg    5040 ttaatccac gattacaccc gtaaacgcgg cgttgatgat gcggtcattc tcacccctgc    5100 aatgcaccg tcctggtgtg ttgaccgttc cgttctttgg aatgcggtcg agaaagccga    5160
```

```
cagcgccgg aactcccagc tggcaaggga ggttgaactc gccattcccc gtgagatttc      5220 cgcgaggcc gcacgggaga ccgttctcgc tttgtccggg aaaactttgt cagtcggggc      5280 tgattgccg atgtggcgtt ccatcacatg gaccggacca atccccatgc gcacatcatg      5340 tgaccacga gagctgtcgg ggaaacggga ttcgcaggaa aggtcaggga tggaacgacc      5400 ggcactcgc cgagacgtgg cgcgcatcat gggctgacca tgcgaacaga gcgcttgcga      5460 cgccggcta ccaggaagag atagaccatc gttcatacga gcgtcaggga ctggagaaag      5520 gccgcctt cacctcggaa aggctgcctg tgcgatgaa aaacggggga tggaaacaga      5580 cgcggtgag cagaaccgtc tgattaacag ccttaacctg gaaatacagg tttcccgcac      5640 cagcttgct ctcaggacgg ttcaggaaac gcagcgtaag cgggaactca gcgatgctgc      5700 cgtcgtgca gtggaagccc ttaacctgac cattcccgct gcgaatgcct cagcggatac      5760 ctgcgggaa ttcattgcca cgctgccgca ggaatgcggg aacgcgtggg agatgacccc      5820 gagttcctg gcgatgagcg ggaaggtgaa cgacatcgaa cgtgagggga atgcgctgct      5880 aaagagcag gccattctcg aaaaggagat gaccggactc aaaaaagcac gccctgtcgc      5940 tcccttctg tcagagattc ccctgatgac atgggctgaa ccggaatacc gcaaaagaca      6000 ctccgtttc ttggaaactc gggaaacaga ttgaatctct tcgccgcacc tacagggccg      6060 gaaagaacg ggacattccc gcccgtcgtc aggcctttga acgcagtgg aatacgtgga      6120 tgcgccgga atggcagagc tgaaagaaaa actgtcagca cgggaagcgg agcggcgcag      6180 gaggagccc gaagcggaag cgcgccggaa ggaacaggag catgaggcgc ggctgaaacg      6240 catgataac caccgtctga gccgtgaaac ggcattagtc ggggttatta cggagctggg      6300 cgtgccaga gagccgggaa cgggcaggat aacccgctac atgatgttga gtaacagagc      6360 ggagaattc acggtatggg gtgatgagct ggcgcattac ccccagagtg ttcatgaccc      6420 gtgaatgtt tacctgtcgc caggcggggc tgtgatggtc tcggatatac gtgagggaat      6480 ccagaatct catgagacga tggcgcggcc tgagcgtgtg agaatgtatt ccggtgcgac      6540 gtccggcat gtactggaac agatgcgcca ggggtggccc tcttacggtt ttccggcgct      6600 ccgcatcac tggccggata attttttattt cagcgacgac cgcaggcccg tagcctctcc      6660 ctgccgtct gcgcaccggg tggacgtcac cgcttatgcg gcaccgagc aactcatgcc      6720 gttgtattt tcgacagagc gaaacagcag gacgctgaat ctgctgttgt gcaaagggcc      6780 gaggaagtg cttgtcggat ttgtgcgcca ggaggacggg ctgcgtcccg ttcttgcgct      6840 ccgtcgccg gattacagtc atctgatggt cagcaccatc acggagaacg gggtatgcct      6900 gcaggttac ggagaagcta taaccatga tgcggatact ccgtacccac cggaaccgca      6960 ctgatgcag ttccggctca aaggccatca tgacaggctt ttggctgctg tccacaaacc      7020 gaagagatg ccggattatc tcttccgtca actcggtttt aatcagacct ggcatgagtg      7080 aagcgggac gaacagcaca ggcaacaaca acgccgc      7117
```

<210> SEQ ID NO 35
<211> LENGTH: 30
<212> TYPE: DNA
<213> ORGANISM: Artificial Sequence
<220> FEATURE:
<223> OTHER INFORMATION: Forward primer

<400> SEQUENCE: 35
gtgtcatgaa aatgggtaac caatggcaac      30

<210> SEQ ID NO 36
<211> LENGTH: 35
<212> TYPE: DNA
<213> ORGANISM: Artificial Sequence
<220> FEATURE:
<223> OTHER INFORMATION: Reverse primer

<400> SEQUENCE: 36
cacagagctc gcgctaacaa aacagcacaa gggag                      35

<210> SEQ ID NO 37
<211> LENGTH: 37
<212> TYPE: DNA
<213> ORGANISM: Artificial Sequence
<220> FEATURE:
<223> OTHER INFORMATION: Forward primer

<400> SEQUENCE: 37
gtgtccatgg ctaaaacatt attaatagct gcatcgc                    37

<210> SEQ ID NO 38
<211> LENGTH: 29
<212> TYPE: DNA
<213> ORGANISM: Artificial Sequence
<220> FEATURE:
<223> OTHER INFORMATION: Reverse primer

<400> SEQUENCE: 38
gtgtctgcag aactgactga attgagatg                             29

<210> SEQ ID NO 39
<211> LENGTH: 37
<212> TYPE: DNA
<213> ORGANISM: Artificial Sequence
<220> FEATURE:
<223> OTHER INFORMATION: Forward primer

<400> SEQUENCE: 39
gtgtagatct ttaagaccca ctttcacatt taagttg                    37

<210> SEQ ID NO 40
<211> LENGTH: 30
<212> TYPE: DNA
<213> ORGANISM: Artificial Sequence
<220> FEATURE:
<223> OTHER INFORMATION: Reverse primer

<400> SEQUENCE: 40
cacaggatcc ttactgaacc gcgatccccg                            30

<210> SEQ ID NO 41
<211> LENGTH: 40
<212> TYPE: DNA
<213> ORGANISM: Artificial Sequence
<220> FEATURE:
<223> OTHER INFORMATION: Forward primer

<400> SEQUENCE: 41
gtgtgagctc gatcaaccag caagccgtta accctctgac                 40

<210> SEQ ID NO 42
<211> LENGTH: 67
<212> TYPE: DNA
<213> ORGANISM: Artificial Sequence
<220> FEATURE:
<223> OTHER INFORMATION: Reverse primer

<400> SEQUENCE: 42
gtgtgcatgc gggggggccat ataggccggg gatttaaatg caaacgtccg ccgaaacgcc      60
gacgcac      67

<210> SEQ ID NO 43
<211> LENGTH: 71
<212> TYPE: DNA
<213> ORGANISM: Artificial Sequence
<220> FEATURE:
<223> OTHER INFORMATION: Forward primer

<400> SEQUENCE: 43
gtgtgcatgc ggggttaatt aaggggggcgg ccgcgtggta ttggttgaac cgacggtgct      60
catgacatcg c      71

<210> SEQ ID NO 44
<211> LENGTH: 37
<212> TYPE: DNA
<213> ORGANISM: Artificial Sequence
<220> FEATURE:
<223> OTHER INFORMATION: Reverse primer

<400> SEQUENCE: 44
gtgtctcgag gatatcattc tggcctctga cgttgtg      37

<210> SEQ ID NO 45
<211> LENGTH: 45
<212> TYPE: DNA
<213> ORGANISM: Artificial Sequence
<220> FEATURE:
<223> OTHER INFORMATION: Forward primer

<400> SEQUENCE: 45 tttttttccat ggctattatg actgaaatcg ttgcagataa aacgg      45

<210> SEQ ID NO 46
<211> LENGTH: 46
<212> TYPE: DNA
<213> ORGANISM: Artificial Sequence
<220> FEATURE:
<223> OTHER INFORMATION: Reverse primer

<400> SEQUENCE: 46 tttttttaagc ttcccgggtc agacttcagg tacctcaaag agtgtc      46

<210> SEQ ID NO 47
<211> LENGTH: 33
<212> TYPE: DNA
<213> ORGANISM: Artificial Sequence
<220> FEATURE:
<223> OTHER INFORMATION: Forward primer

<400> SEQUENCE: 47
ccgctcgaga tgcacggctc caacaagctc cca      33

<210> SEQ ID NO 48
<211> LENGTH: 33
<212> TYPE: DNA
<213> ORGANISM: Artificial Sequence
<220> FEATURE:
<223> OTHER INFORMATION: Reverse primer

<400> SEQUENCE: 48

```
cgcggatcct taggcactcg ccttgagtgc ctg                                    33
```

<210> SEQ ID NO 49
<211> LENGTH: 102
<212> TYPE: DNA
<213> ORGANISM: Artificial Sequence
<220> FEATURE:
<223> OTHER INFORMATION: Oligonucleotide

<400> SEQUENCE: 49

```
gatcccatgg cttatggcag aaaaaaacgc cgtcagcgcc gtcgcatgaa cgcgctgcag       60
gaagataccc cgccgggccc gtccaccgtg tttcgcccgc cg                         102
```

<210> SEQ ID NO 50
<211> LENGTH: 103
<212> TYPE: DNA
<213> ORGANISM: Artificial Sequence
<220> FEATURE:
<223> OTHER INFORMATION: Oligonucleotide

<400> SEQUENCE: 50

```
gggacagggt gatggtgatg cccgcgatgc cgatgcggat ttcgcggcaa tgcggggttt       60
ccagcgggcg ggaggaggtc ggcgggcgaa acacggtgga cgg                        103
```

<210> SEQ ID NO 51
<211> LENGTH: 102
<212> TYPE: DNA
<213> ORGANISM: Artificial Sequence
<220> FEATURE:
<223> OTHER INFORMATION: Oligonucleotide

<400> SEQUENCE: 51

```
ggcatcgcgg gcatcaccat caccctgtcc ctgtgcggct gcgcgaacgc gcgcgcgccg       60
accctgcgct ccgcgaccgc ggataactcc gaaaacaccg gc                         102
```

<210> SEQ ID NO 52
<211> LENGTH: 111
<212> TYPE: DNA
<213> ORGANISM: Artificial Sequence
<220> FEATURE:
<223> OTHER INFORMATION: Oligonucleotide

<400> SEQUENCE: 52

```
gcgatattcg gacggatcgc aggagcgttt tttggacggc ggtttcggct gatcggtgcg       60
cagatccgga acgtttttaa agccggtgtt ttcggagtta ccgcggtcg c               111
```

<210> SEQ ID NO 53
<211> LENGTH: 111
<212> TYPE: DNA
<213> ORGANISM: Artificial Sequence
<220> FEATURE:
<223> OTHER INFORMATION: Oligonucleotide

<400> SEQUENCE: 53

```
cctgcgatcc gtccgaatat cgcgtctccg aactgaaaga atccctgatc accaccaccc      60
cgtcccgccc gcgcaccgcc cgccgctgca tccgcctctg aaagcttcat g              111
```

<210> SEQ ID NO 54
<211> LENGTH: 41
<212> TYPE: DNA
<213> ORGANISM: Artificial Sequence
<220> FEATURE:
<223> OTHER INFORMATION: Oligonucleotide

```
<400> SEQUENCE: 54
catgaagctt tcagaggcgg atgcagcggc gggcggtgcg c                               41

<210> SEQ ID NO 55
<211> LENGTH: 98
<212> TYPE: DNA
<213> ORGANISM: Artificial Sequence
<220> FEATURE:
<223> OTHER INFORMATION: Oligonucleotide

<400> SEQUENCE: 55
gatcccatgg ctcatcacca tcaccaccat tatggccgca aaaaacgccg tcagcgccgt          60
cgcatgaacg cgctgcagga agatacccccg ccgggccc                                 98

<210> SEQ ID NO 56
<211> LENGTH: 100
<212> TYPE: DNA
<213> ORGANISM: Artificial Sequence
<220> FEATURE:
<223> OTHER INFORMATION: Oligonucleotide

<400> SEQUENCE: 56
gatcccatgg ctaaaaagac ggctctggcg cttctgctct tgctgttagc gctgactagt          60
gtagcgcagg cctatggccg caaaaaacgc cgtcagcgcc                                100

<210> SEQ ID NO 57
<211> LENGTH: 551
<212> TYPE: DNA
<213> ORGANISM: Bacteriophage
<220> FEATURE:
<221> NAME/KEY: CDS
<222> LOCATION: (7)...(408)
<221> NAME/KEY: modified_base
<222> LOCATION: (1)...(1)
<223> OTHER INFORMATION: n=a, c, g, or t

<400> SEQUENCE: 57 nagacc atg gct tat ggc aga aaa aaa aga aga cag aga aga aga atg             48
       Met Ala Tyr Gly Arg Lys Lys Arg Arg Gln Arg Arg Arg Met
         1               5                  10 aac gcg ctg cag gaa gat acc ccg ccg ggc ccg tcc acc gtg ttt cgc            96
Asn Ala Leu Gln Glu Asp Thr Pro Pro Gly Pro Ser Thr Val Phe Arg
 15                  20                  25                  30 ccg ccg acc tcc tcc cgc ccg ctg gaa acc ccg cat tgc cgc gaa atc           144
Pro Pro Thr Ser Ser Arg Pro Leu Glu Thr Pro His Cys Arg Glu Ile
                 35                  40                  45 cgc atc ggc atc gcg ggc atc acc atc acc ctg tcc ctg tgc ggc tgc           192
Arg Ile Gly Ile Ala Gly Ile Thr Ile Thr Leu Ser Leu Cys Gly Cys
             50                  55                  60 gcg aac gcg cgc gcg ccg acc ctg cgc tcc gcg acc gcg gat aac tcc           240
Ala Asn Ala Arg Ala Pro Thr Leu Arg Ser Ala Thr Ala Asp Asn Ser
 65                  70                  75 gaa aac acc ggc ttt aaa aac gtc ccg gat ctg cgc acc gat cag ccg           288
Glu Asn Thr Gly Phe Lys Asn Val Pro Asp Leu Arg Thr Asp Gln Pro
         80                  85                  90 aaa ccg ccg tcc aaa aaa cgc tcc tgc gat ccg tcc gaa tat cgc gtc           336
Lys Pro Pro Ser Lys Lys Arg Ser Cys Asp Pro Ser Glu Tyr Arg Val
 95                 100                 105                 110 tcc gaa ctg aaa gaa tcc ctg atc acc acc acc ccg tcc cgc ccg cgc           384
Ser Glu Leu Lys Glu Ser Leu Ile Thr Thr Thr Pro Ser Arg Pro Arg
                115                 120                 125
```

```
acc gcc cgc cgc tgc atc cgc ctc tgaaagcttg gctgttttgg cggatgagag      438
Thr Ala Arg Arg Cys Ile Arg Leu
            130 aagattttca gcctgataca gattaaatca gaacgcagaa gcggtctgat aaaacagaat      498 ttgcctggcg gcagtagcgc ggtggtccca cctgacccca tgccgaactc aga            551

<210> SEQ ID NO 58
<211> LENGTH: 134
<212> TYPE: PRT
<213> ORGANISM: Bacteriophage

<400> SEQUENCE: 58

Met Ala Tyr Gly Arg Lys Lys Arg Gln Arg Arg Met Asn Ala
1               5                   10                  15

Leu Gln Glu Asp Thr Pro Pro Gly Pro Ser Thr Val Phe Arg Pro Pro
            20                  25                  30

Thr Ser Ser Arg Pro Leu Glu Thr Pro His Cys Arg Glu Ile Arg Ile
        35                  40                  45

Gly Ile Ala Gly Ile Thr Ile Thr Leu Ser Leu Cys Gly Cys Ala Asn
    50                  55                  60

Ala Arg Ala Pro Thr Leu Arg Ser Ala Thr Ala Asp Asn Ser Glu Asn
65                  70                  75                  80

Thr Gly Phe Lys Asn Val Pro Asp Leu Arg Thr Asp Gln Pro Lys Pro
                85                  90                  95

Pro Ser Lys Lys Arg Ser Cys Asp Pro Ser Glu Tyr Arg Val Ser Glu
            100                 105                 110

Leu Lys Glu Ser Leu Ile Thr Thr Pro Ser Arg Pro Arg Thr Ala
        115                 120                 125

Arg Arg Cys Ile Arg Leu
            130

<210> SEQ ID NO 59
<211> LENGTH: 444
<212> TYPE: DNA
<213> ORGANISM: Bacteriophage
<220> FEATURE:
<221> NAME/KEY: modified_base
<222> LOCATION: (1)...(1)
<223> OTHER INFORMATION: n=a, c, g, or t
<221> NAME/KEY: CDS
<222> LOCATION: (7)...(427)

<400> SEQUENCE: 59 nagacc atg gct cat cac cat cac cac cat tat ggc cgc aaa aaa cgc        48
       Met Ala His His His His His His Tyr Gly Arg Lys Lys Arg
           1               5                   10 cgt cag cgc cgt cgc atg aac gcg ctg cag gaa gat acc ccg ccg ggc        96
Arg Gln Arg Arg Arg Met Asn Ala Leu Gln Glu Asp Thr Pro Pro Gly
15                  20                  25                  30 ccg tcc acc gtg ttt cgc ccg ccg acc tcc tcc cgc ccg ctg gaa acc       144
Pro Ser Thr Val Phe Arg Pro Pro Thr Ser Ser Arg Pro Leu Glu Thr
                35                  40                  45 ccg cat tgc cgc gaa atc cgc atc ggc atc gcg ggc atc acc atc acc       192
Pro His Cys Arg Glu Ile Arg Ile Gly Ile Ala Gly Ile Thr Ile Thr
            50                  55                  60 ctg tcc ctg tgc ggc tgc gcg aac gcg cgc gcg ccg acc ctg cgc tcc       240
Leu Ser Leu Cys Gly Cys Ala Asn Ala Arg Ala Pro Thr Leu Arg Ser
        65                  70                  75 gcg acc gcg gat aac tcc gaa aac acc ggc ttt aaa aac gtc ccg gat       288
Ala Thr Ala Asp Asn Ser Glu Asn Thr Gly Phe Lys Asn Val Pro Asp
```

```
ctg cgc acc gat cag ccg aaa ccg ccg tcc aaa aaa cgc tcc tgc gat      336
Leu Arg Thr Asp Gln Pro Lys Pro Pro Ser Lys Lys Arg Ser Cys Asp
 95             100                 105                 110 ccg tcc gaa tat cgc gtc tcc gaa ctg aaa gaa tcc ctg atc acc acc      384
Pro Ser Glu Tyr Arg Val Ser Glu Leu Lys Glu Ser Leu Ile Thr Thr
                115                 120                 125 acc ccg tcc cgc ccg cgc acc gcc cgc cgc tgc atc cgc ctc t            427
Thr Pro Ser Arg Pro Arg Thr Ala Arg Arg Cys Ile Arg Leu
        130                 135                 140 gaaagcttgg ctgtttt                                                   444
```

<210> SEQ ID NO 60
<211> LENGTH: 140
<212> TYPE: PRT
<213> ORGANISM: Bacteriophage

<400> SEQUENCE: 60

```
Met Ala His His His His His His Tyr Gly Arg Lys Lys Arg Arg Gln
 1               5                  10                  15

Arg Arg Arg Met Asn Ala Leu Gln Glu Asp Thr Pro Pro Gly Pro Ser
            20                  25                  30

Thr Val Phe Arg Pro Pro Thr Ser Ser Arg Pro Leu Glu Thr Pro His
        35                  40                  45

Cys Arg Glu Ile Arg Ile Gly Ile Ala Gly Ile Thr Ile Thr Leu Ser
    50                  55                  60

Leu Cys Gly Cys Ala Asn Ala Arg Ala Pro Thr Leu Arg Ser Ala Thr
65                  70                  75                  80

Ala Asp Asn Ser Glu Asn Thr Gly Phe Lys Asn Val Pro Asp Leu Arg
                85                  90                  95

Thr Asp Gln Pro Lys Pro Pro Ser Lys Lys Arg Ser Cys Asp Pro Ser
            100                 105                 110

Glu Tyr Arg Val Ser Glu Leu Lys Glu Ser Leu Ile Thr Thr Thr Pro
        115                 120                 125

Ser Arg Pro Arg Thr Ala Arg Arg Cys Ile Arg Leu
    130                 135                 140
```

<210> SEQ ID NO 61
<211> LENGTH: 1565
<212> TYPE: DNA
<213> ORGANISM: Salmonella

<400> SEQUENCE: 61

```
gatatcattc tggcctctga cgttgtgatg gtcgcacgtg gcgatctggg cgttgaaatc      60
ggcgatccgg agctggttgg tatccagaaa gcgctgattc gccgtgcgcg tcagctaaac     120
cgcgcagtca tcaccgcaac gcaaatgatg gagtcgatga tcaccaaccc gatgccgacc     180
cgtgcggaag tgatggacgt ggcgaacgcc gtcctggatg gcacggatgc ggttatgctg     240
tctgccgaaa ccgcagccgg tcagtatcct tctgaaaccg ttgccgcaat ggcgcgcgtc     300
tgcctgggcg cagaaaaaat ccccagcatc aatgtgtcta acaccgtctc gacgtgcag      360 ttcgacaacg ttgaagaagc cattgccatg tctgcgatgt atcgcggcaaa ccatctgaaa   420 ggcgttaccg cgatcatcac catgacggaa tccggtcgta ccgcgctaat gacttcccgt     480
atcagctccg gcctgccgat tttcgccatg tcgcgccatg aacgcacgct gaacctgacc     540
gcgctctatc gcggagtaac gccggtgcat tttgatagcg cggctgatgg cgttgtcgcg     600
```

```
                                                  -continued
gcacatgaag ctgttaatct gctgcgcgat aaagggtatc tggtttccgg cgacctggtt    660
atcgtgaccc agggcgatgt catgagcacc gtcggttcaa ccaataccac gcggccgccc    720
ccttaattaa ccccgcatgc gggggggccat ataggccggg gatttaaatg caaacgtccg   780
ccgaaacgcc gacgcactgt gttccagata tagtcaaaaa ccggattacc ctgattatga    840
aacatcgccg ccattttttg cccctgagag gccatcagca tggctggaat gtcgacgccc    900
cagccatgcg gtacgagaaa aatgactttt tcgtcgttac gacgcatctc ctcgataatc    960
tccagaccct cccagtcaac acgctgttga attttttcg gaccgcgcat cgccaactca    1020
gccatcatcg ccattgcctg tggcgcggtg gcgaacatct catcgacaat cgcttcgcgc   1080
tcagcttcgc tacgctgcgg aaagcacaac gacagattaa ttagcgcccg gcgacgagaa   1140
ctcttcccca gccgtccggc aaaacgcccc agcgtcgcca gcaaagggtc gcggaatgat   1200
gccggtgtta atgcgatccc cgccattgcc gccgcgccca accaggcgcc ccaatactgt   1260
ggatagcgaa aggattttc gaattcaggg atatactcac tattattttt tttggtttcc    1320
atgcttttcc agggtctgct gacgcgaaaa ggaattgtga atagtgtagc gacgtctgcg   1380
tctcacacaa aacaaaaaag ccggcacaca tcgcgtaccg gctctgtcag cgcatttgtt   1440
aatcgaagcg cagttgcggc agaacctctt tcacctgtgc caggtattca cgacgatctg   1500
accccgtcag accttccgtg cgcggcaatt ttgctgtcag agggttaacg gcttgctggt   1560
tgatc                                                               1565
```

COMPOSITIONS AND METHODS FOR TUMOR-TARGETED DELIVERY OF EFFECTOR MOLECULES

This application claims priority to U.S. provisional patent applications Nos. 60/157,500, 60/157,581, and 60/157,637, filed on Oct. 4, 1999, the contents of each of which is incorporated herein by reference its entirety.

1. FIELD OF THE INVENTION

The present invention relates to the delivery of one or more primary effector molecule(s) to a solid tumor for the treatment or inhibition of the tumor. More particularly, the invention is related to the preparation and use of attenuated tumor-targeted bacteria, such as e.g., *Salmonella*, as a vector for the delivery of one or more primary effector molecule(s) to an appropriate site of action, e.g., the site of a solid tumor. Specifically, the attenuated tumor-targeted bacteria of the invention is a facultative aerobe or facultative anaerobe which is modified to encode one or more primary effector molecule(s). The primary effector molecule(s) of the invention include members of the TNF cyokine family, anti-angiogenic factors, and cytotoxic polypeptides or peptides. The primary effector molecules of the invention are useful, for example, to treat a solid tumor cancer such as a carcinoma, melanoma, lymphoma, sarcoma, or metastases derived from these tumors. The invention further relates to the surprising discovery that primary effector molecule(s) such as TNF family members, anti-angiogenic factors, and cytotoxic polypeptides or peptides can be delivered locally to tumors by attenuated tumor-targeted bacteria with reduced toxicity and reduced immunological complications to the host. The invention also relates to the delivery of one or more optional effector molecule(s) (termed "secondary effector molecules") which may be delivered by the attenuated tumor-targeted bacteria in conjunction with the primary effector molecule(s). The secondary effector molecule(s) provide additional anti-tumor therapeutic activity, enhance release of the primary effector molecule(s) from the attenuated tumor-targeted bacteria, and/or enhance uptake of the primary effector molecule(s) at the appropriate site of action, e.g., at the site of a solid tumor.

2. BACKGROUND OF THE INVENTION

A neoplasm, or tumor, is a neoplastic mass resulting from abnormal cell growth, which can be benign or malignant. Benign tumors generally remain localized. Malignant tumors generally have the potential to invade and destroy neighboring body tissue and spread to distant sites and cause death (for review, seq Robins and Angell, 1976, *Basic Pathology*, 2d Ed., W. B. Saunders Co., Philadelphia, pp. 68–122). A tumor is said to have metastasized when it has spread from one organ or tissue to another.

A major problem in the chemotherapy of solid tumor cancers is delivery of therapeutic agents, such as drugs, in sufficient concentrations to eradicate tumor cells while at the same time minimizing damage to normal cells. Thus, studies in many laboratories are directed toward the design of biological delivery systems, such as antibodies, cytokines, and viruses for targeted delivery of drugs, pro-drug converting enzymes, and/or genes into tumor cells (see, e.g., Crystal, R. G., 1995, Science 270:404–410).

2.1. Cellular Immunity and Cytokines

One strategy for the treatment of cancer involves enhancing or activating a cellular immune response. Successful induction of a cellular immune response directed toward autologous tumors offers several advantages over conventional chemotherapy: 1) immune recognition is highly specific, being directed exclusively toward tumors; 2) growth at metastatic sites can be suppressed through immune surveillance; 3) the diversity of immune response and recognition can compensate for different resistance mechanisms employed by tumor cells; 4) clonal expansion of cytotoxic T cells can occur more rapidly than the expanding tumor, resulting in antitumor mechanisms which ultimately overwhelm the tumor; and 5) a memory response can suppress disease recurrence in its earliest stages, prior to physical detection. Clinical studies of responding patients have borne out results from animal models demonstrating that successful immunotherapy involves the activation of CD8+ T cells (class I response), although evidence exists for participation of CD4+ T cells, macrophages, and NK cells. See, e.g., Chapoval et al., 1998, J. Immunol. 161:6977–6984; Gollub et al., 1998, J. Clin. Invest. 102:561–575; Kikuchi et al., 1999, Int. J. Cancer 80:425–430; Pan et al., 1995, Int. J. Cancer 80:425–430; Saffran et al., 1998, Cancer Gene Ther. 5:321–330; and Zimmerrmann et al., 1999, Eur. J. Immunol. 29:284–290.

2.2. Tumor Necrosis Factor (TNF) Family of Cytokines

The best characterized member of the TNF family is TNF-α. TNF-α is known to exert pleiotropic effects on the immune system. TNF-α is a cytokine which can exert potent cytotoxic effects directly on tumor cells. TNF-α is generally thought to exert its anti-tumor effects via other mechanisms such as stimulation of proliferation and differentiation, and prevention of apoptosis in monocytes (see, e.g., Mangan et al., 1991, J. Immunol. 146:1541–1546; and Ostensen et al., 1987, J. Immunol. 138:4185–4191), promotion of tissue factor-like procoagulant activity and suppression of endothelial cell surface anticoagulant activity, ultimately leading to clot formation within the tumor (reviewed in Beutler and Cerami, 1989, Ann. Rev. Immunol. 7:625–655; and Vassalli, P., 1992, Ann. Rev. Immunol. 10:411–452). However, as a result of the properties, systemic administration of TNF-α results in lethal consequences in the host due to disseminated intravascular coagulation.

Other cytokines have also been implicated in anti-tumor responses. IL-2 is a class I cytokine and is also thought to play a role in anti-tumor response. For example, spontaneously regressing melanomas have been associated with elevated intratumoral levels of TNF-α and IL-2. See, e.g., Beutler and Cerami, 1989, Annu. Rev. Immunol. 7:625–655; Lowes et al., 1997, J. Invest. Dermatol. 108:914–919; Mangan et al., 1991, J. Immunol. 146:1541–1546; Scheruich et al., 1987, J. Immunol. 138: 1786–1790.

Both TNF-α and IL-2 aid in lymphocyte homing, and IL-2 has been shown to induce tumor infiltration of natural killer (NK) cells, T-cells, and lymphokine activated killer (LAK) cells (see, e.g., Etter et al., 1998, Cytokine 10:395–403; Reinhardt et al., 1997, Blood 89:3837–46; Chen et al., 1997, Neuropathol. Exp. Neurol. 56:541–50; Vora et al., 1996, Clin. Exp. Immunol. 105:155–62; Luscinskas et al., 1996, J. Immunol. 157:326–35; Kjaergaard et al., 1998, Scand. J. Immunol. 47, 532–540; Johansson et al., 1996, Nat. Immun. 15:87–97; and Watanabe et al., 1997, Am. J. Pathol. 150:1869–80). In the presence of both TNF-α and IL-2, the cytolytic activity of NK and LAK cells is increased, even when directed against TNF-insensitive cell lines (see, e.g. Ostensen et al., 1987, J. Immunol. 138:4185–4191). However, therapeutic levels of IL-2 have also been shown to be toxic to the host.

Clearly, dose-limiting toxicity from systemic cytokine administration poses a significant barrier to realizing the potential of cytokines in cancer therapy. Moreover, systemic cytokine delivery can result in decreased homing of syngeneic T cells, thus opposing targeted immunotherapy, in addition to resulting in unwanted clinical side effects. See Addison et al., 1998, Gene Ther. 5:1400–1409; Albertini et al., 1997, Clin. Cancer Res. 3:1277–1288; Becker et al., 1996, Proc. Natl. Acad. Sci. USA 93:7826–7831; Book et al., 1998, J. Neuroimmunol. 92:50–59; Cao et al., 1998, J. Cancer Res. Clin. Oncol. 124:88–92; D'Angelica et al., 1999, Cancer Immunol. Immunother. 47:265–271; Deszo et al., 1996, Clin. Cancer Res. 2:1543–1552; Kjaergaard et al., 1998, Scand: J. Immunol. 47:532–540; Ostensen et al., 1987, J. Immunol. 138:4185–4191; and Schirrmacher et al., 1998, Clin. Cancer Res. 4:2635–2645.

2.3. Delivery of Cytokines

Recent experimental animal and clinical studies have attempted to bypass systemic toxicity of cytokines and administer higher doses, through sub-systemic or alternative methods of delivery of cytokines. In murine models, sarcoma-180 tumors have been treated with administration of a fusogenic liposome-encapsulated TNF-α gene, and systemic administration of polyethylene glycol-encapsulated TNF-α, which could localize to the tumor vasculature (see Tsutsumi et al., 1996, Jpn. J. Cancer Res. 87:1078–1085). Sensitization of tumors to TNF-α by endothelial-monocyte-activating polypeptide II has also been reported (see, Marvin et al., 1999, J. Surg. Res. 63:248–255; Wu et al., 1996, Cancer Res.59:205–212).

In clinical studies, complete tumor eradication has been observed following high-dose TNF-α administration to patients via isolated limb perfusion, in combination with interferon-α or melphalan. However, this technique presents severe risks to the patient if the cytokines are not completely removed following treatment. Further, these treatments require limb isolation, which, in itself presents risks to the patient. See Eggermont et al., 1997, Semin. Oncol. 24:547–555 Fraker et al., 1995, Cancer J. Sci. Am. 1:122–130; Lejeune et al., 1998, Curr. Opin. Immunol. 10:573–580; Marvin et al., 1996, J. Surg. Res. 63:248–255; Mizuguchi et al., 1998, Cancer Res. 58:5725–5730; Tsutsumi et al., 1996, Jpn. J. Cancer Res. 87:1078–1085; and Wu t al., 1996, Cancer Res. 59, 205–212.

Previous studies by Carrier et al., 1992, J. Immunol. 148:1176–81, Saltzman et al., 1997, Cancer Biother. Radiopharm. 12:37–45, Saltzman et al., 1997, J. Pediat. Surgery 32:301–306 have reported the use of attenuated *Salmonella* strains to deliver IL-1β (Carrier) and IL-2 (Saltzman) directly to livers and spleens, the natural sites of *Salmonella* infection, to serve as vaccine strains or affect hepatic metastases. Saltzman's studies used oral administration of *Salmonella* in which bacteria are taken up by GALT (gut associated lymphoid tissue) and transported to liver and spleen. However, these infections are limited to the natural sites of infection.

2.4. Angiogenesis and Tumorigenesis

Another strategy for the treatment of cancer involves the inhibition of angiogenesis. Angiogenesis is the process of growth of new capillaries from preexisting blood vessels. New capillaries are formed by a process in which the endothelial cells of the preexisting blood vessel, using proteolytic enzymes such as matrix metalloproteases, degrade the basement membranes in their vicinity, proliferate, migrate into surrounding stromal tissue and form microtubes. The process of angiogenesis is very tightly regulated by an interplay between negative and positive factors, and in adults is normally restricted to the female reproductive cycle and wound repair (Malonne et al., 1999, Clin. Exp. Metastasis 17:1–14). Aberrant or abnormal regulation of angiogenesis has been implicated in many human disorders, including diabetic retinopathy, psoriasis, rheumatoid arthritis, cardiovascular disease, and tumorigenesis (Folkman, 1995, Nat. Med. 1:27–31).

Angiogenesis is a critical process for tumor growth and metastasis. Tumor formation is divided into two stages, the prevascular and vascular stages. Studies have shown that cells of prevascular tumors proliferate as rapidly as do cells from vascularized tumors. However, prevascular tumors rarely grow to more than 2–3 mm$^3$ because of the existence of an equilibrium between cell proliferation and cell death, the latter resulting from the hypoxic nature of the prevascular tumor (Folkman, 1995, Nat. Med. 1:27–31). The switch from the prevascular to vascular stage requires a shift in the balance of the regulatory factors of angiogenesis from a net balance favoring negative factors to one in which the positive factors, such as fibroblast growth factor (FGF) and vascular endothelial growth factor (VEGF), predominate (Cao, 1998, Prog. Mol. Subcell. Biol. 20:161–176). The shift in balance between regulatory factors is a result of the up-regulation of the angiogenic factors and the simultaneous down-regulation of anti-angiogenic factors (Folkman, 1995, N. Eng. J. Med. 333:1757–1763).

2.5. Anti-Angiogenic Factors

Anti-angiogenic factors were postulated to exist on the basis of several related phenomena that led to the conclusion that primary tumors often inhibited the growth of their metastases (Cao, 1998, Prog. Mol. Subcell. Biol. 20:161–176). The first of these factors to be isolated was mouse angiostatin, a 38 kDa proteolytic fragment of plasminogen that is released into the circulation by primary Lewis lung carcinoma tumors and prevents the growth of secondary metastases (O'Reilly et al., 1994, Cell 79:315–328). In humans, peptides of 40, 42 and 45 kDa produced by the limited proteolysis of plasminogen with metalloelastase have anti-angiogenic activity comparable to mouse angiostatin (O'Reilly et al., 1994, Cell 79:315–328). Plasminogen itself has no such activity. It is also thought that tumor-associated macrophages are responsible for the production of angiostatin, since tumor cells themselves have no detectable angiostatin mRNA. Macrophage metalloelastase expression is induced by granulocyte colony stimulating factor (GM-CSF) secreted by the tumor cells (Dong et al., 1997, Cell 88:801–810). In certain tumors, angiostatin production is catalyzed by serine proteases rather than metalloelastase, where serine proteases are produced directly by the tumor cells (Gately et al., 1997, Cancer Res. 56:4887–4890). Administration of angiostatin at a concentration of 100 mg/kg/day to experimental mice with primary tumors resulted in a strong inhibition of tumor growth without toxic side effects. The tumors regrew within 2 weeks of cessation of the angiostatin treatment, indicating that the tumors regress into a dormant state rather than completely die as a result of the treatment (O'Reilly et al., 1996, Nat. Med. 2:689–692).

After the discovery of angiostatin, other angiogenesis inhibitors, including several angiogenesis-inhibiting peptides, were discovered and isolated. A more potent inhibitor of angiogenesis than angiostatin is kringle 5, a peptide comprising the fifth kringle domain of plasminogen (angiostatin comprises kringle domains 1–4). Kringle 5 can be produced by the proteolysis of plasminogen, and recombinant forms are also active (Cao et al., 1997, J. Biol. Chem. 272:22924–22928).

Endostatin was isolated in a manner similar to the isolation of angiostatin (O'Reilly et al., 1997, Cell 88:1–20), the source being a murine hemangioendothelioma rather than a Lewis lung carcinoma. The peptide has an apparent molecular mass of 20 kDa whose sequence corresponds to the C-terminal of collagen XVIII (O'Reilly et al., 1997, Cell 88:1–20), a region called NC1 that is divergent among various collagen molecules (Oh et al., 1994, Proc. Natl. Acad. Sci. USA 91:4229–4233; and Rehn et al., 1994, Proc. Natl. Acad. Sci. USA 91:4234–4238). In mice, the growth of Lewis lung carcinoma metastases is suppressed by the administration 0.3 mg/kg/day of recombinant endostatin, and the primary tumor regresses to a dormant state when the peptide is administered at 20 mg/kg/day. Functional recombinant endostatin can be produced from inclusion bodies, either in vitro by denaturation and refolding, or in vivo by the sustained release of subcutaneously administered endostatin inclusion body preparations (O'Reilly et al., 1997, Cell 88:1–20). An alternative method of endostatin delivery consisting of intramuscular administration of an endostatin expression plasmid results in only the partial inhibition of tumor growth in a mouse model system (Blezinger et al., 1999, Nat. Biotech. 17:343–348). Similarly, endostatin or angiotensin-encoding plasmids complexed to liposomes that were delivered intravenously resulted in a partial inhibition of tumor growth in a nude mouse model of breast cancer (Chen et al., 1999, Cancer Res. 59:3308–3312).

Recently, a novel anti-angiogenic activity has been attributed to a C-terminal truncation peptide of the Serpin (Serine Protease Inhibitor) anti-thrombin (O'Reilly et al., 1999, Science 285:1926–1928). Full length anti-thrombin has no inherent anti-angiogenic activity, but upon cleavage of the C-terminal reactive loop of the protein by thrombin, antithrombin acquires potent angiogenic activity. The proteolytic fragment is referred to hereinafter as anti-angiogenic anti-thrombin.

Other angiogenesis-inhibiting peptides known in the art include the 29 kDa N-terminal and a 40 kDa C-terminal proteolytic fragments of fibronectin (Homandberg et al., 1985, J. Am. Pathol. 120:327–332); the 16 kDa proteolytic fragment of prolactin (Clapp et al., 1993, Endocrinology 133:1292–1299); and the 7.8 kDa proteolytic fragment of platelet factor-4 (Gupta et al., 1995, Proc. Natl. Acad. Sci. USA 92:7799–7803).

In addition to those naturally produced proteolytic fragments that have demonstrated anti-angiogenic effects, several synthetic peptides that correspond to regions of known extracellular matrix proteins have been assessed for activity in inhibiting angiogenesis. Synthetic peptides which have been demonstrated to be functional endothelial inhibitors, i.e. angiogenesis inhibitors, include a 13 amino acid peptide corresponding to a fragment of platelet factor-4 (Maione et al., 1990, Cancer Res. 51:2077–2083); a 14 amino acid peptide corresponding to a fragment of collagen I (Tolma et al., 1993, J. Cell Biol. 122:497–511); a 19 amino acid peptide corresponding to a fragment of Thrombospondin I (Tolsma et al., 1993, J. Cell Biol. 122:497–511); and a 20 amino acid peptide corresponding to a fragment of SPARC (Sage et al., 1995, J. Cell. Biochem. 57:1329–1334), a secreted cysteine-rich extracellular matrix glycoprotein whose expression in human melanoma cells leads to reduced cellular invasion in vitro and reduced tumorigenicity in an in vivo nude mouse model (Ledda et al., 1996, Nature Med. 3:171–176). Other peptides of less than 10 amino acids that inhibit angiogenesis and correspond to fragments of laminin, fibronectin, procollagen, and EGF have also been described (see the review by Cao, 1998, Prog. Mol. Subcell. Biol. 20:161–176).

The small fibronectin peptides that inhibit angiogenesis generally comprise the motif RGD. RGD is a peptide motif (amino acids Arg-Gly-Asp) used by proteins for recognition and binding to integrin molecules. The expression of integrin $\alpha_v\beta_3$ is associated with angiogenic blood vessels and inhibition of its activity by monoclonal antibodies blocks vascularization (Brooks et al., 1994, Science 264:569–571). This has been confirmed by a study showing that the administration of cyclic pentapeptides containing the RGD motif inhibits the activity of vitronectin receptor-type integrins and block retinal neovascularization (Hammes et al., 1996, Nature Medicine 2:529–533). The anti-angiogenic effect of integrin blockers such as cyclic pentapeptides and monoclonal antibodies has been shown to promote tumor regression by inducing the apoptosis of angiogenic blood vessels (Brooks et al., 1994, Cell 79:1157–1164). Peptides comprising the RGD motif, and another integrin binding motif, NGR (amino acids Asn-Gln-Arg), showed markedly enhanced anti-tumor activity.

The inhibition of the activity of another type of cell surface receptor, namely the urokinase plasminogen activator (uPA) receptor, also results in the inhibition of angiogenesis. The uPA receptor, upon ligand binding, initiates a proteolytic cascade that is necessary for the basement membrane invasion step of angiogenesis. Inhibition of the uPA receptor by receptor antagonists inhibits angiogenesis, tumor growth (Min et al., 1996, Cancer Res. 56: 2428–2433) and metastasis (Crowley et al., 1993, Proc. Natl. Acad. Sci. USA 90:5021–5025). Such antagonists have been identified by bacteriophage peptide display of random peptides (Goodson et al., Proc. Natl. Acad. Sci. USA 91:7129–7133). Dominant negative forms of the receptor's ligand, uPA, have also been identified (Min et al., 1996, Cancer Res. 56: 2428–2433).

While the discovery of angiostatin, endostatin and other anti-angiogenic peptides provided an exciting new approach for cancer therapy, the reality of a course of treatment involving one or more of these peptides is the impracticality of the production of immense amounts of peptides (stemming from the cost and/or labor of having to produce, for an average person of 65 kg or 143 lbs, approximately 1.3 or 6.5 grams of protein per day, depending on the peptide) and the duration of the treatment (which has to be sustained if the tumor is to stay in regression). It is thought that the two main reasons that these peptides have to be administered in such large quantities are that, first, a majority are degraded in the blood stream and, second, of the molecules that do survive degradation only a very limited proportion make their way to the tumor. Thus, it would be a great advantage to the field of tumor therapy if anti-angiogenic proteins or peptides could be delivered more efficiently to the tumor and in a more cost-effective and patient-friendly manner.

2.6. Bacteriocin Family

Colicin E3 (referred to hereinafter as ColE3) is a bacteriocin, i.e., a bacterial proteinaceous toxin with selective activity, in that its host is immune to the toxin. Bacteriocins may be encoded by the host genome or by a plasmid, may have a broad or narrow range of hosts, and may have a simple structure comprising one or two subunits or may be a multi-subunit structure (Konisky, 1982, Ann. Rev. Microbiol. 36:125–144). In addition, a bacteriocin host has an immunity against the bacteriocin. The immunity is found in all cells of a given host population, even those that do not express the bacteriocin.

Thee cytotoxicity of ColE3 results from its inhibition of protein synthesis (Nomura, 1963, Cold Spring Harbor Symp. Quant. Biol. 28:315–324). The target of ColE3 activity is the 16S component of bacterial ribosomes, which is common to the 30S and 70S ribosomes (Bowman et al., 1971, Proc. Natl. Acad. Sci. USA. 68:964–968), and the activity results in the degradation of the ribosome (Meyhack, 1970, Proc. Natl. Acad. Sci. USA). ColE3 activity is unique among RNAses, in that it does not cause the overall degradation of RNA, but cleaves mRNA molecules 49 nucleotides from the end, resulting in the separation of the rRNA from the mRNA and thereby inhibiting translation. The ribonuclease activity of ColE3 resides in the molecule itself, rather than being mediated by another protein (Saunders, 1978, Nature 274:113–114). ColE3 is also able to penetrate the inner and outer membranes of the target cell.

In its naturally occurring form, ColE3 is a 60 kDa protein complex consisting of a 50 kDa and a 10 kDa protein in a 1:1 ratio, the larger subunit having the nuclease activity and the smaller subunit having inhibitory function of the 50 kDa subunit. Thus, the 50 kDa protein acts as a cytotoxic protein (or toxin), and the 10 kDa protein acts as an anti-toxin. The 50 kDa subunit comprises at least two functional domains, an N-terminal region required for translocation across target cell membranes, and a C-terminal region with catalytic (RNAse) activity. Within the host organism, the activity of the large subunit is inhibited by the small subunit. The subunits are thought to dissociate upon entry of the toxin into the target cell as a result of interaction with the target cell's outer membrane (reviewed by Konisky, 1982, Ann. Rev. Microbiol. 36:125–144).

The toxicity of the large subunit of ColE3 has been utilized to prevent the lateral spread of cloned genes among microorganisms. Diaz et al. (1994, Mol. Microbiol. 13:855–861) separated the two components of ColE3 such that the small (anti-toxic) subunit was expressed as a chromosomally integrated coding sequence and the large subunit was expressed from a plasmid. Bacteria with the chromosomally integrated small subunit are immune to plasmids that express the ColE3 large subunit, but if the plasmid were to be laterally transferred to another recipient that lacked the small subunit, that cell would be killed.

Colicin E3 (ColE3) has also been shown to have a profoundly cytotoxic effect on mammalian cells (see Smarda et al., 1978, Folia Microbiol. 23:272–277), including a leukemia cell model system (see Fiska et al., 1979, Experimentia 35:406–407). ColE3 activity targets the 40S subunit of the 80S mammalian ribosome (Turnowsky et al., 1973, Biochem. Biophys. Res. Comm. 52:327–334).

2.7. Bacterial Infections and Cancer

Early clinical observations reported cases in which certain cancers were reported to regress in patients with bacterial infections, See Nauts et al., 1953, Acta Medica. Scandinavica 145:1–102, (Suppl. 276); and Shear, 1950, J. A. M. A. 142:383–390. Since these observations, Lee et al., 1992, Proc. Natl. Acad. Sci. USA 89:1847–1851 (Lee et al.) and Jones et al., 1992, Infect. Immun. 60:2475–2480 (Jones et al.) isolated mutants of Salmonella typhimurium that were able to invade HEp-2 (human epidermoid carcinoma) cells in vitro in significantly greater numbers than the wild-type strain. The "hyperinvasive" mutants were isolated under conditions of aerobic growth of the bacteria that normally repress the ability of wild-type strains to invade HEp-2 animal cells. However, such hyperinvasive Salmonella typhimurium as described by Lee et al. and Jones et al. carry the risk of pan-invasive infection and could lead to wide-spread bacterial infection in the cancer patient.

Carswell et al., 1975, Proc. Natl. Acad. Sci. USA 72:3666–3669, demonstrated that mice injected with bacillus Calmette-Guerin (BCG) have increased serum levels of TNF and that TNF-positive serum caused necrosis of the sarcoma Meth A and other transplanted tumors in mice. As a result of such observations, immunization of cancer patients with BCG injections is currently utilized in some cancer therapy protocols. See Sosnowski, 1994, Compr. Ther. 20:695–701; Barth and Morton, 1995, Cancer 75 (Suppl. 2):726–734; Friberg, 1993, Med. Oncol. Tumor. Pharmacother. 10:31–36 for reviews of BCG therapy.

However, TNF-α-mediated septic shock is among the primary concerns associated with bacteria, and can have toxic or lethal consequences for the host (Bone, 1992, JAMA 268:3452–3455; Dinarello et al., 1993, JAMA 269:1829–1835). Further, dose-limiting, systemic toxicity of TNF-α has been the major barrier to effective clinical use. Modifications which reduce this form of an immune response would be useful because TNF-α levels would not be toxic, and a more effective concentration and/or duration of the therapeutic vector could be used.

2.8. Tumor-Targeted Bacteria

Genetically engineered Salmonella have been demonstrated to be capable of tumor targeting, possess anti-tumor activity and are useful in delivering effector genes such as the herpes simplex thymidine kinase (HSV TK) to solid tumors (Pawelek et al., WO 96/40238).

2.9. Decreased Induction of TNF-α by Modified Bacterial Lipid A

Modifications to the lipid composition of tumor-targeted bacteria which alter the immune response as a result of decreased induction of TNFα production were suggested by Pawelek et al. (Pawelek et al., WO 96/40238). Pawelek et al. provided methods for isolation of genes from Rhodobacter responsible for monophosphoryl lipid A (MLA) production. MLA acts as an antagonist to septic shock. Pawelek et al. also suggested the use of genetic modifications in the lipid A biosynthetic pathway, including the mutation firA, which codes for the third enzyme UDP-3-O (R-30 hydroxylmyristoyl)-glucosamine-acyltransferase in lipid A biosynthesis (Kelley et al., 1993, J. Biol. Chem. 268:19866–19874). Pawelek et al. showed that mutations in the firA gene induce lower levels of TNFα.

In Escherichia coli, the gene msbB (mlt) which is responsible for the terminal myristalization of lipid A has been identified (Engel, et al., 1992, J. Bacteriol. 174:6394–6403; Karow and Georgopoulos 1992, J. Bacteriol. 174:702–710; Somerville et al., 1996, J. Clin. Invest. 97:359–365). Genetic disruption of this gene results in a stable non-conditional mutation which lowers TNFα induction (Somerville et al., 1996, J. Clin. Invest. 97:359–365; Somerville, WO 97/25061). These references, however, do not suggest that disruption of the msbB gene in tumor-targeted Salmonella vectors would result in bacteria which are less virulent and more sensitive to chelating agents.

The problems associated with the use of bacteria as gene delivery vectors center on the general ability of bacteria to directly kill normal mammalian cells as well as their ability to overstimulate the immune system via TNFα which can have toxic consequences for the host (Bone, 1992, JAMA 268:3452–3455; and Dinarello et al, 1993, JAMA 269:1829–1835). In addition to these factors, resistance to antibiotics can severely complicate coping with the presence of bacteria within the human body (Tschape, 1996, D T W Dtsch Tierarztl Wochenschr 1996 103:273–7; Ramos et al., 1996, Enferm Infec. Microbiol. Clin. 14: 345–51).

Hone and Powell, WO97/18837 ("Hone and Powell"), disclose methods to produce gram-negative bacteria having non-pyrogenic Lipid A or LPS.

Maskell, WO98/33923, describes a mutant strain of *Salmonella* having a mutation in the msbB gene which induces TNFα at a lower level as compared to a wild type strain.

Bermudes et al., WO 99/13053, teach compositions and methods for the genetic disruption of the msbB gene in *Salmonella*, which results in *Salmonella* possessing a lesser ability to elicit TNFα and reduced virulence compared to the wild type. In certain embodiments, some such mutant *Salmonella* have increased sensitivity to chelating agents as compared to wild type *Salmonella*. See also, Low et al., 1999, Nature Biotech. 17:37–47.

Citation or identification of any reference in Section 2, or any section of this application shall not be construed as an admission that such reference is available as prior art to the present invention.

3. SUMMARY OF THE INVENTION

The present invention provides methods for delivering one or more primary effector molecule(s) to a solid tumor. In an embodiment, the methods provide for delivery of a high level of one or more primary effector molecules. In particular, the invention provides methods by which a primary effector molecule(s), which may be toxic or induce unwanted effects (e.g., unwanted immunological effects) when delivered systemically to a host, can be delivered locally to tumor by an attenuated tumor-targeted bacteria, such as *Salmonella* with reduced toxicity to the host. The present invention encompasses the preparation and the use of attenuated tumor-targeted bacteria, such as, e.g., *Salmonella*, as a vector for the delivery of one or more primary effector molecule(s) and optionally, one or more secondary effector molecule(s), to an appropriate site of action, e.g., the site of a solid tumor. Specifically, the attenuated tumor-targeted bacteria of the invention are facultative aerobes or facultative anaerobes which are engineered to encode one or more primary effector molecule(s) and optionally; one or more secondary effector molecule(s).

The present invention provides attenuated tumor-targeted bacteria engineered to express nucleic acid molecules encoding primary effector molecules at the site of a solid tumor. In a specific embodiment, attenuated tumor-targeted bacteria are engineered to express a nucleic acid molecule encoding a primary effector molecule. In another embodiment, attenuated tumor-targeted bacteria are engineered to express one or more nucleic acid molecules encoding one or more primary effector molecules. In accordance with this embodiment, a single bacterial strain is engineered to express one or more nucleic acid molecules encoding one or more primary effector molecules at the site of a solid tumor. In another embodiment, more than one attenuated tumor-targeted bacterial strain is engineered to express one or more nucleic acid molecules encoding one or more primary effector molecules. In a mode of this embodiment, the attenuated tumor-targeted bacterial strains are of the same species. In another mode of this embodiment, the attenuated tumor-targeted bacterial strains are of different species (e.g., *Listeria* and *Salmonella*).

The primary effector molecules of the invention are useful for the treatment of a solid tumor cancer such as a carcinoma, melanoma, lymphoma, or sarcoma. As used herein, "treatment of a solid tumor" or "treat a solid tumor" encompasses inhibiting the growth of a tumor or tumor cells, reducing the volume of a tumor, killing tumor cells, or spreading of tumor cells (metastasis). In a specific embodiment, the primary effector molecules of the invention induce a local immune response at the site of the tumor that results in the inhibition of growth of a tumor or tumor cells, the killing of tumor cells, or the prevention of the spread of tumor cells to other parts of the body. Accordingly, the primary effector molecules provide a therapeutic effect for treatment of a tumor.

The primary effector molecules can be derived from any known organism, including, but not limited to, animals, plants, bacteria, fungi, and protista, or viruses. In a preferred mode of one embodiment of the invention, the primary effector molecule(s) is derived from a mammal. In a more preferred mode of this embodiment, the primary effector molecule(s) is derived from a human. The primary effector molecules of the invention include members of the TNF family, anti-angiogenic factors, cytotoxic polypeptides or peptides, tumor inhibitory enzymes, and functional fragments thereof.

In a specific embodiment, the primary effector molecules of the invention are members of the TNF family or functional fragments thereof. Examples of TNF family members, include, but are not limited to, tumor necrosis factor-α (TNF-α), tumor necrosis factor-β (TNF-β), TNF-α-related apoptosis-inducing ligand (TRAIL), TNF-α-related activation-induced cytokine (TRANCE), TNF-α-related weak inducer of apoptosis (TWEAK), CD40 ligand (CD40L), LT-α (lymphotoxin alpha), LT-β (lymphotoxin beta), OX40L (OX40 ligand), FasL, CD27L (CD27 ligand), CD30L (CD30 ligand), 4-1BBL, APRIL (a proliferation-inducing ligand), LIGHT (a 29 kDa type II transmembrane protein produced by activated T cells), TL1 (a tumor necrosis factor-like cytokine), TNFSF16, TNFSF17, and AITR-L (ligand of the activation-inducible TNFR family member). In a preferred embodiment, a primary effector molecule of the invention is tumor necrosis factor-α (TNF-α), tumor necrosis factor-β (TNF-β), TNF-α-related apoptosis-inducing ligand (TRAIL), TNF-α-related activation-induced cytokine (TRANCE), TNF-α-related weak inducer of apoptosis (TWEAK), and CD40 ligand (CD40L), or a functional fragment thereof.

In another specific embodiment, the primary effector molecules of the invention are anti-angiogenic factors or functional fragments thereof. Examples of anti-angiogenic factors, include, but are not limited to, endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the anti-angiogenic 24 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, and peptide antagonists of integrin $\alpha_v\beta_3$ and the VEGF receptor. In a preferred embodiment of the invention, a primary effector molecule of the invention is a functional fragment of endostatin, apomigren or thrombospondin I.

In another specific embodiment, the primary effector molecules of the invention are cytotoxic polypeptides or peptides, or functional fragments thereof. Examples of cytotoxic polypeptides or peptides include, but are not limited to, members of the bacteriocin family, verotoxin, cytotoxic necrotic factor 1 (CNF1), cytotoxic necrotic factor 2 (CNF2), *Pasteurella multiocida* toxin (PMT), *Pseudomonas* endotoxin, hemolysin, CAAX tetrapeptides which are potent competitive inhibitors of farnesyltransferase, cyclin inhibitors, Raf kinase inhibitors CDC kinase inhibitors, caspases, p53, p16, and p21. In a preferred embodiment, the primary effector molecule is a member of the bacteroicin family, with the proviso that said bacteriocin family member is not a bacteriocin release protein (BRP). Examples of bacteriocin family members, include, but are not limited to, ColE1, ColE1a, ColE1b ColE2, ColE3, ColE4, ColE5, ColE6, ColE7, ColE8, ColE9, Colicins A, Colicin K, Colicin L, Colicin M, cloacin DF13, pesticin A1122, staphylococcin 1580, butyricin 7423, pyocin R1 or AP41, megacin A-216, and vibriocin. In a specific embodiment, the primary effector molecule is colicin E3.

In another specific embodiment, the primary effector molecules of the invention are tumor inhibitory enzymes or functional fragments thereof. Examples of tumor inhibitory enzymes include, but are not limited to, methionase, asparaginase, lipase, phospholipase, protease, ribonuclease (excluding colE3), DNAase, and glycosidase. In a preferred embodiment, the primary effector molecule is methionase.

The present invention also provides methods for local, combinatorial delivery of one or more primary effector molecule(s) and one or more secondary effector molecule(s) to solid tumors by attenuated tumor-targeted bacteria, such as *Salmonella*. In a specific embodiment, attenuated tumor-targeted bacteria are engineered to express a nucleic acid molecule encoding a primary effector molecule and a secondary effector molecule. In another embodiment, attenuated tumor-targeted bacteria are engineered to express one or more nucleic acid molecules encoding one or more primary effector molecules and one or more secondary effector molecules. In accordance with this embodiment, a single bacterial strain is engineered to express one or more nucleic acid molecules encoding one or more primary effector molecules and one or more secondary effector molecules at the site of a solid tumor. In another embodiment, more than one attenuated tumor-targeted bacterial strain is engineered to express one or more nucleic acid molecules encoding one or more primary effector molecules and one or more secondary effector molecules at the site of a solid tumor. In a mode of this embodiment, the attenuated tumor-targeted bacterial strains are of the same species. In another mode of this embodiment, the attenuated tumor-targeted bacterial strains are of different species (e.g., *Listeria* and *Salmonella*).

The secondary effector molecule(s) of the invention provide additional anti-tumor therapeutic activity, enhance release of the primary effector molecule(s) from the attenuated tumor-targeted bacteria, and/or enhance internalization at the site of action, e.g., at the site of a solid tumor. The secondary effector molecule(s) of the invention comprise a molecule (such as an anti-tumor protein, including but not limited to a cytotoxins, an enzyme abd a bacteriocin; a pro-drug converting enzyme; an antisense molecule; a ribozyme; an antigen; etc.) which is delivered in addition to the primary effector molecule(s) by the methods of the invention to treat a solid tumor cancer such as a carcinoma, melanoma, lymphoma, or sarcoma.

The secondary effector molecules can be derived from any known organism, including, but not limited to, animals, plants, bacteria, fungi, and protista, or viruses. In certain embodiments, the secondary effector molecule is derived from a bacteria or virus. In certain preferred embodiments of the invention, the secondary effector molecule(s) is derived from a bacterium (e.g. BRP). In other preferred embodiments of the invention, the secondary effector molecule(s) is derived from a virus (e.g., TAT). In yet other preferred embodiments of the invention, the secondary effector molecule(s) is derived from a mammal. In certain preferred embodiments, the secondary effector molecule(s) is derived from a human.

The invention provides attenuated tumor-targeted bacteria comprising effector molecule(s) which are encoded by a plasmid or transfectable nucleic acid. In a preferred embodiment of the invention, the attenuated tumor-targeted bacteria is *Salmonella*. When more than one effector molecule (e.g., primary or secondary) is expressed in an attenuated tumor-targeted bacteria, such as *Salmonella*, the effector molecules may be encoded by the same plasmid or nucleic acid, or by more than one plasmid or nucleic acid. The invention also provides attenuated tumor-targeted bacteria comprising effector molecule(s) which are encoded by a nucleic acid which is integrated into the bacterial genome. Integrated effector molecule(s) may be endogenous to an attenuated tumor-targeted bacteria, such as *Salmonella*, or may be introduced into the attenuated tumor-targeted bacteria (e.g., by introduction of a nucleic acid which encodes the effector molecule, such as a plasmid, transfectable nucleic acid, transposon, etc.) such that the nucleic acid encoding the effector molecule becomes integrated into the genome of the attenuated tumor-targeted bacteria. The invention provides a nucleic acid molecule encoding an effector molecule which nucleic acid is operably linked to an appropriate promoter. A promoter operably linked to a nucleic acid encoding an effector molecule may be homologous (i.e., native) or heterologous (i.e., not native to the nucleic acid encoding the effector molecule). Examples of suitable promoters include but are not limited to the Tet promoter, trc, pepT, lac, sulA, pol II (dinA), ruv, recA, uvrA, uvrB, uvrD, umuDC, lexA, cea, caa, recN and pagC.

The present invention also provides methods for local delivery of one or more fusion proteins comprising a signal sequence and an effector molecule by attenuated tumor targeted bacteria. In a preferred embodiment, attenuated tumor-targeted bacteria are engineered to express one or more nucleic acid molecules encoding one or more fusion proteins comprising an Omp-like protein, or portion thereof (e.g., signal sequence, leader sequence, periplasmic region, transmembrane domain, multiple transmembrane domains, or combinations thereof; see infra, Section 3.1 for definition of "Omp-like protein") and an effector molecule. Without intending to be limited as to mechanism, the present inventors believe that the Omp-like protein acts as an anchor or tether for the effector molecule to the outer membrane, or serves to localize the effector molecule to the bacterial outer membrane. In certain embodiments, the effector molecule has enhanced delivery to the outer membrane of the bacteria. In one embodiment, the fusion of an effector molecule to an Omp-like protein is used to enhance localization of an effector molecule to the periplasm. In certain other embodiments, the fusion of an effector molecule to an Omp-like protein is used to enhance release of the effector molecule. Examples of Omp-like proteins include, but are not limited to, at least a portion of each of the following: OmpA, OmpB, OmpC, OmpD, OmpE, OmpF, OmpT, a porin-like protein, PhoA, PhoE, lamB, β-lactamase, an enterotoxin, protein A, endoglucanase, peptidoglycan-associated lipoprotein (PAL), FepA, FhuA, NmpA, NmpB, NmpC, and a major outer membrane lipoprotein (such as LPP). In other embodiments of the invention, a fusion protein of the invention comprises a proteolytic cleavage site. The proteolytic cleavage site may be endogenous to the effector molecule or endogenous to the Omp-like protein, or the proteolytic cleavage site may be constructed into the fusion protein.

The present invention also provides methods for local delivery of one or more fusion proteins comprising a ferry peptide and an effector molecule to a solid tumor by attenuated tumor-targeted bacteria. Ferry peptides used in fusion proteins have been shown to facilitate the delivery of a polypeptide or peptide of interest to virtually any cell within diffusion limits of its production or introduction (see., e.g., Bayley, 1999, Nature Biotechnology 17:1066–1067; Fernandez et al., 1998, Nature Biotechnology 16:418–420; and Derossi et al., 1998, Trends Cell Biol. 8:84–87). Accordingly, engineering attenuated tumor-targeted bacteria to express fusion proteins comprising a ferry peptide and an effector molecule enhances the ability of an effector molecule to be internalized by tumor cells. In a specific embodiment, attenuated tumor-targeted bacteria are engineered to express a nucleic acid molecule encoding a fusion protein comprising a ferry peptide and an effector molecule. In another embodiment, attenuated tumor-targeted bacteria are engineered to express one or more nucleic acid molecules encoding one or more fusion proteins comprising a ferry peptide and an effector molecule. In accordance with these embodiments, the effector molecule may be a primary or secondary effector molecule. Examples of ferry peptides include, but are not limited to, peptides derived from the HIV TAT protein, the antennapedia homeodomain (penetratin), Kaposi fibroblast growth factor (FGF) membrane-translocating sequence (MTS), and herpes simplex virus VP22.

The present invention also provides methods for local delivery of one or more fusion proteins comprising a signal peptide, ferry peptide and an effector molecule to a solid tumor by attenuated tumor-targeted bacteria. In a specific embodiment, attenuated tumor-targeted bacteria are engineered to express one or more nucleic acid molecules encoding one or more fusion proteins comprising a signal sequence, a ferry peptide and an effector molecule. In accordance with this embodiment, the effector molecule may be a primary or secondary effector molecule.

The present invention also provides methods for local delivery of one or more fusion proteins comprising a signal peptide, a protolytic cleavage site, a ferry peptide and an effector molecule to a solid tumor by attenuated tumor-targeted bacteria. In a specific embodiment, attenuated tumor-targeted bacteria are engineered to express one or more nucleic acid molecules encoding one or more fusion proteins comprising a signal sequence, a protolytic cleavage site, a ferry peptide and an effector molecule. In accordance with this embodiment, the effector molecule may be a primary or secondary effector molecule.

In certain embodiments, a single bacterial strain is engineered to express one or more nucleic acid molecules encoding a fusion protein of the invention at the site of a solid tumor. In certain other embodiments, more than one attenuated tumor-targeted bacterial strain is engineered to express one or more nucleic acid molecules encoding one or more fusion proteins of the invention at the site of a solid tumor. In modes of these embodiments, the attenuated tumor-targeted bacterial strains are of the same species. In another modes of these embodiments, the attenuated tumor-targeted bacterial strains are of different species (e.g., *Listeria* and *Salmonella*).

The present invention also provides methods for local delivery of one or more fusion proteins of the invention and one or more effector molecules of the invention to the site of a solid tumor by attenuated tumor-targeted bacteria. Preferably, the expression of both the fusion protein(s) and effector molecule(s) at the site of the solid tumor by an attenuated tumor-targeting bacteria improves the level of tumor or tumor cell growth inhibited compared to when either fusion protein(s) alone or the effector molecule(s) alone is expressed.

The present invention also provides expression of a primary effector molecule and optionally, a secondary effector molecule in an attenuated tumor-targeted bacteria, such as *Salmonella*, which bacteria has an enhanced release system. In a preferred embodiment of the invention, the enhanced release is associated with expression of a release factor by the attenuated tumor-targeted bacteria. In one embodiment, the release allows enhanced release of effector molecules from the cytoplasmic or periplasmic space. A release factor may be endogenous to the attenuated tumor-targeted bacteria or it may exogenous (i.e., encoded by a nucleic acid molecule that is not native to the attenuated tumor-targeted bacteria). A release factor may be encoded by a nucleic acid comprising a plasmid, or by a nucleic acid which is integrated into the genome of the attenuated tumor-targeted bacteria. A release factor may be encoded by the same nucleic acid or plasmid that encodes a primary effector molecule, or by a separate nucleic acid or plasmid. A release factor may be encoded by the same nucleic acid or plasmid that encodes a secondary effector molecule, or by a separate nucleic acid or plasmid. In a preferred embodiment, the release factor is a Bacteriocin Release Protein (BRP). In a specific embodiment, the BRP is that of the cloacin DF13 plasmid, one of colicin E1–E9 plasmids, or the colicin A, N or D plasmids. In a preferred embodiment, the BRP is of cloacin DF13 (pCloDF13 BRP). In another embodiment of the invention, the enhanced release system comprises overexpression of a porin protein.

The present invention also provides expression of a fusion protein of the invention in an attenuated tumor-targeted bacteria, such as *Salmonella*, which bacteria has an enhanced release system. In a specific embodiment, the release factor is expressed in a cell which also expresses a fusion protein comprising a primary effector molecule fused to an Omp-like protein. In this embodiment, the co-expression of the release factor allows for enhanced release of the fusion protein from the periplasmic space.

In one embodiment, the present invention provides methods of delivering high levels of effector molecules or fusion proteins using modified, attenuated tumor-targeted strains of bacteria, which selectively accumulate within tumors while expressing the effector molecules or fusion proteins. In a specific mode, a modified, attenuated tumor-targeted strain of bacteria selectively amplifies effector molecules within tumors. While the teachings of the following sections are discussed, for simplicity, with reference specifically to *Salmonella*, the compositions and methods of the invention are in no way meant to be restricted to *Salmonella* but encompass any other bacteria to which the teachings apply. Specifically, the invention provides an attenuated tumor-targeted bacterium which is a facultative aerobe or facultative anaerobe. Examples of attenuated tumor-targeted bacteria include, but are not limited to, *Escherichia coli*, including enteroinvasive *Escherichia coli*, *Salmonella* spp., *Shigella* spp., *Yersinia enterocohtica*, *Listeria monocytogenies*, *Mycoplasma hominis*, and *Streptococcus* spp.

The present invention also provides pharmaceutical compositions comprising a pharmaceutically acceptable carrier and an attenuated tumor-targeted bacteria engineered to contain one or more nucleic acid molecules encoding one or more primary effector molecules. The present invention also provides pharmaceutical compositions comprising a pharmaceutically acceptable carrier and an attenuated tumor-targeted bacteria engineered to contain one or more nucleic acid molecules encoding one or more primary effector molecules and one or more secondary effector molecules. The present invention also provides pharmaceutical compositions comprising a pharmaceutically acceptable carrier and an attenuated tumor-targeted bacteria engineered to contain one or more nucleic acid molecules encoding one or more fusion proteins of the invention. Further, the present invention provides pharmaceutical compositions comprising a pharmaceutically acceptable carrier and an attenuated tumor-targeted bacteria engineered to contain one or more nucleic acid molecules encoding one or more fusion proteins of the invention and one or more effector molecules (i.e., primary or/and secondary molecules). In a preferred embodiment, the attenuated tumor-targeted bacteria is *Salmonella*.

The pharmaceutical compositions of the invention are useful for the treatment of solid tumors. Solid tumors include, but are not limited to, sarcomas, carcinomas, lymphomas, and other solid tumor cancers, including, but not limited to germ line tumors, tumors of the central nervous system, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, melanoma, renal cancer, bladder cancer, and mesothelioma.

The present invention provides methods for delivering a primary effector molecule for the treatment of a solid tumor cancer comprising administering, to an animal, preferably a mammal and most preferably a human, in need of such treatment, a pharmaceutical composition comprising an attenuated tumor-targeted bacteria engineered to contain one or more nucleic acid molecules encoding one or more primary effector molecules. The present invention also provides methods for delivering a primary effector molecule for the treatment of a solid tumor cancer comprising administering, to an animal, preferably a mammal and most preferably a human, in need of such treatment, a pharmaceutical composition comprising an attenuated tumor-targeted bacteria engineered to contain one or more nucleic acid molecules encoding one or more primary effector molecules and one or more secondary effector molecules. The present invention also provides methods for delivering a primary effector molecule for the treatment of a solid tumor cancer comprising administering, to an animal, preferably a mammal and most preferably a human, in need of such treatment, a pharmaceutical composition comprising an attenuated tumor-targeted bacteria engineered to contain one or more nucleic acid molecules encoding one or more fusion proteins of the invention. Further, the present invention provides methods for delivering a primary effector molecule for the treatment of a solid tumor cancer comprising administering, to an animal, preferably a mammal and most preferably a human, in need of such treatment, a pharmaceutical composition comprising an attenuated tumor-targeted bacteria engineered to contain one or more nucleic acid molecules encoding one or more fusion proteins of the invention and one or more effector molecules (i.e., primary or/and secondary molecules). In a preferred embodiment, the attenuated tumor-targeted bacteria is *Salmonella*. In a specific mode, the attenuated tumor-targeted bacteria comprises an enhanced release system.

In certain embodiments, attenuated tumor-targeted bacteria engineered to express one or more nucleic acid molecules encoding one or more effector molecules and/or fusion proteins can be used in conjunction with other known cancer therapies. For example, attenuated tumor-targeted bacteria engineered to express one or more nucleic acid molecules encoding one or more effector molecules and/or fusion proteins can be used in conjunction with a chemotherapeutic agent. Examples of chemotherapeutic agents include, but are not limited to, cisplatin, ifosfamide, paclitaxol, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, taxol, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, melphalan, glucocorticoids, procaine, tetracaine, lidocaine, propranolol, and puromycin homologs, and cytoxan. Alternatively, attenuated tumor-targeted bacteria engineered to express one or more nucleic acid molecules encoding one or more effector molecules and/or fusion proteins can be used in conjunction with radiation therapy.

The present invention includes the sequential or concomitant administration of anti-cancer agents and attenuated tumor-targeted bacteria engineered to express one or more nucleic acid molecules encoding one or more effector molecules and/or fusion proteins. The invention encompasses combinations of anti-cancer agents and attenuated tumor-targeted bacteria engineered to express one or more nucleic acid molecules encoding one or more effector molecules and/or fusion proteins that are additive or synergistic.

The invention also encompasses combinations of anticancer agents and attenuated tumor-targeted bacteria engineered to express one or more nucleic acid molecules encoding one or more effector molecules and/or fusion proteins that have different sites of action. Such a combination provides an improved therapy based on the dual action of these therapeutics whether the combination is synergistic or additive. Thus, the novel combinational therapy of the present invention yields improved efficacy over either agent used as a single-agent therapy.

3.1. Definitions and Abbreviations

As used herein, *Salmonella* encompasses all *Salmonella* species, including: *Salmonella typhi*, *Salmonella choleraesuis*, and *Salmonella enteritidis*. Serotypes of *Salmonella* are also encompassed herein, for example, *typhimurium*, a subgroup of *Salmonella enteritidis*, commonly referred to as *Salmonella typhimurium*.

Analog: As used herein, the term "analog" refers to a polypeptide that possesses a similar or identical function as a primary or secondary effector molecule but does not necessarily comprise a similar or identical amino acid sequence of a primary or secondary effector molecule, or possess a similar or identical structure of a primary or secondary effector molecule. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a primary or secondary effector molecule described herein; (b) a polypeptide encoded by a nucleotide sequence that hybridizes under stringent conditions to a nucleotide sequence encoding a primary or secondary effector molecule described herein of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence-encoding a primary or secondary effector molecule described herein. A polypeptide with similar structure to a primary or secondary effector molecule described herein refers to a polypeptide that has a similar secondary, tertiary or quaternary structure of primary or secondary effector molecule described herein. The structure of a polypeptide can be determined by methods known to those skilled in the art, including but not limited to, peptide sequencing, X-ray crystallography, nuclear magnetic resonance, circular dichroism, and crystallographic electron microscopy.

Anti-angiogenic factor: An anti-angiogenic factor is any proteinaceous molecule which has anti-angiogenic activity, or a nucleic acid encoding such a proteinaceous molecule. In a preferred embodiment, the anti-angiogenic factor is a peptide fragment or cleavage fragment of a larger protein.

Attenuation: Attenuation is a modification so that a microorganism or vector is less pathogenic. The end result of attenuation is that the risk of toxicity as well as other side-effects is decreased, when the microorganism or vector is administered to the patient.

Bacteriocin: A bacteriocin is a bacterial proteinaceous toxin with selective activity, in that the bacterial host is immune to the toxin. Bacteriocins may be encoded by the bacterial host genome or by a plasmid, may be toxic to a broad or narrow range of other bacteria, and may have a simple structure comprising one or two subunits or may be a multi-subunit structure. In addition, a host expressing a bacteriocin has immunity against the bacteriocin.

Chelating agent sensitivity: Chelating agent sensitivity is defined as the effective concentration at which bacteria proliferation is affected, or the concentration at which the viability of bacteria, as determined by recoverable colony forming units (c.f.u.), is reduced.

Derivative: As used herein, the term "derivative" in the context of a "derivative of a polypeptide" refers to a polypeptide that comprises an amino acid sequence of a polypeptide, such as a primary or secondary effector molecule, which has been altered by the introduction of amino acid residue substitutions, deletions or additions, or by the covalent attachment of any type of molecule to the polypeptide. The term "derivative" as used herein in the context of a "derivative of a primary or a secondary effector molecule" refers to a primary or secondary effector molecule which has been so modified, e.g., by the covalent attachment of any type of molecule to the primary or secondary molecule. For example, but not by way of limitation, a primary or secondary effector molecule may be modified, e.g., by proteolytic cleavage, linkage to a cellular ligand or other protein, etc. A derivative of a primary or secondary effector molecule may be modified by chemical modifications using techniques known to those of skill in the art (e.g., by acylation, phosphorylation, carboxylation, glycosylation, selenium modification and sulfation). Further, a derivative of a primary or secondary effector molecule may contain one or more non-classical amino acids. A polypeptide derivative possesses a similar or identical function as a primary or secondary effector molecule described herein. The term "derivative" in the context of a "derivative of an msbB⁻ attenuated tumor-targeted $Salmonella$ mutant" refers to a modified msbB⁻ $Salmonella$ mutant as defined in International Publication No. WO 99/13053 at page 17, incorporated herein by reference in its entirety.

Fragment: As used herein, the term "fragment" refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a primary or secondary effector molecule.

Functional fragment: As used herein, the term "functional fragment" refers to a fragment of a primary or secondary effector molecule that retains at least one function of the primary or secondary effector molecule (e.g., enzymatic activity, anti-angiogenic activity, or anti-tumor activity of the effector molecule).

Fusion protein: As used herein, the term "fusion protein" refers to a polypeptide that comprises an amino acid sequence of primary or secondary effector molecule, or functional fragment or derivative thereof, and an amino acid sequence of a heterologous polypeptide (e.g., a non-primary or non-secondary effector molecule).

Omp-like protein: As used herein, an Omp-like protein includes any bacterial outer membrane protein, or portion thereof (e.g., signal sequence, leader sequence, periplasmic region, transmembrane domain, multiple transmembrane domains, or combinations thereof). In specific embodiments, the Omp-like protein is at least a portion of OmpA, OmpB, OmpC, OmpD, OmpE, OmpF; OmpT, a porin-like protein, PhoA, PhoE, lamB, β-lactamase, an enterotoxin, protein A, endoglucanase, peptidoglycan-associated lipoprotein (PAL), FepA, FhuA, NmpA, NmpB, NmpC, or a major outer membrane lipoprotein (such as LPP), etc.

Purified: As used herein, "purified" attenuated tumor-targeted bacterial strain is substantially free of contaminating proteins or amino acids (e.g., debris from dead bacteria), or media. An attenuated tumor-targeted bacterial strain that is substantially free of contaminating proteins or amino acids includes preparations of attenuated tumor-targeted bacteria having less than about 30%, 20%, 10%, or 5% (by dry weight) of contaminating protein or amino acid.

Release factor: As used herein, a release factor includes any protein, or functional portion thereof which enhances release of bacterial components. In one embodiment a release factor is a bacteriocin release protein. Release factors include, but are not limited to, the bacteriocin release protein (BRP) encoded by the cloacin D113 plasmid, the BRPs encoded by the colicin E1–E9 plasmids, or BRPs encoded by the colicin A, N or D plasmids.

Septic shock: Septic shock is a state of internal organ failure due to a complex cytokine cascade, initiated by TNF-α. The relative ability of a microorganism or vector to elicit TNF-α is used as one measure to indicate its relative ability to induce septic shock.

Tumor-targeted: Tumor-targeted is defined as the ability to preferentially localize to a cancerous target cell or tissue relative to a non-cancerous counterpart cell or tissue and replicate. Thus, a tumor-targeted bacteria such as *Salmonella* preferentially attaches to, infects and/or remains viable in the cancerous target cell or the tumor environment.

Virulence: Virulence is a relative term describing the general ability to cause disease, including the ability to kill normal cells or the ability to elicit septic shock (see specific definition below).

As used herein, the strain designations VNP20009 (International Publication No. WO 99/13053), YS1646 and 41.2.9 are used interchangeably and each refer to the strain deposited with the American Type Culture Collection and assigned Accession No. 202165. As used herein, the strain designations YS1456 and 8.7 are used interchangeably and each refer to the strain deposited with the American Type Culture Collection and assigned Accession No. 202164.

The present invention may be understood more fully by reference to the following detailed description, illustrative examples of specific embodiments and the appended figures.

4. BRIEF DESCRIPTION OF THE FIGURES

FIG. 1. Coding sequence for the mature human TNF-α. Both DNA (SEQ ID NO:3) and protein (SEQ ID NO:4) sequences are indicated.

FIG. 2. Derivation of the *Salmonella* VNP20009 serC-strain.

FIG. 3. TNF-α, expression from a chromosomally-integrated trc promoter driven TNF-α, gene in *Salmonella typhimurium*.

FIG. 4. Coding sequence for the synthetic OmpA signal sequence (nucleotides 1–63) fusion to the mature human TNF-α (nucleotides 67–543). Both DNA (SEQ ID NO:7) and protein (SEQ ID NO:8) sequences are indicated for the fusion construct.

Figure 5:
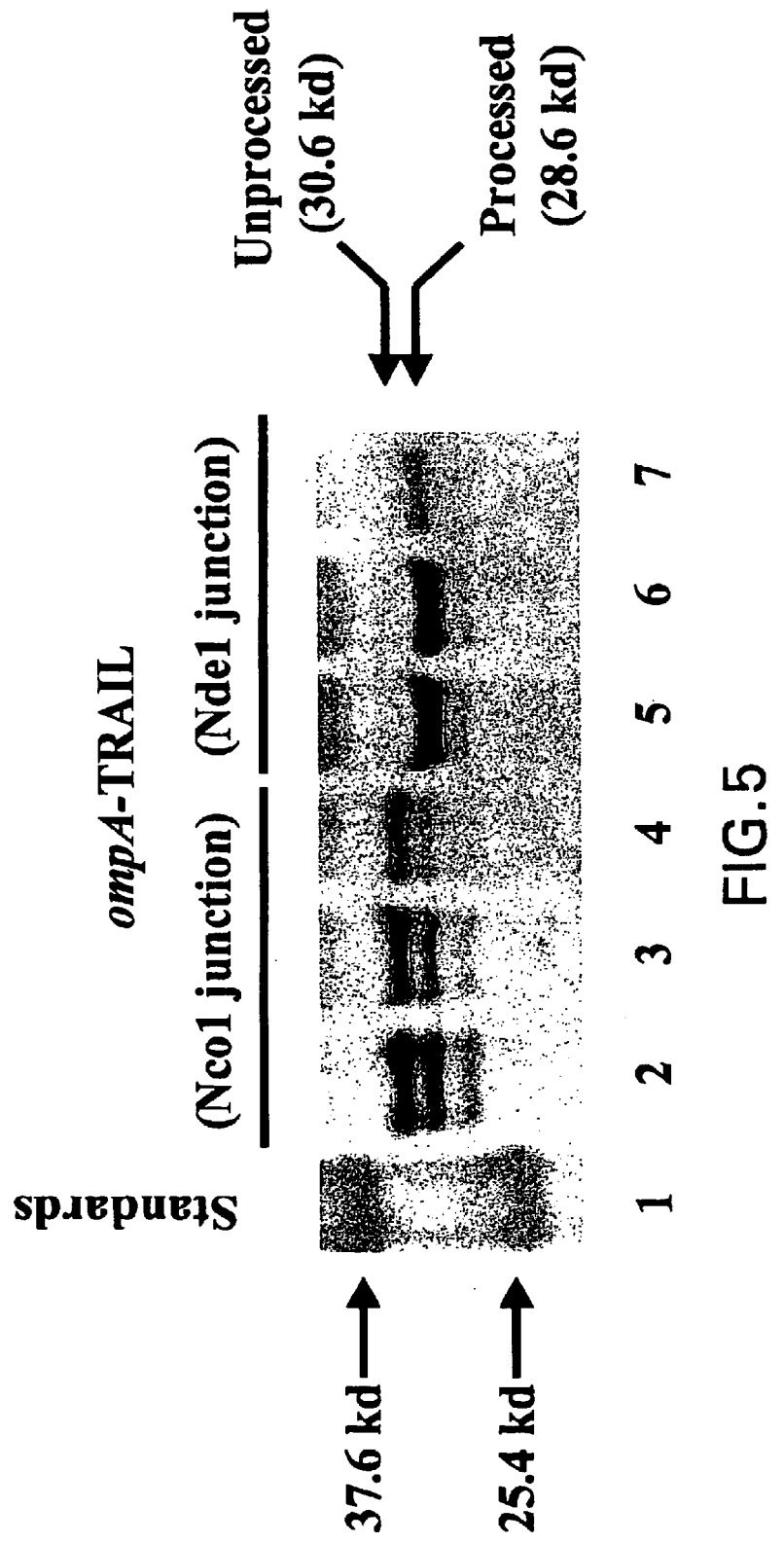

FIG. 5. Periplasmic localization and processing of an OmpA/TNF-α, fusion protein in *E-coli* (JM 109 strain).

FIG. 6. Coding sequence for the OmpA signal sequence (nucleotides 1–63) fusion to the mature human TRAIL (nucleotides 67–801). Both DNA (SEQ ID NO:9) and protein (SEQ ID NO:10) sequences are indicated for the fusion construct.

Figure 7:
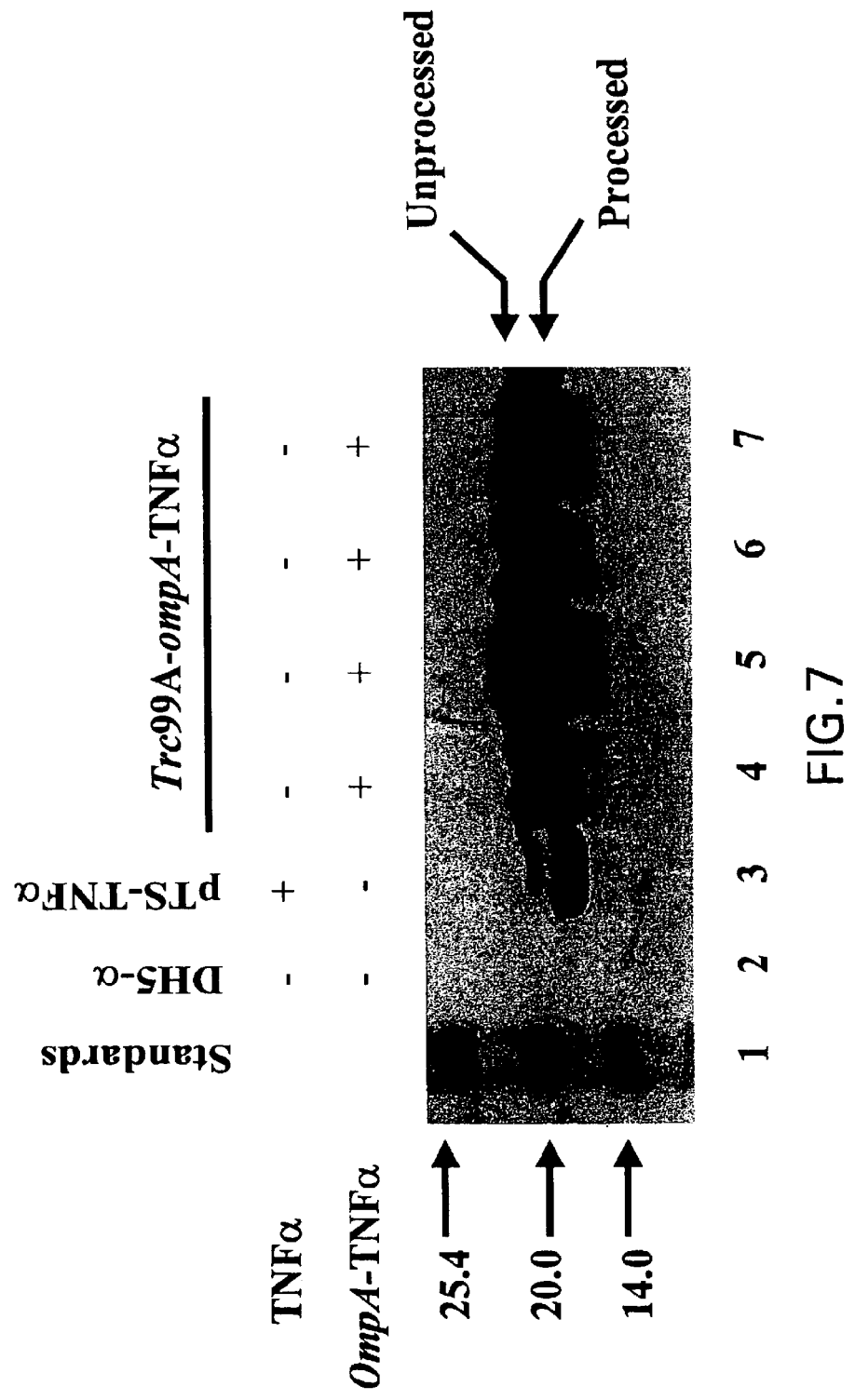

FIG. 7. Expression and processing of an OmpA TRAIL fusion protein in *E-coli* (JM 109 strain).

FIG. 8. Coding sequence for the modified OmpA signal sequence (nucleotides 1–63) fusion to the mature (C125A) human IL-2 (nucleotides 64–462). Both DNA (SEQ ID NO:11) and protein (SEQ ID NO:12) sequences are indicated for the fusion construct.

Figure 9:
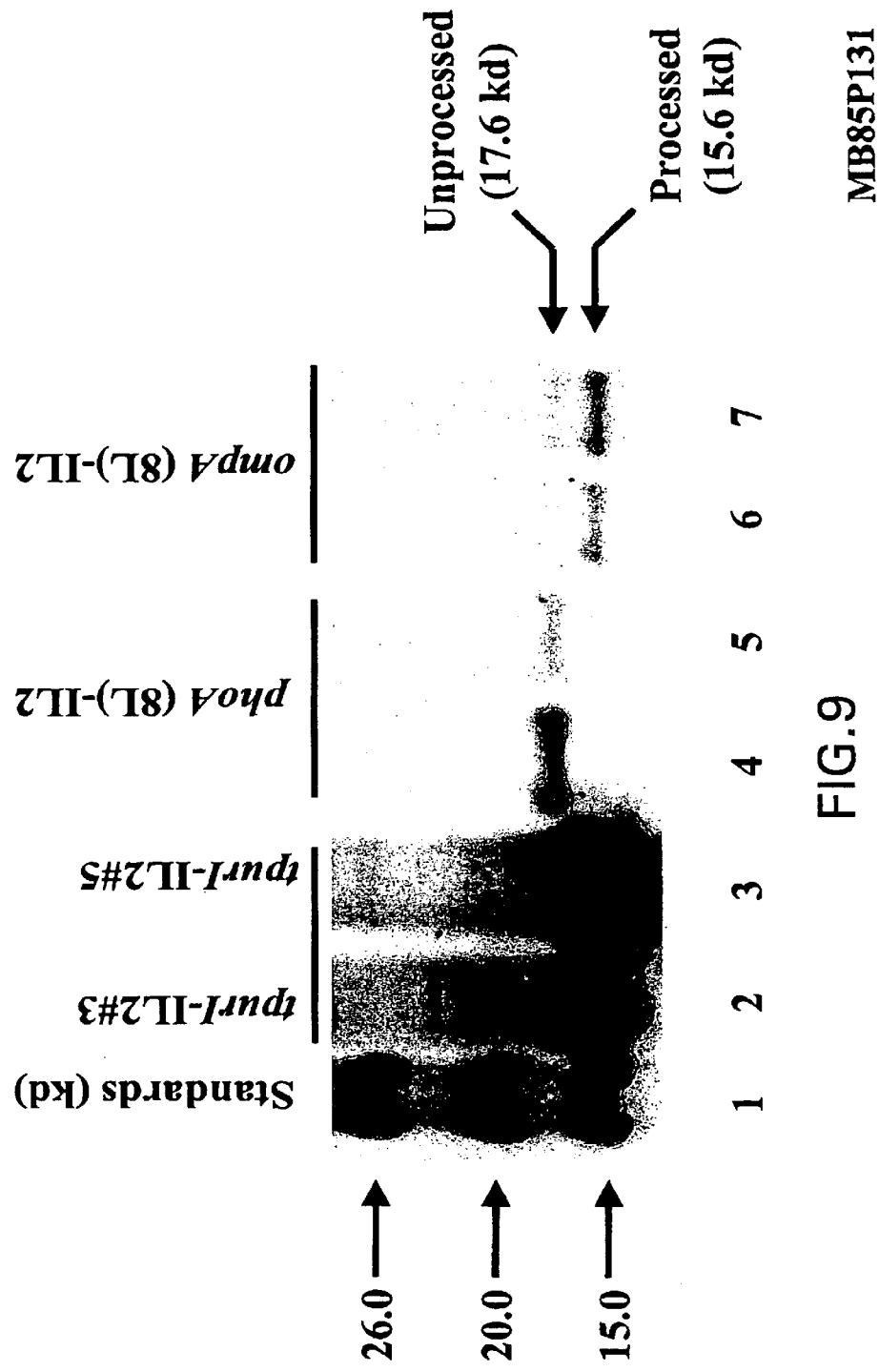

FIG. 9. Expression and processing of mature human IL-2 fused to the phoA(8L) or ompA (8L) synthetic signal peptides.

FIG. 10. Coding sequence for the modified phoA signal sequence (nucleotides 1–63) fusion to the mature (C125A) human IL-2 (nucleotides 64–462). Both DNA (SEQ ID NO:13) and protein (SEQ ID NO:14) sequences are indicated for the fusion construct.

Figure 11:
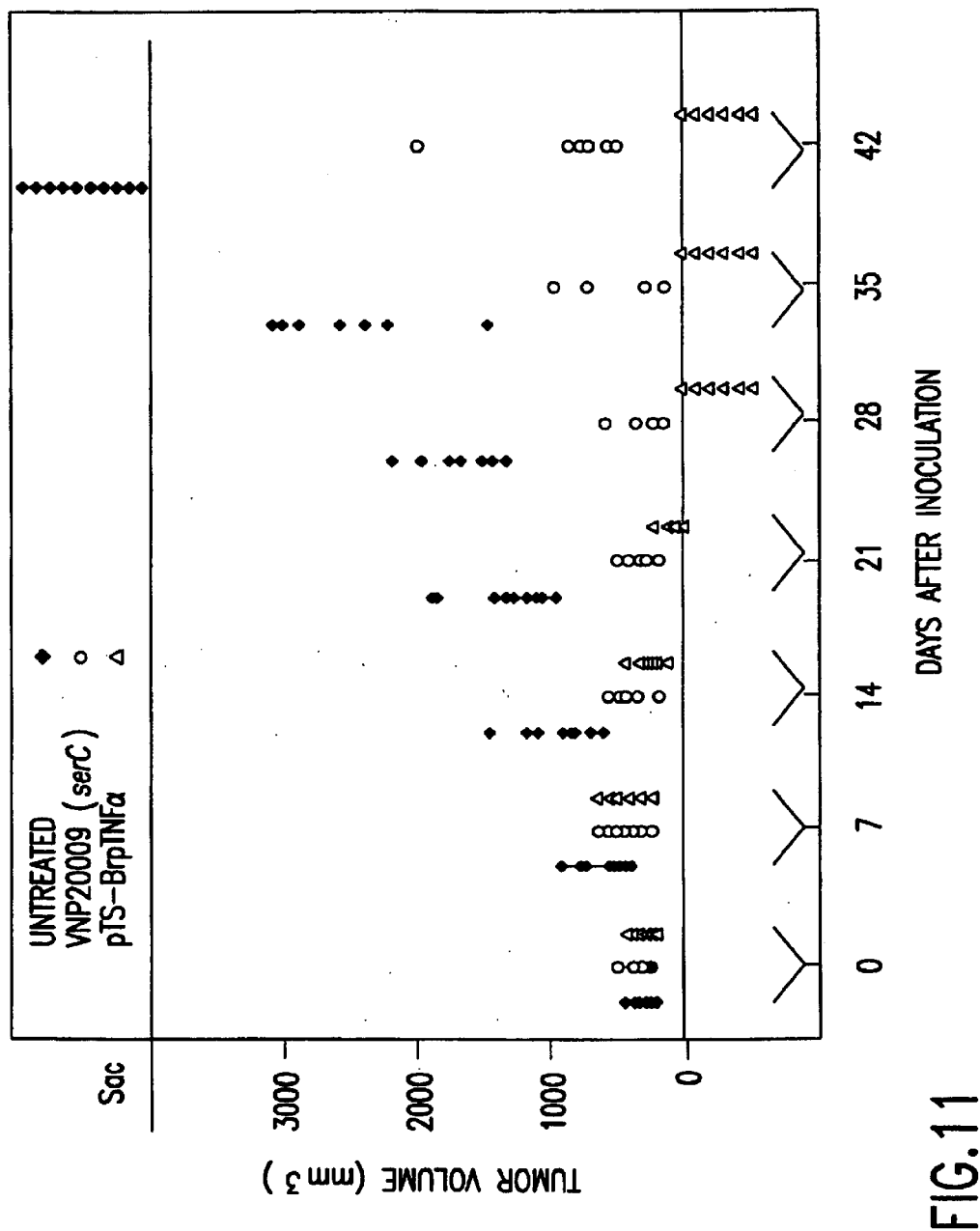

FIG. 11. In vivo anti-tumor efficacy of an attenuated strain of *Salmonella typhimurium* expressing the mature form of human TNF-α.

Figure 12:
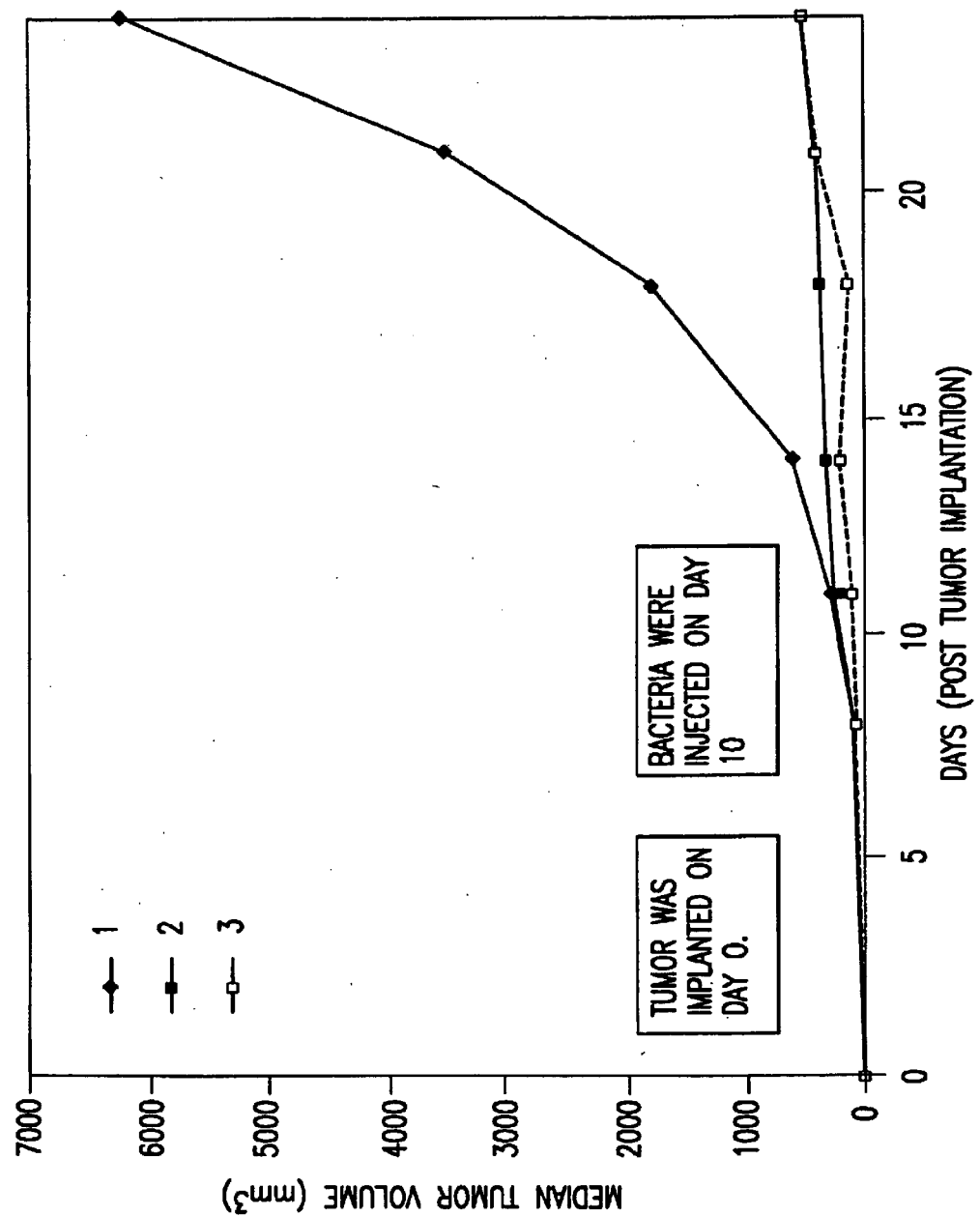

FIG. 12. Effect of BRP expression on anti-tumor efficacy in vivo. The figure shows a graphic representation of mean tumor size over time of a C57BL/6 mouse population with B16 melanoma tumors treated with (1) a PBS control; (2) VNP20009; and (3) VNP20009 harboring the pSW1 plasmid, which comprises the BRP gene.

Figure 13A:
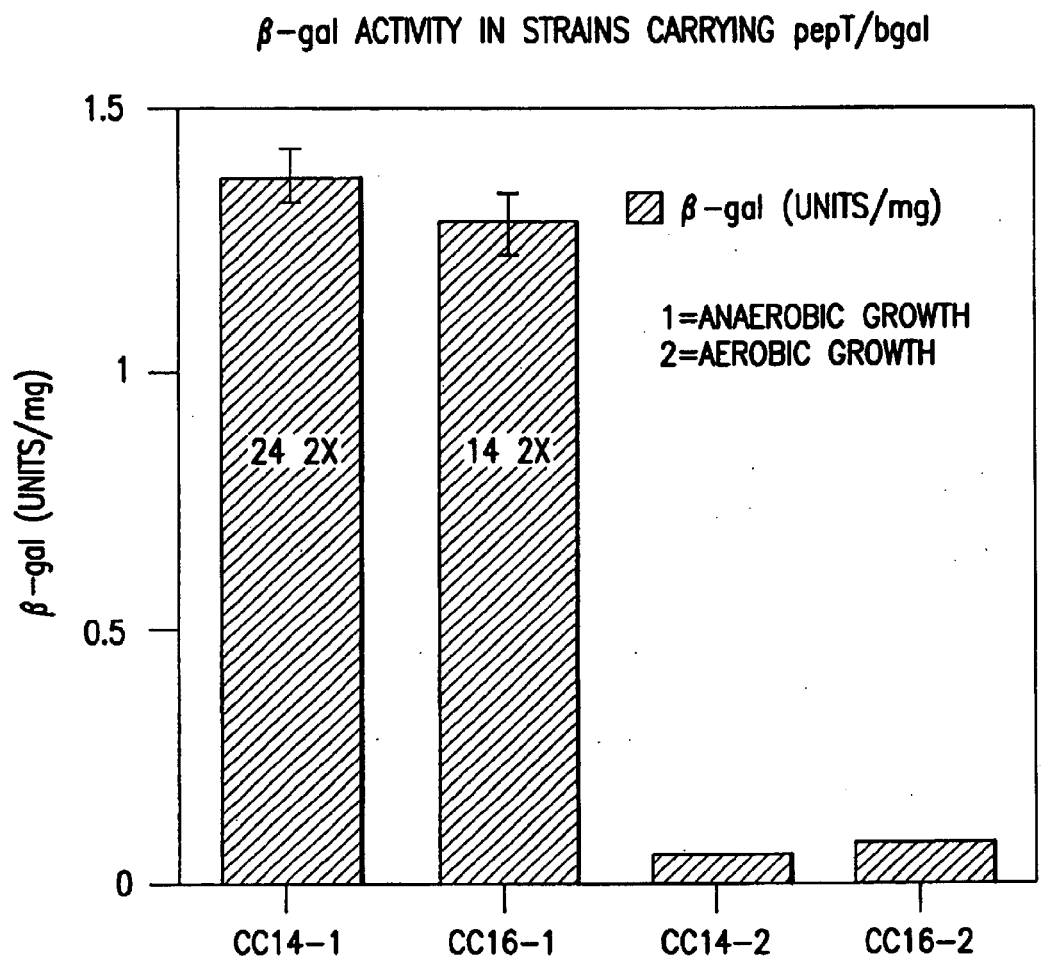
Figure 13B:
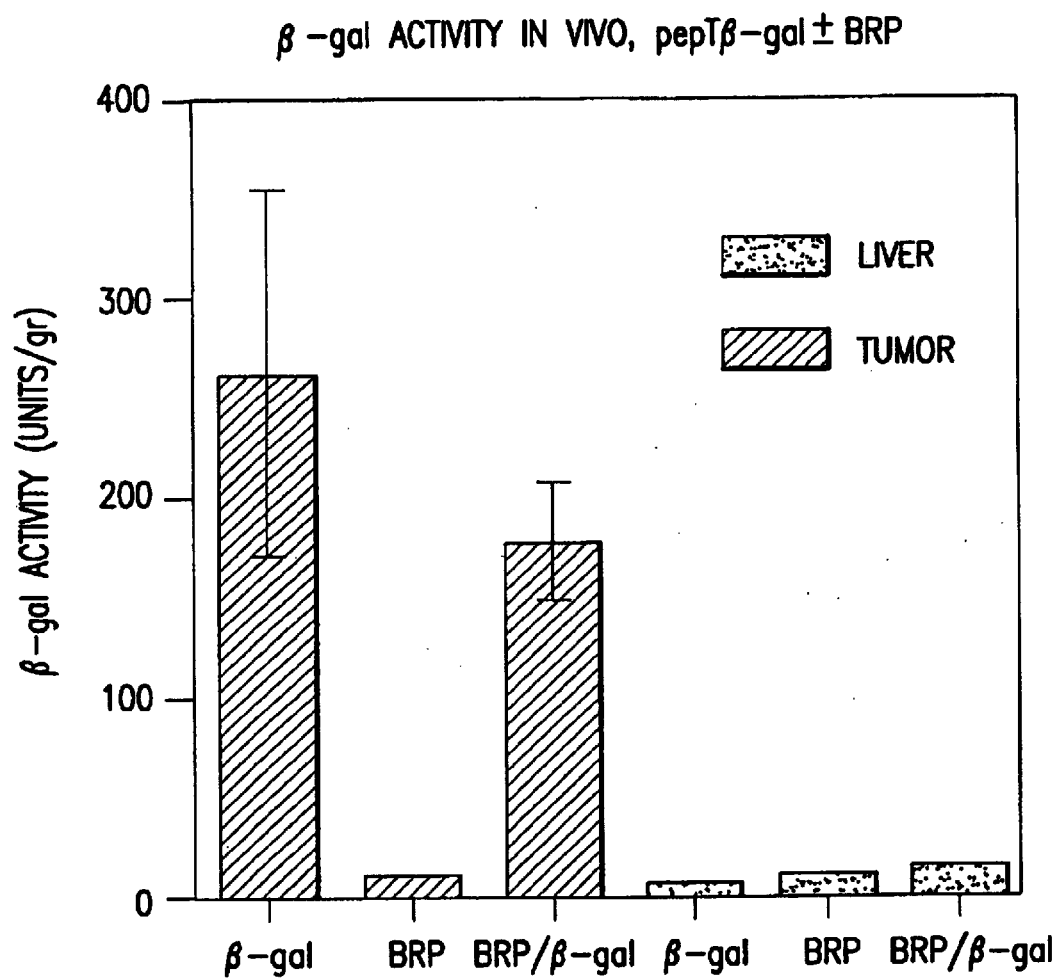

FIG. 13. Anaerobic induction of β-gal gene expression under the control of the pepT promoter in *Salmonella*. FIG. 13A demonstrates the in vitro induction of β-gal expression in response to anaerobic conditions of two strains of *Salmonella*, YS1456 and VNP20009. FIG. 13B demonstrates the in vivo induction of β-gal in tumor v. liver cells of VNP20009 *Salmonella* expressing-BRP, β-gal, or BRP and β-gal.

Figure 14:
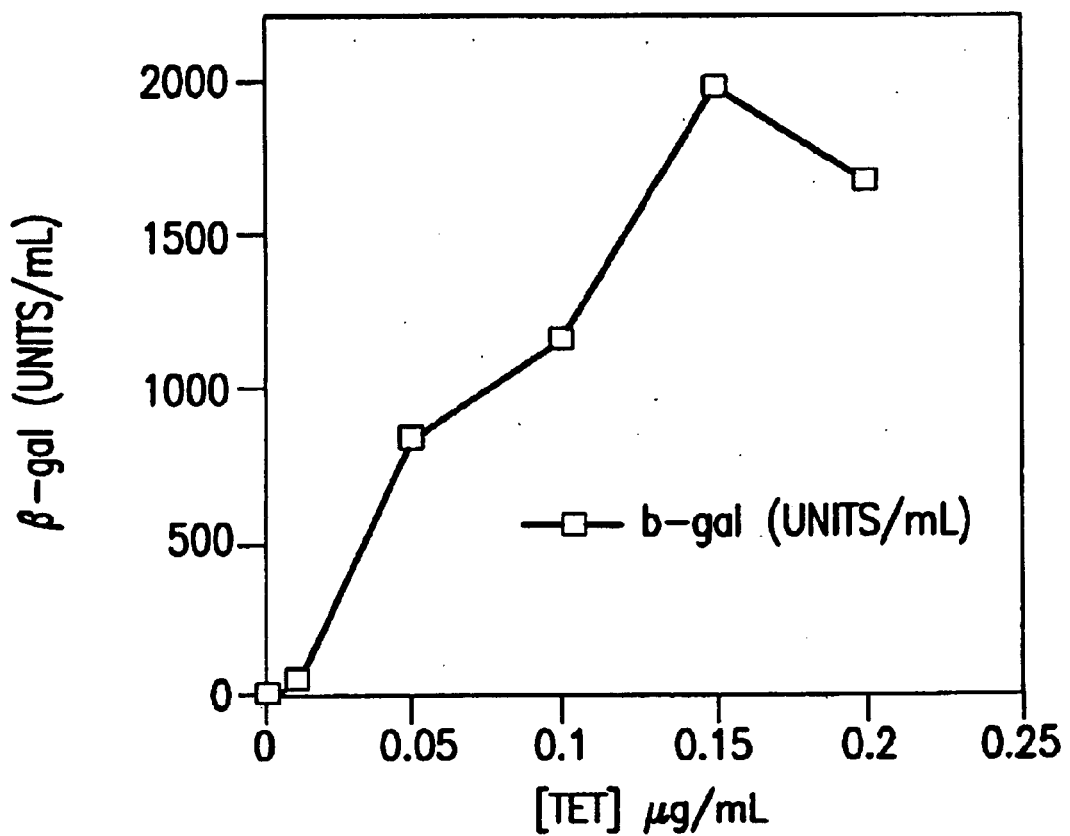

FIG. 14. Tetracycline induction of β-gal gene expression under the control of the Tet promoter in *Salmonella*. The dose-response indicates a linear response to Tetracycline up to a concentration of approximately 0.15 μg/ml, after which there response declines, presumably as a result of the antibiotic function of Tetracycline.

Figure 15A:
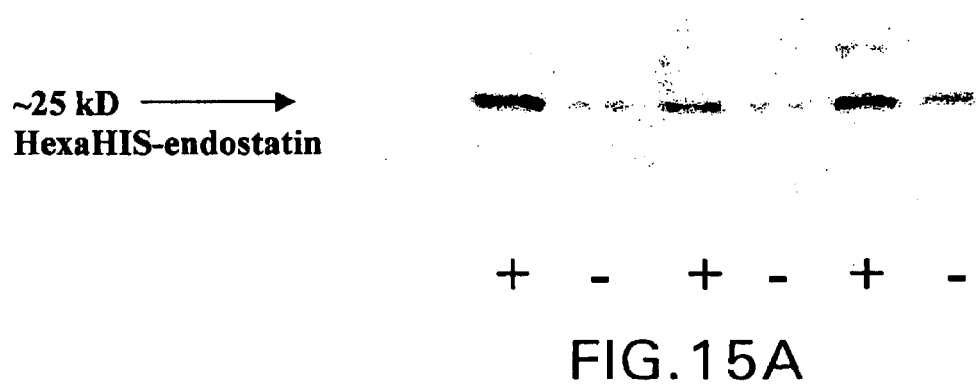
Figure 15B:
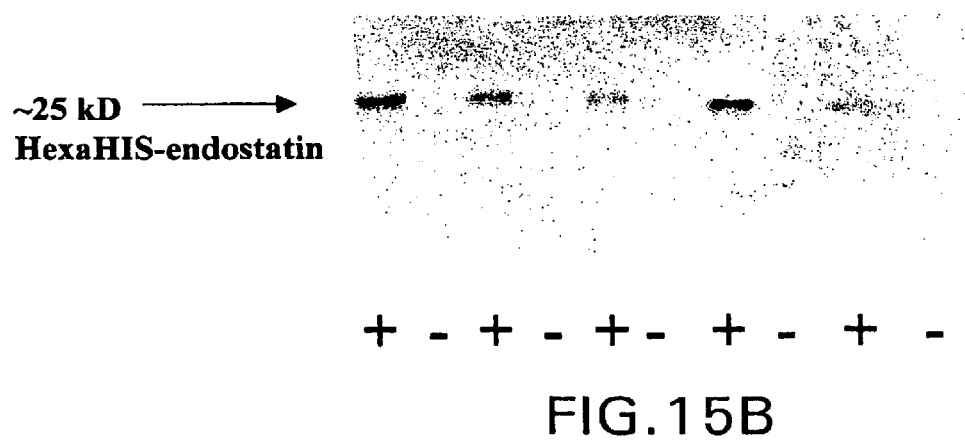

FIG. 15. Hexahistidine-endostatin (HexaHIS-endostatin) expression from the pTrc99a vector. FIG. 15A shows the expression of HexaHIS-endostatin from three independent clones transformed into *Salmonella* (VNP20009). FIG. 15B shows the expression of HexaHIS-endostatin from five independent clones transformed into *E. coli* (DH5α). Even numbered lanes indicate extracts from uninduced cultures, whereas odd numbered lanes indicate the corresponding IPTG-induced cultures.

Figure 16:
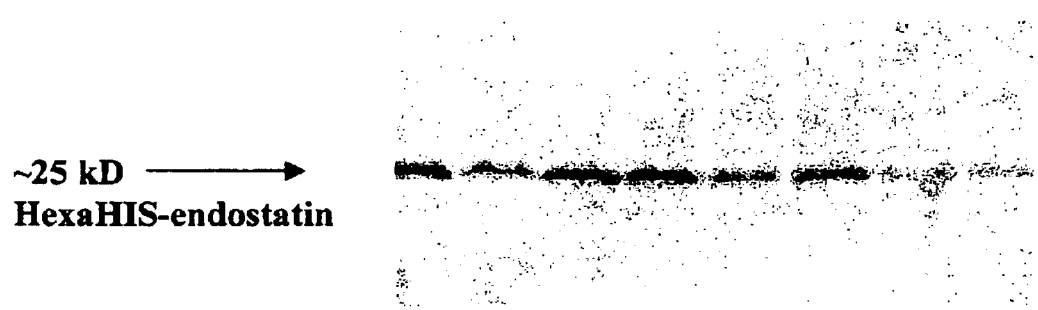

FIG. 16. Expression of HexaHIS-endostatin from the plasmid YA3334: HexaHIS-endostatin in the asd system (utilizing the trc promoter) is able to express a band of the correct size for HexaHIS-endostatin (~25 kD) by Western analysis with a anti-histidine antibody (lanes 1–8 correspond to eight independent clones).

Figure 17:
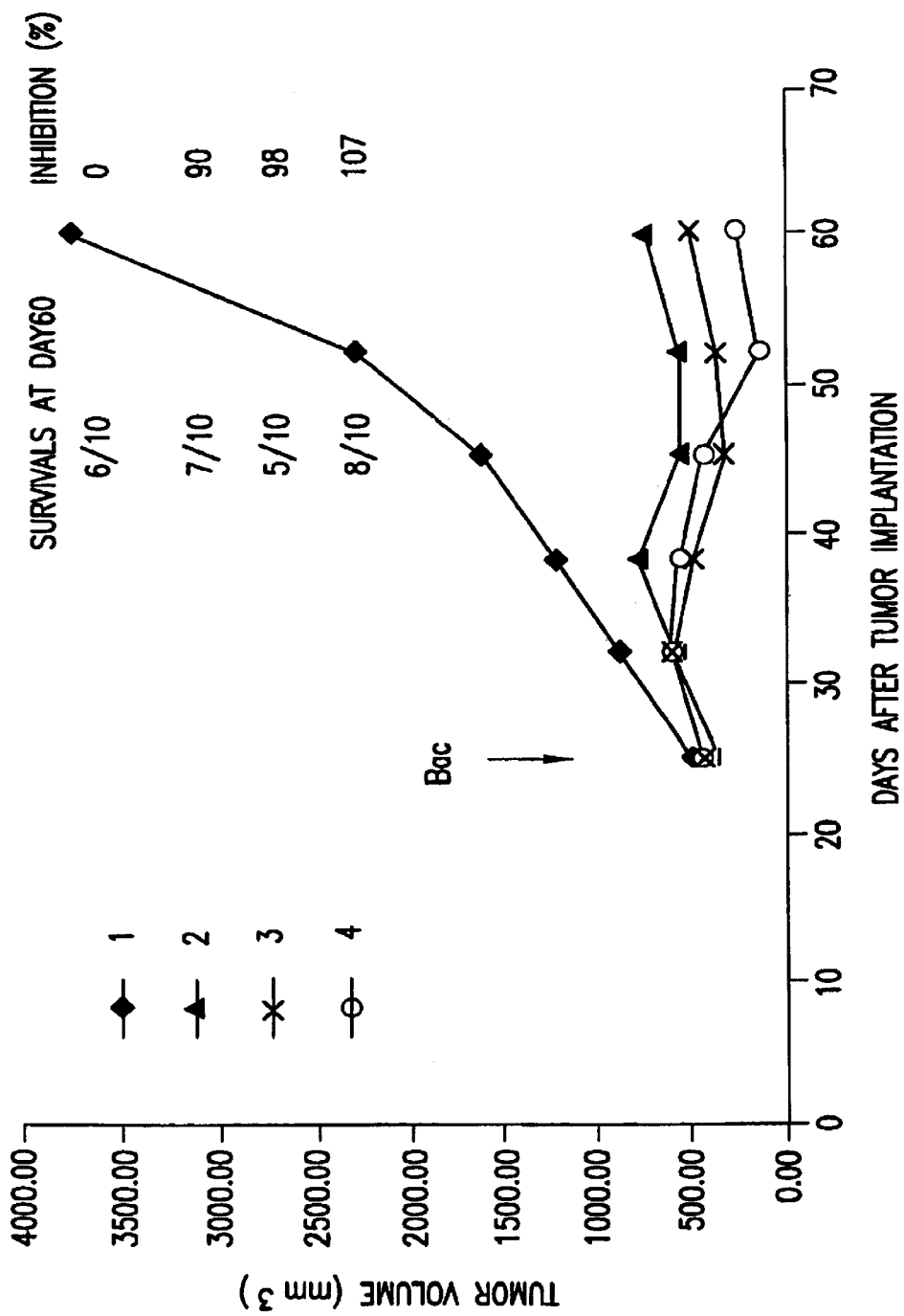

FIG. 17. Efficacy of VNP20009 cells expressing endostatin on C38 murine colon carcinoma. The figure shows a graphic representation of mean tumor size over time of a mouse population with established C38 tumors treated with (1) a PBS control; (2) asd⁻ VNP20009 carrying an empty YA3334 vector; (3) asd ⁻VNP20009 which expresses hexahistidine-endostatin; (4) and VNP20009 which expresses hexahistidine-endostatin and BRP.

Figure 18:
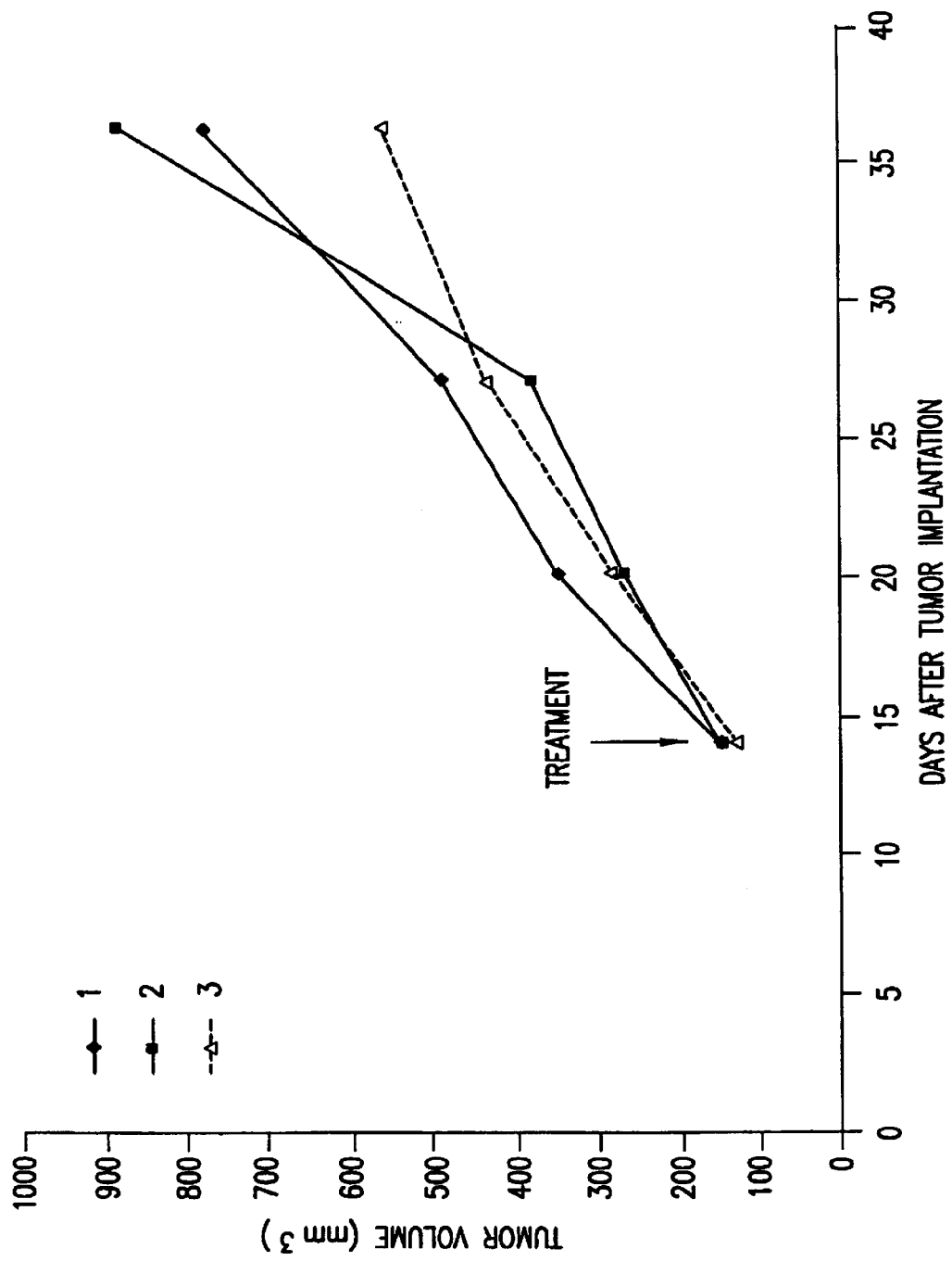

FIG. 18. Efficacy of VNP20009 cells expressing endostatin on DLD1 human colon carcinoma. The figure shows a graphic representation of mean tumor size over time of a nude mouse population with established DLD1 tumors treated with (1) a PBS control; (2) asd⁻ VNP20009 carrying an empty YA3334 vector; and (3) VNP20009 which expresses hexahistidine-endostatin and BRP.

Figure 19:
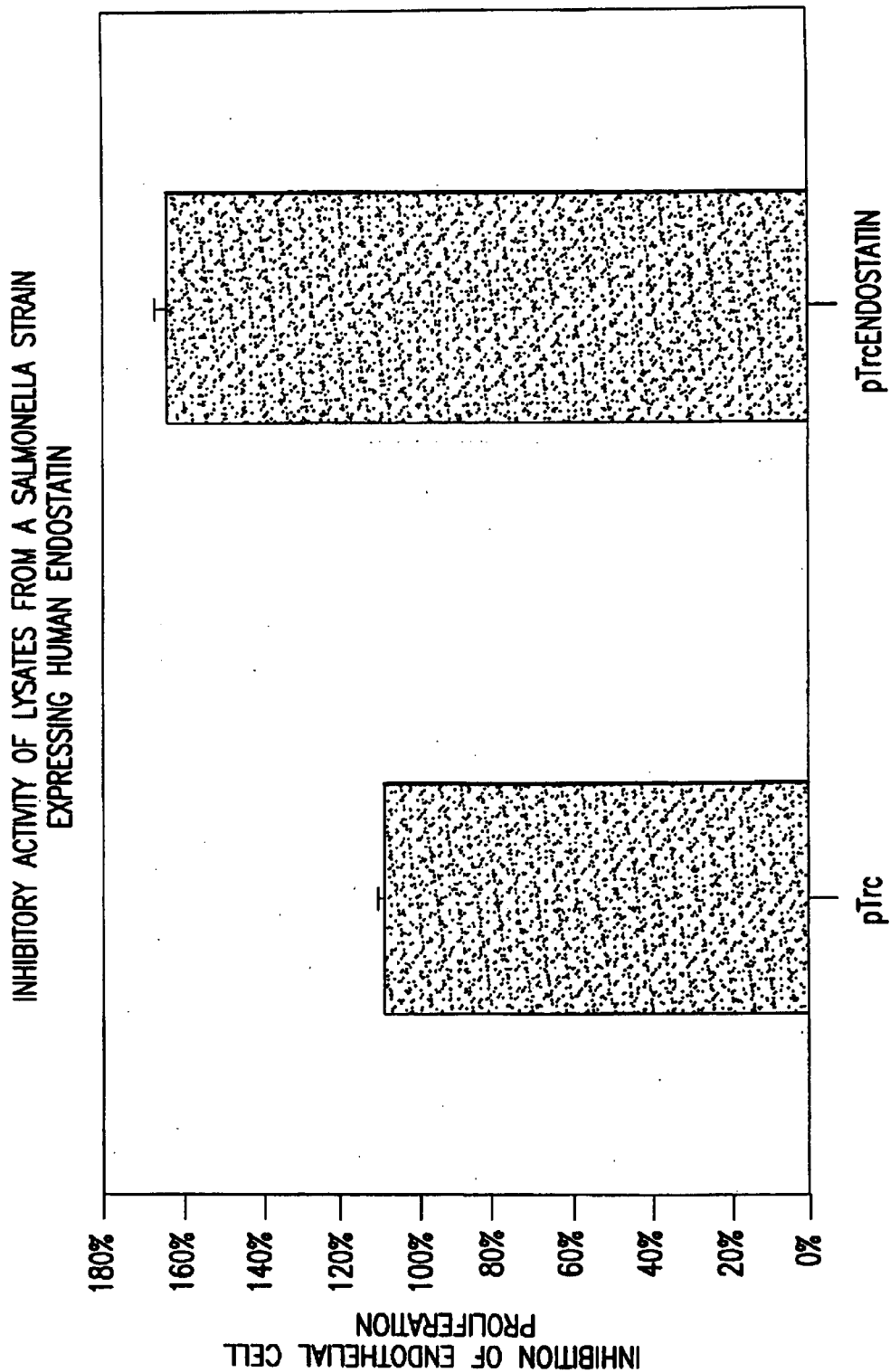

FIG. 19. Anti-proliferative activity of lysates from attenuated tumor-targeted *Salmonella* expressing human endostatin on endothelial cells. This figure shows the inhibition of human vein endothelial cell (HUVEC) proliferation in response to bFGF and lysates corresponding to $8 \times 10^8$ bacteria. As a control *Salmonella* containing the empty pTrc vector was used. Each data point is a mean of quadruplicate values from a representative experiment. Samples were normalized by the number of bacteria.

Figure 20:
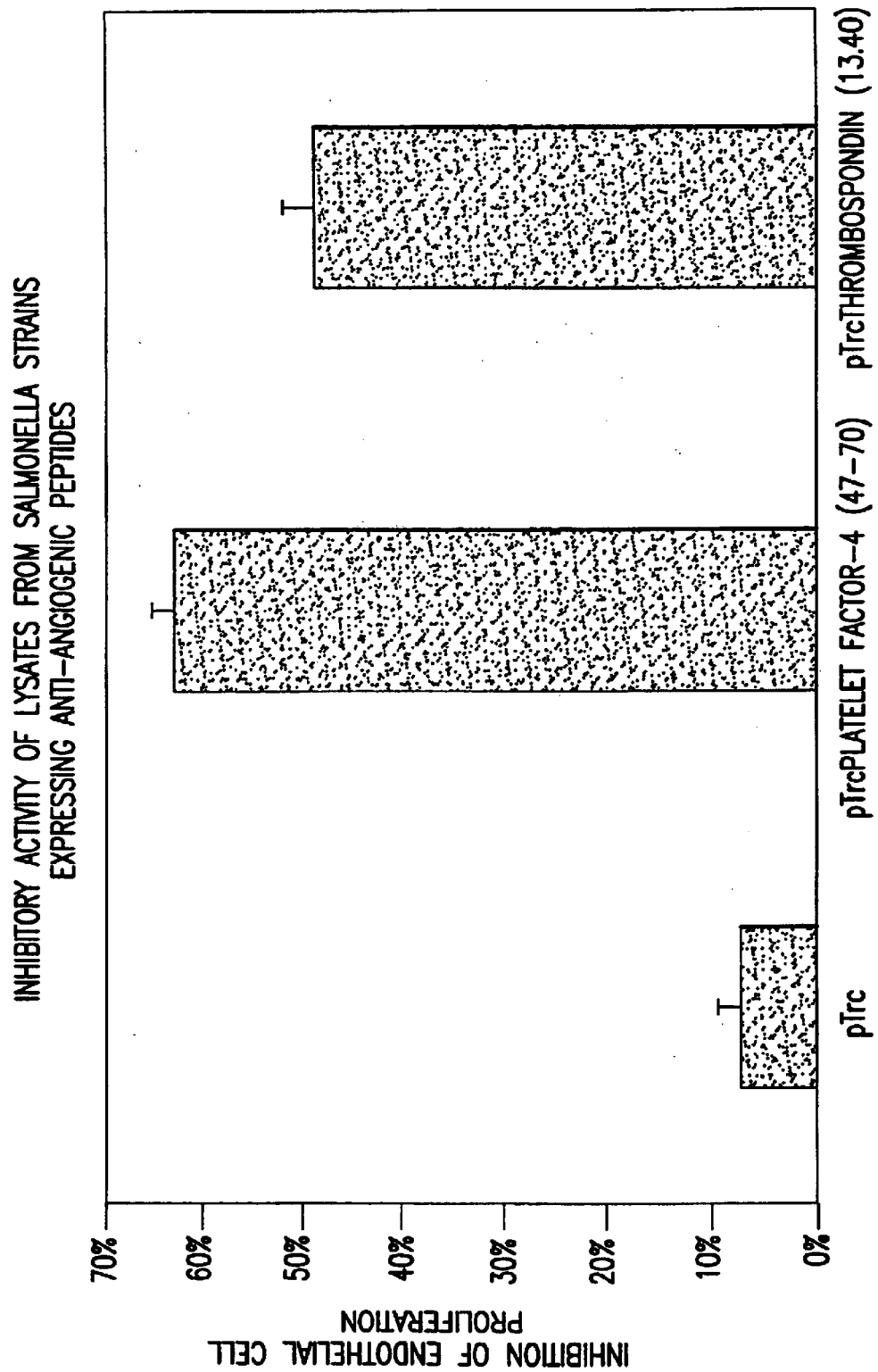

FIG. 20. Anti-proliferative activity of lysates from attenuated tumor-targeted *Salmonella* expressing platelet factor-4 peptide (amino acids 47–70 of platelet factor-4) and thrombospondin peptide(13.40) on endothelial cells. This figure shows the inhibition of human vein endothelial cell (HUVEC) proliferation in response to bFGF and lysates corresponding to $3.2 \times 10^8$ bacteria. As a control *Salmonella* containing the empty pTrc vector was used. Each data point is a mean of quadruplicate values from a representative experiment. Samples were normalized by the number of bacteria.

Figure 21:
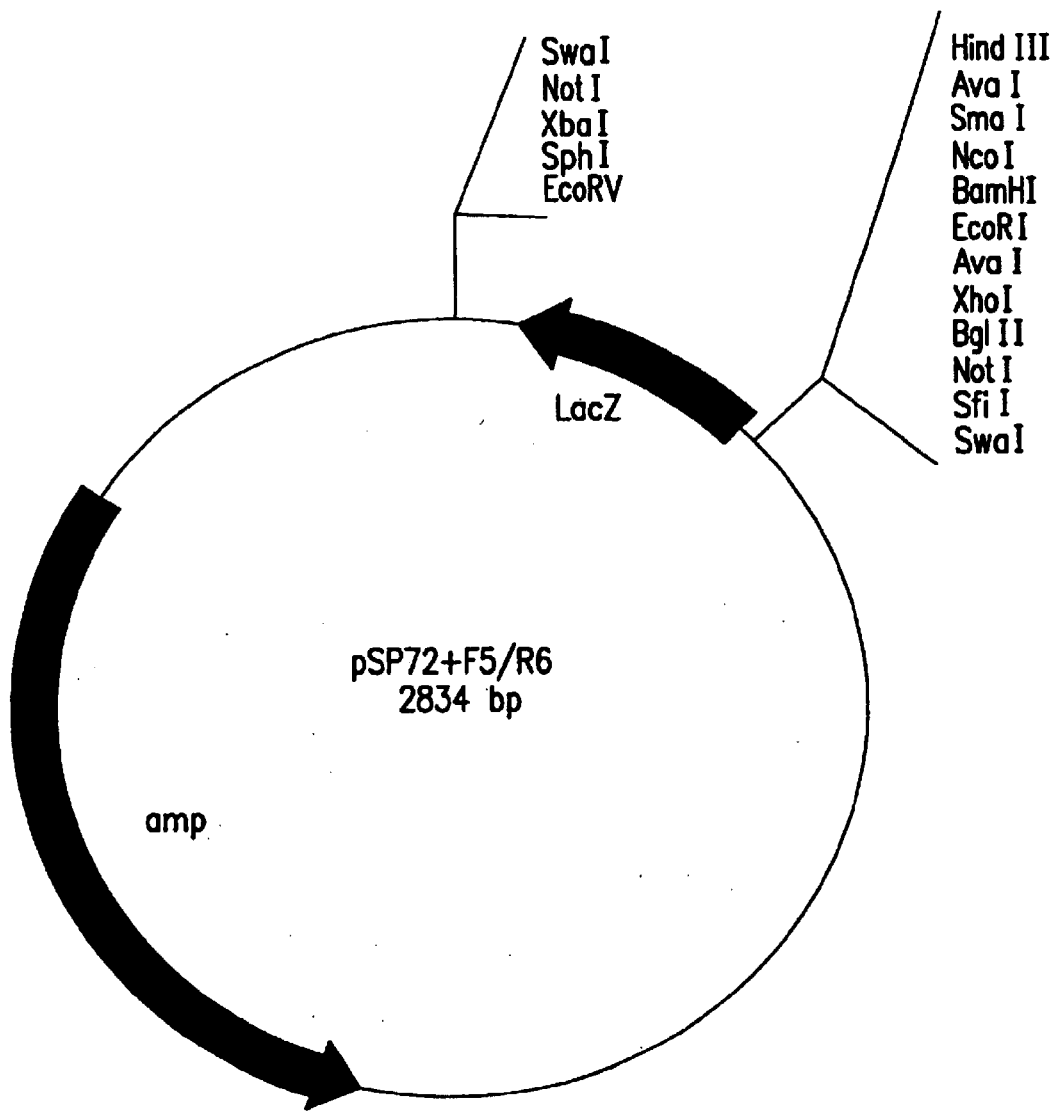

FIG. 21. Construction of the pE3.shuttle-1 Vector.

Figure 22:
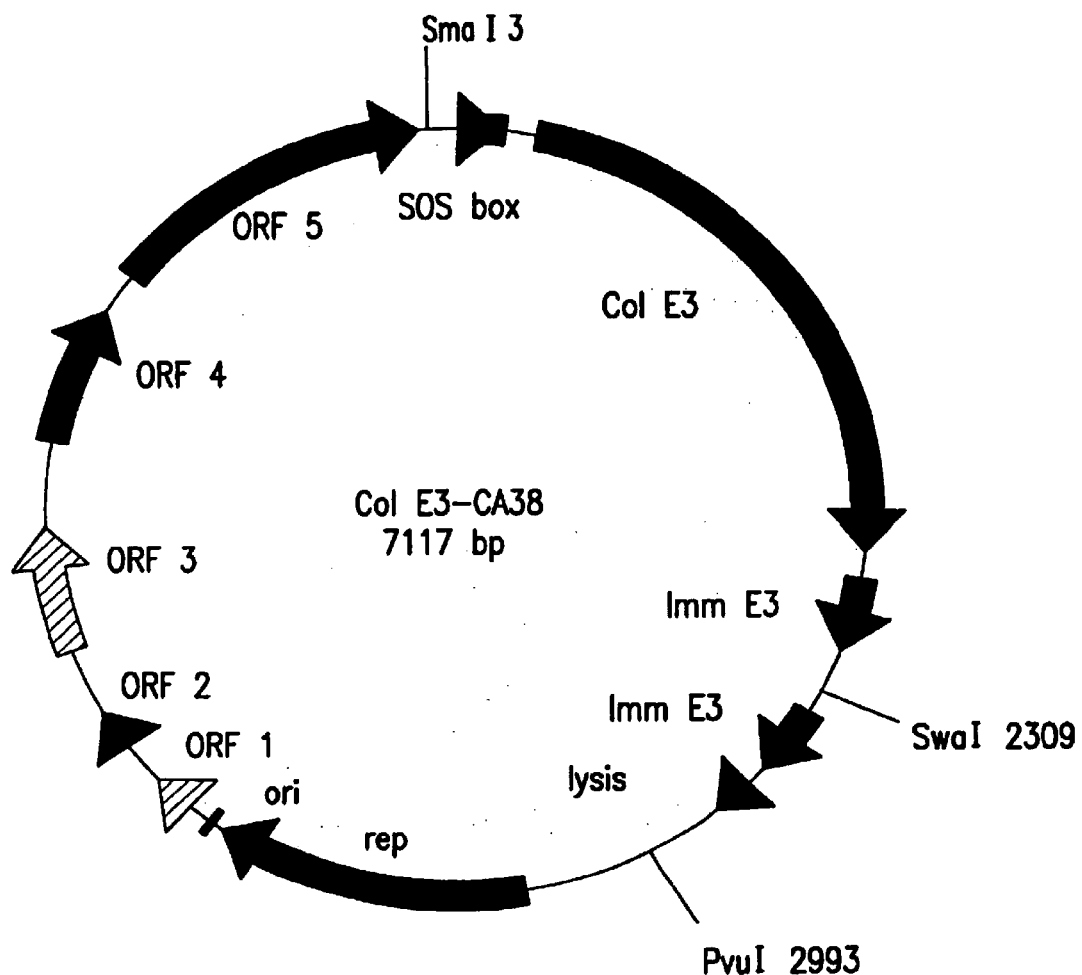

FIG. 22. Construction of the Col E3-CA38 Vector (GenBank Accession Number AF129270). The nucleotide sequence of the Col E3-CA38 Vector is as depicted in SEQ ID NO: 1. The Col E3-CA38 Vector contains 5 open reading frames as depicted in SEQ ID Nos: 2–5, respectively.

Figure 23:
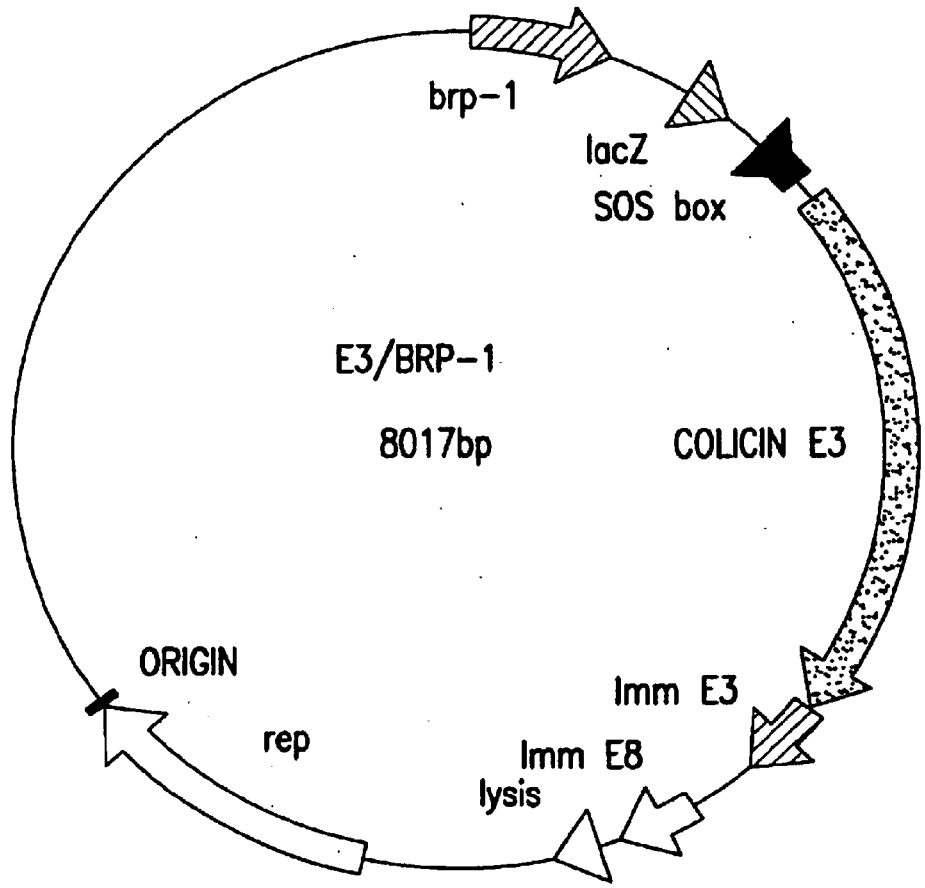

FIG. 23. Construction of the Col E3-CA38/BRP-1 vector.

Figure 24:
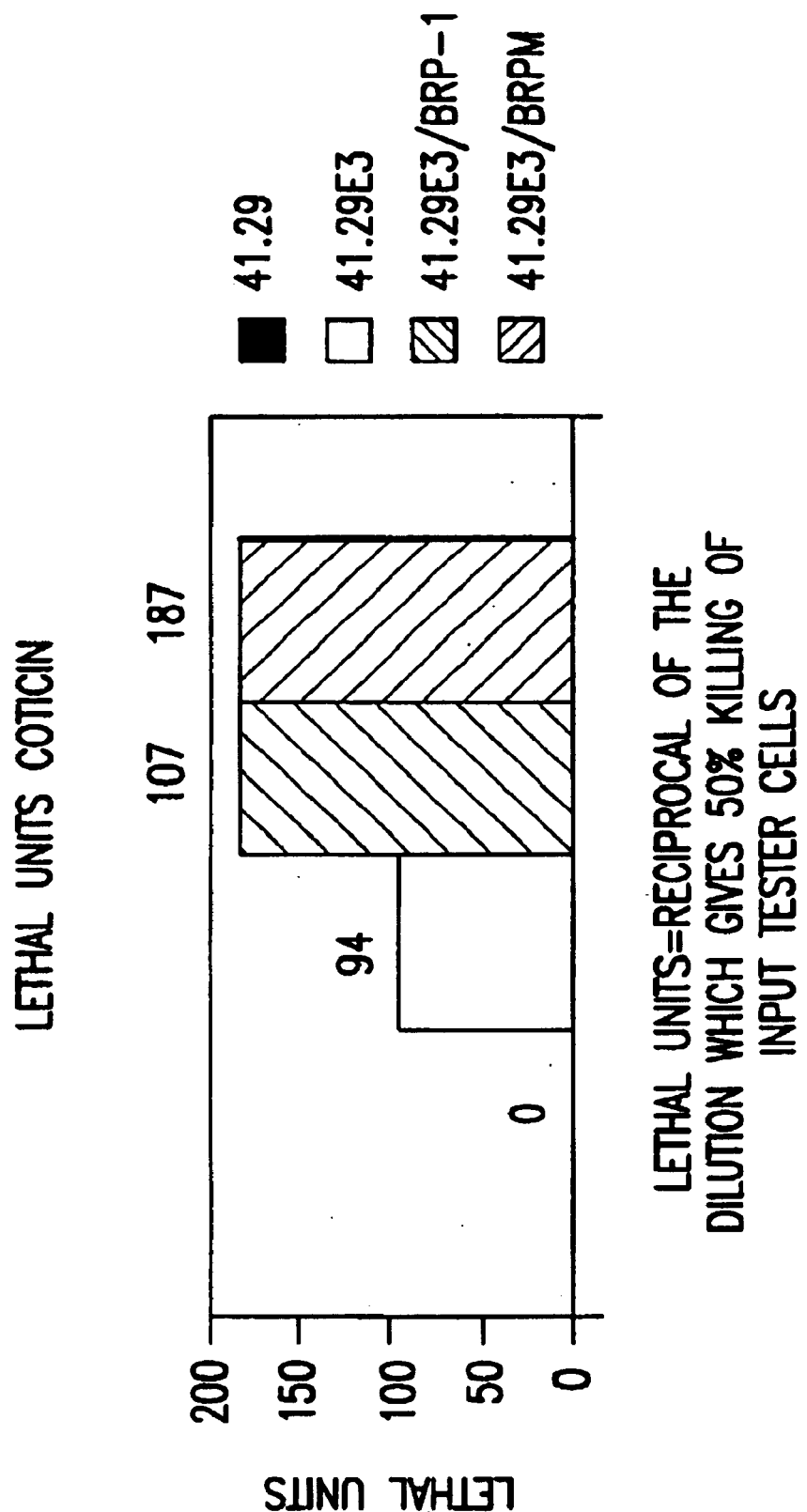

FIG. 24. Bar Graph showing the amount of lethal units of colicin E3 produced by each strain.

Figure 25:
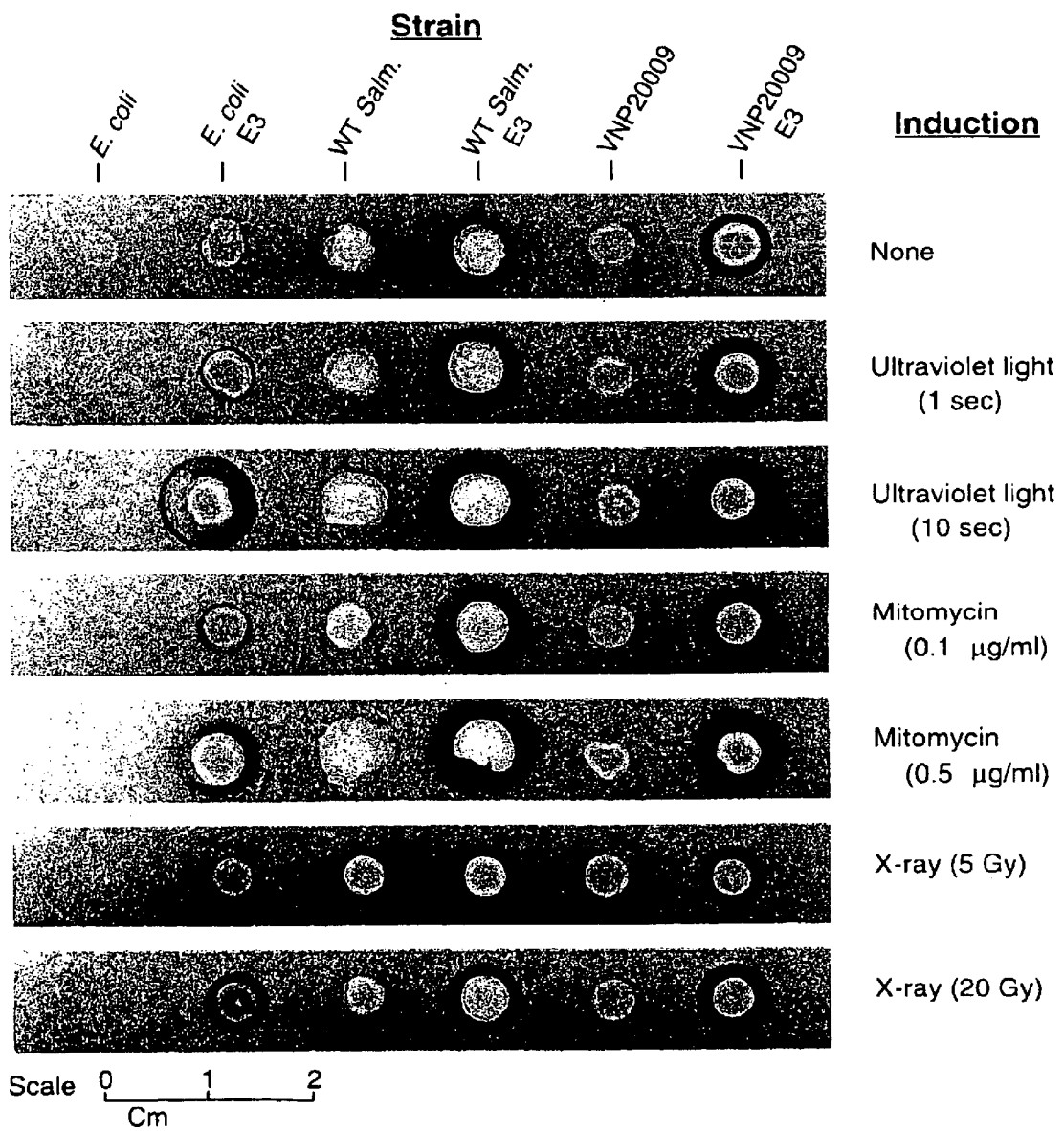

FIG. 25. Halo assay for various strains exposed to ultraviolet light or x-rays.

Figure 26:
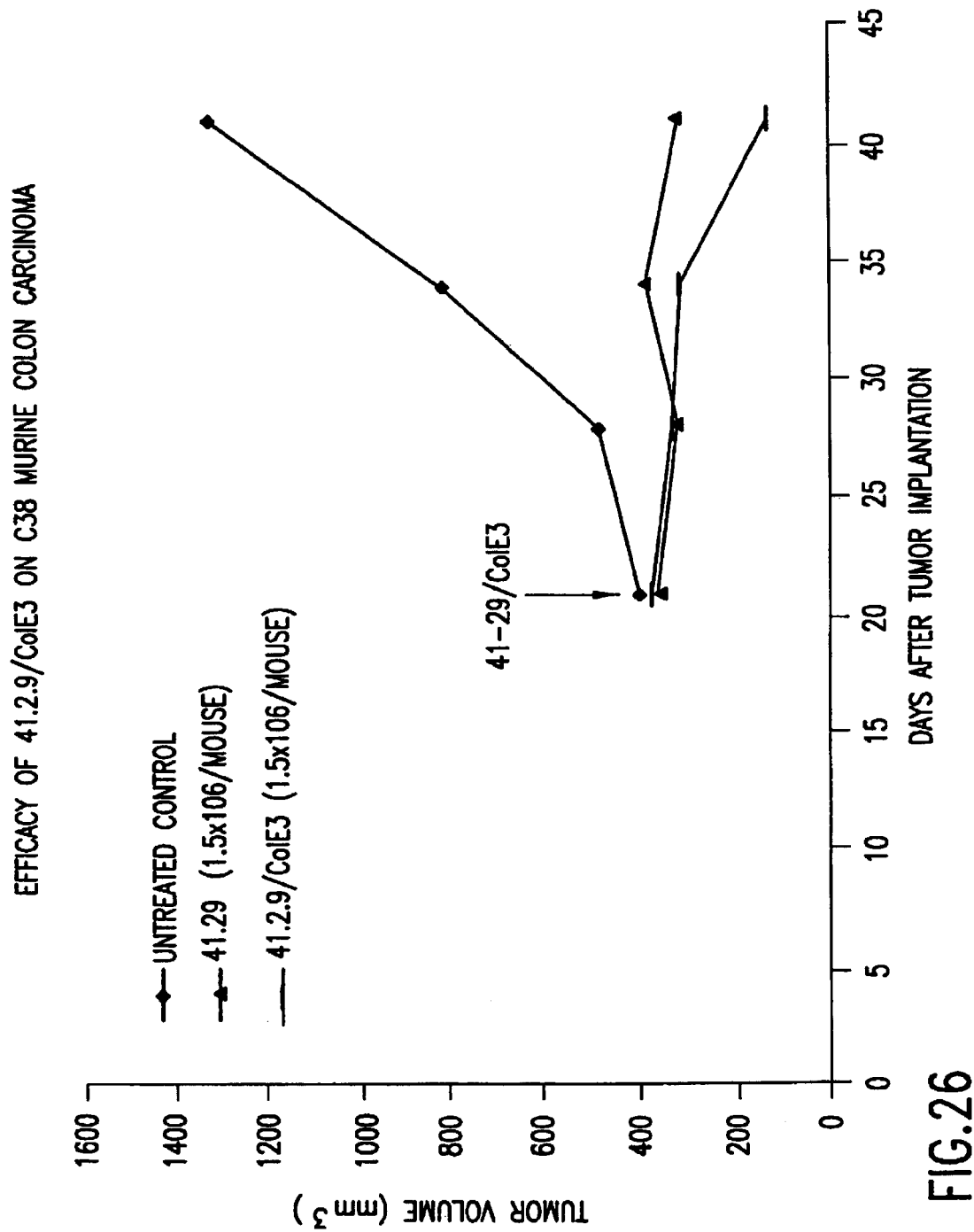

FIG. 26. Efficacy of 41.2.9/Col E3 on C38 murine colon carcinoma.

Figure 27:
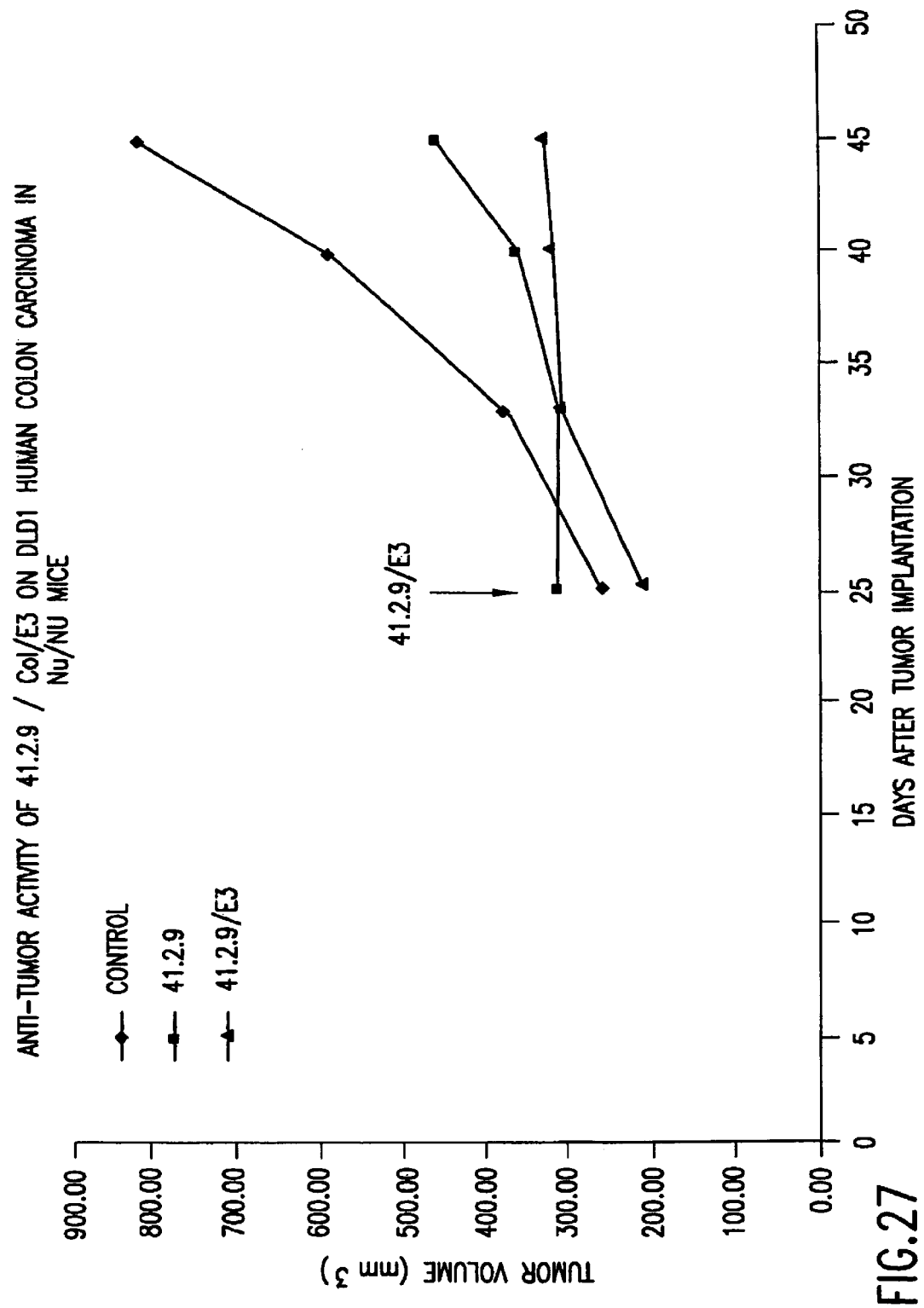

FIG. 27. Anti-tumor activity of 41.2.9/Col/E3 on DLD1 human colon carcinoma in NU/Nu mice.

Figure 28:
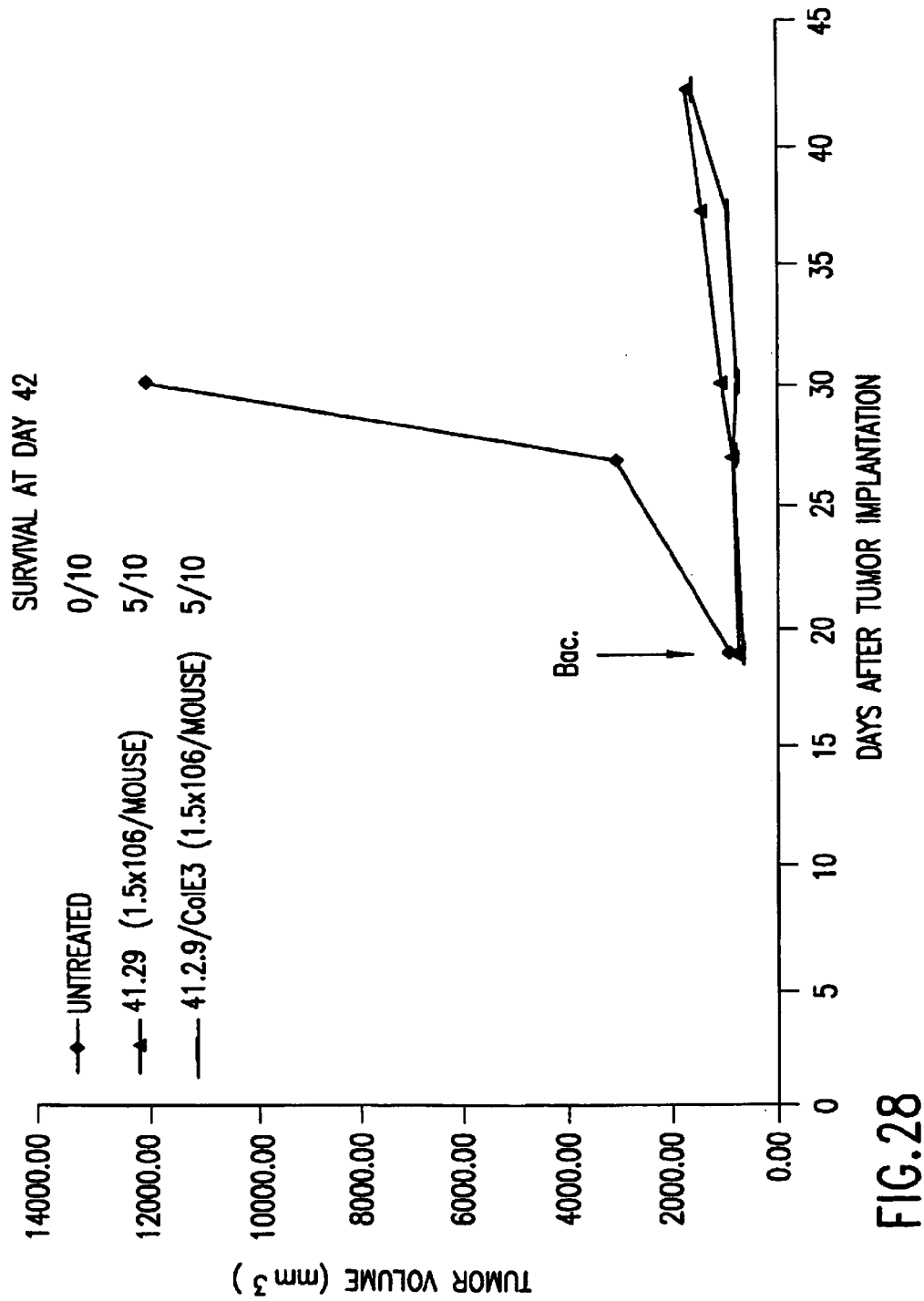

FIG. 28. Efficacy of 41.2.9/Col E3 on B16 murine melanoma.

FIG. 29. Cytotoxicity of *Salmonella* expressing cloned *E. coli* CNF1.

Figure 30A:
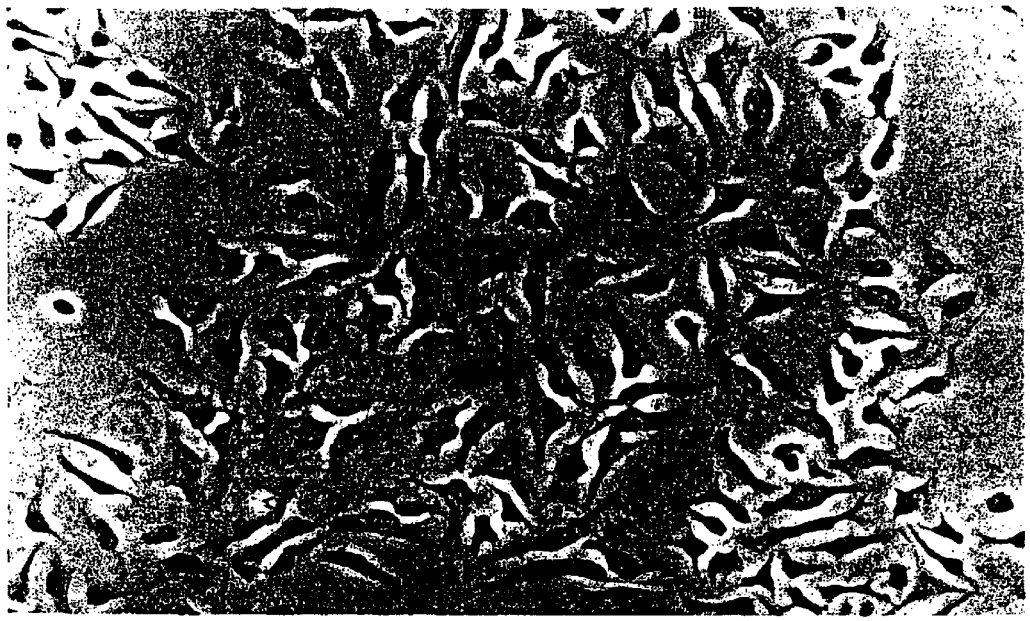
Figure 30B:

FIG. 30. Hela cells exposed to CNF1 (A) show enlargement and multinucleation relative to normal Hela cells (B).

FIG. 31. The msbB portion of the pCVD442-msbB vector in the 3' to 5' orientation (as viewed in th FIG. 32 map), with a deletion in the middle of msbB and containing internal NotI, PacI, SphI, SfiI, SwaI and DraI polylinker in its place (SEQ ID NO:61). See FIG. 32.

Figure 32:
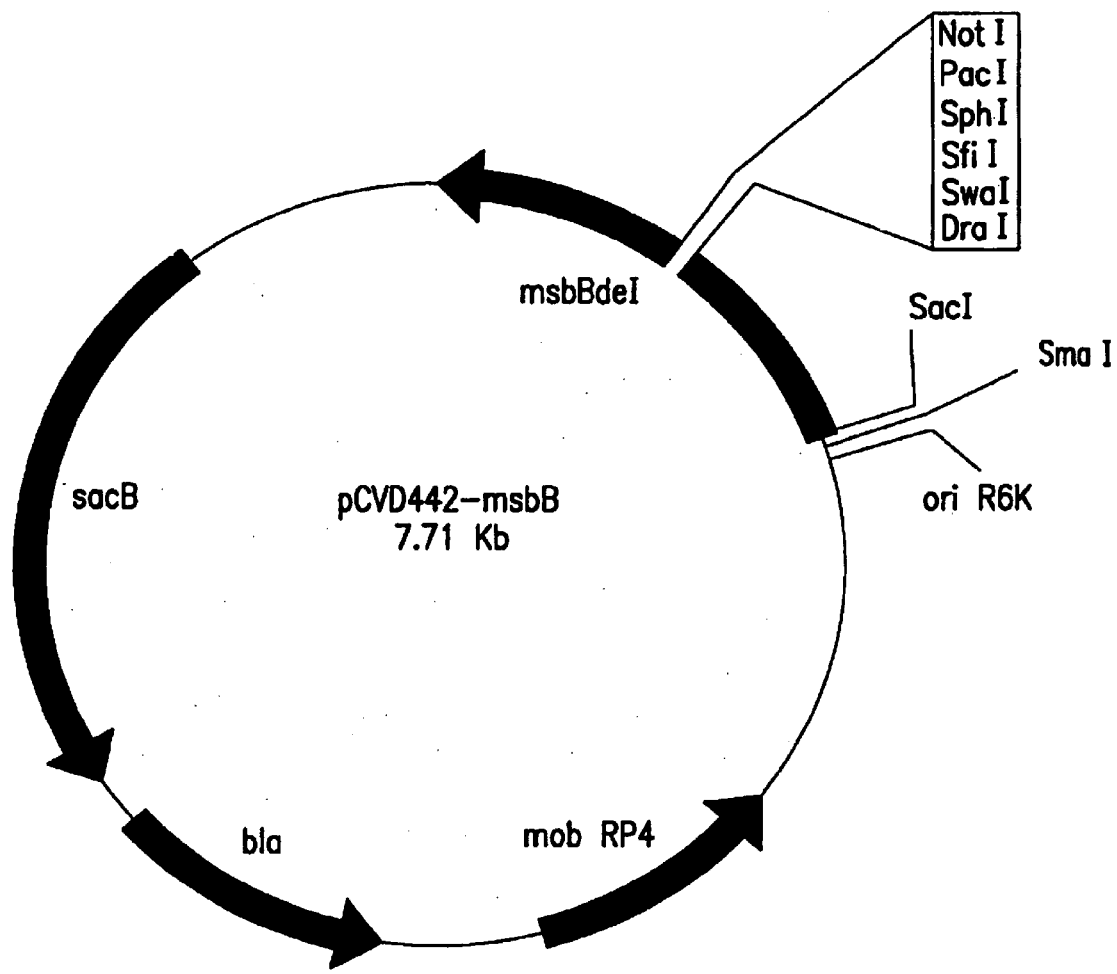

FIG. 32. Restriction map and schematic of the pCVD442-msbB vector for cloning DNA in the DmsbB region and subsequent insertion on the chromosome. msbBdel, the 5' and 3' regions of DmsbB; mob RP4, the mobilization element in order for the plasmid to be transferred from one strain to another. bla; the beta-lactamase gene which confers sensitivity to b-lactam antibiotic such as carbenicillin and ampicillin. sacB, the gene which confers sensitivity to sucrose.

Figure 33:
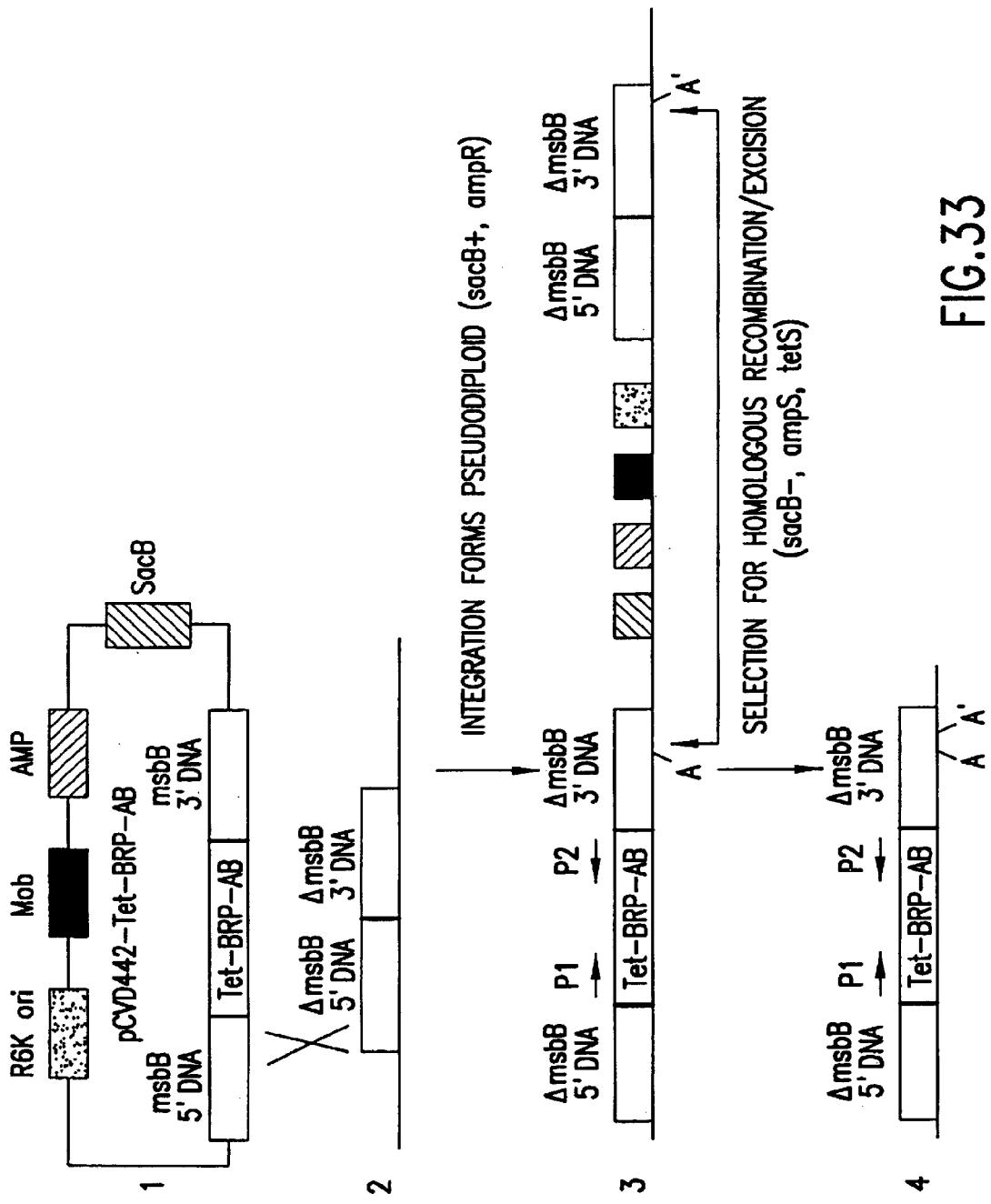

FIG. 33. 1) pCVD442-Tet-BRP-AB vector, 2) homologous recombination with the DmsbB chromosomal copy in *Salmonella* YS50102, 3) chromosomal integration in *Salmonella* YS50102, and following phage transduction to strain VNP20009, 4) sucrose resolution resulting in strain 41.2.9-Tet-BRP-AB. oriR6K, the plasmid origin of replication; mobRP4, the mobilization element in order for the plasmid to be transferred from one strain to another. amp; the beta-lactamase gene which confers sensitivity to b-lactam antibiotic such as carbenicillin and ampicillin. sacB, the gene which confers sensitivity to sucrose. Note: not drawn to scale.

Figure 34:
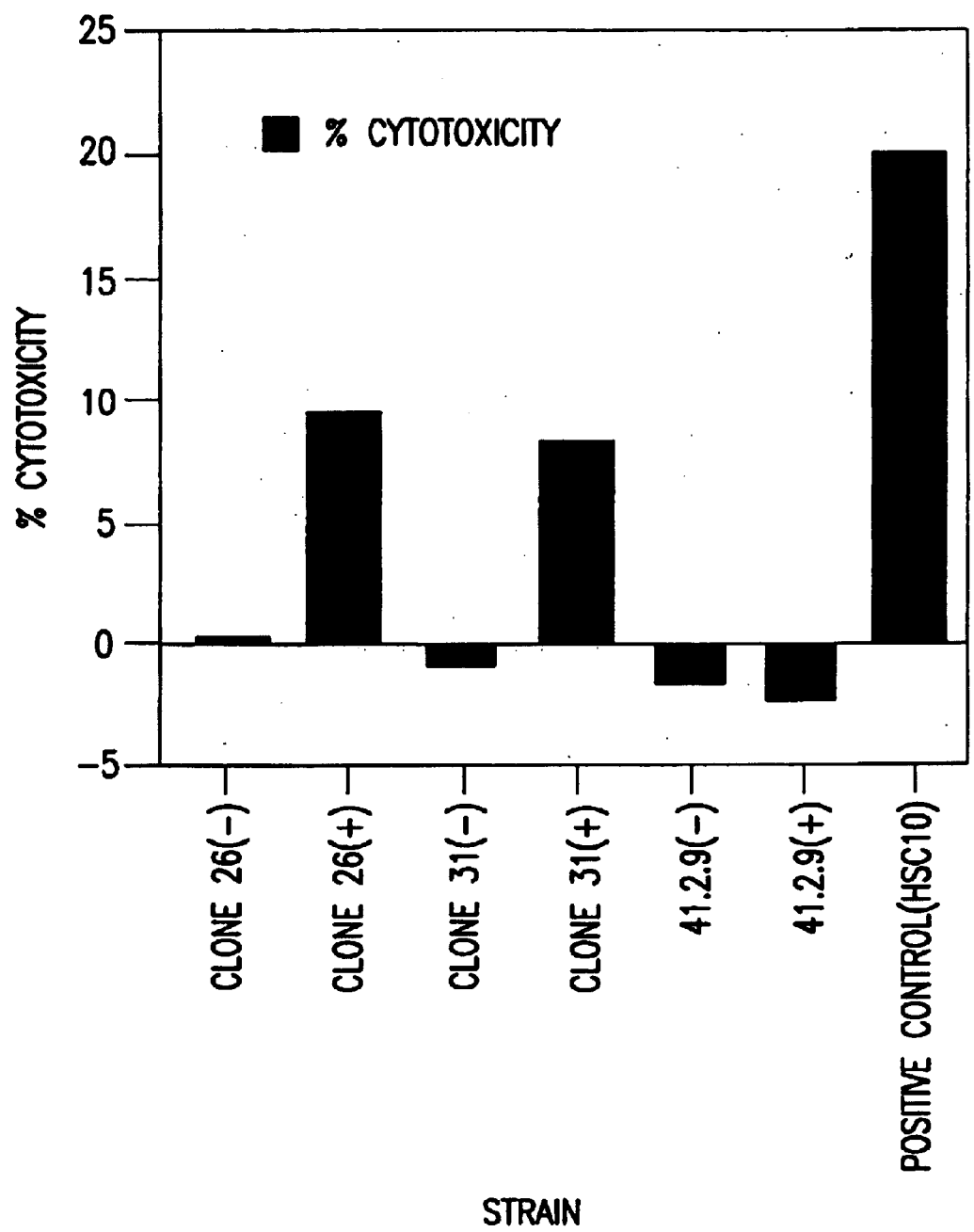

FIG. 34. Percent cytotoxicity of tetBRPAB clone #26 and clone #31 compared to positive and negative controls (HSC10 and 41.2.9) following 72 hours of exposure to SKOV3 cells (Ave N=8). Expression of verotoxin was induced by tetracycline (see clones 26 and 31). Tetracycline treatment (+); and no tetracycline treatment (−). The *E. coli* strain HSC10 was used as a positive control for percent cytotoxicity.

Figure 35:
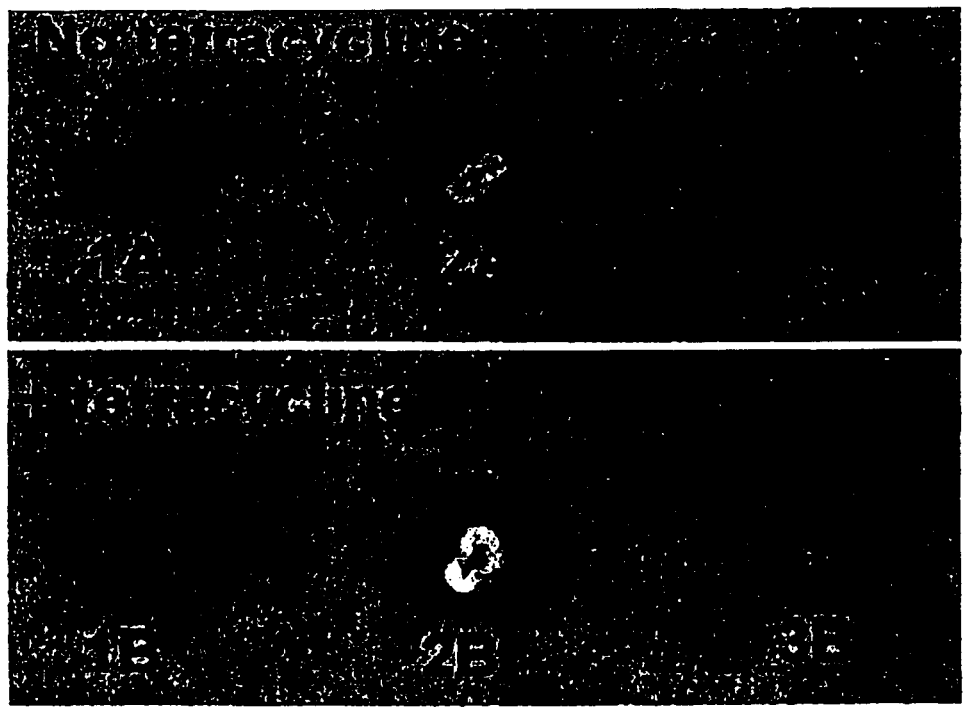

FIG. 35. Halo formation on blood agar for attenuated tumor-targeted *Salmonella* in the absence of tetracycline (1A) and the presence of tetracycline (1B). Halo formation for attenuated tumor-targeted *Salmonella* engineered to constitutively express SheA. in the absence of tetracycline (2A) and the presence of tetracycline (2B). Halo formation for attenuated tumor-targeted *Salmonella* engineered to express tetracycline inducible SheA in the absence of tetracycline (3A) and the presence of tetracycline (3B).

FIG. 36. (A) An illustration of the TAT-apoptin fusion protein without the hexahistadine tag. (B) An illustration of the TAT-apoptin fusion protein with the hexahistadine tag. (C) A) An illustration of the TAT-apoptin fusion protein with an OmpA-8L signal sequence.

FIG. 37. Coding sequence for TAT-apoptin fusion protein. Both DNA (SEQ ID NO:57) and protein (SEQ ID NO:58) sequences are indicated.

FIG. 38. Coding sequence for hexahistidine-TAT-apoptin fusion protein. Both DNA (SEQ ID NO:59) and protein (SEQ ID NO:60) sequences are indicated.

Figure 39:
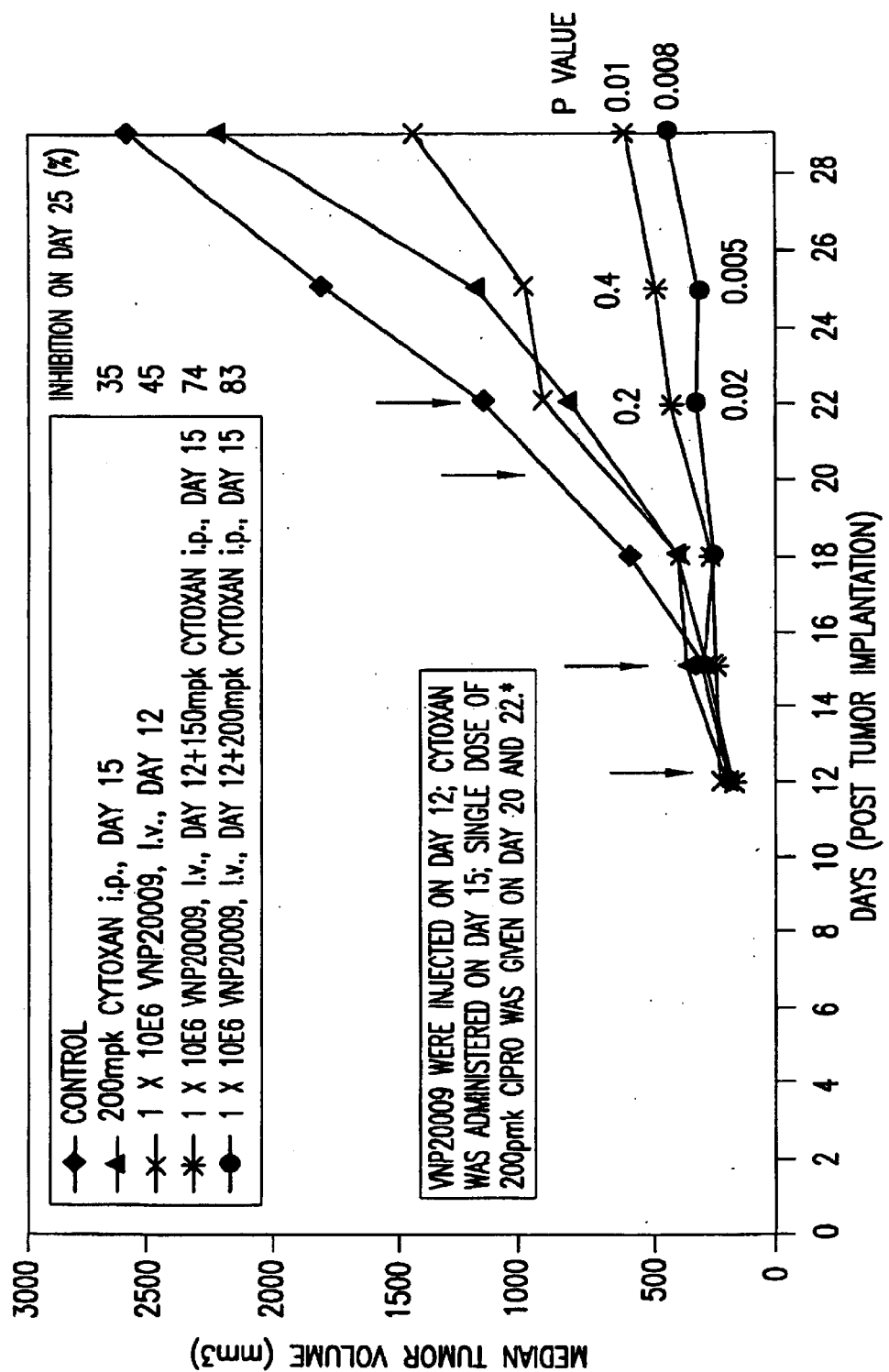

FIG. 39. Efficacy of VNP20009/cytoxan combination therapy on M27 lung carcinoma growth in C57BL/6 mice.

Figure 40:
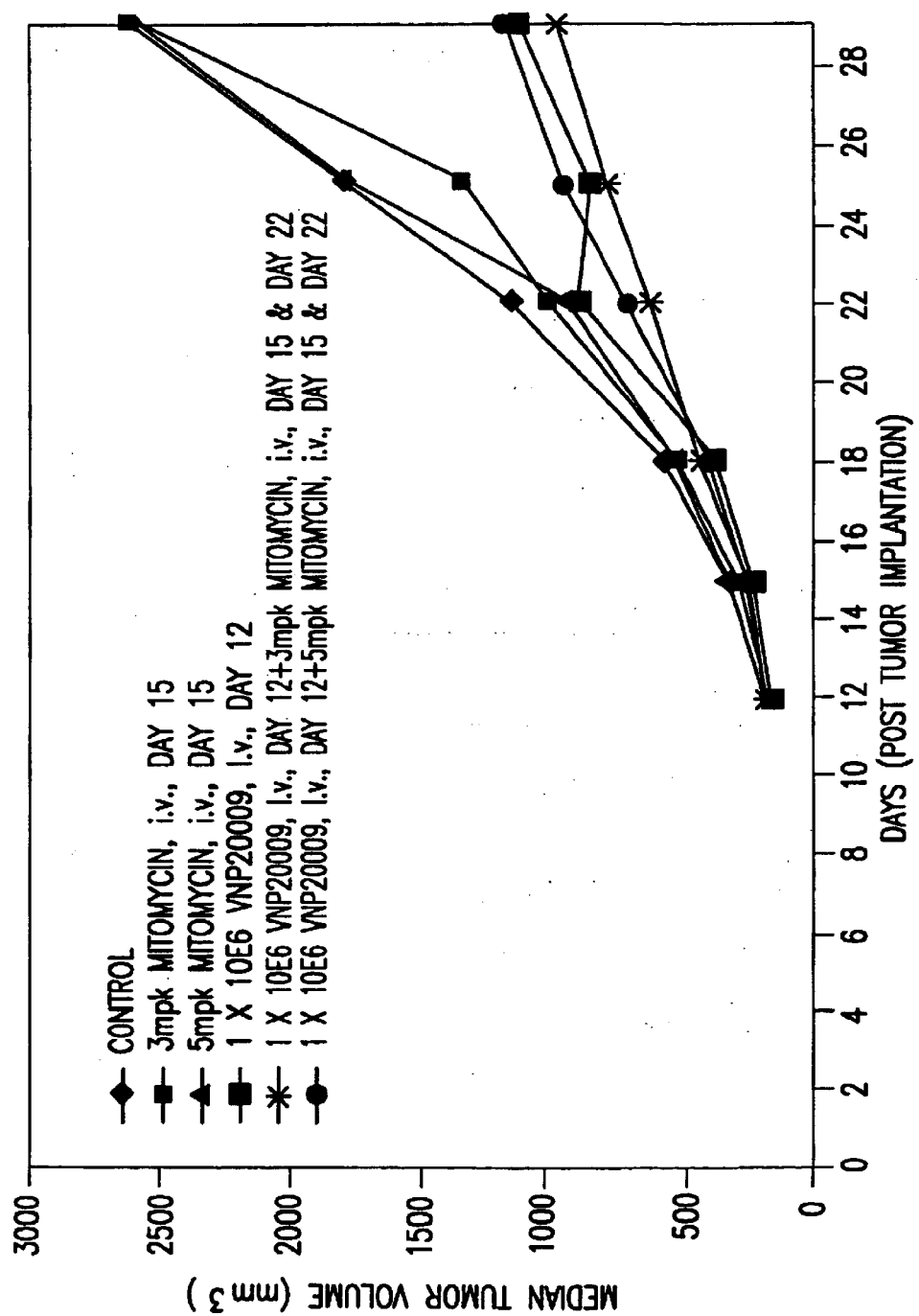

FIG. 40. Efficacy of VNP20009/mitomycin combination therapy on M27 lung carcinoma growth in C57BL/6 mice.

Figure 41:
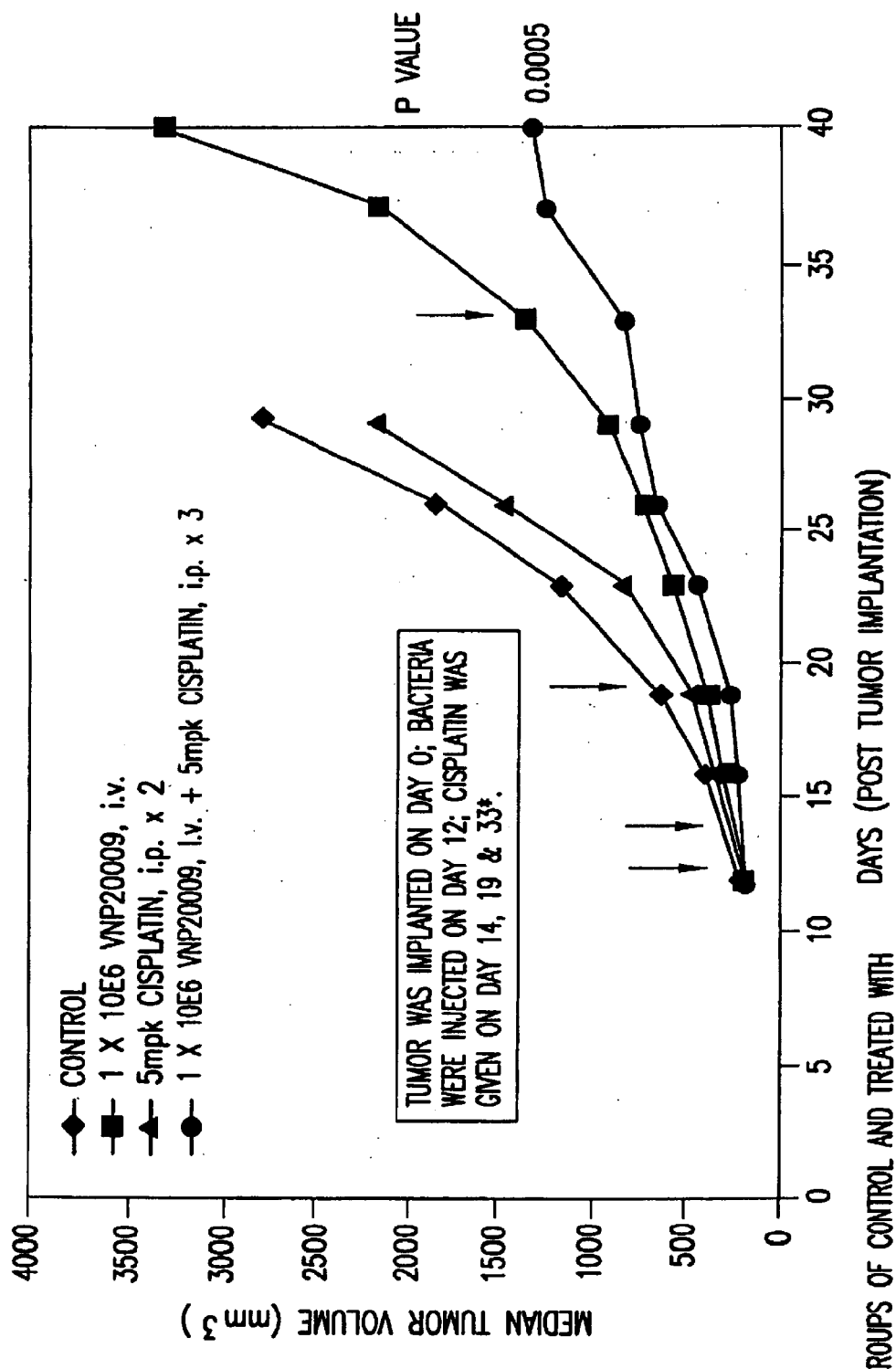

FIG. 41. Efficacy of VNP20009/cisplatin combination therapy on M27 lung carcinoma growth in C57BL/6 mice.

5. DETAILED DESCRIPTION OF THE INVENTION

The present invention utilizes attenuated tumor-targeted strains of bacteria to deliver high levels of therapeutic primary effector molecule(s) to tumors. The present invention provides the advantage of bypassing potential systemic toxicity of certain primary effector molecules (e.g., septic shock caused by TNF-α). The present invention provides delivery of one or more primary effector molecule(s) and optionally, one or more secondary effector molecule(s) to a solid tumor. More particularly, the invention encompasses the preparation and the use of attenuated tumor-targeted bacteria, such as, e.g., *Salmonella*, as a vector for the delivery of one or more primary effector molecule(s) and optionally, one or more secondary effector molecule(s), to an appropriate site of action, e.g., the site of a solid tumor. Specifically, the attenuated tumor-targeted bacteria of the invention are facultative aerobes or facultative anaerobes, which are engineered to encode one or more primary effector molecule(s) and optionally, one or more secondary effector molecule(s).

The attenuated tumor-targeted bacterial-based delivery system presently described provides local delivery of one or more effector molecule(s) to the site of solid tumors. The invention provides safe and effective methods by which a primary effector molecule(s), which may be toxic or induce an unwanted side effect (e.g., an unwanted immunological effect) when delivered systemically to a host, can be delivered locally to tumors by an attenuated tumor-targeted bacteria, such as *Salmonella* with reduced toxicity to the host. The invention also provides combinatorial delivery of one or more primary effector molecule(s) and optionally, one or more secondary effector molecule(s) which are delivered by an attenuated tumor-targeted bacteria, such as *Salmonella*. The invention also provides combinatorial delivery of different attenuated tumor-targeted bacteria carrying one or more different primary effector molecule(s) and/or optionally, one or more different secondary effector molecule(s).

The present invention also provides methods for local delivery of one or more fusion proteins comprising an effector molecule by attenuated tumor-targeted bacteria engineered to express said fusion proteins at the site of the solid tumor(s). In one embodiment, attenuated tumor-targeted bacteria are engineered to express a fusion protein comprising a signal peptide and an effector molecule. In another embodiment, attenuated tumor-targeted bacteria are engineered to express a fusion protein comprising a signal peptide, a proteolytic cleavage site, and an effector molecule. In another embodiment, attenuated tumor-targeted bacteria are engineered to express a fusion protein comprising a ferry peptide and an effector molecule. In another embodiment, attenuated tumor-targeted bacteria are engineered to express a fusion protein comprising a signal peptide, a ferry peptide and an effector molecule. In yet another embodiment, attenuated tumor-targeted bacteria are engineered to express a fusion protein comprising a signal peptide, a proteolytic cleavage site, a ferry peptide and an effector molecule. Attenuated tumor-targeted bacteria are engineered to express one or more fusion proteins of the invention and one or more effector molecules of the invention.

The present invention also provides pharmaceutical compositions comprising a pharmaceutically acceptable carrier and an attenuated tumor-targeted bacteria engineered to contain one or more nucleic acid molecules encoding one or more primary effector molecules. The present invention also provides pharmaceutical compositions comprising a pharmaceutically acceptable carrier and an attenuated tumor-targeted bacteria engineered to contain one or more nucleic acid molecules encoding one or more primary effector molecules and one or more secondary effector molecules. Further, the present invention provides pharmaceutical compositions comprising a pharmaceutically acceptable carrier and an attenuated tumor targeted bacteria engineered to contain one or more nucleic acid molecules encoding one or more fusion proteins and one or more effector molecules.

The present invention provides methods of treating solid tumor cancers in an animal, said methods comprising administering to an animal in need thereof an attenuated tumor-targeted bacteria engineered to express one or more nucleic acid molecules encoding one or more primary effector molecules. The present invention also provides methods of treating solid tumor cancers in an animal, said methods comprising administering to an animal in need thereof an attenuated tumor-targeted bacteria engineered to express one or more nucleic acid molecules encoding one or more primary effector molecules and one or more secondary effector molecules. Further, the present invention provides methods of treating solid tumor cancers in an animal, said methods comprising administering to an animal in need thereof an attenuated tumor-targeted bacteria engineered to contain one or more nucleic acid molecules encoding one or more fusion proteins and one or more effector molecules. Preferably, the animal is a mammal (e.g., a dog, a cat, a horse, a cow, a monkey, or a pig) and more preferably the animal is a human. Examples of solid tumor cancers include, but are not limited to, sarcomas, carcinomas, lymphomas, and other solid tumor cancers, including but not limited to, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, central nervous system cancer, germ cell line cancer, melanoma, renal-cancer, bladder cancer, and mesothelioma.

Although not intending to be limited to any one mechanism, the inventors believe that the present invention results in the targeted expression of the effector molecule(s) at the site of a tumor by delivery of the attenuated tumor-targeted bacterial vector containing the effector molecule(s).

For reasons of clarity, the detailed description is divided into the following subsections: Bacterial Vectors; Primary Effector Molecules for Tumor Therapy; Secondary Effector Molecules for Co-expression With Primary Effector Molecules; Derivatives and Analogs; Fusion Proteins; Expression Vehicles; and Methods and Compositions for Delivery.

5.1. Bacterial Vectors

Any attenuated tumor-targeted bacteria may be used in the methods of the invention. More specifically, the attenuated tumor-targeted bacteria used in the methods of the invention are facultative aerobes or facultative anaerobes. Examples of attenuated tumor-targeted bacteria that are facultative aerobes or facultative anaerobes which may be used in the methods of the invention include, but are not limited to, *Escherichia coli* including enteroinvasive *Escherichia coli*, *Salmonella* spp., *Shigella* spp., *Yersinia enterocohtica*, *Listeria monocytogenies*, *Mycoplasma hominis*, and *Streptococcus* spp.

Factors contributing to attenuation and tumor-targeting are described herein and may be used to construct or select an appropriate bacterial strain for use in the methods of the invention. For example, methods to select and isolate tumor-targeted bacteria are described in Section 6.1, and methods to attenuate bacteria are described in Section 6.2 of International publication WO96/40238, which are incorporated herein by reference. Examples of attenuated tumor-targeted bacteria are also described in International Application WO99/13053, which is incorporated herein by reference in its entirety. In certain embodiments of the invention, a bacteria may be modified by methods known in the art to be attenuated or highly attenuated.

The present invention provides attenuated tumor-targeted bacteria as a vector for the delivery of one or more primary effector molecules (e.g., a TNF family member, a cytotoxic peptide or polypeptide, a tumor inhibitory enzyme, or an anti-angiogenic factor) alone or in combination with a one or more secondary effector molecule(s). The present invention also provides attenuated tumor-targeted bacteria as a vector for the delivery of one or more fusion proteins of the invention alone or in combination with one or more effector molecules. In a preferred embodiment of the invention, the attenuated tumor-targeted bacteria which is engineered to express one or more nucleic acid molecule encoding effector molecules and/or fusion proteins is *Salmonella*.

While the teachings of the following section refers specifically to *Salmonella*, the compositions and methods of the invention are in no way meant to be restricted to *Salmonella* but encompass any other bacterium to which the teachings apply. Suitable bacterial species include, but are not limited to, *Escherichia coli* including enteroinvasive *Escherichia coli*, *Salmonella* spp., *Shigella* spp., *Yersinia enterocohtica*, *Listeria monocytogenies*, *Mycoplasma hominis*, *Streptococcus* spp., wherein the bacterium is a facultative aerobe or facultative anaerobe.

5.1.1 Salmonella Vectors

Any attenuated tumor-targeted bacteria can be modified using the teaching of the invention to encode one or more primary effector molecules and optionally, one or more secondary effector molecules to produce a novel attenuated tumor-targeted bacteria useful for the delivery of one or more effector molecules of the invention to a solid tumor. Further, any attenuated tumor-targeted bacteria can be modified using the teaching of the invention to encode one or more fusion proteins of the invention and optionally, one or more effector molecules to produce a novel attenuated tumor-targeted bacteria useful for the delivery of fusion proteins and effector molecules of the invention to a solid tumor.

Bacteria such as *Salmonella* is a causative agent of disease in humans and animals. One such disease that can be caused by *Salmonella* is sepsis, which is a serious problem because of the high mortality rate associated with the onset of septic shock (Bone, 1993, Clinical Microbiol. Revs. 6:57–68). Therefore, to allow the safe use of *Salmonella* vectors in the present invention, the bacterial vectors such as *Salmonella* are attenuated in their virulence for causing disease. In the present application, attenuation, in addition to its traditional definition in which a microorganism vector is modified so that the microorganism vector is less pathogenic, is intended to include also the modification of a microorganism vector so that a lower titer of that derived microorganism vector can be administered to a patient and still achieve comparable results as if one had administered a higher titer of the parental microorganism vector. The end result serves to reduce the risk of toxic shock or other side effects due to administration of the vector to the patient. Such attenuated bacteria are isolated by means of a number of techniques. For example, attenuation can be achieved by the deletion or disruption of DNA sequences which encode for virulence factors that insure survival of the bacteria in the host cell, especially macrophages and neutrophils. Such deletion or disruption techniques are well known in the art and include, for example, homologous recombination, chemical mutagenesis, radiation mutagenesis, or transposon mutagenesis. Those virulence factors that are associated with survival in macrophages are usually specifically expressed within the macrophages in response to stress signals, for example, acidification, or in response to host cell defensive mechanisms such macropinocytosis (Fields et al., 1986, Proc. Natl. Acad. Sci. USA 83:5189–5193). Table 4 of International Publication WO 96/40238 is an illustrative list of *Salmonella* virulence factors whose deletion results in attenuation.

Yet another method for the attenuation of the bacterial vectors, such as *Salmonella*, is to modify substituents of the bacteria which are responsible for the toxicity of that bacteria. For example, lipopolysaccharide (LPS) or endotoxin is primarily responsible for the pathological effects of bacterial sepsis. The component of LPS which results in this response is lipid A ("LA"). Elimination or mitigation of the toxic effects of LA results in an attenuated bacteria since 1) the risk of septic shock in the patient is reduced and 2) higher levels of the bacterial vector can be tolerated.

Altering the LA content of bacteria, such as *Salmonella*, can be achieved by the introduction of mutations in the LPS biosynthetic pathway. Several enzymatic steps in LPS biosynthesis and the genetic loci controlling them in *Salmonella* have been identified (Raetz, 1993, J. Bacteriol. 175:5745–5753 and references therein), as well as corresponding mutants. One such illustrative mutant is firA, a mutation within the gene that encodes the enzyme UDP-3-O(R-30 hydroxymyristoyl)-glycocyamine N-acyltransferase, which regulates the third step in endotoxin biosynthesis (Kelley et al., 1993, J. Biol. Chem. 268:19866–19874). Bacterial strains bearing this type of mutation produce a lipid A that differs from wild type lipid A in that it contains a seventh fatty acid, a hexadecanoic acid (Roy and Coleman, 1994, J. Bacteriol. 176:1639–1646). Roy and Coleman demonstrated that in addition to blocking the third step in endotoxin biosynthesis, the firA$^-$ mutation also decreases enzymatic activity of lipid A 4' kinase that regulates the sixth step of lipid A biosynthesis.

In addition to being attenuated, the bacterial vectors of the invention are tumor-targeted, i.e. the bacteria preferentially attaches to, infects, and/or remains viable in a tumor or tumor cell versus a normal tissue, non-tumor or non-tumor cell. Suitable methods for obtaining attenuated tumor-targeted bacteria are described in Section 6.1 (pages 25–32; tumor-targeting) and Section 6.2.2 (pages 43–51;attenuation) of International Publication WO 96/40238, which are incorporated herein by reference. As the resulting vectors are highly specific and super-infective, the difference between the number of infecting bacteria found at the target tumor or tumor cell as compared to the non-cancerous counterparts becomes larger and larger as the dilution of the microorganism culture is increased such that lower titers of microorganism vectors can be used with positive results. The techniques described in International Publication WO 96/40238 can also be used to produce attenuated tumor-targeted *Salmonella* or non-*Salmonella* bacterial vectors.

An illustrative example of an attenuated tumor-targeted bacterium having an LPS pathway mutant is the msbB$^-$ *Salmonella* mutant described in International Publication WO99/13053, which is incorporated herein by reference in its entirety; see especially Section 6.1.2 which describes the characteristic of the msbB– *Salmonella* mutant. One characteristic of the msbB$^-$ *Salmonella* is decreased ability to induce a TNF-α response compared to the wild-type bacterial vector. The msbB$^-$ *Salmonella* induce TNF-α expression at levels of about 5 percent to about 40 percent compared to the levels induced by wild-type *Salmonella*.

The TNF-α response induced by whole bacteria or isolated or purified LPS can be assessed in vitro or in vivo using commercially available assay systems such as by enzyme linked immunoassay (ELISA). Comparison of TNF-α production on a per colony forming unit ("c.f.u.") or on a μg/kg basis, is used to determine relative activity. Lower TNF-α levels on a per unit basis indicate decreased induction of TNF-α production. In a preferred embodiment, the msbB$^-$ *Salmonella* vector is modified to contain one or more primary effector molecule(s) and optionally, one or more secondary effector molecule(s) of the invention.

The present invention also encompasses the use of derivatives of msbB$^-$ attenuated tumor-targeted *Salmonella* mutants. Derivatives of msbB$^-$ attenuated tumor-targeted *Salmonella* mutants can be modified using the teaching of the invention to encode one or more primary effector molecule(s) and optionally, one or more secondary effector molecule(s) to produce a novel attenuated tumor-targeted bacteria useful for the delivery of one or more effector molecule(s) of the invention to a solid tumor.

The stability of the attenuated phenotype is important such that the strain does not revert to a more virulent phenotype during the course of treatment of a patient. Such stability can be obtained, for example, by providing that the virulence gene is disrupted by deletion or other non-reverting mutations on the chromosomal level rather than epistatically.

Another method of insuring the attenuated phenotype is to engineer the bacteria such that it is attenuated in more than one manner, e.g., a mutation in the pathway for lipid A production, such as the msbB$^-$ mutation (International Publication WO 99/13053) and one or more mutations to auxotrophy for one or more nutrients or metabolites, such as uracil biosynthesis, purine biosynthesis, and arginine biosynthesis as described by Bochner, 1980, J. Bacteriol. 143:926–933. In a preferred embodiment, the tumor-targeted msbB$^-$ *Salmonella* encoding or expressing at least one primary effector molecule is also auxotrophic for purine. In certain embodiments, the attenuated tumor-targeted bacteria encoding or expressing at least one primary effector molecule are attenuated by the presence of a mutation in AroA, msbB, PurI or SerC. In other embodiments, the attenuated tumor targeted bacteria encoding at least one primary effector molecule are attenuated by the presence of a deletion in AroA, msbB, PurI or SerC.

Accordingly, any attenuated tumor-targeted bacteria may be used in the methods of the invention to express and deliver one or more primary effector molecule(s) and optionally, one or more secondary effector molecule(s) to a solid tumor cancer. In preferred embodiments, the attenuated tumor-targeted bacteria are constructed to express one or more primary effector molecule(s) and optionally, one or more secondary effector molecule(s). Further, any attenuated tumor-targeted bacteria may be used in the methods of the invention to express and deliver one or more fusion proteins and optionally, one or more effector molecules to a solid tumor cancer. In preferred embodiments, the attenuated tumor-targeted bacteria are constructed to express one or more fusion proteins and optionally, one or more effector molecules.

5.2. Primary Effector Molecules for Tumor Therapy

The invention provides for delivery of primary (and optionally secondary) effector molecule(s) by attenuated tumor-targeted bacteria, such as *Salmonella*. The effector molecules of the invention are proteinaceous molecules, (e.g., protein (including but not limited to peptide, polypeptide, protein, post-translationally modified protein, etc.). The invention further provides nucleic acid molecules which encode the primary effector molecules of the invention.

The primary effector molecules can be derived from any known organism, including, but not limited to, animals, plants, bacteria, fungi, and protista, or viruses. In a preferred embodiment of the invention, the primary effector molecule (s) is derived from a mammal. In a more preferred embodiment, the primary effector molecule(s) is derived from a human. The primary effector molecules of the invention comprise members of the TNF family, anti-angiogenic factors, cytotoxic polypeptides or peptides, tumor inhibitory enzymes, and functional fragments thereof.

In a specific embodiment, the primary effector molecules of the invention are members of the TNF family or functional fragments thereof. Examples of TNF family members, include, but are not limited to, tumor necrosis factor-α (TNF-α), tumor necrosis factor-β (TNF-β), TNF-α-related apoptosis-inducing ligand (TRAIL), TNF-α-related activation-induced cytokine (TRANCE), TNF-α-related weak inducer of appptosis (TWEAK), CD40 ligand (CD40L), LT-α, LT-β, OX4OL, CD4OL, FasL, CD27L, CD30L, 4-1BBL, APRIL, LIGHT, TL1, TNFSF16, TNFSF17, and AITR-L. In a preferred embodiment, a primary effector molecule of the invention is tumor necrosis factor-α (TNF-α), tumor necrosis factor-β (TNF-β), TNF-α-related apoptosis-inducing ligand (TRAIL), TNF-α-related activation-induced cytokine (TRANCE), TNF-α-related weak inducer of apoptosis (TWEAK), and CD40 ligand (CD40L), or a functional fragment thereof. For review see, e.g., Kwon, B. et al., 1999, Curr. Opin. Immunol. 11:340–345, which describes members of the TNF family. Also, Table 1 herein below, lists classic and standardized nomenclature of exemplary members of the TNF family. In a preferred embodiment of the invention the primary effector molecule of the invention is tumor necrosis factor-α (TNF-α), tumor necrosis factor-β (TNF-β), TNF-α-related apoptosis-inducing ligand (TRAIL), TNF-α-related activation-induced cytokine (TRANCE), TNF-α-related weak inducer of apoptosis (TWEAK), or CD40 ligand (CD40L).

TABLE 1

TNF FAMILY MEMBERS

| Classic Nomencalture | Standardized Nomenclature |
|---|---|
| LT-α | TNFSF1 |
| TNF-α | TNFSF2 |
| Lt-β | TNFSF3 |
| OX4OL | TNFSF4 |
| CD4OL | TNFSF5 |
| $F_{as}L$ | TNFSF6 |
| CD27L | TNFSF7 |
| CS30L | TNFSF8 |
| 4-BBL | TNFSF9 |
| TRAIL | TNFSF10 |
| TRANCE | TNFSF11 |
| TWEAK | TNFSF12 |
| APRIL | TNFSF13 |
| LIGHT | TNFSF14 |
| TL1 | TNFSF15 |
| — | TNFSF16 |
| — | TNFSF17 |
| AITR-L | TNFSF18 |

In another specific embodiment, the primary effector molecules of the invention are anti-angiogenic factors or functional fragments thereof. Examples of anti-angiogenic factors, include, but are not limited to, endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the anti-angiogenic 24 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, and peptide antagonists of integrin $\alpha_v\beta_3$ and the VEGF receptor.

In a preferred embodiment of the invention, a primary effector molecule of the invention is endostatin. Naturally occurring endostatin consists of the C-terminal ~180 amino acids of collagen XVIII (cDNAs encoding two splice forms of collagen XVIII have Genbank Accession No. AF18081 and AF18082).

In another preferred embodiment of the invention, a primary effector molecule of the invention is plasminogen fragments (the coding sequence for plasminogen can be found in Genbank Accession No. NM_000301 and A33096). Angiostatin peptides naturally include the four kringle domains of plasminogen, kringle 1 through kringle 4. It has been demonstrated that recombinant kringle 1, 2 and 3 possess the anti-angiogenic properties of the native peptide, whereas kringle 4 has no such activity (Cao et al., 1996, J. Biol. Chem. 271:29461–29467). Accordingly, the angiostatin effector molecule of the invention comprises at least one and preferably more than one kringle domain selected from the group consisting of kringle 1, kringle 2 and kringle 3. In a specific embodiment, the primary effector molecule of the invention is a human angiostatin molecule selected from the group consisting of 40 kDa isoform, the 42 kDa isoform, the 45 kDa isoform, or a combination thereof. In another embodiment, the primary effector molecule is the kringle 5 domain of plasminogen, which is a more potent inhibitor of angiogenesis than angiostatin (angiostatin comprises kringle domains 1–4).

In another preferred embodiment of the invention, a primary effector molecule of the invention is antithrombin III. Antithrombin III, which is referred to hereinafter as antithrobin, comprises a heparin binding domain that tethers the protein to the vasculature walls, and an active site loop which interacts with thrombin. When antithrombin is tethered to heparin, the protein elicits a conformational change that allows the active loop to interact with thrombin, resulting in the proteolytic cleavage of said loop by thrombin. The proteolytic cleavage event results in another change of conformation of antithrombin, which (i) alters the interaction interface between thrombin and antithrombin and (ii) releases the complex from heparin (Carrell, 1999, Science 285:1861–1862, and references therein). O'Reilly et al. (1999, Science 285:1926–1928) have discovered that the cleaved antithrombin has potent anti-angiogenic activity. Accordingly, in one embodiment, the anti-angiogenic factor of the invention is the anti-angiogenic form of antithrombin. For the delivery of said protein to a solid tumor according to the methods of the invention, the bacterial vector is modified to express full length antithrombin Genbank Accession No. NM_000488 and a proteolytic enzyme that catalyzes the cleavage of antithrombin to produce the anti-angiogenic form of the protein. The proteolytic enzyme is selected from the group comprising thrombin, pancreatic elastases, and human neutrophil elastase. In a preferred embodiment, the proteolytic enzyme is pancreatic elastase. Methods for the recombinant expression of functional pancreatic elastase are taught by Shirasu (Shirasu et al., 1987, J. Biochem. 102:1555–1563).

In another preferred embodiment of the invention, a primary effector molecule of the invention is the 40 kDa and/or 29 kDa proteolytic fragment of fibronectin. The expression vehicles for these fragments can be generated by standard methods using the full length nucleic acid sequence encoding the fibronectin precursor protein (Genbank Accession No. X02761), and a description of the maturation of the encoded protein. In a preferred embodiment the 40 kDa and/or the 29 kDa fragment of fibronectin is expressed as a cytoplasmic protein under the control of the trc promoter, for example by insertion into the pTrc99A plasmid.

In another preferred embodiment of the invention, a primary effector molecule of the invention is a urokinase plasminogen activator (uPA) receptor antagonist. In one mode of the embodiment, the antagonist is a dominant negative mutant of uPA (see, e.g., Crowley et al., 1993, Proc. Natl. Acad. Sci. USA 90:5021–5025). In another mode of the embodiment, the antagonist is a peptide antagonist or a fusion protein thereof (Goodson et al., 1994, Proc. Natl. Acad. Sci. USA 91:7129–7133). In yet another mode of the embodiment, the antagonist is a dominant negative soluble uPA receptor (Min et al., 1996, Cancer Res. 56:2428–2433).

In another preferred embodiment of the invention, a primary effector molecule of the invention is the 16 kDa N-terminal fragment of prolactin, comprising approximately 120 amino acids, or a biologically active fragment thereof (the coding sequence for prolactin can be found in Genbank Accession No. NM_000948). In a specific embodiment, said prolactin fragment has a Cys58-Ser58 mutation to circumvent undesired cross-linking of the protein by disulfide bonds.

In another preferred embodiment of the invention, a primary effector molecule of the invention is the 7.8 kDa platelet factor-4 fragment. In a specific embodiment, the 7.8 kDa platelet factor-4 fragment is expressed as a fusion protein wherein the amino terminal comprises the first 35 amino acids of E. coli β-glucoronidase. In another embodiment, the heparin binding lysines of platelet factor-4 are mutated to glutamic acid residues, which results in a variant protein having potent anti-angiogenic activity (Maione et al., 1991, Cancer Res. 51:2077–2083). The coding sequence for platelet factor-4 has the Genbank Accession No. NM_002619.

In another preferred embodiment of the invention, a primary effector molecule of the invention is a small peptide corresponding to the anti-angiogenic 13 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, the small anti-angiogenic peptides of laminin, fibronectin, procollagen, or EGF, or small peptide antagonists of integrin $\alpha_v\beta_3$ or the VEGF receptor. In a specific embodiment, the small peptides are expressed in tandem to increase protein stability. The sequences of the small peptides are provided by Cao (1998, Prog. Mol. Subcell. Biol. 20:161–176), with the exception of VEGF receptor antagonists (Soker et al., 1993, J. Biol. Chem. 272:31582–31588). In a highly preferred embodiment, the small peptide comprises an RGD or NGR motif. In certain modes of the embodiment, the RGD or NGR containing peptide is presented on the cell surface of the host bacteria, for example by fusing the nucleic acid encoding the peptide in frame with a nucleic acid encoding one or more extracellular loops of OmpA.

In another specific embodiment, the primary effector molecules of the invention are cytotoxic polypeptides or peptides, or functional fragments thereof. A cytotoxic polypeptide or peptide is cytotoxic or cytostatic to a cell, for example, by inhibiting cell growth through interference with protein synthesis or through disruption of the cell cycle. Such a product may act by cleaving rRNA or ribonucleoprotein, inhibiting an elongation factor, cleaving mRNA, or other mechanism that reduced protein synthesis to a level such that the cell cannot survive.

Examples of cytotoxic polypeptides or peptides include, but are not limited to, members of the bacteriocin family, verotoxin, cytotoxic necrotic factor 1 (CNF1; e.g., E. coli CNF1 and Vibrio fischeri CNF1), cytotoxic necrotic factor 2 (CNF2), Pasteurella multiocida toxin (PMT), hemolysin, CAAX tetrapeptides which are potent competitive inhibitors of farnesyltransferase, saporin, the ricins, abrin, other ribosome inactiviting proteins (RIPs), Pseudomonas exotoxin, inhibitors of DNA, RNA or protein synthesis, antisense nucleic acids, other metabolic inhibitors (e.g., DNA or RNA cleaving molecules such as DNase and ribonuclease, protease, lipase, phospholipase), prodrug converting enzymes (e.g., thymidine kinase from HSV and bacterial cytosine deaminase), light-activated porphyrin, ricin, ricin A chain, maize RIP, gelonin, cytolethal distending toxin, diphtheria toxin, diphtheria-toxin A chain, trichosanthin, tritin, pokeweed antiviral protein (PAP), mirabilis antiviral protein (MAP), Dianthins 32 and 30, abrin, monodrin, bryodin, shiga, a catalytic inhibitor of protein biosynthesis from cucumber seeds (see, e.g., International Publication WO 93/24620), Pseudomonas exotoxin, E. coli heat-labile toxin, E. coli heat-stable toxin, EaggEC stable toxin-1 (EAST), biologically active fragments of cytotoxins and others known to those of skill in the art. See, e.g., O'Brian and Holmes, Protein Toxins of Escherichia coli and Salmonella in Escherichia and Salmonella, Cellular and Molecular Biology, Neidhardt et al. (eds.), pp. 2788–2802, ASM Press, Washington, D.C. for a review of E. coli and Salmonella toxins.

In a preferred embodiment, the primary effector molecule is a member of the bacteroicin family (see e.g., Konisky, 1982, Ann. Rev. Microbiol. 36:125–144), with the proviso that said bacteriocin family member is not a bacteriocin release protein (BRP). Examples of bacteriocin family members, include, but are not limited to, ColE1, ColE1a, ColE1b ColE2, ColE3, ColE4, ColE5, ColE6, ColE7, ColE8, ColE9, Colicin A, Colicin K, Colicin L, Colicin M, cloacin DF13, pesticin A1122, staphylococcin 1580, butyricin 7423, pyocin R1 or AP41, megacin A-216, microcin M15, and vibriocin (Jayawardene and Farkas-Himsley, 1970, J. Bacteriology vol. 102 pp 382–388). Most preferably the primary effector molecule(s) is colicin E3 or V, although colicins A, E1, E2, Ia, Ib, K, L, and M (see, Konisky, 1982, Ann. Rev. Microbiol. 36:125–144) are also suitable as a primary effector molecule(s). In another preferred mode of this embodiment, the bacteriocin is a cloacin, most preferably cloacin DF13.

In a preferred embodiment, the primary effector molecule(s) is ColE1, ColE2, ColE3, ColE4, ColE5, ColE6, ColE7, ColE8, or ColE9. Colicin E3 (ColE3) has been shown to have a profoundly cytotoxic effect on mammalian cells (Smarda et al., 1978, Folia Microbiol. 23:272–277), including a leukemia cell model system (Fiska et al., 1978, Experientia 35:406–40. ColE3 cytotoxicity is a function of protein synthesis arrest, mediated by inhibition of 80S ribosomes (Turnowsky et al., 1973, Biochem. Biophys. Res. Comm. 52:327–334). More specifically, ColE3 has ribonuclease activity (Saunders, 1978) Nature 274:113–114). In its naturally occurring form, ColE3 is a 60 kDa protein complex consisting of a 50 kDa and a 10 kDa protein in a 1:1 ratio, the larger subunit having the nuclease activity and the smaller subunit having inhibitory function of the 50 kDa subunit. Thus, the 50 kDa protein acts as a cytotoxic protein (or toxin), and the 10 kDa protein acts as an anti-toxin. Accordingly, in one embodiment, when ColE3 is used as a secondary effector molecule, the larger ColE3 subunit or an active fragment thereof is expressed alone or at higher levels than the smaller subunit. In another embodiment of the invention, the ColE3 50 kDa toxin and 10 kDa anti-toxin are encoded on a single plasmid within an attenuated tumor-targeted bacteria, such as *Salmonella*. In this embodiment, the toxin/anti-toxin can act as a selection system for the *Salmonella* which carry the plasmid, such that *Salmonella* which lose the plasmid are killed by the toxin. In another embodiment, the 10 kDa anti-toxin is on the chromosome, separate form the colE3 toxin on the plasmid, resulting in a barrier to transmission to other bacteria. (See Section 5.6, infra).

In another preferred embodiment, the primary effector molecule(s) is cloacin DF13. Cloacin DF13 functions in an analogous manner to ColE3. The protein complex is of 67 KDa molecular weight. The individual components are 57 kDa and 9 kDa in size. In addition to its ribonuclease activity, DF13 can cause the leakage of cellular potassium.

In another preferred embodiment, the primary effector molecule(s) is colicin V (Pugsley, A. P. and Oudega, B. "Methods for Studying Colicins and Their Plasmids" in Plasmids, a Practical Approach 1987, ed. By K. G. Hardy; Gilson, L. et al. EMBO J. 9: 3875–3884).

In another embodiment, the primary effector molecule(s) is colicin E2 (a dual subunit colicin similar to ColE3 in structure but with endonuclease rather than ribonuclease activity); colicins A, E1, Ia, Ib, or K, which form ion-permeable channels, causing a collapse of the proton motive force of the cell and leading to cell death; colicin L which inhibits protein, DNA & RNA synthesis; colicin M which causes cell sepsis by altering the osmotic environment of the cell; pesticin A1122 which functions in a manner similar to colicin B function; staphycoccin 1580, a pore-forming bacteriocin; butyricin 7423 which indirectly inhibits RNA, DNA and protein synthesis through an unknown target; Pyocin P1, or protein resembling a bacteriophage tail protein that kills cells by uncoupling respiration from solute transport; Pyocin AP41 which has a colicin E2-like mode of action; or megacin A-216 which is a phospholipase that causes leakage of intracellular material (for a general review of bacteriocins, see Konisky, 1982, Ann. Rev. Microbiol. 36:125–144); colicin A (Pugsley, A. P. and Oudega, B. "Methods for Studying Colicins and Their Plasmids" in Plasmids, a Practical Approach 1987, ed. By K. G. Hardy).

Accordingly, a primary effector molecule may comprise any bacteriocin described herein or known in the art, with the proviso that said bacteriocin is not a bacteriocin release protein.

In another specific embodiment, the primary effector molecules of the invention are tumor inhibitory enzymes or functional fragments thereof. Examples of tumor inhibitory enzymes include, but are not limited, methionase, asparaginase, lipase, phospholipase, protease, ribonuclease, DNAase, and glycosidase. In a preferred embodiment, the primary effector molecule is methionase.

The primary effector molecules of the invention are useful, for example, to treat, or prevent a solid tumor cancer such as a carcinoma, melanoma, lymphoma, or sarcoma.

The invention provides nucleic acid molecules encoding a primary effector molecule. The invention also provides nucleic acid molecules encoding one or more primary effector molecule(s) and optionally, one or more secondary effector molecule(s). The invention provides nucleic acids encoding effector molecule(s) of the invention which is operably linked to an appropriate promoter. Optionally, the nucleic acids encoding an effector molecule(s) may be operably linked to other elements that participate in transcription, translation, localization, stability and the like.

The nucleic acid molecule encoding a primary effector molecule is from about 6 to about 100,000 base pairs in length. Preferably, the nucleic acid is from about 20 base pairs to about 50,000 base pairs in length. More preferably, the nucleic acid molecule is from about 20 base pairs to about 10,000 base pairs in length. Even more preferably, the nucleic acid molecule is about 20 base pairs to about 4000 base pairs in length.

5.3. Secondary Effector Molecules for Co-Expression with Primary Effector Molecules In certain embodiments of the invention, the primary effector molecule (e.g., a TNF family member, a cytotoxic peptide or polypeptide, an anti-angiogenic factor, or a tumor inhibitory enzyme) is optionally co-expressed in a bacterial vector with another molecule, i.e. a secondary effector molecule. The secondary effector molecule provides additional therapeutic value and/or facilitates the release of the contents of the modified bacterial vector (which expresses at least one primary effector molecule and optionally one or more secondary effector molecules) into the surrounding environment. As used herein, the term "additional therapeutic value" indicates that the secondary effector molecule provides an additive or synergistic, cytostatic, or cytotoxic effect on a tumor, e.g., in addition to that provided by the primary effector molecule(s). Thus, a secondary effector molecule functions as an additional therapeutic factor and/or a release factor. Preferably, the secondary effector molecule, whether a therapeutic or release factor (or both), is preferentially or specifically activated or expressed at the desired site, i.e. at the site of the tumor. In certain embodiments, the secondary effector molecule can serve two functions, i.e. promote the release of the bacterial cell contents (e.g., by promoting bacterial cell lysis or quasi lysis) and provide therapeutic value (e.g., by cytotoxicity to the tumor cells). In certain non-limiting embodiments, the cytotoxicity of the secondary effector molecule can be mediated by the patient's immune system; accordingly such a secondary effector molecule can function as an immunomodulator.

In certain embodiments of the invention, the attenuated tumor-targeted bacterial vector of the invention is engineered to express at least one secondary effector molecule which has anti-tumor activity, i.e. expression of the secondary effector molecule results in killing or inhibition of the growth of a tumor or tumor cells.

The secondary effector molecule is proteinaceous or a nucleic acid molecule. The nucleic acid molecule can be double-stranded or single-stranded DNA or double-stranded or single-stranded RNA, as well as triplex nucleic acid molecules. The nucleic acid molecule can function as a ribozyme, or antisense nucleic acid, etc.

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. Nos. 5,168,053; 5,190,931; 5,135,917; and 5,087,617). Triplex molecules refer to single DNA strands that bind duplex DNA forming a colinear triplex molecule, thereby preventing transcription (see, e.g., U.S. Pat. No. 5,176,996).

A ribozyme is an RNA molecule that specifically cleaves RNA substrates, such as mRNA, resulting in inhibition or interference with cell growth or expression. There are at least five known classes of ribozymes involved in the cleavage and/or ligation of RNA chains. Ribozymes can be targeted to any RNA transcript and can catalytically cleave that transcript (see, e.g., U.S. Pat. No. 5,272,262; U.S. Pat. No. 5,144,019; and U.S. Pat. Nos. 5,168,053, 5,180,818, 5,116,742 and 5,093,246).

As described above for the primary effector molecule, a nucleic acid encoding or comprising a secondary effector molecule is provided in operative linkage with a selected promoter, and optionally in operative linkage with other elements that participate in transcription, translation, localization, stability and/or the like. Further, the secondary effector molecule can be expressed using the same promoter as the primary effector molecule and an internal ribosome binding site, or using a different promoter than the primary effector molecule.

The nucleic acid molecule encoding the secondary effector molecule is from about 6 base pairs to about 100,000 base pairs in length. Preferably the nucleic acid molecule is from about 20 base pairs to about 50,000 base pairs in length. More preferably the nucleic acid molecule is from about 20 base pairs to about 10,000 base pairs in length. Even more preferably, it is a nucleic acid molecule from about 20 pairs to about 4,000 base pairs in length.

The nucleotide sequences of the effector molecules encoding the secondary effector molecules described below are well known (see GenBank). A nucleic acid molecule encoding a secondary effector molecule, which secondary effector molecule is a cytotoxic or cytostatic factor or a biologically active fragment, variant or derivative thereof, may be isolated by standard methods, such as amplification (e.g., PCR), probe hybridization of genomic or cDNA libraries, antibody screening of expression libraries, chemically synthesized or obtained from commercial or other sources.

Nucleic acid molecules and oligonucleotides for use as described herein can be synthesized by any method known to those of skill in this art (see, e.g., International Publication WO 93/01286, U.S. Pat. Nos. 5,218,088; 5,175,269; and 5,109,124). Identification of oligonucleotides and ribozymes for use as antisense agents involve methods well known in the art.

5.3.1. Factors Providing Additional Therapeutic Value

In certain embodiments of the invention, the attenuated tumor-targeted bacterial vector of the invention, which expresses at least one primary effector molecule and is preferably a *Salmonella* vector, expresses at least one secondary effector molecule which has anti-tumor activity, i.e. expression of the secondary effector molecule results in killing or inhibition of the growth of a tumor or tumor cells or spread of tumor cells, thereby augmenting the cytotoxic or cytostatic action of the primary effector molecule. In one embodiment, the effects on the tumor of the secondary effector molecule are additive to those of the primary effector molecule. In a preferred embodiment, the effects are supra-additive or synergistic, i.e. greater than the sum of the effects of the primary and secondary effector molecules if administered separately.

In certain embodiments, the secondary effector molecule is cytotoxic or cytostatic to a cell by inhibiting cell growth through interference with protein synthesis or through disruption of the cell cycle. Such a product may act, for example, by cleaving rRNA or ribonucleoprotein, inhibiting an elongation factor, cleaving mRNA, or other mechanism that reduced protein synthesis to a level such that the cell cannot survive. Examples of such secondary effector molecules include but are not limited to saporin, the ricins, abrin, and other ribosome inactivating proteins (RIPs).

In another embodiment, the secondary effector molecule is a pro-drug converting enzyme or nucleic acid encoding the same, i.e. an enzyme that modulates the chemical nature of a drug to produce a cytotoxic agent. Illustrative examples of pro-drug converting enzymes are listed on page 33 and in Table 2 of WO 96/40238 by Pawelek et al., which is incorporated herein by reference., WO 96/40238 also teaches methods for production of secreted fusion proteins comprising such pro-drug converting enzymes. According to the present invention, a pro-drug converting enzyme need not be a secreted protein if co-expressed with a release factor such as BRP (See, infra, Section 5.3.2). In a specific embodiment, the pro-drug converting enzyme is cytochrome p450 NADPH oxidoreductase which acts upon mitomycin C and porfiromycin (Murray et al., 1994, J. Pharmacol. Exp. Therapeut. 270:645–649). In another embodiment, the secondary effector molecule(s) is co-expressed with a release factor such as BRP, and cause the release of co-factors (e.g., NADH, NADPH, ATP, etc.) which enhance pro-drug converting enzyme activity. In another mode of the embodiment, a secondary effector molecule is co-expressed with a release factor such as BRP, leading to the release of an activated drug (e.g., a drug which is activated within the bacterial cytoplasm or periplasm, and then released from the bacterial vector).

In another embodiment, a secondary effector molecule is an inhibitor of inducible nitric oxide synthase (NOS) or of endothelial nitic oxide synthase. Nitric oxide (NO) is implicated to be involved in the regulation of vascular growth and in arterosclerosis. NO is formed from L-arginine by nitric oxide synthase (NOS) and modulates immune, inflammatory and cardiovascular responses.

In another embodiment, the secondary effector molecule is cytotoxic or cytostatic to a cell by inhibiting the production or activity of a protein involved in cell proliferation, such as an oncogene or growth factor, (e.g., bFGF, int-2, hst-1/K-FGF, FGF-5, hst-2/FGF-6, FGF-8) or cellular receptor or ligand. The inhibition can be at the level of transcription or translation (mediated by a secondary effector molecule that is a ribozyme or triplex DNA), or at the level of protein activity (mediated by a secondary effector molecule that is an inhibitor of a growth factor pathway, such as a dominant negative mutant).

In another embodiment, a secondary effector molecule is a cytokine, chemokine, or an immunomodulating protein or a nucleic acid encoding the same, such as interleukin-1 (IL-1), interleukin-2 (IL-2), interleukin-4 (IL-4), interleukin-5 (IL-5), interleukin-10 (IL-10), interleukin-15 (IL-15), interleukin-18 (IL-18), endothelial monocyte activating protein-2 (EMAP2), GM-CSF, IFN-γ, IFN-α, MIP-3α, SLC, MIP-3β, or an MHC gene, such as HLA-B7. Delivery of such immunomodulating effector molecules will modulate the immune system, increasing the potential for host antitumor immunity. Alternatively, nucleic acid molecules encoding costimulatory molecules, such as B7.1 and B7.2, ligands for both CD28 and CTLA-4, can also be delivered to enhance T cell mediated immunity. Yet another immunomodulating agent is, α-1,3-galactosyl transferase, whose expression on tumor cells allows complement-mediated cell killing. Further, another immunomodulating agent is a tumor-associated antigen, i.e. a molecule specifically that is expressed by a tumor cell and not in the non-cancerous counterpart cell, or is expressed in the tumor cell at a higher level than in the non-cancerous counterpart cell. Illustrative examples of tumor-associated antigens are described in Kuby, *Immunology*, W. H. Freeman and Company, New York, N.Y., 1$^{st}$ Edition (1992), pp. 515–520 which is incorporated by reference herein. Other examples of tumor-associated antigens are known to those of skill in the art.

In another embodiment, a secondary effector molecule is a Flt-3 ligand or nucleic acid encoding the same. In another embodiment, a secondary molecule is BRP.

In a specific embodiment, a secondary effector molecule is not a TNF family member when the primary effector molecule is a TNF family member. In another specific embodiment, a secondary effector molecule is not an anti-angiogenic factor when the primary effector molecule is an anti-angiogenic factor. In another specific embodiment, a secondary molecule is not a cytotoxic peptide or polypeptide when the secondary molecule is a cytotoxic peptide or polypeptide. In another specific embodiment, a secondary molecule is not a tumor inhibiting enzyme when the primary effector molecule is a a tumor inhibiting enzyme.

5.3.2. Factors that Promote the Release of Anti-Tumor Effector Molecules into the Tumor Environment In certain other embodiments of the invention, the attenuated tumor-targeted bacterial vector of the invention, which expresses at least one primary effector molecule and is preferably a *Salmonella* vector, expresses at least one secondary effector molecule which functions to permeabilize the bacteria cell membrane(s) or enhance the release of intracellular components into the extracellular environment, e.g. at the tumor site, thereby enhancing the delivery of the primary and/or secondary effector molecule(s). Such secondary effector molecule which permeabilizes the bacterial cell or enhances release is designated "a release factor". In certain embodiments, the release factor also advantageously has anti-tumor activity.

The release factor expressed by the bacterial vector of the invention may be endogenous to the modified attenuated tumor-targeted bacteria or it may be exogenous (e.g., encoded by a nucleic acid that is not native to the attenuated tumor-targeted bacteria). A release factor may be encoded by a nucleic acid comprising a plasmid, or by a nucleic acid which is integrated into the genome of the attenuated tumor-targeted bacteria. A release factor may be encoded by the same nucleic acid or plasmid that encodes a primary effector molecule, or by a separate nucleic acid or plasmid. A release factor may be encoded by the same nucleic acid or plasmid that encodes a secondary effector molecule, or by a separate nucleic acid or plasmid. In one embodiment, the release factor is expressed in a cell which also expresses a fusion protein comprising a primary effector molecule fused to an Omp-like protein. In this embodiment, the co-expression of the release factor allows for enhanced release of the fusion protein from the periplasmic space.

In a preferred embodiment, such a factor is one of the Bacteriocin Release Proteins, or BRPs (herein referred to in the generic as BRP). The BRP employed in the invention can originate from any source known in the art including but not limited to the cloacin DF13 plasmid, one of colicin E1–E9 plasmids, or from colicin A, N or D plasmids. In a preferred embodiment, the BRP is of cloacin DF 13 (pCloDF13 BRP).

Generally, BRPs are 45–52 amino acid peptides that are initially synthesized as precursor molecules (PreBRP) with signal sequences that are not cleaved by signal endopeptidases. BRP activity is thought to be mediated, at least in part, by the detergent-resistant outer membrane phopholipase A (PldA) and is usually associated with an increase in the degradation of outer membrane phospholipid (for a general review on BRPs, see van der Wal et al., 1995, FEMS Microbiology Review 17:381–399). Without limitation as to mechanism, BRP promotes the preferential release of periplasmic components, although the release of cytoplasmic components is also detected to a lesser extent. When moderately overexpressed, BRP may cause the bacterial membrane to become fragile, inducing quasi-lysis and high release of cytoplasmic components. Additionally, it is thought that when BRP is expressed at superhigh levels, the protein can cause bacterial cell lysis, thus delivering cellular contents by lytic release. In this embodiment, BRP expression may be correlated with BRP activity (e.g., release of bacterial contents). For example, superhigh BRP activity results in bacterial cell lysis of substantially all bacteria. Thus, as used herein, "superhigh expression" is defined as the expression level of BRP which results in bacterial cell lysis of substantially all bacteria. Moderate BRP activity, is associated with partial or enhanced release of bacterial contents as compared to a control bacteria which is not expressing BRP, without obligate lysis of the bacteria. Thus, in this embodiment, moderate overexpression of BRP is defined as the expression level at which release of cytoplasmic components is enhanced, without bacterial lysis of substantially all of the bacteria. Substantially all of the bacteria, as used herein, is more than 60% of the bacteria, preferably more than 70%, more preferably 80%, still more preferably more than 90% and most preferably 90–100% of bacteria.

In a specific embodiment of the invention, the BRP protein is a pCloDF13 BRP mutant whose lytic function has been uncoupled from its protein release function, thereby enhancing protein release without bacterial lysis (van der Wal et al., 1998, App. Env. Microbiol. 64:392–398). This embodiment allows for prolonged protein release from the bacterial vector, while reducing the need for frequent administration of the vector. In another specific embodiment, the BRP of the invention is a pCloDF13 BRP with a shortened C-terminus, which in addition to protein release causes cell lysis (Luirink et al., 1989, J. Bacteriol. 171:2673–2679).

In another embodiment of the invention, the enhanced release system comprises overexpression of a porin protein; see e.g., Sugawara, E. and Nikaido, H., 1992, J. Biol. Chem. 267:2507–11.

In certain embodiments when a BRP is expressed by the bacterial vector of the invention, the BRP may be endogenous to the modified attenuated tumor-targeted bacteria or it may be exogenous (e.g., encoded by a nucleic acid that is not native to the attenuated tumor-targeted bacteria). A BRP may be encoded by a nucleic acid comprising a plasmid, or by a nucleic acid which is integrated into the genome of the attenuated tumor-targeted bacteria. A BRP may be encoded by the same nucleic acid or plasmid that encodes a primary effector molecule, or by a separate nucleic acid or plasmid. A BRP may be encoded by the same nucleic acid or plasmid that encodes a secondary effector molecule, or by a separate nucleic acid or plasmid. In one embodiment, the BRP-like protein is expressed in a cell which also expresses a fusion protein comprising an effector molecule fused to an Omp-like protein. In this embodiment, the co-expression of the BRP allows for enhanced release of the fusion protein.

In a preferred specific embodiment of the invention a BRP encoding nucleic acid is encoded by a colicin plasmid. In another specific embodiment of the invention, the BRP encoding nucleic acid is expressed under the control of the native BRP promoter, which is an SOS promoter that responds to stress (e.g., conditions that lead to DNA damage such as UV light) in its native host (for BRP, *Enterococcus cloacae*), yet is partially constitutive in *Salmonella*. In a preferred embodiment, the BRP encoding nucleic acid is expressed under the control of the pepT promoter, which is activated in response to the anaerobic nature of the tumor environment (see e.g., Lombardo et al., 1997, J. Bacteriol. 179:1909–17).

Alternatively, the promoter can be an antibiotic-induced promoter, such as the tet promoter of the Tn10 transposon. In a preferred embodiment, the tet promoter is a singlemer, which singlemer responds in an all-or-nothing manner to the presence of tetracycline or analogs thereof such as doxicycline and anhydrotetracycline and provides a genetically stable on-off switch. In another embodiment, the let promoter is multimerized, for example three-fold. Such a multimer responds in a graded manner to the presence of tetracycline and provides a more manipulable system for control of effector molecule levels. Promoter activity would then be induced by administering to a subject who has been treated with the attenuated tumor-targeted bacteria of the invention an appropriate dose of tetracycline. Although the let inducible expression system was initially described for eukaryotic systems such as *Schizosaccharomyces pombe* (Faryar and Gatz, 1992, Current Genetics 21:345–349) and mammalian cells (Lang and Feingold, 1996, Gene 168:169–171), recent studies extend its applicability to bacterial cells. For example, Stieger et al. (1999, Gene 226:243–252) have shown 80-fold induction of the firefly luciferase gene upon let induction when operably linked to the let promoter. An advantage of this promoter is that it is induced at very low levels of tetracycline, approximately $\frac{1}{10}$th of the dosage required for antibiotic activity.

5.4. Derivatives and Analogs

The invention further encompasses bacterial vectors that are modified to encode or deliver a derivative, including but not limited to a fragment, analog, or variant of a primary and/or secondary effector molecule, or a nucleic acid encoding the same. The derivative, analog or variant is functionally active, e.g., capable of exhibiting one or more functional activities associated with a full-length, wild-type effector molecule. As one example, such derivatives, analogs or variants which have the desired therapeutic properties can be used to inhibit tumor growth or the spread of tumor cells (metastasis). Derivatives or analogs of an effector molecule can be tested for the desired activity by procedures known in the art, including those described herein.

In particular, variants can be made by altering effector molecule encoding sequences by substitutions, additions (e.g., insertions) or deletions that provide molecules having the same or increased anti-tumor function relative to the wild-type effector molecule. For example, the variants of the invention include, but are not limited to, those containing, as a primary amino acid sequence, all or part of the amino acid sequence of an effector molecule, including altered sequences in which functionally equivalent amino acid residues are substituted for residues within the sequence resulting in a silent change, i.e., the altered sequence has at least one conservative substitution.

Any of the primary or secondary effector-encoding nucleic acids that are of mammalian origin can be altered to employ bacterial codon usage by methods known in the art. Preferred codon usage is exemplified in Current Protocols in Molecular Biology, Green Publishing Associates, Inc., and John Wiley & Sons, Inc. New York, and Zhang et al., 1991, Gene 105:61–72.

In a specific embodiment, a derivative, analog or variant of a primary or secondary molecule comprises a nucleotide sequence that hybridizes to the nucleotide sequence encoding the primary or secondary molecule, or fragment thereof under stringent conditions, e.g., hybridization to filter-bound DNA in 6× sodium chloride/sodium citrate (SSC) at about 45° C. followed by one or more washes in 0.2×SSC/0.1% SDS at about 50–65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1–6.3.6 and 2.10.3).

Derivatives or analogs of a primary or secondary effector molecule include but are not limited to those molecules comprising regions that are substantially homologous to the primary or secondary effector molecule or fragment thereof (e.g., in various embodiments, at least 60% or 70% or 80% or 90% or 95% identity over an amino acid sequence of identical size without any insertions or deletions or when compared to an aligned sequence in which the alignment is done by a computer homology program known in the art) or whose encoding nucleic acid is capable of hybridizing to an effector molecule protein effector molecule encoding sequence, under high stringency, moderate stringency, or low stringency conditions.

To determine the percent identity of two amino acid sequences or of two nucleic acids, e.g. between the sequences of a primary effector molecule and other known sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264–2268, modified as in Karlin and Altschul, 1993, Proc. Natl. Acad. Sci. USA 90:5873–5877. Such an algorithm is incorporated into the NBLAST and XBLAST programs of Altschul, et al., 1990, J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res. 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci., 10:3–5; and FASTA described in Pearson and Lipman, 1988, Proc. Natl. Acad. Sci. 85:2444–8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see http://bioweb.pasteur.fr/docs/man/man/fasta.1.html#sect2, the contents of which are incorporated herein by reference.

Alternatively, protein sequence alignment may be carried out using the CLUSTAL W algorithm, as described by Higgins et al., 1996, Methods Enzymol. 266:383–402.

The percent identity between two sequences can be determined using techniques similar to those described above, with or without allowing gaps. In calculating percent identity, only exact matches are counted.

A primary effector molecule or a secondary effector molecule, or derivatives, or analogs thereof can be produced by various methods known in the art. The manipulations which result in their production can occur at the nucleic acid or protein level. For example, a cloned effector molecule encoding sequence encoding, for example, an effector molecule can be modified by any of numerous strategies known in the art (Sambrook et al., 1989, *Molecular Cloning, A Laboratory Manual*, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of a modified effector molecule encoding a derivative or analog of a primary or secondary effector molecule, care should be taken to ensure that the modified effector molecule encoding sequence remains within the same translational reading frame as the native protein, uninterrupted by translational stop signals, in the effector molecule encoding sequence region where the desired primary or secondary effector molecule activity is encoded.

Additionally, a nucleic acid sequence encoding an effector molecule can be mutated in vitro or in vivo, to create and/or destroy translation, initiation, and/or termination sequences, or to create variations in coding regions and/or to form new restriction endonuclease sites or destroy preexisting ones, to facilitate further in vitro modification. In a preferred specific embodiment, an effector molecule encoding nucleic acid sequence is mutated, for example, to produce a more potent variant. Any technique for mutagenesis known in the art can be used, including but not limited to, chemical mutagenesis, in vitro site-directed mutagenesis (Hutchinson et al., 1978, J. Biol. Chem. 253:6551), use of TAB® linkers (Pharmacia), PCR with primers containing a mutation, etc. In a preferred embodiment, conservative amino acid substitutions are made at one or more predicted non-essential amino acid residues of an effector molecule. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In other embodiments, the effector molecules or fusion proteins of the invention are constructed to contain a protease cleavage site.

5.5. Fusion Proteins

In certain embodiments, the invention provides a primary or secondary effector molecule which is constructed as a fusion protein (e.g., covalently bonded to a different protein). The invention provides nucleic acids encoding such fusion proteins. In certain other embodiments of this invention, the nucleic acid encoding a fusion protein of the invention is operably linked to an appropriate promoter.

In a specific embodiment, an effector molecule is constructed as a chimeric or fusion protein comprising an effector molecule or fragment thereof (preferably consisting of at least a domain or motif of the effector molecule, or at least 5, at least 10, at least 25, at least 50, at least 75, or at least 100 amino acids of the effector molecule) joined at its amino- or carboxy-terminus via a peptide bond to an amino acid sequence of a different protein. In specific embodiments, fusion comprises at least 2, at least 6, at least 10, at least 20, at least 30, at least 50, at least 75, or at least 100 contiguous amino acids of a heterologous polypeptide or fragment thereof that is functionally active. In one embodiment, such a fusion protein or chimeric protein is produced by recombinant expression of a nucleic acid encoding the primary effector molecule (e.g., a TNF-coding sequence, an anti-angiogenic factor-coding sequence, a tumor inhibitory enzyme-coding sequence, or a cytotoxic polypeptide-coding sequence) joined in-frame to a coding sequence for a different protein. Such a chimeric product can be made by ligating the appropriate nucleic acid sequences encoding the desired amino acid sequences to each other by methods known in the art, in the proper coding frame, and expressing the chimeric product into the expression vehicle of choice by methods commonly known in the art. Chimeric nucleic acids comprising portions of a nucleic acid encoding an effector molecule fused to any heterologous polypeptide-encoding sequences may be constructed. A specific embodiment relates to a chimeric protein comprising a fragment of a primary or secondary effector molecule of at least 5, at least 10, at least 25, at least 50, or at least 100 amino acids, or a fragment that displays one or more functional activities of the full-length primary or secondary effector molecule.

In a specific embodiment, a fusion protein comprises an affinity tag such as a hexahistidine tag, or other affinity tag that may be used in purification, isolation, identification, or assay of expression. In another specific embodiment, a fusion protein comprises a protease cleavage site such as a metal protease or serine cleavage site. In this embodiment, it is in some cases preferred that a protease site corresponding to a protease which is active at the site of a tumor is constructed into a fusion protein of the invention. In several embodiments, an effector molecule is constructed as a fusion protein to an Omp-like protein, or fragment thereof (e.g., signal sequence, leader sequence, periplasmic region, transmembrane domain, multiple transmembrane domains, or combinations thereof; see infra, Section 3.1 for definition of "Omp-like protein").

In a preferred embodiment, an effector molecule (primary or secondary) of the invention is expressed as a fusion protein with an outer membrane protein (Omp-like protein). Bacterial outer membrane proteins are integral membrane proteins of the bacterial outer membrane, possess multiple membrane-spanning domains and are often attached to one or more lipid moieties. Outer membrane proteins are initially expressed in precursor form (the pro-Omp) with an amino terminal signal peptide that directs the protein to the membrane, upon which the signal peptide is cleaved by a signal peptidase to produce the mature protein. In one embodiment, an effector molecule is constructed as a fusion protein with an Omp-like protein. In this embodiment, the primary effector molecule has enhanced delivery to the outer membrane of the bacteria. Without intending to be limiting as to mechanism, the Omp-like protein is believed by the inventors to act as an anchor or tether for the effector molecule to the outer membrane, or serves to localize the protein to the bacterial outer membrane. In one embodiment, the fusion of an effector molecule to an Omp-like protein is used to enhance localization of an effector molecule to the periplasm. In another embodiment, the fusion of an effector molecule to an Omp-like proteins is used to enhance release of an effector molecule. In specific embodiments, the Omp-like protein is at least a portion of OmpA, OmpB, OmpC, OmpD, OmpE, OmpF, OmpT, a porin-like protein, PhoA, PhoE, lamB, β-lactamase, an enterotoxin, protein A, endoglucanase, peptidoglycan-associated lipoprotein (PAL), FepA, FhuA, NmpA, NmpB, NmpC, or a major outer membrane lipoprotein (such as LPP), etc. In certain embodiments of the invention, the signal sequence is constructed to be more hydrophobic (e.g., by the insertion or replacement of amino acids within the signal sequence to hydrophobic amino acids, e.g., leucine). As illustrative examples, see Sections 7.1–7.4, infra.

In other embodiments of the invention, a fusion protein of the invention comprises a proteolytic cleavage site. The protolytic cleavage site may be endogenous to the effector molecule or endogenous to the Omp-like protein, or the proteolytic cleavage site may be constructed into the fusion protein. In certain specific embodiments, the Omp-like protein of the invention is a hybrid Omp comprising structural elements that originate from separate proteins.

In an exemplary mode of the embodiment, the Omp-like protein is OmpA; the same principles used in the construction of OmpA-like fusion proteins are applied to other Omp fusion proteins, keeping in mind the structural configuration of the specific Omp-like protein.

For example, the native OmpA protein contains eight anti-parallel transmembrane β-strands within the 170 amino acid N-terminal domain of the protein. Between each pair of transmembrane domains is an extracellular or intracellular loop, depending on the direction of insertion of the transmembrane domain. The C-terminal domain consists of 155 amino acids which are located intracellularly and presumably contact the peptidoglycan occupying the periplasmic space. Expression vectors have been generated that facilitate the generation of OmpA fusion proteins. For example, Hobom et al. (1995, Dev. Biol. Strand. 84:255–262) have developed vectors containing the OmpA open reading frame with linkers inserted within the sequences encoding the third or fourth extracellular loops that allow the in-frame insertion of the heterologous protein of choice.

In one embodiment of the invention, the portion of the OmpA fusion protein containing the primary effector molecule has enhanced expression in the periplasm. In one aspect of the embodiment, the fusion protein comprises prior to maturation either the signal sequence or the signal sequence followed by at least one membrane-spanning domain of OmpA, located N-terminal to the primary effector molecule. The signal sequence is cleaved and absent from the mature protein. In another aspect of the embodiment, the primary effector molecule is at the N-terminus of the OmpA fusion, rending inconsequential to the positioning of the primary effector molecule the number of membrane spanning domains of OmpA utilized, as long as the fusion protein is stable. In yet another aspect of the embodiment, the primary effector molecule is situated between the N- and C-terminal domains of OmpA such that a soluble periplasmic protein containing the primary effector molecule upon cleavage by a periplasmic protease within the periplasm. In certain aspects of this embodiment, it is preferred that a bacterial vector which expresses a periplasmic primary effector molecule also coexpresses BRP to enhance release of the effector molecule from the bacterial cell.

In another embodiment of the invention, the portion of the OmpA fusion protein containing the primary effector molecule is at the extracellular bacterial surface. In one aspect of the embodiment, the fusion protein comprises an even number or odd number of membrane-spanning domains of OmpA located N-terminal to the primary effector molecule. In another aspect of the embodiment, the primary effector molecule is situated between two extracellular loops of OmpA for presentation to the tumor cell by the bacterial cell. In specific embodiments, the invention provides expression plasmids of effector molecule fusion proteins at the bacterial extracellular surface. For example, the plasmid denoted Trc(lpp)ompA, comprises a trc promoter-driven lipopolyprotein (lpp) anchor sequence fused to a truncated ompA transmembrane sequence. As another example, the plasmid is denoted TrcompA comprises a trc promoter-driven ompA encoding signal sequence. Such plasmids may be constructed to comprise a nucleic acid encoding one or more effector molecule(s) of the invention.

Optionally, an effector molecule is preceded or flanked by consensus cleavage sites for a metalloprotease or serine protease that is abundant in tumors, for release of the effector molecule into the tumor environment. Whether the primary effector molecule is preceded or flanked by protease cleavage sites depends on whether it is located terminally or internally in the fusion protein, respectively.

Similar fusion proteins may be constructed with any of the Omp-like proteins using the strategies described above in terms of OmpA. In the construction of such fusion proteins, as will be apparent to one of ordinary skill in the art, the selection of the portion of the Omp-like protein to be fused to an effector molecule will depend upon the location that is desired for the expression of the effector molecule (e.g., periplasmic, extracellular, membrane bound, etc.). Such fusion protein constructions as described herein for primary effector molecules are also appropriate for secondary effector molecules.

In a preferred embodiment, an effector molecule is fused to a ferry peptide. Ferry peptides used in fusion proteins have been shown to facilitate the delivery of a polypeptide or peptide of interest to virtually any cell within diffusion limits of its production or introduction (see., e.g., Bayley, 1999, Nature Biotechnology 17:1066–1067; Fernandez et al., 1998, Nature Biotechnology 16:418–420; and Derossi et al., 1998, Trends Cell Biol. 8:84–87). Accordingly, engineering attenuated tumor-targeted bacteria to express fusion proteins comprising a ferry peptide and an effector molecule enhances the ability of an effector molecule to be internalized by tumor cells. In a specific embodiment, attenuated tumor-targeted bacteria are engineered to express a nucleic acid molecule encoding a fusion protein comprising a ferry peptide and an effector molecule. In another embodiment, attenuated tumor-targeted bacteria are engineered to express one or more nucleic acid molecules encoding one or more fusion proteins comprising a ferry peptide and an effector molecule. In accordance with these embodiments, the effector molecule may be a primary or secondary effector molecule. Examples of ferry peptides include, but are not limited to, peptides derived from the HIV TAT protein, the antennapedia homeodomain (penetratin), Kaposi fibroblast growth factor (FGF) membrane-translocating sequence (MTS), herpes simplex virus VP22, polyhistadine (e.g., hexahistadine; 6H), polylysine (e.g., hexalysine; 6K), and polyarginine (e.g., hexaarginine; 6R) (see, e.g., Blanke et al., 1996, Proc. Natl. Acad. Sci. USA 93:8437–8442).

In another preferred embodiment, a fusion protein comprises a signal peptide, ferry peptide and an effector molecule. In a specific mode of this embodiment, attenuated tumor-targeted bacteria are engineered to express one or more nucleic acid molecules encoding one or more fusion proteins comprising a signal sequence, a ferry peptide and an effector molecule. In accordance with this mode, the effector molecule is a primary or secondary effector molecule.

In another preferred embodiment, a fusion protein comprises a signal peptide, a protolytic cleavage site, a ferry peptide and an effector molecule to a solid tumor by attenuated tumor-targeted bacteria. In a specific embodiment, attenuated tumor-targeted bacteria are engineered to express one or more nucleic acid molecules encoding one or more fusion proteins comprising a signal sequence, a protolytic cleavage site, a ferry peptide and an effector molecule. In accordance with this embodiment, the effector molecule may be a primary or secondary effector molecule.

By way of non-limiting example, colicin activity may be enhanced by addition of internalizing peptides derived from HIV TAT, herpes simplex virus VP22, antennapaedia, 6H, 6K, and 6R. The fusion can be either C-terminal, N-terminal, or internal. Internal fusions are especially preferred where the fusion follows the N-terminal signal sequence cleavage peptide. The fusion protein may further comprise an N-terminal signal sequence such OmpA or a C-terminal signal sequence such as hlyA.

In a preferred embodiment, an effector molecule is fused to the delivery portion of a toxin. Various toxins are known to have self-delivery capacity, where one portion of the toxin acts as a delivery agent for the second portion of the toxin. For example, Ballard et al., 1996, Proc. Natl. Acad. Sci. USA 93:12531–12534 demonstrated that the anthrax protective agent (PA) which mediates the entry of lethal factor (LF) and edema factor into the cytosolic compartment of mammalian cells, is also capable of mediating entry of protein fusions to a truncated form of LF (LFn; 255 amino acid residues). Thus, effector molecules of the invention, except those that function outside the cell, can be fused to the LFn, or other toxin systems, including, but not limited to, diptheria toxin A chain residues 1–193 (Blanke et al., 1996, Proc. Natl. Acad. Sci. USA 93:8437–8442), cholera toxin, verotoxin, $E.\ coli$ heat labile toxins (LTs), $E.\ coli$ heat stable toxins (STs), enterohemolysins, enterotoxins, cytotoxins, EAggEC stable toxin 1 (EAST), CNFs, cytolethal distending toxin, α-hemolysins, β-hemolysins, and SheA hemolysins (for review see, e.g., O'Brien and Holmes, 1996. Protein toxins of $Escherichia\ coli$ and $Salmonella$. Cellular and Molecular Biology, Neidhardt et al. (eds), ASM Press, Washington, D.C., pp2788–2802). In a specific embodiment, a primary effector molecule is fused to the delivery portion of a toxin. In another specific embodiment, a secondary effector molecule is fused to the delivery portion of a toxin.

Construction of fusion proteins for expression in bacteria are well known in the art and such methods are within the scope of the invention. (See, e.g., Makrides, S., 1996, Microbiol. Revs 60:512–538 which is incorporated herein by reference in its entirety).

5.6. Expression Vehicles

The present invention provides attenuated tumor-targeted bacteria which have been engineered to encode one or more primary effector molecules and optionally, one or more secondary effector molecules. The invention provides attenuated tumor-targeted bacteria comprising effector molecule(s) which are encoded by a plasmid or transfectable nucleic acid. In a preferred embodiment of the invention, the attenuated tumor-targeted bacteria is $Salmonella$. When more than one effector molecule (e.g., primary or secondary) is expressed in an attenuated tumor-targeted bacteria, such as $Salmonella$, the effector molecules may be encoded by the same plasmid or nucleic acid, or by more than one plasmid or nucleic acid molecule. The invention also provides attenuated tumor-targeted bacteria comprising effector molecule(s) which are encoded by a nucleic acid molecule which is integrated into the bacterial genome. Integrated effector molecule(s) may be endogenous to an attenuated tumor-targeted bacteria, such as *Salmonella*, or may be introduced into the attenuated tumor-targeted bacteria (e.g., by introduction of a nucleic acid which encodes the effector molecule, such as a plasmid, transfectable nucleic acid, transposon, etc.) such that the nucleic acid molecule encoding the effector molecule becomes integrated into the genome of the attenuated tumor-targeted bacteria. In a preferred embodiment of the invention, the attenuated tumor-targeted bacteria is *Salmonella*. The invention provides a nucleic acid molecule encoding an effector molecule which nucleic acid is operably linked to an appropriate promoter. A promoter operably linked to a nucleic acid molecule encoding an effector molecule may be homologous (i.e., native) or heterologous (i.e., not native to the nucleic acid molcule encoding the effector molecule).

The nucleotide sequence coding for an effector molecule of the invention or a functionally active analog or fragment or other derivative thereof, can be inserted into an appropriate expression vehicle, e.g., a plasmid which contains the necessary elements for the transcription and translation of the inserted protein-coding sequence. The necessary transcriptional and translational signals can be supplied by the effector molecule and/or its flanking regions. Alternatively, an expression vehicle is constructed by inserting a structural DNA sequence encoding a desired protein together with suitable translation initiation and termination signals in operable reading phase with a functional promoter using one of a variety of methods known in the art for the manipulation of DNA. See, generally, Sambrook et al., 1989, *Molecular Biology: A Laboratory Manual*, Cold Spring Harbor Press, Cold Spring Harbor, N.Y.; Ausubel et al., 1995, *Current Protocols in Molecular Biology*, Greene Publishing, New York, N.Y. These methods may include in vitro recombinant DNA and synthetic techniques and in vivo recombinants (genetic recombination). The invention provides a nucleic acid molecule encoding an effector molecule which nucleic acid is operably linked to an appropriate promoter.

The present invention also provides attenuated tumor-targeted bacteria which have been modified to encode one or more fusion proteins and optionally, one or more effector molecules. The invention provides attenuated tumor-targeted bacteria comprising fusion proteins which are encoded by a plasmid or transfectable nucleic acid. When more than one fusion protein and/or effector molecule (e.g., primary or secondary) is expressed in an attenuated tumor-targeted bacteria, such as *Salmonella*, the fusion proteins and/or effector molecules may be encoded by the same plasmid or nucleic acid, or by more than one plasmid or nucleic acid. The invention also provides attenuated tumor-targeted bacteria comprising fusion proteins which are encoded by a nucleic acid which is integrated into the bacterial genome. The invention also provides a nucleic acid molecule encoding an fusion protein which nucleic acid molecule is operably linked to an appropriate promoter. The nucleotide sequence coding for a fusion protein of the invention can be inserted into an appropriate expression vehicle, e.g., a plasmid which contains the necessary elements for the transcription and translation of the inserted protein-coding sequence.

In certain specific embodiments of the invention, the expression vehicle of the invention is a plasmid. Large numbers of suitable plasmids are known to those of skill in the art and are commercially available for generating the recombinant constructs of the present invention.

Such commercial plasmids include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed. pBR322 is considered to be a low copy number plasmid. If higher levels of expression are desired, the plasmid can be a high copy number plasmid, for example a plasmid with a pUC backbone. pUC plasmids include but are not limited to pUC19 (see e.g., Yanisch-Perron et al. 1985, Gene 33:103–119) and pBluescript (Stratagene).

The following plasmids are provided by way of example and may be used in conjunction with the methods of the invention. Bacterial: pBs, phagescript, phiX174, pbluescript SK, pBs KS, pNH8a, pNH16a, pNH18a, pNH46a (Stratagene); pTrc99A, pKK223-3, pKK233-3, pDR540, pRIT5 (Pharmacia). A commercial plasmid with a pBR322 "backbone" may also be used, for example, pKK223-3 (Pharmacia Fine Chemicals, Uppsala, Sweden) and GEM 1 (Promega Biotec, Madison, Wis., USA). These are combined with an appropriate promoter and the structural sequence to be expressed. pCET, pTS (as described in Section 6 herein).

In specific embodiments of the invention, a plasmid encoding an effector molecule is the pTS-TNF-$\alpha$ plasmid, the pTS-BRP plasmid, or the pTS-BRPTNF-$\alpha$ plasmid as described in Section 6 herein.

In a specific embodiment of the invention, the fusion protein of the invention for secretion into the periplasmic space comprising the OmpA signal sequence and the primary effector protein are encoded by the plasmid pIN-III-ompA-Hind, which contains the DNA sequence encoding the ompA signal sequence upstream of a linker sequence into which the coding sequence for the primary effector molecule can be cloned. In a preferred specific embodiment, the lac inducible promoter of pIN-III-ompA-Hind vector is replaced by a pepT or tet promoter. (See, Rentier-Delrue et al. (1988), Nuc. Acids Res. 16:8726).

The present invention also provides transposon-mediated chromosomal integration of effector molecules. Any transposon plasmid known in the art may be used in the methods of the invention so long as a nucleic acid encoding an effector molecule can be constructed into the transposon cassette. For example, the invention provides a transposon plasmid, comprising a transposon or minitransposon, and an MCS.

In certain embodiments of the invention, the plasmid of the invention is a transposon plasmid, i.e., comprises a transposon in which the sequence encoding an effector molecule of interest is inserted. Transposon plasmids contain trasposon cassettes which cassette becomes integrated into the bacterial genome. Accordingly, a nucleic acid encoding an effector molecule or fusion protein thereof is inserted into the transposon cassette. Thus, a transposon insertion integrates the cassette into the bacterial genome. The coding sequence of the effector molecule can be operably linked to a promoter, or can be promoterless. In the latter case, expression of the selectable marker is driven by a promoter at the site of transposon insertion into the bacterial genome. Colonies of bacteria having a transposon insertion are screened for expression levels that meet the requirements of the invention, e.g. that express sufficient levels of cytokine to promote tumor cytotoxicity, stasis, or regression.

In certain embodiments, in addition to the transposon, the transposon plasmid comprises, outside the inverted repeats of the transposon, a transposase gene to catalyse the insertion of the transposon into the bacterial genome without being carried along with the transposon, so that bacterial strains with stable transposon insertions are generated.

Transposons to be utilized by the present invention include but are not limited to Tn7, Tn9, Tn10 and Tn5. In a preferred embodiment, the transposon plasmid is pNK2883 (ATCC) having an ampicillin resistance gene located outside the Tn10 insertion elements and the nucleic acids encoding one or more effector molecule(s) is inserted between the two Tn10 insertion elements (e.g., within the transposon cassette). Preferably, the construct is made such that additional sequences encoding other elements is inserted between the two Tn10 insertion elements. In specific embodiments, such elements may optionally include (1) a promoterless copy a selectable marker (e.g., SerC, AroA, etc) for positive selection of the bacteria containing the plasmid; (2) a BRP gene, (3) a promoter for the effector molecule (such as trc) operably linked to the nucleic acid encoding the one or more primary effector molecule(s) (such as TNF-α, or a fusion protein thereof, e.g., an OmpA-TNF-α fusion), (4) a terminator for the nucleic acid encoding the one or more effector molecule(s).

In one embodiment, after the manipulation of the plasmid as appropriate and selection of those clones having the desired construct using the ampicillin resistance properties encoded by the plasmid, the antibiotic selection is removed through plasmid loss and strains having a chromosomal transposon insert are chosen for administering to human subjects (e.g., by plating on selective media).

In another specific embodiment, the plasmid pTS is used which comprises an altered target specificity transposase gene and a minitransposon, containing the coding sequences for a promoterless serC gene and an MCS. In another specific embodiment, the plasmid pTS-BRP is used which comprises an altered target specificity transposase gene and a minitransposon, containing the coding sequences for a promoterless serC gene, and alkylating agent-inducible bacteriocin release factor, and an MCS.

In a preferred embodiment, a transposon plasmid for selection of transposon-mediated chromosomal integrants, comprises:
  a) a transposase gene, for transposon excision and integration, located outside of the transposon insertion sequence (e.g., outside of the transposon cassette);
  b) a wild-type coding sequence corresponding to the selection gene deleted in the bacterial strain (e.g., serC) as well as a ribosomal binding site and terminator for the wild-type gene, but lacking a promoter. This sequence is preferably located immediately following the left TN10 transposon insertion sequence;
  optionally, between the right-and-left insertion sequences is a nucleic acid sequence encoding a release enhancing nucleic acid (e.g., BRP); and
  d) a multiple cloning site (MCS) located between the right and left insertion sequences, containing unique restriction sites within the plasmid, for the incorporation of effector molecule. The MCS is preferably located immediately following the release enhancing nucleic acid (if used) and just prior to the right TN10 insertion sequence.

In another embodiment, the gene disruption resulting from random integration of effector molecules onto the host chromosome, identifies the suitability of the gene location for effector insertion.

In yet another embodiment, the expression vehicle is an extrachromosomal plasmid that is stable without requiring antibiotic selection, i.e. is self-maintained. In one non-limiting example, the self-maintained expression vehicle is a *Salmonella* virulence plasmid.

For example, in one embodiment of the invention, the plasmid selection system is maintained by providing a function which the bacteria, such as *Salmonella*, lacks and on the basis of which those *Salmonella* having the function can be selected for at the expense of those that do not. In one embodiment, the *Salmonella* of the invention is an auxotrophic mutant strain and the expression plasmid provides the mutant or absent biosynthetic enzyme function. The *Salmonella* which contain the expression plasmid can be selected for by growing the cells on growth medium which lacks the nutrient that only the desired cells, i.e. those with the expression plasmid, can metabolize. In a highly preferred aspect of this embodiment, the *Salmonella* of the invention has an obligatory requirement for DAP (meso-diaminopimelic acid), most preferably by deletion of the asd gene. DAP is a component of the peptidoglycan present in the periplasm of Gram-negative bacteria, which is required for the integrity of the bacterial outer membrane. Absence of DAP results in bacterial cell lysis resulting from the loss of outer membrane integrity. The asd (βaspartate semialdehyde dehydrogenase) gene encodes an enzyme in the DAP biosynthetic pathway. Gram-negative bacteria which lack asd function can be grown by supplying DAP to the culture media. Plasmids, e.g. the expression plasmids of the invention, that carry the asd gene sequence operably linked to a homologous or heterologous promoter can be selected for by growing Gram-negative bacteria that lack asd activity in the absence of DAP (see, e.g., U.S. Pat. No. 5,840,483 to Curtiss, III).

Other non-antibiotic selection systems are known in the art and are within the scope of the invention. For example, a selection system utilizing a plasmid comprising a stable toxin and less stable anti-toxin may be used to select for bacteria which maintain such a plasmid.

In another embodiment, the expression vehicle is an extrachromosomal plasmid that is selectable by non-antibiotic means, for example a colicin plasmid. As used herein, a colicin plasmid minimally encodes a colicin toxin and an anti-colicin, the colicin toxin being more stable than the anti-colicin, such that any bacteria which loses the colicin plasmid is killed as a result of the perdurance of the colicin toxin. In a preferred embodiment, the colicin toxin is the large subunit of ColE3 and the anti-colicin is the small subunit of ColE3.

In other embodiments of the invention, the expression vehicle is a λ vector, more specifically a lysogenic λ vector. In a preferred embodiment, the bacterial host comprising the λ vector further comprises a temperature-sensitive λ repressor which is functional at 30° C. but not 37° C. Consequently, the bacterial host can be grown and manipulated in vivo at 30° C. without expression of the primary and/or secondary effector molecule which may be toxic to the bacterial cell. Upon introduction of the bacterial strain into the subject, the λ repressor is inactivated by normal body temperature and expression of the primary effector molecule, and optionally a secondary effector molecule, is activated.

Expression of a nucleic acid sequence encoding an effector molecule or fusion protein may be regulated by a second nucleic acid sequence so that the effector molecule is expressed in a bacteria transformed with the recombinant DNA molecule. For example, expression of an effector molecule may be controlled by any promoter/enhancer element known in the art. A promoter/enhancer may be homologous (i.e., native) or heterologous (i.e., not native). Promoters which may be used to control the expression of an effector molecule, e.g. a cytokine, or fusion protein in bacteria include, but are not limited to prokaryotic promoters such as the β-lactamase promoter (Villa-Kamaroff et al., 1978, Proc. Natl. Acad. Sci. U.S.A. 75:3727–3731), or the lac promoter (DeBoer et al., 1983, Proc. Natl. Acad. Sci. U.S.A. 80:21–25; Scientific American, 1980, 242:74–94). Other promoters emcompassed by the present invention include, but are not limited to, lacI, lacZ, T3, T7, gpt, lambda $P_R$, lambda $P_L$, trc, pagC, sulA, pol II (dinA), ruv, recA, uvrA, uvrB, uvrD, umuDC, lexA, cea, caa, and recN (see, e.g., Schnarr et al., 1991. Biochimie 73:423–431). In a preferred embodiment, the promoter is trc, (see, e.g., Amann et al., 1988, Gene 69:301–15).

In a particular embodiment, in which the primary effector molecule is a colicin expressed under the control of a SOS-responsive promoter, the attenuated bacterial strain may be treated with x-rays, ultraviolet radiation, an alkylating agent or another DNA damaging agent such that expression of the colicin is increased. Exemplary SOS-responsive promoters include, but are not limited to, recA, sulA, umuC, dinA, ruv, uvrA, uvrB, uvrD, lexA, cea, caa, recN, etc.

In another preferred embodiment, the promoter has enhanced activity in the tumor environment; for example, a promoter that is activated by the anaerobic environment of the tumor such as the P1 promoter of the pepT gene. Activation of the P1 promoter is dependent on the FNR transcriptional activator (Strauch et al., 1985, J. Bacteriol. 156:743–751). In a specific embodiment, the P1 promoter is a mutant promoter that is induced at higher levels under anaerobic conditions than the native P1 promoter, such as the pepT200 promoter whose activity in response to anaerobic conditions is induced by CRP-cAMP instead of FNR (Lombardo et al., 1997, J. Bacteriol. 179:1909–1917). In another embodiment, the anaerobically-induced promoter is used, e.g., the potABCD promoter. potABCD is an operon that is divergently expressed from pepT under anaerobic conditions. The promoter in the pepT gene responsible for this expression has been isolated (Lombardo et al., 1997, J. Bacteriol. 179:1909–1917) and can be used according to the methods of the present invention.

Alternatively, the promoter can be an antibiotic-induced promoter, such as the tet promoter of the Tn10 transposon. In a preferred embodiment, the tet promoter is multimerized, for example three-fold. Promoter activity would then be induced by administering to a subject who has been treated with the attenuated tumor-targeted bacteria of the invention an appropriate dose of tetracycline. Although the let inducible expression system was initially described for eukaryotic systems such as *Schizosaccharomyces pombe* (Faryar and Gatz, 1992, Current Genetics 21:345–349) and mammalian cells (Lang and Feingold, 1996, Gene 168:169–171), recent studies extend its applicability to bacterial cells. For example, Stieger et al. (1999, Gene 226:243–252) have shown 80-fold induction of the firefly luciferase gene upon tet induction when operably linked to the tet promoter. An advantage of this promoter is that it is induced at very low levels of tetracycline, approximately ⅒th of the dosage required for antibiotic activity.

Once a plasmid is constructed comprising an effector molecule or fusion protein is introduced into the attenuated tumor-targeted bacteria, effector molecule expression or fusion protein expression can be assayed by any method known in the art including but not limited to biological activity, enzyme activity, Northern blot analysis, and Western blot analysis. (See Sambrook et al., 1989, *MolecularBiology: A Laboratory Manual*, Cold Spring Harbor Press, Cold Spring Harbor, N.Y.; Ausubel et al., 1995, *Current Protocols in Molecular Biology*, Greene Publishing, New York, N.Y.).

5.7. Combination Therapy

In certain embodiments, attenuated tumor-targeted bacteria are used in conjunction with other known cancer therapies to treat a solid cancer tumor. In certain other embodiments, attenuated tumor-targeted bacteria engineered to express one or more nucleic acid molecules encoding one or more effector molecules and/or fusion proteins are used in conjunction with other known cancer therapies to treat a solid cancer tumor. For example, attenuated tumor-targeted bacteria engineered to express one or more nucleic acid molecules encoding one or more effector molecules and/or fusion proteins can be used in conjunction with a chemotherapeutic agent. Examples of chemotherapeutic agents include, but are not limited to, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan. Alternatively, attenuated tumor-targeted bacteria engineered to express one or more nucleic acid molecules encoding one or more effector molecules and/or fusion proteins can be used in conjunction with radiation therapy (e.g., gamma radiation or x-ray radiation). Any radiation therapy protocol can be used depending upon the type of cancer to be treated. For example, but not by way of limitation, x-ray radiation can be administered, in particular, high-energy megavoltage (radiation of greater that 1 MeV energy) can be used for deep tumors, and electron beam and orthovoltage x-ray radiation can be used for skin cancers. Gamma ray emitting radioisotopes, such as radioactive isotopes of radium, cobalt and other elements may also be administered to expose tissues to radiation.

The present invention includes the sequential or concomitant administration of an anti-cancer agent and attenuated tumor-targeted bacteria. The invention encompasses combinations of anti-cancer agents and attenuated tumor-targeted bacteria that are additive or synergistic.

The invention also encompasses combinations of one or more anti-cancer agents and attenuated tumor-targeted bacteria that have different sites of action. Such a combination provides an improved therapy based on the dual action of these therapeutics whether the combination is synergistic or additive. Thus, the novel combinational therapy of the present invention yields improved efficacy over either agent used as a single-agent therapy.

The present invention also includes the sequential or concomitant administration of an anti-cancer agent and attenuated tumor-targeted bacteria engineered to express one or more nucleic acid molecules encoding one or more effector molecules and/or fusion proteins. The invention encompasses combinations of anti-cancer agents and attenuated tumor-targeted bacteria engineered to express one or more nucleic acid molecules encoding one or more effector molecules and/or fusion proteins that are additive or synergistic.

The invention also encompasses combinations of one or more anti-cancer agents and attenuated tumor-targeted bacteria engineered to express one or more nucleic acid molecules encoding one or more effector molecules and/or fusion proteins that have different sites of action. Such a combination provides an improved therapy based on the dual action of these therapeutics whether the combination is synergistic or additive. Thus, the novel combinational therapy of the present invention yields improved efficacy over either agent used as a single-agent therapy.

5.8. Methods and Compositions for Delivery

The invention provides methods by which one or more primary effector molecules which may be toxic when delivered systemically to a host, can be delivered locally to tumors by an attenuated tumor-targeted bacteria with reduced toxicity to the host. In one embodiment, the primary effector molecule is useful to treat sarcomas, lymphomas, carcinomas, or other solid tumor cancers. In certain non-limiting embodiments, the effector molecule is useful for inducing local immune response at the site of the tumor.

According to the present invention, the attenuated tumor-targeted bacterial vectors containing a nucleic acid molecules encoding one or more primary effector molecules and optionally one or more primary effector molecules are advantageously used in methods to inhibit the growth of a tumor, reduce the volume of a tumor, or prevent the spread of tumor cells in an animal, including a human patient, having a solid tumor cancer.

The present invention provides methods for delivering one or more primary effector molecules for the treatment of a solid tumor cancer comprising administering, to an animal in need of such treatment, a pharmaceutical composition comprising an attenuated tumor-targeted bacteria comprising one or more nucleic acid molecules encoding one or more primary effector molecules operably linked to one or more appropriate promoters. The present invention also provides methods for delivering one or more primary effector molecules for the treatment of a solid tumor cancer comprising administering, to an animal in need of such treatment, a pharmaceutical composition comprising an attenuated tumor-targeted bacteria comprising one or more nucleic acid molecules encoding one or more primary effector molecules and one or more secondary effector molecules operably linked to one or more appropriate promoters. In one embodiment, the primary effector molecule is a TNF family member, a cytotoxic peptide or polypeptide, an anti-angiogenic factor, a tumor inhibitory enzyme, or a functional fragment thereof.

The present invention provides methods for delivering one or more fusion proteins of the invention for the treatment of a solid tumor cancer comprising administering, to an animal in need of such treatment, a pharmaceutical composition comprising an attenuated tumor-targeted bacteria comprising one or more nucleic acid molecules encoding one or more fusion proteins of the invention operably linked to one or more appropriate promoters. The present invention also provides methods for delivering one or more fusion proteins of the invention and one or more effector molecules for the treatment of a solid tumor cancer comprising administering, to an animal in need of such treatment, a pharmaceutical composition comprising an attenuated tumor-targeted bacteria comprising one or more nucleic acid molecules encoding one or more fusion proteins of the invention and one or more effector molecules operably linked to one or more appropriate promoters.

In a preferred embodiment, the attenuated tumor-targeted bacteria is *Salmonella*. In another embodiment, the attenuated tumor-targeted bacteria comprises an enhanced release system. In a preferred embodiment, the animal is a mammal. In a highly preferred embodiment, the animal is a human.

The invention also provides combinatorial delivery of one or more primary effector molecules and optionally, one or more secondary effector molecules which are delivered by an attenuated tumor-targeted bacteria such as *Salmonella*. The invention also provides combinatorial delivery of different attenuated tumor-targeted bacteria carrying one or more different primary effector molecules and/or optionally, one or more different secondary effector molecules.

The invention also provides delivery of one or more fusion proteins of the invention which are delivered by an attenuated tumor-targeted bacteria such as *Salmonella*. The invention also provides combinatorial delivery of one or more fusion proteins of the invention and optionally, one or more effector molecules of the invention, which are delivered by an attenuated tumor-targeted bacteria such as *Salmonella*. The invention also provides combinatorial delivery of different attenuated tumor-targeted bacteria carrying one or more different fusion proteins and/or optionally, one or more different effector molecules.

Solid tumors include, but are not limited to, sarcomas, carcinomas and other solid tumor cancers, including, but not limited to germ line tumors, tumors of the central nervous system, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, melanoma, renal cancer, bladder cancer, and mesothelioma. The subject is preferably an animal, including but not limited to animals such as cows, pigs, chickens, dogs, cats, horses, etc., and is preferably a mammal, and most preferably human. As used herein, treatment of a solid tumor, includes but is not limited to, inhibiting tumor growth, inhibiting tumor cell proliferation, reducing tumor volume, or inhibiting the spread of tumor cells to other parts of the body (metastasis).

The present invention provides a pharmaceutical composition comprising a pharmaceutically acceptable carrier and an attenuated tumor-targeted bacteria comprising one or more nucleic acid molecules encoding one or more primary effector molecules operably linked to one or more appropriate promoters. The present invention provides a pharmaceutical composition comprising a pharmaceutically acceptable carrier and an attenuated tumor-targeted bacteria comprising one or more nucleic acid molecules encoding one or more primary effector molecules and one or more secondary effector molecules operably linked to one or more appropriate promoters.

The present invention provides a pharmaceutical composition comprising a pharmaceutically acceptable carrier and an attenuated tumor targeted bacteria comprising one or more nucleic acid molecules encoding one or more fusion proteins of the invention operably linked to one or more appropriate promoters. The present invention provides a pharmaceutical composition comprising a pharmaceutically acceptable carrier and an attenuated tumor-targeted bacteria comprising one or more nucleic acid molecules encoding one or more fusion proteins of the invention and one or more effector molecules operably linked to one or more appropriate promoters.

The present invention also provides a pharmaceutical composition comprising a pharmaceutically acceptable carrier and an attenuated tumor-targeted bacteria. The present invention also provides a pharmaceutical composition comprising a pharmaceutically acceptable carrier and an attenuated tumor-targeted bacteria comprising one or more primary effector molecules and optionally, one or more secondary effector molecules. Such compositions comprise a therapeutically effective amount of an attenuated tumor-targeted *Salmonella* vector comprising one or more primary effector molecules and optionally one or more secondary effector molecules, and a pharmaceutically acceptable carrier. The present invention also provides a pharmaceutical composition comprising a pharmaceutically acceptable carrier and an attenuated tumor-targeted *Salmonella* comprising one or more fusion proteins of the invention and optionally, one or more effector molecules. Such compositions comprise a therapeutically effective amount of an attenuated tumor-targeted *Salmonella* vector comprising one or more fusion proteins of the invention and optionally one or more effector molecules, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, and the like. Saline is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic attenuated tumor-targeted bacteria, in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a suspending agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the pharmaceutical composition of the invention which will be effective in the treatment or prevention of a solid tumor cancer will depend on the nature of the cancer, and can be determined by standard clinical techniques. In addition, in vitro assays may optionally be employed to help identify optimal dosage ranges. The precise dose to be employed in the formulation will also depend on the route of administration, and the seriousness of the cancer, and should be decided according to the judgment of the practitioner and each patient's circumstances. However, suitable dosage ranges are generally from about 1.0 c.f.u./kg to about $1\times10^{10}$ c.f.u./kg; optionally from about 1.0 c.f.u./kg to about $1\times10^{8}$ c.f.u./kg; optionally from about $1\times10^{2}$ c.f.u./kg to about $1\times10^{8}$ c.f.u./kg; optionally from about $1\times10^{4}$ c.f.u./kg to about $1\times10^{8}$ c.f.u./kg; and optionally from about $1\times10^{4}$ c.f.u./kg to about $1\times10^{10}$ c.f.u./kg. Effective doses may be extrapolated from dose-response curves derived from in vitro or animal model test systems.

Various delivery systems are known and can be used to administer a pharmaceutical composition of the present invention. Methods of introduction include but are not limited to intradermal, intramuscular, intraperitoneal, intravenous, subcutaneous, intrathecal, intranasal, epidural, and oral routes. Methods of introduction may also be intratumoral (e.g., by direct administration into the area of the tumor).

The compositions may be administered by any convenient route, for example by infusion or bolus injection, by absorption through epithelial or mucocutaneous linings (e.g., oral mucosa, rectal and intestinal-mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or preneoplastic tissue.

The attenuated tumor-targeted bacteria comprising one or more primary effector molecules and optionally, one or more secondary effector molecules may be delivered in a controlled release system. The attenuated tumor-targeted bacteria comprising one or more fusion proteins of the invention and optionally, one or more effector molecules may also be delivered in a controlled release system. In one embodiment, a pump may be used (see Langer, supra; Sefton, CRC Crit. Ref. Biomed. Eng. 14:201 (1987); Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem: 23:61 (1983); see also Levy et al., 1985, Science 228:190; During et al., 1989, Ann. Neurol. 25:351; and Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (1990, Science 249:1527–1533) and may be used in connection with the administration of the attenuated tumor-targeted bacteria comprising one or more primary effector molecule(s) and optionally, one or more secondary effector molecule(s).

The invention also provides a pharmaceutical pack or kit comprising one or more containers filled with one or more of the ingredients of the pharmaceutical compositions of the invention. Optionally associated with such container(s) can be a notice in the form prescribed by governmental agency regulating the manufacture, use or sale of pharmaceuticals or biological products, which notice reflects approval by the agency of manufacture, use or sale for human administration.

The present invention also provides methods for treating a solid tumor comprising administering to an animal in need thereof, a pharmaceutical composition of the invention and at least one other known cancer therapy. In a specific embodiment, an animal with a solid tumor cancer is administered a pharmaceutical composition of the invention and at least one chemotherapeutic agent. Examples of chemotherapeutic agents include, but are not limited to, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan.

The present invention includes the sequential or concomitant administration of pharmaceutical composition of the invention and an anti-cancer agent such as a chemotherapeutic agent. In a specific embodiment, the pharmaceutical composition of the invention is administered prior to (e.g., 2 hours, 6 hours, 12 hours, 1 day, 4 days, 6 days, 12 days, 14 days, 1 month or several months before) the administration of the anti-cancer agent. In another specific embodiment, the pharmaceutical composition of the invention is administered subsequent to (e.g., 2 hours, 6 hours, 12 hours, 1 day, 4 days, 6 days, 12 days, 14 days, 1 month or several months after) the administration of an anti-cancer agent. In a specific embodiment, the pharmaceutical composition of the invention is administered concomitantly with an anti-cancer agent. The invention encompasses combinations of anti-cancer agents and attenuated tumor-targeted bacteria engineered to express one or more nucleic acid molecules encoding one or more effector molecules and/or fusion proteins that are additive or synergistic.

The invention also encompasses combinations of anti-cancer agents and attenuated tumor-targeted bacteria engineered to express one or more nucleic acid molecules encoding one or more effector molecules and/or fusion proteins that have different sites of action. Such a combination provides an improved therapy based on the dual action of these therapeutics whether the combination is synergistic or additive. Thus, the novel combinational therapy of the present invention yields improved efficacy over either agent used as a single-agent therapy.

In one embodiment, an animal with a solid tumor cancer is administered a pharmaceutical composition of the invention and treated with radiation therapy (e.g., gamma radiation or x-ray radiation). In a specific embodiment, the invention provides a method to treat or prevent cancer that has shown to be refractory to radiation therapy. The pharmaceutical composition may be administered concurrently with radiation therapy. Alternatively, radiation therapy may be administered subsequent to administration of a pharmaceutical composition of the invention, preferably at least an hour, five hours, 12 hours, a day, a week, a month, more preferably several months (e.g., up to three months), subsequent to administration of a pharmaceutical composition.

The radiation therapy administered prior to, concurrently with, or subsequent to the administration of the pharmaceutical composition of the invention can be administered by any method known in the art. Any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma ray emitting radioisotopes, such as radioactive isotopes of radium, cobalt and other elements may also be administered to expose tissues to radiation.

Additionally, the invention also provides methods of treatment of cancer with a Pharmaceutical composition as an alternative to radiation therapy where the radiation therapy has proven or may prove too toxic, i.e., results in unacceptable or unbearable side effects, for the subject being treated.

5.9. Demonstration of Therapeutic or Prophylactic Utility of Pharmaceutical Compositions of the Invention The pharmaceutical compositions of the invention are preferably tested in vitro, and then in vivo for the desired therapeutic or prophylactic activity, prior to use in humans. For example, in vitro assays which can be used to determine whether administration of a specific pharmaceutical composition is indicated, include in vitro cell culture assays in which a patient tissue sample is grown in culture, and exposed to or otherwise administered a pharmaceutical composition, and the effect of such composition upon the tissue sample is observed.

Pharmaceutical compositions of the invention can be tested for their ability to augment activated immune cells by contacting immune cells with a test pharmaceutical composition or a control and determining the ability of the test pharmaceutical composition to modulate (e.g., increase) the biological activity of the immune cells. The ability of a test composition to modulate the biological activity of immune cells can be assessed by detecting the expression of cytokines or antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Cytokine and antigen expression can be assayed, for example, by immunoassays including, but are not limited to, competitive and non-competitive assay systems using techniques such as western blots, immunohisto-chemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A, immunoassays and FACS analysis. The activation of signaling molecules can be assayed, for example, by kinase assays and electromobility shift assays (EMSAs). The effector function of T-cells can be measured, for example, by a 51Cr-release assay (see, e.g., Palladino et al., 1987, Cancer Res. 47:5074–5079 and Blachere et al., 1993, J. Immunotherapy 14:352–356).

Pharmaceutical compositions of the invention can be tested for their ability to reduce tumor formation in animals suffering from cancer. Pharmaceutical compositions of the invention can also be tested for their ability to alleviate of one or more symptoms associated with a solid tumor cancer. Further, pharmaceutical compositions of the invention can be tested for their ability to increase the survival period of patients suffering from a solid tumor cancer. Techniques known to those of skill in the art can be used to analyze the function of the pharmaceutical compostions of the invention in animals.

In various specific embodiments, in vitro assays can be carried out with representative cells of cell types involved in a solid tumor cancer, to determine if a pharmaceutical composition of the invention has a desired effect upon such cell types.

Pharmaceutical compositions of the invention for use in therapy can be tested in suitable animal model systems prior to testing in humans, including but not limited to rats, mice, chicken, cows, monkeys, pigs, dogs, rabbits, etc. For in vivo testing, prior to administration to humans, any animal model system known in the art may be used.

The following series of examples are presented by way of illustration and not by way of limitation on the scope of the invention.

6. EXAMPLE

Expression of TNF-α by Attenuated Tumor-Targeted *Salmonella*

The following example demonstrates that attenuated tumor-targeted bacteria, such as *Salmonella*, containing a nucleic acid molecule encoding a TNF family member are capable of expressing the TNF family member.

6.1. Construction of TNF-α Plasmids

The plasmids described herein serve to illustrate examples of specific embodiments of the invention. As will be apparent to one of ordinary skill in the art, promoter and/or effector molecule-encoding nucleic acids such as the trc promoter and/or TNF-α encoding nucleic acids may be replaced with other appropriate promoter or effector molecules by methods known in the art.

For plasmid-based bacterial expression of effector molecule-encoding nucleic acids using the trc promoter, the plasmid Trc99A (commercially available from Pharmacia) or TrcHisB (commercially available from InVitrogen) were used. Both plasmids employ an Nco I site, as the start codon, followed by a multiple cloning site.

6.1.1. The pCET Plasmid

For plasmid-based bacterial expression of effector molecule encoding nucleic acids using a dual $\lambda P_L$, or $\lambda P_R$ promoter, the pCET plasmid was constructed as follows. Plasmid pCE33 (Elvin et al., 1990, Gene 87:123–126) was sequentially cleaved with the restriction enzyme Cla I and blunt-ended with mung bean nuclease, followed by cleavage with the restriction enzyme BamHI. Next, the resulting 1.4 kb fragment was ligated into a 2.1 kb Ssp I/Bam HI fragment of pUC19 (commercially available from GIBCO) to create plasmid pCI. Plasmid pCI was cleaved with restriction enzyme BamHI and blunt-ended with mung bean nuclease, followed by cleavage with restriction enzyme Afl III. The resultant 3.1 kb band was isolated. Plasmid TrcHisB was partially digested with the restriction enzyme ClaI, blunt-ended with T4 DNA polymerase, followed by cleavage with Afl III. The resultant 0.6 kb band, containing the minicistron and terminator, was then ligated into the 3.1 kb pCI fragment to give plasmid pCET. As with Trc99A or TrcHisB, pCET employs an NcoI site as the start codon, followed by the TrcHisB multiple cloning site. Growth of bacteria harboring any plasmid containing the $\lambda P_L$, or $\lambda P_R$ promoter, was performed at 30° C.

6.1.2. The pTS Plasmid

A plasmid, denoted pTS, employing transposon-mediated chromosomal integration and serine prototrophic selection of effector molecule-encoding nucleic acids, was constructed as follows. The plasmid pNK2883 (commercially available from the American Type Culture Collection (ATCC)) was cleaved with restriction enzyme Bam HI and the 4.8 kb band isolated. The *Salmonella typhimurium* serC encoding nucleic acid was isolated from *S. typhimurium* strain 14028 (commercially available from the ATCC) by PCR using a forward primer of sequence GAAGATCTTC-CGGAGGAGGGGAAATG (SEQ ID NO:1), and a reverse primer, of sequence CGGGATCCGAGCTCGAGGGC-CCGGGAAAGGATCTAAGAAGATCC (SEQ ID NO:2). The PCR reaction mixture was cleaved with restriction enyzymes Bgl II and Bam HI, and the 1.1 kb PCR product isolated and ligated into the 4.8 pNK2883 fragment to give a plasmid, denoted pTS. A cloning sited immediately 3' to the serC encoding nucleic acid was present for the insertion of effector molecule-encoding nucleic acids.

6.13. The pTS-TNF-α Plasmid

A plasmid (pTS-TNF-α), for the pTS-mediated chromosomal integration of a trc promoter-driven human TNF-α encoding nucleic acid, was constructed as follows. Plasmid PYA3332 is the ASD plasmid PYA272 (see, e.g., U.S. Pat. No. 5,840,483 to Curtiss, III) with the origin of replication replaced by that of the colE1 plasmid (see, e.g., Bazaral and Helsinki, 1970, Biochem 9:399–406). Plasmid PYA3332 was cleaved with restriction enzyme Nco I and blunt-ended with mung bean nuclease. The blunt-ended fragment was then cleaved with restriction enzyme Hind III and the 3.3 kb DNA fragment was isolated. An *E. coli*-optimized human TNF-α encoding nucleic acid (see, Pennica et al., 1984 Nature 312:724–729; and Salztman, et al., 1996, Cancer Biotherapy 11:145–153) as depicted in FIG. 1, was then cleaved with restriction enzyme Nde I, blunt-ended with T4 DNA polymerase, and then cleaved with restriction enzyme with Hind III. The resulting 0.5 kb fragment was ligated into the 3.3 kb PYA3332 fragment to give plasmid Asd34TNF-α. Asd34TNF-α was then cleaved with restriction enzyme Bgl II, and the 1.1 kb fragment, encoding the trc promoter-driven TNF-α encoding nucleic acid, and ligated into the Bam HI site of pTS to give plasmid pTS-TNF-α.

6.1.4. The pTS-BRP Plasmid

A plasmid, denoted pTS-BRP, employing transposon-mediated chromosomal integration of the BRP encoding nucleic acid and serine prototrophic selection of effector molecule-encoding nucleic acids, was constructed as follows. A BRP encoding nucleic acid was isolated from plasmid pSWI (commercially available from Bio101, Vista, Calif.) by PCR using a forward primer, of sequence CCGACGCGTTGACACCTGAAAACTGGAG (SEQ ID NO:5), and a reverse primer, of sequence CCGACGCGT-GAAAGGATCTCAAGAAGATC (SEQ ID NO:6), and cloned into a TOPO-TA cloning plasmid (commercially available from InVitrogen, Carlsbad, Calif.) to give a plasmid, denoted pBRP#5. Plasmid pBRP#5 was cleaved with restriction enzymes Apa I and Bam HI, and the resultant 0.6 kb band, containing the BRP encoding nucleic acid, was ligated into the 5.9 kb Apa I/Bam HI proto-pTS fragment to give the plasmid pTS-BRP. Cloning sites both 5' and 3' to the BRP encoding nucleic acids were present for the insertion of effector molecule-encoding nucleic acids.

6.1.5. The pTS-BRPTNF-α Plasmid

A plasmid-(pTS-BRPTNF-α), for the pTS-mediated chromosomal integration of the BRP and trc promoter-driven TNF-α encoding nucleic acids, was constructed as follows. Plasmid Asd34TNF-α, described above for the construction of pTS-TNF-α, was cleaved with restriction enzyme Bgl II, and the 1.1 kb fragment, encoding the trc promoter-driven TNF-α encoding nucleic acid, was ligated into the Bam HI site of pTS-BRP to give plasmid pTS-BRPTNF-α.

6.2. Integration of Effector Molecule-Encoding Nucleic Acid into the *Salmonella* Host Chromosome The system described here employs ΔserC-*Salmonella* strains auxotrophic for serine or glycine, and plasmids which restore serine/glycine prototrophy upon chromosomal integration into an actively transcribed region. However, it is well known in the art that other selection markers can be used to select for chromosomal integrants, and such markers are within the scope of the invention. See, e.g., Kleckner et al., 1991, Meth.

Enzymol. 204:139–180.

pTS or pTS-BRP plasmids containing effector molecule-encoding nucleic acids may be introduced into serC-*Salmonella* strains by a number of means well-known in the art, including chemical transformation and electroporation. Following the introduction of effector molecule-encoding nucleic acids, *Salmonella* are grown in ampicillin-containing growth medium for a minimum of 2 hours, and more preferably 6 hours or longer. Bacteria are then placed in medium capable of selecting bacteria prototrophic for serine, e.g., M56 medium. Atlas, R. M. "Handbook of Microbiological Media." L. C. Parks, ed. CRC Press, Boca Raton, Fla., 1993. Bacteria harboring chromosomal integrations of effector molecule-encoding nucleic acids are capable of growth in the selective media. Effector molecule-encoding nucleic acid expression is then measured, as illustrated below. Effector molecule-encoding nucleic acid expression may be measured by any of several methods known to those skilled in the art, such as by enzymatic activity, biological activity, Northern blot analysis, or Western blot analysis.

6.2.1. Delivery and Expression of *Salmonella*-Expressed TNF-α

A trc promoter-driven TNF-α encoding nucleic acid was inserted into the Bam HI site of pTS-BRP to give a plasmid, denoted pTS-BRPTNF-α, as described above. Plasmid pTS-BRPTNF-α was electroporated into an attenuated strain of *S. typhimurium*, strain VNP20009, (see International Publication WO 99/13053) constructed to be serC- such that the genotype was ΔmsbB, ΔpurI, ΔserC (FIG. 2), by standard methods known in the art. Without limitation as to mechanism, integration of the plasmid into the bacterial genome allows for activation of the serC encoding nucleic acid and leads to a serC$^+$ phenotype. Accordingly, bacteria harboring a chromosomal integration of the TNF-α encoding nucleic acid were selected by plating the electroporated bacteria on M56 agar plates supplemented with adenine. Bacteria were further characterized for loss of ampicillin resistance, indicative of plasmid loss, and concomitant loss of plasmid-based TNF-α expression.

In order to examine and quantify TNF-α expression by the tumor-targeted bacteria of the invention, *Salmonella* harboring a chromosomal integration of the TNF-α encoding nucleic acids were grown overnight, and a measured sample of the culture was used in Western blot analysis. Specifically, TNF-α expression from a representative serC$^+$, ampicillin-sensitive clone, denoted pTS-BRPTNF-α Clone 2, is shown in FIG. 3. Western blot analysis revealed that bacterial protein, corresponding to $3.9 \times 10^7$ cfu of pTS-BRPTNF-α Clone 2 bacteria (Lane 1), expressed more than 50 ng TNF-α (Lane 5), indicating expression of TNF-α at levels greater than 10 ng/$10^7$ bacteria. Therefore, the human TNF-α was successfully expressed from a chromosomally-integrated, trc promoter-driven, TNF-α encoding nucleic acid in *Salmonella*.

7. EXAMPLE

Attenuated Tumor-Targeted Bacteria Expressing OMPA Fusion Proteins

Periplasmic localization of proteins by fusion to various signal peptides is dependent on both the signal peptide and the protein. For example, proteins can be localized to the periplasmic compartment of bacteria by fusion of a signal peptide to the amino terminus of the protein. Without limitation, periplasmic localization is believed to facilitate release of bacterial components (such as proteins) by requiring the component to traverse only a single membrane in order to be released into the surrounding environment. In contrast, cytoplasmic localization requires that the component traverse both the inner and outer membranes of bacteria in order to be released into the surrounding environment. Further, periplasmic localization of certain protiens may aid in biological activity.

A variety of methods known in the art may be used to target an effector molecule of the invention to the periplasm. This example demonstrates that the fusion of the ompA signal peptide to the amino terminus of an effector molecule such as a TNF-α, TRAIL (TNF-α-related apoptosis-inducing ligand), and interleukin-2 (IL-2) results in the periplasmic localization and subsequent processing of proteins.

7.1. Processing of an OMPA-TNF-α Fusion Protein

TNF-α expression in four different clones, expressing a plasmid-based trc promoter-driven ompA-TNF-α fusion protein in JM 109 bacteria, was examined by Western blot analysis of whole cell lysate. Periplasmic localization was demonstrated by cleavage of the precursor fusion proteins to mature TNF-α by signal peptidase, an enzyme located in the periplasm. In all four clones, following induction with IPTG, overexpression of TNF-α resulted in the appearance of TNF-α as a doublet migrating at approximately 20 kd (FIG. 5, lanes 4–7), corresponding to both unprocessed and processed forms. For comparison, a *Salmonella* strain harboring a chromosomally-integrated TNF-α encoding nucleic acids, expressing the mature (processed) form of TNF-α, was used as a positive control (FIG. 5, lane 3). TNF-α expression was not detected in bacteria lacking the TNF-α encoding nucleic acids (FIG. 5, lane 2).

These results demonstrated that fusion of the mature human TNF-α protein to the *E. coli* ompA signal peptide (as depicted in FIG. 4) resulted in periplasmic localization and processing when expressed in *E. coli*. Further, it was unknown whether overexpression of a secreted protein would be toxic to the bacterial host as a result of overwhelming the normal secretory apparatus. The present demonstration of expression of a processed ompA-TNF-α fusion protein indicated that the normal secretory apparatus was capable of accommodating the high-level expression of secreted proteins.

7.2. Processing of an ompA-TRAIL Fusion Protein

The ability of the ompA signal peptide to periplasmically localize TNF family members was extended to TRAIL (TNF-α-related apoptosis-inducing ligand), another member of the TNF family. For these experiments, a trc promoter-driven TRAIL encoding nucleic acids, encoding the mature form of human TRAIL (hTRAIL), was fused to the coding sequence of the ompA signal peptide (as depicted in FIG. 6). Two different ompA/TRAIL junctions were examined, one encoding an Nco I site and one encoding an Nde I site (See FIG. 6 for Nde I containing sequence). Western analysis of both types of clones is shown in FIG. 7. Using an anti-hTRAIL antibody, Western blot analysis revealed that bacteria over-expressing the ompA-TRAIL with the Nco I junction expressed both processed (28.2 kd) and unprocessed (30.2 kd) forms of hTRAIL (FIG. 7, lanes 2–4), whereas bacteria over-expressing the ompA-TRAIL with the Nde I junction expressed the processed form exclusively (FIG. 7, lanes 4–7), indicating that the Nde I junction provided more efficient processing.

These results demonstrated that fusion of the mature human TRAIL protein to the *E. coli* ompA signal peptide resulted in periplasmic localization and processing. Further, it was unknown whether overexpression of the secreted protein would be toxic to the bacterial host as a result of overwhelming the normal secretory apparatus. The present demonstration of expression of a processed ompA-TRAIL fusion protein indicated that the normal secretory apparatus was capable of accommodating the high-level expression of secreted proteins.

7.3. Processing of an ompA(8L)-IL-2 Fusion Protein

A secondary effector molecule (IL-2) was expressed as a fusion protein. Fusion of mature (C125A) hIL-2 to the wild-type OmpA signal sequence, used above for TNF-α and TRAIL, did not permit processing of IL-2. In order to examine the periplasmic localization and processing of the human IL-2 cytokine, mature human (C125A) IL-2 was fused to a modified ompA signal peptide, denoted ompA (8L), as depicted in FIG. 8. The modified ompA signal peptide was modified by replacing amino acids 6–17 of the ompA signal with those depicted in FIG. 8. Expression and processing are shown in FIG. 9 (lanes 6 and 7). Each lane represents a single clone. Results of Western blot analysis indicated that virtually complete processing was observed with the ompA(8L) signal peptide (FIG. 9, lanes 6 and 7).

7.4. Processing of an phoA(8L)-IL-2 Fusion Protein

A second fusion protein was examined for periplasmic localization and processing of human IL-2, and compared with the fusion protein of Section 7.3. The expression and processing of mature human (C125A) IL-2 fused to a modified phoA signal peptide, denoted phoA(8L), as depicted in FIG. 10 was examined. Expression and processing are shown in FIG. 9. Partial processing was observed with the synthetic phoA(8L) signal peptide (FIG. 9, lanes 4 and 5), whereas more complete processing was observed with the ompA(8L) signal peptide (FIG. 9, lanes 6 and 7).

These results indicate that localization and processing of IL-2 was provided by different signal peptides. The results also demonstrate that periplasmic localization of proteins by fusion to various signal peptides is dependent on both the signal peptide and the protein.

The results of the fusion protein studies indicate that a secondary effector protein of the invention, such as IL-2, can be expressed and localized to the bacterial periplasm by fusion with the a protein signal peptide such as OmpA or PhoA. As will be apparent to one of ordinary skill in the art, other signal sequences can be used to cause periplasmic localization of an effector molecule can be used. As will further be apparent to one of ordinary skill in the art, other effector molecules of the invention can be substituted for the effector molecules described in the examples herein.

8. EXAMPLE

Anti-Tumor Efficacy of *Salmonella* (ΔmsbB, ΔpurI) Expressing the Mature Form of TNF-α

The following experiment demonstrates that an attenuated tumor-targeted bacteria such as *Salmonella* containing a nucleic acid encoding a primary effector molecule (e.g., a TNF family member) can deliver the primary effector to mammalian tumors and cause a decrease in tumor volume.

The ability of TNF-α expression to increase the anti-tumor efficacy of *Salmonella typhimurium* was evaluated in a staged murine Colon 38 carcinoma model. For these experiments, 1 mm$^3$ tumor fragments, derived from a Colon 38 tumor, were implanted into C57BL/6 mice and tumors were allowed to grow to a mean size of approximately 0.3 g, at which time animals were randomly placed into the following treatment groups (n=10): 1) untreated; 2) *Salmonella typhimurium* (ΔmsbB, ΔpurI, serC) (parental strain); and 3) pTS-BRPTNF-α (Clone 2 described above). Mice in each group either remained untreated or received a single intravenous injection of 1×10$^6$ cfu of the appropriate bacterial strain. Tumor size was measured weekly, beginning at the time of bacteria inoculation.

In the group receiving attenuated tumor-targeted *Salmonella* expressing TNF-α, tumor regression was apparent by the second week following treatment, with complete regression observed in 6 of the animals within 4 weeks following treatment (FIG. 11). Tumors in the untreated group progressively increased in size, whereas tumors in the group treated with the parental *Salmonella typhimurium* (ΔmsbB, ΔpurI, ΔverC) strain displayed partial regression between weeks 3–4 following treatment, after which tumors progressively increased in size (FIG. 11).

These results demonstrate that attenuated tumor-targeted *Salmonella* are able to express and deliver an effector molecule such as a TNF family member to a tumor. Such *Salmonella* are useful in the treatment of tumors and provide enhanced tumor regression results as compared to parent *Salmonella* strains which do not express the TNF family member.

The demonstration of complete tumor regression, by *Salmonella* expressing TNF-α from chromosomally-integrated nucleic acid, indicates that biologically effective expression can result from chromosomally integrated-effector molecule encoding nucleic acids.

9. EXAMPLE

Enhanced Delivery of Nucleic Acid Molecules by BRP Expressing Bacteria

In order to demonstrate that BRP activity could enhance the release of a plasmid from a tumor-targeted attenuated bacteria such as *Salmonella*, a tumor-targeted attenuated *Salmonella* strain was constructed that contained BRP on a plasmid as well as a second plasmid used as a marker for release (pTrc99a with AMP marker). To assay activity of BRP, the *Salmonella* with or without BRP was grown in culture by standard methods. The resulting supernatant was then cleared of any remaining bacteria by centrifugation and filtration and the cleared supernatant was then added to competent cells and underwent a transformation reaction. These "recipient" cells were then plated onto LB amp to look for uptake of the AMP marker plasmid. An increase in the number of AMP resistant colonies with BRP would indicate that more plasmid was released into the media from strains expressing BRP. Results are summarized in Table 2 below:

TABLE 2

| Plasmid | Average # of Amp Colonies/Transformation |
| --- | --- |
| pTrc99a alone | 125 |
| pTrc99a + BRP (pSW1) | 383 |

These results demonstrate that the presence of BRP increased the amount of amp plasmid secreted to the media. Thus, transformation into "recipient cells" with supernatants from cells expressing BRP gave higher number of colonies. These results demonstrate that BRP enhanced release of a secondary effector molecule, which comprised a nucleic acid plasmid. Accordingly, the results show that BRP is useful for plasmid release or DNA delivery. In addition, these *Salmonella* strains that expressed BRP and were able to deliver DNA and remained replication competent as a population.

10. EXAMPLE

BRP Expression Does not Impair Tumor-Targeting or Tumor-Inhibiting Ability of Attenuated Tumor-Targeted *Salmonella*

The following example demonstrates that attenuated tumor-targeted bacteria can be engineered to express BRP in conjunction with one or more effector molecules to enhance the delivery of effector molecules to tumors without inhibiting the ability of bacteria to target the tumor.

Solid tumor models were obtained by subcutaneous injection of B16 melanoma cells in the right hind flank of C57BL/6 mice. For tumor implantation, cells were detached from the flask by trypsinization, washed, and suspended in phosphate buffered saline at $2.5 \times 10^6$ cells/ml. An aliquot of 0.2 ml of the cell suspension, for a total of $5 \times 10^5$ cells/mouse, was injected on Day 0. When tumor volumes reached 150–200 mm$^3$, approximately 10 days after implantation, the mice were randomized into three groups of ten mice and each group received a different treatment. The control group (curve #1 on FIG. 12) received 0.2 mls of PBS. Another group received 0.2 ml containing $2 \times 10^6$ c.f.u./mouse of the attenuated tumor-targeted strain of *Salmonella* VNP20009 (curve #2 on FIG. 12). The third group received 0.2 ml containing $2 \times 10^6$ c.f.u./mouse of the attenuated tumor-targeted strain of *Salmonella* comprising pSW1, a plasmid comprising the BRP gene under the control of its native promoter (curve #3 on FIG. 12). The BRP gene is SOS inducible in *E. coli*, although the inventors believe, without limitation as to mechanism, that it is partially constitutive in *Salmonella*, producing low to moderate levels of the BRP protein, which are further enhanced by the SOS nature of the tumor environment. Mice injected with BRP-expressing VNP20009 *Salmonella* showed nearly identical anti-tumor responses to those injected with non-BRP-expressing VNP20009, indicating that the survival or tumor-targeting ability of these *Salmonella* is not altered by BRP expression, nor is their ability to inhibit tumor growth. The outcome of BRP-expression on attenuated tumor-targeted *Salmonella* is in direct contrast to the effect of the expression of secreted HSV-thymidine kinase (HSV-TK), which HSV-TK expression results in the loss of VNP20009's tumor-inhibiting abilities (Pawelek et al., 1997, Cancer Res. 57:4537–4544). Thus, the BRP system can be used to enhance the delivery of primary and/or secondary effector molecules to tumors without further modification.

11. EXAMPLE pepT Promoter Expression Vehicles

This example demonstrates the in vitro and in vivo expression of a nucleic acid molecule encoding reporter such as β-gal under the control of the pepT promoter in an attenuated tumor-targeted bacteria such as *Salmonella*.

11.1. Construction of pepT-BRP-βGAL Expression Plasmids

The pepT promoter was cloned by PCR amplification of the region from an isolated colony of wild type *Salmonella typhimurium* (ATCC 14028) using the following primers:

Forward: 5'-AGT CTA GAC AAT CAG GCG AAG AAC GG-3' (SEQ ID NO:15)

Reverse: 5'AGC CAT GGA GTC ACC CTC ACT TTT C-3' (SEQ ID NO:16).

The PCR conditions consisted of 1 cycle of 95° C. for 5 minutes, 35 cycles of 95° C. for 1 minute, 65° C. for 1 minute, 72° C. for 2 minutes and 1 cycle of 72° C. for 10 minutes. The PCR product was cloned into the PCR 2.1 cloning vector (Invitrogen, Carlsbad, Calif.), and is referred to as PepT/PCR 2.1.

The PepT/PCR 2.1 vector was digested with NcoI and XbaI. The pepT fragment was gel isolated and ligated into the β-gal Zterm vector digested with the same enzymes. Zterm (Temporary Genbank Bankit No. 296495) is a promoterless β-gal plasmid generated by cloning the βGal open reading frame into pUC19. The resultant plasmid was called pepT-βGAL.

11.2. In Vitro Expression of pepT-βGAL and Measurement of pepT-βGAL Activity

*Salmonella* strains YS1456 (CC14 in FIG. 13A; for the genetic make up of the strain, see WO 96/40238) or VNP20009 (CC16 in FIG. 13A) harboring pepT-βGAL were grown under either anaerobic or aerobic conditions to an OD$_{600}$ of ~0.5–0.8. β-gal activity was measured by the method of Birge and Low (1974, J. Mol. Biol. 83:447–457). The results are shown in FIG. 13A, and demonstrate approximately 14- to 24-fold induction of β-gal activity upon growth of the bacteria under anaerobic conditions.

11.3. In Vivo Expression of pepT-βGAL and Measurement of pepT-βGAL Activity

Cells of the *Salmonella* strain YS1456 harboring the pepT-βgal expression plasmids, a BRP expression plasmid (pSW1 from BIO101 (Vista, Calif.), which comprises the pCloDF13 BRP coding sequence under the control of its native promoter) or both expression plasmids were injected intravenously into tumor bearing mice. Five days post injection, tumors and livers were homogenized and bacteria were isolated to show that the presence of plasmids for pepT-βgal and/or BRP did not interfere with the ability of these bacteria to target tumors. In addition, the tumor and liver homogenates were used to measure βgal activity to determine whether active βgal could be measured in vivo and whether the pepT promoter was induced in an anaerobic tumor environment. The results, shown in FIG. 13B, indicate very high levels of pepT promoter activity in the tumor environment. There is no significant increase in liver expression of βgal over the background level, which is thought to arise from the low activity of the pepT promoter in the aerobic liver environment and/or the low targeting of the bacterial vector to the liver.

12. EXAMPLE

Tetracycline Inducible Expression System

This example demonstrates the expression of a nucleic acid molecule encoding a reporter gene such as β-gal under the control of the tet promoter in an attenuated tumor-targeted bacteria such as *Salmonella*.

The let promoter was cloned from a mini-TN10 transposon by PCR amplification using the following primers:
Forward: 5'-GGA TCC TTA AGA CCC ACT TTC ACA TTT AAG T-3' (SEQ ID NO:17)
Reverse: 5'-GGT TCC ATG GTT CAC TTT TCT CTA TCA C-3' (SEQ ID NO:18).

The PCR conditions were as follows: one cycle of 95° C. for 5 minutes; 35 cycles of 95° C. for 1 minute, 60° C. for 1 minute, 72° C. for 2 minutes; and one cycle of 72° C. for 10 minutes.

The ~400 bp PCR fragment was gel isolated and cloned into the PCR 2.1 vector (Invitrogen). The PCR2.1/tet promoter vector was digested with NcoI and BamHI. The ~400 bp tet promoter fragment was gel isolated and ligated into the promoterless β-gal vector Zterm that had been digested with the same two enzymes. The ligation mixture was transformed and the transformed bacteria were plated to tetracycline/X-gal plates. Positive colonies were isolated on the basis of their blue color. Extracts from several positive clones were made, and assayed by the method of Birge and Low (1974, J. Mol. Biol. 83:447–457) for β-gal activity in the presence of tetracycline. One clone was isolated and assayed for β-gal expression over a range of tetracycline concentrations. The results of the assay, which demonstrate the induction of β-gal activity by tetracycline in a dose dependent manner, are shown in FIG. 14.

13. EXAMPLE

Inhibition of Tumor Growth by Attenuated Tumor-Targeted *Salmonella* Expressing Endostatin The following example demonstrates the generation of endostatin-expressing attenuated tumor-targeted *Salmonella*, and the in vivo efficacy of tumor treatment by such *Salmonella*.

13.1 Construction of Endostatin Expression Plasmids

Endostatin was PCR amplified from a human placental cDNA library using the following primers:
Forward: 5'-GTG TCC ATG GGG CAC AGC CAC CGC GAC TTC CAG-3' (SEQ ID NO:19)
Reverse: 5'-ACA CGA GCT CCT ACT TGG AGG CAG TCA TGA AGC T-3' (SEQ ID NO:20).

The resulting PCR product was cloned into the PCR2.1 vector (Invitrogen). Hexahistidine-endostatin was PCR amplified using the above constructed plasmid as a template with the following primers:
Forward: 5'-GTG TCC ATG GCT CGG CGG GCA AGT GTC GGG ACT GAC CAT CAT CAT CAT CAT CAT CAC AGC CAC CGC GAC TTC-3' (SEQ ID NO:21)
Reverse: 5'-GTG CGG ATC CCT ACT TGG AGG CAG TCA TGA AGC TG-3' (SEQ ID NO:22).

The conditions for the PCR amplification consisted of 1 cycle of 95° C. 5 min; 30 cycles of 95° C. for 1 min, 55° C. for 1 minute, and 72° C. for 2 minutes; and 1 cycle of 72° C. for 10 minutes.

The resulting product was a DNA fragment with NcoI (5') and BamHI (3') restriction sites encoding human endostatin having the peptide sequence MARRASVGTDHHHHHH (SEQ ID NO:23) at its amino terminus.

The PCR product was digested with NcoI and BamHI and the 550 bp product was gel isolated and ligated into the pTrc99A vector that had been previously cut with the same enzymes. The ligation reaction products were transformed into *E. coli* DH5α and the attenuated tumor-targeted *Salmonella* strain VNP20009.

The hexahistidine-endostatin coding sequence was also cloned into the expression vector YA3334 as a NcoI/BamHI fragment. YA3334 is the asd plasmid PYA272 (Curtiss III, U.S. Pat. No. 5,840,483) with the origin of replication replaced by that of positive clones was isolated and transformed into the *Salmonella* strain 8324, which is VNP20009 with an asd mutation. This strain was generated according to the methods described in Curtiss III (U.S. Pat. No. 5,840, 483).

13.2. In Vitro Expression of Endostatin by Attenuated Tumor-Targeted *Salmonella*

Different strains of *Salmonella* VNP20009 and *E. coli* DH5α strains containing the pTrc99A-hexahistidine-endostatin plasmid were grown to mid-log phase (O.D.$_{600}$ ~0.6–0.8), at which point each culture was split, one half receiving 0.1 mM IPTG for induction of trc promoter activity and the other half receiving no IPTG. After three further hours of growth, bacterial extracts were prepared and the expression of hexahistidine-endostatin was confirmed by Western blot analysis with an anti-histidine antibody (Clontech, Palo Alto, Calif.). FIGS. 15A and 15B show the results of the Western blots which demonstrate pTrc99A hexahistidine-endostatin (HexHIS-endostatin) expression in *E. coli* DH5α and *Salmonella* VNP20009, respectively. While the trc promoter shows no activity in *E. coli*. in the absence of IPTG, the same promoter is constitutively active in *Salmonella* Hexahistidine-endostatin is expressed a single band of approximately 25 kD, which is the predicted molecular weight for the fusion protein.

The hexahistidine-endostatin fusion protein was similarly expressed from the YA3334 plasmid, which utilizes the trc promoter to direct expression. A protein of the predicted mass of 25 kDa was detected using the anti-histidine antibody, as shown in FIG. 16. In FIG. 16, all bacterial cultures from which the samples were derived had been induced with 0.1 mM IPTG for three hours.

13.3. Efficacy of Attenuated Tumor-Targeted *Salmonella* Expressing Endostatin on C38 Murine Colon Carcinoma Colon 38 tumor fragments of 2×2×2 mm$^3$ volume were implanted subcutaneously in 9 week old female C57BL/6 mice. When the tumor volumes reached 1000 mm$^3$, they were removed, cut into fragments of 2×2×2 mm$^3$. The fragments were serially passaged for further cycles and the resulting 2×2×2 mm$^3$ fragments were implanted subcutaneously at the right flanks of female C57BL/6 mice. When tumor volumes reached 150–200 mm$^3$, approximately 24 days after implantation, the mice were randomized into six groups of ten mice and each group received a different treatment. One control group received 0.2 mls of PBS. Another control group received 0.2 ml containing 1×10$^6$ c.f.u. of the attenuated tumor-targeted strain of *Salmonella*

VNP20009 carrying a control asd plasmid, i.e. an asd plasmid that has no insert, as described in Section 5.6, supra. The first experimental group received 0.2 ml containing 1×10⁶ c.f.u. of VNP20009 expressing a hexahistidine-endostatin fusion protein in an asd plasmid. The second experimental group received VNP20009 with the same expression construct as the first group and further expressed BRP.

FIG. 17 shows the results of these experiments, which demonstrate the efficacy of tumor inhibition by the VNP20009 strains expressing hexahistine-endostatin. After 60 days of treatment, the median tumor size in those VNP20009 *Salmonella* expressing endostatin was approximately 13% of the median tumor size in control animals, and over 30% less than the median tumor size in animals treated with VNP20009 *Salmonella* harboring an empty vector. Of the surviving animals, many exhibited static tumor growth, as indicated by small changes in net tumor size, and one exhibited a strong regression of the tumor. Incomplete penetrance or effectiveness of the treatment most likely reflects an imperfect delivery system for endostatin, in concordance with O'Reilly et al.'s (1997, Cell 88:277–285) finding that endostatin accumulates in inclusion bodies. The delivery system for endostatin is enhanced by the expression of BRP. BRP expression is controlled by its natural promoter, which normally shows an SOS response in bacteria. BRP expression was shown to decrease mean tumor volume to approximately 6% of the mean tumor volume of the control population. Furthermore, within the mouse populations treated with hexhistidine-endostatin and BRP, several of the mice exhibited striking reductions in tumor volume over time, wherein the tumor volume regressed to approximately 10% or less of the initial tumor volume. The effect of BRP is likely to be two-fold: first, BRP itself may possess anti-tumor activity, and second, BRP promotes the release of periplasmic contents and to some extent the release of cytoplasmic contents, including endostatin, which prevents the protein from accumulating in inclusion bodies.

13.4. Efficacy of attenuated Tumor-Targeted *Salmonella* Expressing Endostatin on DLD Human Colon Carcinoma Cultures of DLD1 cells grown in log phase were trypsinized, washed with PBS and the cells reconstituted to a suspension of 5×10⁷ cells/ml in PBS. 0.1 ml aliquots of single cell suspensions, each containing 5×10⁶ cells, were injected subcutaneously into the right flanks of 9-week old nude female mice (Nu/Nu-CD1 from Charles River). The mice were randomly divided into three groups often animals each, then staged at 10–15 days after injection, or when tumor volume reached 200–400 mm³.

The first group of mice was the control group, and each received an 0.3 ml injection of PBS. The second group of mice received 0.3 ml containing 1×10⁶ c.f.u. of the attenuated tumor-targeted strain of *Salmonella* VNP20009 carrying a control asd plasmid. The third group of mice received 0.3 ml containing 1×10⁶ c.f.u. of the attenuated tumor-targeted strain of *Salmonella* VNP20009 carrying an asd plasmid which expresses a hexahistidine-endostatin fusion protein and BRP. The tumors were monitored and measured twice a week. FIG. 18 is a graphic representation of tumor volume after administration of the three treatments, demonstrating the inhibitory effect of the hexahistidine-endostatin expressing attenuated tumor targeted *Salmonella* on the growth of DLD1 human colon carcinoma.

VNP20009 carrying the empty vector PYA3332 was not able to significantly inhibit tumor growth. However, VNP20009 expressing endostatin and BRP was able to inhibit tumor growth. These results demonstrate that the combination of endostatin plus BRP increases the anti-tumor effect of either the VNP20009 carrying the PYA3332 vector (strain 8324).

14. EXAMPLE

Expression of Anti-Angiogenic Factors by Attenuated Tumor-Targeted *Salmonella*

The following example shows the methodology used to engineer attenuated tumor-targeted bacteria such as *Salmonella* to express the anti-angiogenic factors thrombospondin AHR, platelet factor-4 and apomigren.

14.1. Construction of a Plasmid Containing the Nucleic Acid Sequence Encoding Thrombospondin AHR The peptide sequence, TiP 13.40: AYRWRLSHRPKTG-FIRVVMYEG (SEQ ID NO:24), corresponding to the anti-angiogenic homology region (AHR) of thrombospondin (see, e.g., Patent application No. C07K-14/78), was reverse engineered and codon optimized for expression in *Salmonella*, resulting in the DNA sequence: GCG TAC CGC TGG CGC CTG TCC CAT CGC CCG AAA ACC GGC TTT ATC CGC GTG GTG ATG TAC GAA GGC (SEQ ID NO:25). Complementary oligonucleotides (Oligo 13:40–1 and Oligo 13:40–2) were produced to synthesize this peptide. At the 5' end a sequence coding for the processing region of OMPA and an SpeI restriction site were added. At the 3' end, a stop codon was added with a BamHI restriction site. The two oligos were annealed to generate the double stranded DNA fragment. The DNA fragment was cut with SpeI/BamHI and ligated to the SpeI/BamHI cut vector pTrc801IL2 to produce the plasmid pTrc801-13.40 containing the full length modified OmpA leader sequence. When processed, the sequence produces the full length 13.40 thrombospondin peptide.

Oligo 13.40-1: 5'gtgtactagt<u>gtggcgcaggc</u>GCGTACCGCTG-GCGCCTGTCCCATCGCCCGAAAACC GGCTTTA-TCCGCGTGGTGATGTACGAAGGCTAA*ggatccgcgc* 3' (SEQ ID NO:26)

Oligo 13.40-2: 5'gcgcggatcc*TTAGCCTTCGTACATCAC-CACGCGGATAAAGCCGGTTTTCGGGC GATGGG-ACAGGCGCCAGCGGTACGC<u>cgcctgcgccac</u>actagtacac 3' (SEQ ID NO:27)

(Restriction sites are italicized and the OmpA processing recognition site is underlined.)

14.2. Construction of a Plasmid Containing the Nucleic Acid Sequence Encoding Platelet Factor-4 Peptide (47–70)

The peptide consisting of amino acid residues 47–70 of the C-terminus of platelet factor-4 (PF-4; see, e.g., Maione et al., 1990, Science 247:77–79 and Jouan et al., 1999, Blood 94:984–993) was codon-optimized for expression in *Salmonella*. The peptide, which is depicted below, includes a DLQ-motif responsible for inhibitory activity of PF-4 on CFU-GM progenitor cells and a clusters of basic amino acids which is the major heparin binding domain.

Platelet Factor-4: <u>MSSAAGFCASRPGLLFLGLLLPLV-VAFASAEAEEDGDLQCLCVKTTSQV</u>RPRHITSLEVIKAGPHCPTAQLIATLKNGRKICLDL-QAPLYKKIIKKLLES (SEQ ID NO:28)

Signal peptide=underlined & in bold

Lys 61,62, 65,66=major heparin binding domain (in bold)

DLQ (7–9, 54–56)=inhibitory activity on CFU-GM progenitor cells (in bold)

Complementary oligonucleotides (oligo PF4-1 and oligo PF4-2) were produced to synthesize this peptide. At the 5' end a sequence coding for the processing region of OmpA and a SpeI restriction site were added. At the 3' end, a stop codon was added with a BamHI restriction site. The two oligos were annealed to generate the double stranded DNA fragment. After restriction digest the fragment was ligated into the SpeI/BamHI restricted vector pTrc801 to produce the plasmid pTrc801-PF4. When processed, the sequence produces the full length PF4 (47–70) peptide.

Oligo PF4-1 5'cttcactagt<u>gtggcgcaggcg</u>AACGGCCGCAA-AATCTGCCTGGACCTGCAGGCGCCGCT GTACAAAAAAATCATCAAAAAACTGCTGGAAA-GCTAA ggatcc gcg3' (SEQ ID NO:29)

Oligo PF4-2 5'cgcggatccTTAGCTTTCCAGCAGTTTTTT-GATGATTTTTTTGTACAGCGGCGCCTG CAGGTC-CAGGCAGATTTGCGGCCGTT<u>cgcctgcgccac</u>actagt-gaag3' (SEQ ID NO:30)

(Restriction sites are italicized and the ompA processing recognition site is underlined.)

14.3. Construction of a Plasmid Containing the Nucleic Acid Sequence Encoding Apomigren The anti-angiogenic peptide apomigren (IYSFDGRDIMTDPSWPQKVIWHGSSPHGVRLVDNY-CEA WRTADTAVTGLASPLSTGKILDQKAY-SCANRLIVLCIENSFMTDARK (SEQ ID NO:31; see, e.g., International Publication No. WO99/29856) corresponds to the C-terminus of restin, which is a proteolytic fragment of collagen XV. Oligonucleotides (oligo Apom5F and oligo Apom6F) were designed to amplify the DNA fragment from human cDNA. At the 5' end a sequence coding for the processing region of OmpA and a SpeI restriction site were added. At the 3' end, a stop codon was added with a BamHI restriction site:

Oligo Apom5F: 5'-ggcttc actagt gtggcgcaggcg ATATACTCCTTTGATGGTCG-3' (SEQ ID NO:32)

Oligo Apom6R: 5'-cgc ggatcc TTACTTCCTAGC-GTCTGTCATGAAACTG-3' (SEQ ID NO:33)

(Restriction sites are italicized and the OmpA processing recognition site is underlined.)

A fragment of the correct size was obtained by PCR using placental cDNA as template. The PCR product was cut with SpeI/BamHI and ligated to the SpeI/BamHI restricted vector pTrc801 containing the modified ompA signal sequnce to produce the plasmid pTrc801-Apom. When processed, the sequence produces the Apomigren peptide.

14.4. Anti-Angiogenic Peptides Produced by *Salmonella* Inhibiting Endothelial Cell Proliferation pTrcOmpA-Endostatin, pTrc801-PF4 and pTrc801-13.40 plasmids were electroporated into attenuated tumor-targeted *Salmonella* VNP20009 strains. *Salmonella* strains expressing pTrcOmpA-Endostatin, pTrc801-PF4 and pTrc801-13.40 were screened for anti-proliferative activity as described by Feldman et al., 2000, Cancer Res. 60:1503–1506 and Blezinger et al., 1999, Nature Biotech. 17:343–348. Five-ml cultures of individual colonies were grown for 4 hours. Cell lysates were produced by resuspending the cell pellet in 1/20 volume HUVEC medium containing 100 mg/ml gentamycin and performing 3 consecutive freeze/thaw cycles. The lysates were cleared by centrifugation and filter sterilized using a 0.2 mm syringe filter. Ten, twenty-five or fifty ml of the lysates were added to human vein endothelial cells (HUVECs) in 96 well plates containing 100 ml basal medium 2% FCS plus 10 ng/ml FGF. As a control *Salmonella* containing the empty pTrc vector were used. Plates were incubated for 72 hours and proliferation was measured by MST assay (Mosman et al., 1983, J. Immunol. Methods 65:55–63).

The preliminary results in FIGS. 19 and 20 show that the platelet factor-4 peptide (PF4-2), the thrombospondin peptide 13.40 (13.40-3) and endostatin produced by *Salmonella* seem to have anti-proliferative activity between 40–60%.

15. EXAMPLE

Expression of a Bacteriocin Family Member by Attenuated Tumor-Targeted *Salmonella*

This example demonstrates that attenuated tumor-targeted bacteria, such as *Salmonella*, containing a nucleic acid encoding a bacteriocin family member are capable of expressing the bacteriocin family member.

15.1. Construction of ColE3 Plasmids

The plasmids described herein serve to illustrate examples of specific embodiments of the invention. As will be apparent to one of ordinary skill in the art, promoter and/or effector molecule-encoding nucleic acids such as the trc promoter and/or bacteriocin encoding nucleic acids may be replaced with other appropriate promoter or effector molecules by methods known in the art.

15.1.1. THE pE3.Shuttle-1 Intermediate Vector Plasmid pE3.shuttle-1 represents the intermediate vector used to create a cassette containing a multiple cloning site and lacZ fragment for cloning/selection into the plasmid vector ColE3-CA38 (SEQ ID NO:34). To facilitate the cloning of BRP into E3, BRP was first cloned onto an intermediate shuttle vector (FIG. 21). This vector contains a lacZ fragment which can be used to select clones on lactose in a bacterial strain with a mutation(s) in chromosomal lacZ. The BRP fragment was then cloned into the E3 plasmid SmaI site (FIG. 22) as a cassette containing the lacZ alpha complementation fragment. The lacZ fragment makes insert selection possible (i.e. Lac+) at this step. Although the naturally occurring E3 plasmid has no antibiotic selection markers (FIG. 23), selection for the presence of the plasmid is possible by using a halo assay (Pugsley, A. P. and Oudega, B. "Methods for Studying Colicins and Their Plasmids" in Plasmids, a Practical Approach 1987, ed. By K. G. Hardy; Gilson, L. et al. EMBO J. 9:3875–3884). This shuttle vector should facilitate not only the cloning of BRP onto the E3 plasmid, but any DNA that could be combined with E3 or E3/BRP. The new E3/BRP plasmid was then transformed into 41.2.9 and tested for activity. Preliminary halo forming assays demonstrated that the presence of BRP on the plasmid did not interfere with the ability of this strain to produce E3. To determine if 41.2.9 E3/BRP had enhanced activity over 41.2.9 E3 the amount of lethal units of E3 produced by each strain was determined (FIG. 24). 41.2.9 E3/BRP produces 100% more lethal units than 41.2.9 E3 alone, demonstrating that this strain has an enhanced activity over 41.2.9 E3 alone.

15.1.2. Halo "Stab" Assay for E3 Activity

The sensitive tester strain (SK522) is grown to an $OD_{600}$ of 0.8. One hundred μl of tester strain is added to 3 ml of warm (~55° C.) LB soft agar (for a 100×15 mm dish) and quickly poured onto an LB agar plate. The plate is rocked gently to spread the overlay evenly over the plate and the agar allowed to solidify for 10–15 minutes. Colonies of *E. coli* or *Salmonella* for which E3 activity assay is desired are isolated with a sterile toothpick and "stabbed" into the agar. The agar plates are then inverted and incubated at 37° C. overnight. The following day a halo or clearing zone appears around the E3 stab as the secreted Colicin E3 kills the sensitive strain. The colonies can be further induced to increase E3 production or secretion by treatment with any of a variety of SOS-inducing agents such as an alkyalating agent (e.g., mitomycin), ultraviolet light or X-ray.

The results of one of the halo assays are shown in FIG. 25. When a bacterial strain secretes a colicin in the presence of a sensitive strain grown on a bacterial lawn on a petri dish, the secreted colicin diffuses out and kills the bacterial cells contained in the bacterial lawn, lysing them thus creating a clear zone or halo. The size of the halo corresponds to the amount of colicin secreted. The results shown in FIG. 25 show a number of strains. No halos are ever observed around strains not containing the colE3-CA38 plasmid. In the absence of induction, colicin is produced by the *Salmonella* strains. Also evident is that with various types of induction (i.e., alkylating agents, UV light, X-rays), all of the halos increase in size in a dose-dependent manner.

15.1.3. Overlay Assay for Selective E3 Clones

Transformants are plated with various dilutions (up to 1:10,000) onto LB and grown for 2 hours at 37° C. The sensitive tester strain is then prepared as above in the halo assay and an overlay poured with soft agar. After allowing to solidify for 10 minutes, the plate is then inverted and incubated overnight at 37° C. Small clearing zones then appear the following day (which resemble bacteriophage plaques) with a small colony (or colonies) in the middle of the clearing zone.

15.1.4. "Plaoue" or Halo Purification Assay

The small colony at the center of the clearing zone in the overlay agar described above is then isolated using a sterile pasteur pipette. In the case of either no visible colony or for the case of multiple colonies in one halo, the entire halo is picked with a sterile pasteur pipette. The colony or halo is transferred into 500 μL of LB. Dilutions (up to 1:10,000) are made and replated on LB agar and allowed to grow for 2 hours at 37° C. An overlay is then poured with the sensitive tester strain as outlined above. The following day, all or most of the colonies should have halos around them.

16. EXAMPLE

E3 Injection In Vivo, and Determination of the Percent Retention of Plasmid in *Salmonella*

The following example demonstrates the retention of the colE3-CA38 plasmid in *Salmonella* in vivo.

Homogenates of tumor and liver from two mice 30 days post injection of either 41.29 (or 41.2.9E3-CA38) were used for the studies. In the description to follow, L=Liver, T=Tumor. All four homogenates were plated for CFU and colonies were picked for analysis by msbB PCR and for colicin production. Almost pure cultures of colonies similar to 41.2.9 were obtained from all homogenates. Five colonies were picked from each for colicin and PCR analysis. An additional 30 colonies were picked form the 41.2.9 E3 T and L plates for further analysis as there seemed to be a mixed population of colicin producers and non producers in the 41.2.9E3 liver homogenate. Based on these results, an additional 100 colonies from 41.2.9E3 tumor and liver were picked and tested for colicin production and msbB PCR. Distribution and plasmid retention were calculated from the combined date.

The results of the E3 Injection in vivo, Determination of the Percent retention of plasmid in *Salmonella* are shown below in Table 3.

TABLE 3

| Tissue | CFU/ml | Tissue weight | CFU/gm | number positive for colicin | % positive in msbB PCR | % plasmid retention |
|---|---|---|---|---|---|---|
| 41.29L | 1.07E+03 | 1.33 | 4.02E+03 | 0/5 | 100% | n/a |
| 41.29T | 1.26e+07 | 0.26 | 2.42E+08 | 0/5 | 100% | n/a |
| 41.29E3L | 1.15E+04 | 2.34 | 2.46E+04 | 87/135 | 100% | 64.44 |
| 41.29E3T | 1.09e+06 | 0.35 | 1.56E+07 | 134/135 | 100% | 99.26 |

In order for the colE3 plasmid to have an effect in vivo, and in order for it to carry other genes to the site of the tumor in vivo, the colE3 plasmid must be effectively retained in vivo. The results obtained in this experiment were surprising and also advantageous since the target of the effector is the tumor, and therefore there would be less effect on the liver itself.

17. EXAMPLE

Tumor Targeting of Various 41.2.9. Strains in the M27 Lung Tumor Model

The following experiment demonstrates that the ability of 41.2.9 colE3 and 41.2.9 colE3 BRP and 41.2.9 colE3 BRP-m (modified BRP) *Salmonella* strains to target tumors.

The *Salmonella* strains listed in Table 4 below were injected into M27 lung tumor-bearing animals and animals were sacrificed on Day 7. Organ weights were assayed the next day for calculation of cfu/g. Tumors and livers were homogenized and plated on msbB to determine the colony forming units (c.f.u.). In groups 1, 2, 4, and 6, the strains all accumulated in the tumors to approximately $4 \times 10^8$ cfu/g with varying accumulation in the livers ranging from $6 \times 10^4$ to $4 \times 10^6$ cfu/g. Table 4 summarizes the data for all groups and is represented by the average cfu/g. All strains were found to have good tumor accumulation (better than $10^8$ c.f.u./gram tissue) and all strains gave positive tumor to liver ratios. The BRP colE3 had the best ratio, but was not necessarily better than all other strains available. The E3 and E3BRP strains accumulate to fairly high levels in tumors with tumor to liver ratios between 100–200:1.

TABLE 4

| Group | Strain | Tumor (T) Liver (L) | cfu/g tissue | Ratio (Tumor:Liver) |
|---|---|---|---|---|
| 1 | 41.2.9/E3 | T | $5.1 \pm 1.1 \times 10^8$ | 131:1 |
| 1 | 41.2.9/E3 | L | $3.9 \pm 3.6 \times 10^6$ | |
| 2 | 41.2.9/E3BRP | T | $4.6 \pm 2.7 \times 10^8$ | 209:1 |
| 2 | 41.2.9/E3BRP | L | $2.2 \pm 1.3 \times 10^6$ | |
| $6^1$ | 41.2.9/E3BRP$_m$ | T | $3.5 \pm 0.15 \times 10^8$ | 90:1 |
| $6^1$ | 41.2.9/E3BRP$_m$ | L | $3.9 \pm 3.6 \times 10^6$ | |

BRP$_m$ refers to a modified BRP that contains point mutations at position 96 (G to an A resulting in an amino acid change of a glycine to an arginine) and at position 114 (T to an A resulting in an amino acid change of a serine to a threonine). The mutant BRPm no longer causes quasi lysis but is still able to secrete proteins from the bacteria (van der Wal, F., Koningstein, G., Ten Hagen C. M., Oudega, B. and Luirink, J. (1998) Optimization of Bacteriocin Release Protein (BRP)- Mediated Protein Release by *Escherichia coli*: Random Mutagenesis of the pCloDF13-Derived BRP Gene to Uncouple Lethality and Quasi-Lysis from Protein Release. Applied and Environmental Microbiology vol. 64 pp 392–398).

18. EXAMPLE

Efficacy of 41.2.9/ColE3 on C38 Murine Colon Carcinoma

The following example demonstrates the ability of 41.2.9/ColE3 to inhibit the growth of C38 murine colon carcinoma.

Colon 38 tumor fragment (2×2×2 mm$^3$) was implanted in C57BL/6 mice (female, Age: 9 weeks) subcutaneously. After tumor volume reached to 1,000 mm$^3$, the tumors were removed from the mice under sterile condition and cut into small fragments (about 2×2×2 mm$^3$ mm$^3$/fragment), and repeated above procedure for 5 cycles. The fragments were implanted into mice subcutaneously at the right flank by using a tumor implantation needle on Day 0 of tumor implants.

Animals were randomized on Day 0 of *Salmonella* administration when tumor volume reached 150–200 mm$^3$. Frozen stocks of 41.2.9 and 41.2.9/ColE3 were thawed at room temperature, and diluted in PBS to a final concentration of 7.5×10$^6$ cfu/ml, respectively. Aliquots of 0.2 ml bacterial suspension (1.5×10$^6$ CFU/mouse) were administered intravenously into mice as group indicated on Day 0. The bacteria suspension were diluted to 1×10$^3$ CFU, plated on msbB plates and incubated overnight to determine the number of bacterial cfu which were administered. The tumors were measured twice per week up to the end of the experiment. Three tumors of each group (ColE3) were dissected and processed for determining cfu and retention of plasmid.

| Groups: | |
|---|---|
| | Mice |
| 1. Untreated control | 8 |
| 2. 41.2.9 (1.5 × 10$^6$/mouse) | 8 |
| 3. 41.2.9/ColE3 (1.5 × 10$^6$/mouse) | 8 |

The results for the efficacy of 41.2.9/ColE3 on C38 murine colon carcinoma are shown in FIG. 26. The data demonstrate that mice treated by intravenous injection with VNP20009 (41.2.9) are able to significantly inhibit the growth of C38 murine colon carcinoma. In addition, when mice were treated with VNP20009 containing the ColE3 plasmid, tumor regression (i.e., tumors were smaller at the end of the experiment than at the beginning) was achieved.

19. EXAMPLE

Anti-Tumor Activity of VNP20009/ColE30N DLD1 Human Colon Carcinoma in Nude Mice The following example demonstrates the enhanced ability of *Salmonella* mutant VNP20009/ColE3 (41.2.9/ColE3) to inhibit the growth of DLD1 human colon carcinoma relative to *Salmonella* mutant 41.2.9.

DLD1 cells grown in log phase were removed by trypsinization, washed with PBS, and reconstituted to 5×10$^7$ cell/ml PBS. Single cell suspensions (0.1 ml) were injected into Nude mice (Nu/Nu-CD1 female, Age: 9 weeks; from Charles River) subcutaneously on Day 0 (5×10$^6$ cells/mouse) at right flank. Ten animals were used in each group, randomized and staged at about 10–15 days after tumor implantation, when tumor size reached 300–400 mm$^3$. CFU of *Salmonella* mutant 41.2.9 and 41.2.9/ColE3 were counted one day ahead. Bacteria (41.2.9 and 41.2.9/ColE3) were diluted to 1×10$^7$ CFU/ml. Aliquots of 0.2 ml bacterial suspensions (2×10$^6$ CFU/mouse) were injected intravenously into mice on days indicated. The bacteria suspension was diluted to 1×10$^3$ CFU, plated each solutions 100 ul on msbB plates and the plates incubated overnight. The bacteria colonies were counted next day. The tumors were measured twice per week.

| Groups: | |
|---|---|
| | Mice |
| 1. Untreated control (PBS) | 10 |
| 2. 41.2.9 (2 × 10$^6$/mouse) | 10 |
| 3. 41.2.9/ColE3 (2 × 10$^6$/mouse) | 10 |

The results of the anti-tumor activity of 41.2.9/ColE3 on DLD1 human colon carcinoma in nude mice are shown in FIG. 27. The colicin E3-containing 41.2.9 strain shows enhanced activity as compared to strain 41.2.9 alone.

20. EXAMPLE

Efficacy of 41.2.9/ColE3 on B16 Murine Melanoma in C57BL/6 Mice

The following example demonstrates the ability of *Salmonella* mutant 41.2.9/ColE3 to inhibit the growth B16-F10 melanoma.

B16-F10 cells grown in log phase were removed by trypsinization, washed with PBS, and reconstituted to 5×10$^6$ cell/ml PBS. Single cell suspensions (0.1 ml) were injected into C57BL/6 mice (female, Age: 9 weeks) subcutaneously on Day 0 (5×10$^5$ cells/mouse) at right flank. Ten animals were used in each group, and randomized at day 9, when tumor volume reached 150–200 mm$^3$. Frozen stocks of *Salmonella* clones 41.2.9 and 41.2.9/ColE3 were thawed at room temperature, and diluted in PBS to a final concentration of 7.5×10$^6$ cfu/ml, respectively. Aliquots of 0.2 ml bacterial suspension (1.5×10$^6$ CFU/mouse) were administered intravenously into mice as group indicated on Day 9. The bacteria suspension were diluted to 1×10$^3$ CFU, plated on msbB plates and incubated overnight to determine the number of bacterial cfu which were administered. The tumors were measured twice per week up to the end of the experiment.

| Groups: | |
|---|---|
| | Mice |
| 1. Untreated control | 10 |
| 3. 41.2.9 (1.5 × 10$^6$/mouse) | 10 |
| 5. 41.2.9/ColE3 (1.5 × 10$^6$/mouse) | 10 |

The results of the efficacy of 41.2.9/ColE3 on B16 murine melanoma in C57BL/6 mice are shown in FIG. 28. The data demonstrate that mice treated by intravenous injection with 41.2.9 (41.2.9) are able to significantly inhibit the growth of B16 murine melanoma. In addition, mice treated with 41.2.9/ColE3 showed a significant decrease in tumor size at early time points (up to day 37) compared to 41.2.9 alone. This finding is very important because smaller tumor sizes are more readily susceptible to other therapeutics (e.g., chemotherapeutic agents and radiation such as x-rays).

21. EXAMPLE

Anti-Tumor Efficacy of 41.2.9/E3 Combined with BRP

The following example demonstrates that the coexpression of BRP and E3 in *Salmonella* mutant 41.2.9 increases the anti-tumor efficacy of mutant.

The coexpression of BRP and E3 in *Salmonella* mutant 41.2.9 increases the amount of E3 secreted from the bacteria in vitro. If BRP was able to increase the amount of E3 secreted from the *Salmonella* in vivo then it could be hypothesized that this additional extracellular E3 would be readily available to the tumor cells and thus increase the cytotoxicity to these cells. In this experiment 4 groups of animals (10 animals per group) were tested:

| Group number | Treatment |
| --- | --- |
| 1 | Control (no treatment) |
| 2 | 41.2.9 |
| 3 | 41.2.9/E3 |
| 4 | 41.2.9/E3/BRP |

The model used in this experiment was the human lung carcinoma line HTB177. The cells were implanted into the flank of mice subcutaneously on day 1. When the tumors reached to approximately 500 mm$^3$, on day 14 the animals were injected by intravenous injection with $1 \times 10^6$ cfu of the strain described in the above table, or with saline in the case of group 1. The tumor volume was measured weekly up to day 24. The results in Table 5 show that while 41.2.9 by itself is able to inhibit tumor growth (40% inhibition), the combination with E3 is able to increase the anti-tumor efficacy (63%). However, when the strain carrying both E3 and BRP is used in this model, the anti-tumor efficacy is further enhanced (67% inhibition compared to untreated control) and the enhanced inhibition is quite significant at the earlier time points (Table 5).

TABLE 5

Percent Tumor Growth Inhibition Compared to Untreated Control

| Strain: | Day 17 | Day 20 | Day 24 |
| --- | --- | --- | --- |
| 41.2.9 | 50 | 38 | 40 |
| 41.2.9/E3 | 63 | 58 | 63 |
| 41.2.9/E3/BRP | 97 | 82 | 67 |

In conclusion, treatment with *Salmonella* carrying both the cytotoxic colicin E3 and the enhanced secretion system BRP results in an increase in anti-tumor efficacy compared to the untreated control and to treatment with 41.2.9/E3 alone.

22. EXAMPLE

Combination of Colicin E3-Containing *Salmonella* with X-Ray Treatment

The following example demonstrates that the combination of 41.2.9 with two doses of X-ray significantly increases the survival time of mice above that seen for X-ray alone.

The schedule was as follows: At day 0, tumors were implanted by the administration of B16F10 melanoma ($5 \times 10^5$ cells/mouse) s.c. in the right side, at mid body of 100 C57B6 female mice (5–7 wks of age). At day 8, colicin E3-containing *Salmonella* 41.2.9 was injected and at days 12, and 26, x-rays were administered.

The results of the combination of colicin E3-containing *Salmonella* with x-ray treatment are shown in Table 6.

TABLE 6

| Category | n = ( ) | Days to 1 g | mean | T/C |
| --- | --- | --- | --- | --- |
| A sham 15 Gy | (6) | 12, 12, 18, 18, 18, 21 | 17 | 1.0 |
| J 15 Gy x-rays 12 dpt, 26 dpt | (9) | 14, 14, 18, 21, 25, 35, 35, 67, 67 | 33 | 1.9 |
| K 41.2.9 + 15 Gy x-rays 12 dpt, 26 dpt regression #1,2 | (9) | 21, 28, 35, 35, 56, 60, 60, 60, 67 | 47 | 2.8 |
| L 41.2.9/E3 + 15 Gy x-rays 12 dpt, 26 dpt regression d32 | (9) | 28, 39, 53, 56, 56, 60, 67, 74, 78 | 57 | 3.3 |

This data demonstrates that the combination of 41.2.9 with two doses of X-ray significantly increases the survival time of mice above that seen for X-ray alone. E3 further increased the survival time of mice above that seen for 41.2.9 plus X-ray.

23. EXAMPLE

Expression of Cytotoxic Necrotic Factors by Tumor-Targeted Bacteria

The following example demonstrates that the expression of *E. coli* cytotoxic necrotic factor 1 (CNF1) by tumor-targeted bacteria.

Cytotoxic necrotic factors include, but are not limited to, *E. coli* cytotoxic necrotic factor 1 (CNF1; Falbo et al., 1993, Infect. Immun. 61:4904–4914), *Vibrio fischeri* CNF1 (Lin et al., 1998, Biochem. Biophys. Res. Comm. 250:462–465) and *E. coli* cytotoxic necrotic factor 2 (CNF2; Sugai et al., 1999, Infect. Immun. 67:6550–6557). The CNF-family also includes *Pasteurella multiocida* toxin (PMT) which shares 27% identical residues and 80% conserved residues of the n-terminal portion of CNF2 (Oswald et al., 1994, Proc. Acad, Sci. USA 91:3814–3818).

CNF1 was cloned from *E. coli* J96 (ATCC 700336) by PCR using the primers (forward) 5'-GTGTCAT-GAAAATGGGTAACCAATGGCAAC-3' (SEQ ID NO:35) and (reverse) 5'-CACAGAGCTCGCGCTAACAAAA-CAGCACAAGGGAG-3' (SEQ ID NO:36) using standard PCR. An approximately 3100 bp product was obtained and cloned into the NcoI and SacI sites of pTrc99a for expression of the protein as well as DNA sequencing using *E. coli* as the DNA cloning host. DNA sequencing was performed by standard methods at the Yale University Keck Biotechnology laboratory. The DNA sequencing confirmed that the cloned PCR product was CNF1 with only minor sequence variation of 6 of 3065 base pairs.

The CNF1 plasmid was electroporated into an *E. coli* DNA cloning host DH5α and *Salmonella* strain YS1646 (International Publication No. WO 99/13053). The expression of CNF1 was determined in the *E. coli* DNA cloning host and *Salmonella* strain YS1649 using a standard LDH assay (Promega, Madison, Wis., Cytotox 96®). FIG. 29 shows that the presence of the CNF-containing plasmid results in enhanced cytotoxicity. A subsequent assay was used to show that *Salmonella* carrying the CNF-containing plasmid also exhibit other known properties of CNF1 such as multinucleation (Rycke et al., 1990, J. Clin. Microbiol. 28: 694–699). Hela cells exposed to CNF1 were examined for nuclei by light microscopy. The results in FIG. 30 clearly show that the presence of CNF1 in *Salmonella* results in the expected multinucleation and cell enlargement.

24. EXAMPLE

Expression of Verotoxin by Tumor-Targeted Bacteria

The following example demonstrates the cytotoxicity of verotoxin AB produced by tumor-targeted bacteria engineered to express verotoxin AB.

Verotoxin (syn. HSC10 toxin, Shiga toxin, shiga-like toxin, *Shigella* toxin). This toxin was isolated from a colicin-producing *E. coli* strain HSC10, and was originally thought to be a colicin (Farkas-Himsley et al., 1995, Proc. Natl. Acad. Sci. 92(15):6996–7000). It has a long history of antitumor activity, especially for ovarian cancer and brain tumors, however, the antitumor activity is associated with purified preparations, not with whole live bacteria.

Verotoxin was cloned from *E. coli* HSC10 (ATCC 55227) using primers based upon the published sequence for verotoxin I and confirmed by DNA-sequencing at the Yale Keck Biotechnology Center using standard DNA sequencing techniques. The expression of verotoxin was accomplished using the BRP gene under control of the tetracyclin-inducible promoter polycistronic with the verotoxin A and B subunits. This tetracyclin-inducible BRP verotoxin AB was cloned into a vector for chromosomal integration using the msbB gene.

24.1. Construction of Vectors 24.1.1. Amplification and Cloning of AB

Verotoxin AB (AB) was generated by PCR using the following primers:

H19B-7: forward: 5'-GTGTCCATGGCTAAAACATT-ATTAATAGCTGCATCGC-3' (SEQ ID NO:37); and QSTX-R1: reverse 5'-GTGTCTGCAGAACTGACTGAA-TTGAGATG-3' (SEQ ID NO:38).

These primers also contain outer NcoI(5') and PstI(3') restriction endonuclease sites for cloning into the NcoI and PstI sites of ptrc99A.

24.1.2. Amplification and Cloning of tetBRP

TetBRP-AB was constructed in the intermediate vector pSP72-F6/R6. TetBRP was generated by PCR using the following primers: Tet-5': forward 5'-GTG-TAGATCTTTAAGACCCACTTTCACATTTAAGTTG-3' (SEQ ID NO:39) and BRP-TET-3': reverse 5'-CACAGGATCCTTACTGAACCGCGATCCCCG-3' (SEQ ID NO:40). These primers contain BglII(5') and BamHI(3') restriction endonuclease sites for cloning into BglII and BamHI sites of pSP73-F6/R6 vector.

24.1.3. Subcloning of AB into pSP72-F6/R6-TETBRP ptrc99A-AB was digested with BamHI and AvaI restriction endonucleases to remove AB for insertion into pSP72F6/R6-TetBRP, also digested with BamHI and AvaI restriction endonucleases. The pSP72F6/R6 vector contains multiple restriction endonuclease sites for cloning in addition to a portion of the β-gal gene for lacZ-alpha complementation in trans. Both the vector (pSP72F6/R6-TetBRP) and the AB insert were resolved on a 0.8% 1×TAE agarose gel and purified using the Qiagen gel extraction kit. The vector and insert were ligated using T4 ligase and transformed into DH5a *E. coli* cells using the heat shock method. The cells were plated to LB plates containing 100 μg/ml Amp and 40 μg/ml X-gal. Positive colonies were selected based on ampicillin resistance and the presence of a functional β-gal gene (positive colonies were blue).

24.1.4. Subcloning of tetBRP-AB into pCDV442 pSP72F6/R6-TetBRP-AB was digested with NotI and SfiI restriction endonucleases for subcloning into the pCVD442 vector, also digested with NotI and SfiI restriction endonucleases.

24.1.5. msbB Chromosomal Vector

A vector capable of undergoing homologous recombination with the DmsbB gene in the chromosome of strain VNP20009 (a.k.a. YS1646 in International Publication No. WO 99/13053) was constructed in the suicide vector pCVD442 (Donnenberg and Kaper, 1991, Infection and Immunity 59: 4310–4317). Primers for PCR were designed that would generate portions of the 5' and 3' sections of the msbB deletion occurring in VNP20009 as two separate products (msbB-5': forward 5'-GTG TGA GCT CGA TCA ACC AGC AAG CCG TTA ACC CTC TGA C-3' (SEQ ID NO:41) and reverse 5' GTG TGC ATG CGG GGG GCC ATA TAG GCC GGG GAT TTA AAT GCA AAC GTC CGC CGA AAC GCC GAC GCA C-3' (SEQ ID NO:42); and msbB-3':forward 5'-GTG TGC ATG CGG GGT TAA TTA AGG GGG CGG CCG CGT GGT ATT GGT TGA ACC GAC GGT GCT CAT GAC ATC GC-3' (SEQ ID NO:43) and reverse 5'-GTG TCT CGA GGA TAT CAT TCT GGC CTC TGA CGT TGT G-3' (SEQ ID NO:44). These primers also contain outer SacI (5') and AvaI (3') restriction endonuclease sites to facilitate cloning into the SacI and SalI sites of pCVD442 when these two fragments are joined via a common SphI site and generate internal NotI, PacI, SphI, SfiI, SwaI and DraI, in order to facilitate cloning of DNA fragments into the DmsbB for stable chromosomal integration without antibiotic resistance (FIG. 31). This vector is referred to as pCVD442-msbB (see FIGS. 32 and 33).

In order to clone the Tet-BRP-AB into the pCVD442-msbB, the Tet-BRP-AB plasmid DNA was restriction digested and the appropriate DNA was purified and a ligation reaction containing these two components was performed using T4 ligase. The ligation reaction was then transformed to DH5 1 pir and colonies screened for the presence and orientation of the Tet-BRP-AB. The Tet-BRP-AB clone was transformed into the strain SM10 1 pir (Donnenberg and Kaper, 1991, supra) and the plasmid designated pCVD442-Tet-BRP-AB. Colonies of SM10 1 pir were screened for Tet-BRP-AB gene by PCR, and a SM10 1 pir clone pCVD442-Tet-BRP-AB was chosen for use as a mating donor to *Salmonella* strains. SM10 1 pir containing the pCVD442-Tet-BRP-AB was mated to a *Salmonella* strain YS50101 (a spontaneous derivative of the tetracycline-resistant strain YS82 (Low et al., 1999, supra) with enhanced resistance to Difco MacConkey agar) by standard methods (Davis, R. W., Botstein, D., and Roth, J. R. 1980. *Advanced Bacterial Genetics*, Cold Spring Harbor-Laboratory Press, Cold Spring Harbor) and selected for on plates containing 50 μg/mL carbenicillin (carb) and 300 μg/mL streptomycin (strep). The resulting YS50102-pCVD442-Tet-BRP-AB clones were checked for pCVD442-Tet-BRP-AB gene by PCR.

24.2. Transfer of the Chromosomally Integrated pCVD442-Tet-BRP-AB into 41.2.9 (YS1646) to Generate the strain 41.2.9-Tet-BRP-AB Using bacteriophage P22 (mutant HT105/1 int-201; Davis et al., 1980), 41.2.9 was transduced to carbenicillin resistance using strain YS50102-Tet-BRP-AB as donor. The presence of the bla and sacB genes from pCVD442 allowed the selection of a $carb^r$ (or $amp^r$) $suc^s$ strain denoted 41.2.9-pCVD-Tet-BRP-AB-1 which contained both the DmsbB and DmsbB-Tet-BRP-AB genes (FIG. 33, #3). Strain 41.2.9-Tet-BRP-AB-1 was plated on LB sucrose to select a $suc^r$ $carb^s$ derivative to remove the DmsbB gene and leave the DmsbB-Tet-BRP-AB gene according to the methods of Donnenberg and Kaper, 1991, supra (FIG. 33, #4) except that the LB-sucrose agar plates were made without NaCl, and the plates were incubated at 30° C. After the growth of colonies on these plates, they were gridded to an msbB plate and replica plated to either carbenicillin- or sucrose-containing plates in order to detect the presence of a clone which lacked both the antibiotic and sucrase markers. The resulting clones were checked for the presence of the Tet-BRP-AB gene by PCR. One such derivative containing the chromosomally integrated Tet-BRP-AB and lacking sucrose sensitivity and carbenicillin resistance was denoted as 41.2.9-Tet-BRP-verotoxin AB.

41.2.9-Tet-BRP-verotoxin AB was tested for cytotoxicity in vitro using a standard LDH cytotoxicity assay (Cytotox$^{96}$®; Promega, Madison, Wis.). The results are shown in FIG. 34, demonstrating the toxic properties of verotoxin-expressing clones 26 and 31. Clones 26 and 31 had a significantly higher percentage of cytotoxicity when treated with tetracycline than when not treated with tetracycline.

25. EXAMPLE

Expression of Hemolysin by Tumor-Targeted Bacteria

The following example demonstrates that tumor-targeted bacteria can be engineered to express hemolytic proteins such as hemolysin constitutively or under inducible control.

Hemolysins are well known cytotoxic proteins which have the ability to lyse red blood cells (see, e.g., Beutin, 1991, Med. Microbiol. Immunol 180:167–182). SheA (Genbank Number ECO238954) is a silent hemolysin found in most wild type *E. coli* which is not normally expressed (Fernandez et al., 1998, FEMS Micriobiol Lett 168:85–90). SheA (a.k.a. hlyE; Genbank Number U57430) was cloned by PCR using the following primers (forward) 5'-TTTTTTCCAT GGCTATTATG ACTGAAATCG TTGCAGATAA AACGG-3' (SEQ ID NO:45) and (reverse) 5'-TTTTTTAAGC TTCCCGGGTC AGACTTCAGG TACCTCAAAG AGTGTC-3' (SEQ ID NO:46) from wild type *E. coli* (strain 2507, Yale University *E. coli* Genetic Stock Center) under standard PCR conditions. The PCR product of the correct size was cloned into the NcoI and HindIII sites of ptrc99a (Pharmacia) in order to place it under the partially constitutive trc promoter. The PCR product was also cloned into the tet-bgal-Z-terrn vector (described supra) cut with NcoI and EcoRV. *E. coli* DH5a (Gibco) were then transformed with the plasmids and plated to blood agar (trypic soy agar with 5% sheep blood; BioMerieux, Lombard, Ill.) with and without the addition of 0.2 ug/ml tetracycline. Positive colonies were picked as those containing halos of clearing around the colony which indicates hemolysis. Positive colonies were subjected to standard plasmid purification and transformed to *Salmonella* YS501 and re-screened for halos.

Constitutive halo formation is shown in FIG. 35 (2A and 2B) for the trc99a construct, where a halo is observed with or without added tetracycline. Tetracycline-dependent halo formation is shown in FIG. 35 (3A and 3B) for the tetracycline-promoter driven SheA, where no halo is observed without the addition tetracycline. These results demonstrate that a tumor-targeted bacterium can express a hemolytic protein, either constitutively or under inducible control.

26. EXAMPLE

Expression of Methionase by Tumor-Targeted Bacteria

The following example demonstrates that attenuated tumor-targeted bacteria such as *Salmonella* can be engineered to express methionase.

Methionase is an enzyme that degrades methionine, an essential ammino acid necessary for tumor growth. Methods have been described for administration of purified methionase to inhibit tumor growth or to administer a DNA or viral vector which codes for methionase (International Publication No. WO00/29589 by Xu and Tan). Xu and Tan did not disclose methods for using tumor-specific bacterial vectors for delivery of methionase, and, in order to achieve efficacy with purified protein, large amounts of methionase are required. A novel method for delivering methionase directly to the tumors it to express the enzyme using tumor-targeted bacteria.

The following primers were generated for methionase from *Pneudomas putida* based upon Genbank No. L43133:

Forward: METH-XHOI 5'-CCGCTCGAGATGCACGGCTCCAACAAGCTCCCA-3' (SEQ ID NO:47); and

Reverse: METH-BAM 5'-CGCGGATCCTTAGGCACTCGCCTTGAGTGCCTG-3' (SEQ ID NO:48)

Using the above listed primers (4 mM) and an isolated colony of *Pneudomas putida* as the template, the sequence of methionase was amplified by PCR under the following conditions:

one cycle of 94° C. for 5 minutes, followed by 35 cycles of: 94° C. for 1 minute, 60° C. for 1 minute and 72° C. for 2 minutes. A final amplification step of 72° C. for 10 minutes was included as the last step of the PCR reaction. PCR products were resolved on 0.8% 1× TAE agarose gel and a PCR product of the expected size for methionase (~196 bp) was identified. The band was excised from the gel and purified using the Qiagen gel extraction kit.

Both the pSP72 vector and the isolated gel purifed methionase gene obtained above were digested with the restriction enzymes Xho I and Barn HI. The digested vector and methionase were resolved on a 0.8% 1×TAE agarose gel. The products of the digestion corresponding to the linearized vector and digested methionase gene were excised from the gel and purified using the Qiagen gel extraction kit. The linearized vector and the insert (methionase) were ligated together using T4 ligase. The ligation mixture was transformed into Dh5a *E. coli* cells by a heat shock method. After recovery, the cells were plated to LB media containing 100 mg/mL of ampicillan (Amp) to select for those cells that contain the intact pSP72 vector. Amp resistant colonies were identified and the presence of the pSP72 vector containing the methionase gene were confirmed by plasmid preparation using a Qiagen mini-prep kit and restriction digest with the enzymes Eco RI and Bsp HI. Clone #9, was sent for sequencing to the Yale sequencing Facility, Yale University School of Medicine. Sequence was done using both the SP6 (forward) and T7 (reverse) sequencing primers. Results demonstrate 100% sequence match to published methionase sequence with the exception of the TGA stop codon which was changed to TAA by PCR.

Methionase activity can be determined using the methionase assay described in Hori et al., 1996, Cancer Research 56:2116–2122.

27. EXAMPLE

Expression of Apoptin Protein as a TAT Fusions in Attenuated Tumor-Targeted Bacteria The following example demonstrates that attenuated tumor-targeted bacteria can be engineered to express and secrete fusion proteins comprising an effector molecule and a ferry peptide such as TAT, antennapedia, VP22, and Kaposi FGF MTS.

27.1. Construction of TAT-Apoptin Vectors The canary virus (CAV) protein apoptin is known to induce apoptosis in neoplastic cells, as when delivered by adenoviral vectors (see, e.g., Notebom et al., 1999, Gene Therapy 6:882–892).

In order to generate a protein which could be transcribed in the cytoplasm of *Salmonella* and yet have the ability to be transported to the nucleus of a tumor cell and cause apoptosis, the apoptin protein was fused to a peptide derived from the human immunodeficiency virus (HIV) TAT protein (see, e.g., Schwartze et al., 1999, Science 285:1569–1572). Since TAT protein fusions have also been shown to be functional when fused to poly-histadine (hexahistadine) amino acids which both increase the positive charge and facilitate protein purification (Schwartze et al., 1999, supra), the TAT-apoptin fusion was generated with and without the hexahistadine (FIGS. 36A and B). Further, the TAT-apoptin fusion can be generated with and without an OmpA-8L signal sequence (FIGS. 36A and C).

The apoptin and hexahistadine apoptin are assembled using overlapping oligonucleotides. The nucleic acid sequence encoding apoptin was generated by PCR using the following oligonucleotides:

TAP1: 5'-GATCCCATGG CTTATGGCAG AAAAAAACGC CGTCAGCGCC GTCGCATGAA CGCGCTGCAG GAAGATACCC CGCCGGGCCC GTCCACCGTG TTTCGCCCGC CG-3' (SEQ ID NO:49)

TAP2: 5'-GGGACAGGGT GATGGTGATG CCCGC-GATGC CGATGCGGAT TTCGCGGCAA TGCGGGGTTT CCAGCGGGCG GGAGGAGGTC GGCGGGCGAA ACACGGTGGA CGG-3' (SEQ ID NO:50)

TAP3: 5'-GGCATCGCGG GCATCACCAT CACCCT-GTCC CTGTGCGGCT GCGCGAACGC GCGCGCGCCG ACCCTGCGCT CCGCGACCGC GGATAACTCC GAAAACACCG GC-3' (SEQ ID NO:51)

TAP4: 5'-GCGATATTCG GACGGATCGC AGGAGCGTTT TTTGGACGGC GGTTTCGGCT GATCGGTGCG CAGATCCGGG ACGTTTTTAA AGCCGGTGTT TTCGGAGTTA TCCGCGGTCG C-3' (SEQ ID NO:52)

TAP5: 5'-CCTGCGATCC GTCCGAATAT CGCGTCTCCG AACTGAAAGA ATCCCTGATC ACCACCACCC CGTCCCGCCC GCGCACCGCC CGCCGCTGCA TCCGCCTCTG AAAGCTTCAT G-3' (SEQ ID NO:53)

TAP6: 5'-CATGAAGCTT TCAGAGGCGG ATG-CAGCGGC GGGCGGTGCG C-3' (SEQ ID NO:54)

The nucleic acid sequence encoding the hexahistadine-containing version of the TAT-apoptin fusion protein was generated using TAP2–TAP6 oligonucleotides and TAP6H1 oligonucleotide (5'-GATCCCATGG CTCATCACCA TCACCACCAT TATGGCCGCA AAAACGCCG TCAGCGCCGT CGCATGAACG CGCTGCAGGA AGATACCCCG CCGGGCCC-3'; SEQ ID NO:55). The nucleic acid sequence encoding the OmpA8L-containing version of the TAT-apoptin fusion protein is generated from the PCR product of TAP1–TAP6 oligonucleotides by PCR using TAP6 oligonucleotide and omp8LF1 oligonucleotide (5'-GATCCCATGG CTAAAAAGAC GGCTCTGGCG CTTCTGCTCT TGCTGTTAGC GCTGACTAGT GTAGCGCAGG CCTATGGCCG CAAAAAACGC CGTCAGCGCC-3'; SEQ ID NO:56).

Each oligonucleotide is formulated into a stock solution which is 4 µM in concentration. Using premixed PCR reaction beads (Pharmacia, Ready-to-go beads), 2 µl of each oligonucleotide was used. The PCR reaction consisted of one cycle at 95° for 5 minutes; thirty-five cycles at 95° C. for 1 minute, 60° C. for 1 minute, 72° C. for 1 minute; and one cycle at 72° C. for 10 minutes. The PCR reaction was then extracted with phenol/chloroform, precipitated with ethanol, redissolved in water and subjected to restriction digestion with Nco I and Hind III. The restriction-digested PCR product was resolved by gel electrophoresis and the product of the correct size (approximately 420 and 450 bp for TAT-apoptin and hexahistadine-TAT-apoptin, respectively) were excised from the gel and isolated using standard molecular biology techniques. These products are ligated into Nco I and Hind III digested ptrc99a (Pharmacia) and result in the ptrc99a-TAT-apoptin construct. The correct DNA sequence was obtained for both the TAT-apoptin (FIG. 37) and the hexahistadine TAT-apoptin (FIG. 38).

27.2. Demonstration of Secretion and Uptake of TAT-Apoptin

Attenuated tumor-targeted bacteria are transformed with the ptrc99a-TAT-apoptin construct by standard techniques known in the art (e.g., by heat shock or electroporation) and cultured in medium. The supernatant from the bacterial culture is tested for the presence of TAT-apoptin using techniques known to those of skill in the art (e.g., Western Blot analysis or ELISA). Once the presence of the TAT-apoptin in the supernatant of the bacterial culture is confirmed, the bacterial culture supernatant is incubated with mammalian cells (e.g., NIH3T3, CHO, 293, and 293T cells) and the presence of the TAT-apoptin inside the cells is confirmed by apoptin assays known to those of skill in the art.

27.3. Demonstration the Uptake of TAT-Apoptin Intratumorally

Attenuated tumor-targeted bacteria engineered to express TAT-apoptin or apoptin are administered intravenously to a B16 tumor model. The mice are sacrificed several days after administration of the bacteria and the organ weights are determined. Tumors are assayed for the presence and localization of TAT-aproptin or apoptin using apoptosis assays (e.g., DNA laddering and Fluorescein In Situ Cell Death Detection Kit (Boehringer Mannheim, Mannheim, Germany)) known to those of skill in the art. Further, the size of the tumors are assayed to determine anti-tumor activity of the TAT-apoptin. Tumors are also homogenized and plated to determine the colony forming units (c.f.u.).

28. EXAMPLE

Efficacy of the Combination of VNP20009 and Chemotherapeutic Agents on the Growth of M27 Lung Carcinoma in Mice The following example demonstrates that the administration of attenuated tumor-targeted bacteria in combination with a chemotherapeutic agent may act synergistically or additively to inhibit the growth of solid tumors such as lung carcinoma.

28.1. Efficacy of the Combination of VNP20009 and Cytoxan or VNP20009 and Mitomycin C on the Growth of M27 Lung Carcinoma in Mice Liquid nitrogen stored M27 murine lung carcinoma cells ($1 \times 10^6$/ml×1 ml) were recovered by rapidly thawing the cells at 37° C. and cultured with 10 ml of DMEM culture medium containing 10% fetal calf serum (FCS) at 37° C., 5% $CO_2$. After passing the cells for two generations, M27 cells in log phase were removed by trypsinization, washed with 1×PBS, and reconstituted to $2.5 \times 10^6$ cells/ml with 1×PBS for tumor implantation. An M27 cell suspension was implanted into 100 C57BL/6 mice (female, aged 8 weeks, 20 g; $5×10^5$ cells/mouse) subcutaneously at the right flank on Day 0. The mice were randomly divided into ten groups with each group consisting of 10 mice.

Salmonella strain VNP20009 was diluted to $5×10^6$ CFU/ml with 1×PBS with our standard dilution procedures. Each mouse was intravenously administered 0.2 ml of diluted Salmonella ($1×10^6$ CFU/mouse) on day 12 according to Table 6, infra. In order to determine the actual number of injected bacteria, the $5×10^6$ CFU/ml bacterial suspensions were further diluted to $1×10^3$ CFU/ml and plated on nutrient agar (MsbB plates; International Publication No. WO 99/13053). The colonies formed were counted the next day.

The mitomycin C (Sigma) and cytoxan (Sigma) were administered to mice according to Table 7, infra. The second dose of mitomcyin C was given to the combination groups on day 22 but not those treated with mitomycin C only due to the large size of the tumor. 200 mpk of Cipro (Bayer Inc., West Haven, Conn.) was administered to each mouse treated with VNP20009 alone or VNP20009+chemotherapeutic drugs since severe toxic reactions were observed in groups treated with VNP20009+cytoxan. The tumor volume was measured twice a week until the end of the experiment. The behavior, appearance and mortality of the animals was observed daily. The mice were kept in a clean, temperature constant laboratory. The bedding was changed twice a week and the mice were provided with enough food and drinking water.

TABLE 7

| Group | Number of Mice |
| --- | --- |
| No treatment control | 10 |
| 3 mpk mitomycin C, i.v., day 15 | 10 |
| 5 mpk, mitomycin C, i.v., day 15 | 10 |
| 150 mpk cytoxan, i.p., day 15 | 10 |
| 200 mpk cytoxan, i.p., day 15 | 10 |
| VNP20009, 1 × $10^6$/mouse i.v., day 12 | 10 |
| VNP29009, 1 × $10^6$/mouse i.v., day 12 + 3 mpk mitomycin C, i.v., days 15 & 22 | 10 |
| VNP20009, 1 × $10^6$/mouse i.v., day 12 + 5 mpk mitomycin C, i.v., days 15 & 22 | 10 |
| VNP20009, 1 × $10^6$/mouse i.v., day 12 + 150 mpk cytoxan, i.p., day 15 | 10 |
| VNP20009, 1 × $10^6$/mouse i.v., day 12 + 200 mpk cytoxan, i.p., day 15 | 10 |

As shown to FIG. 39, the combination treatment with VNP20009+cytoxan inhibited the growth of the M27 lung carcinoma more than VNP20009 treatment alone or cytoxan treatment alone. As shown in FIG. 40, the combination of VNP20009+mitomycin C inhibited the growth of the M27 lung carcinoma more than mitomycin C alone. However, the combination of VNP20009+mitomycin C did not inhibit the growth of the M27 lung carcinoma more than VNP20009 treatment alone (FIG. 40). These results suggest that the administration of attenuated tumor-targeted bacteria in combination with a chemotherapeutic agent may act synergistically or additively to inhibit the growth of solid tumors such as lung carcinoma.

28.2. Efficacy of the Combination of VNP20009 and Cisplatin on the Growth of M27 Lung Carcinoma in Mice Liquid nitrogen stored M27 murine lung carcinoma cells ($1×10^6$/ml×1 ml) were recovered by rapidly thawing the cells at 37° C. and cultured with 25 ml of DMEM culture medium containing 10% fetal calf serum (FCS) at 37° C., 5% $CO_2$. After passing the cells for two generations, M27 cells in log phase (about 90–95% saturation) were removed by trypsinization, washed with 1×PBS, and reconstituted to $2.5×10^6$ cells/ml with 1×PBS for tumor implantation. An M27 cell suspension (0.2 ml) was implanted into 36 C57BL/6 mice (female, aged 8 weeks; 20 g; $5×10^5$ cells/mouse) subcutaneously at the right flank on day 0. The mice were randomly divided into groups with each group consisting of 9 mice.

Salmonella strains VNP20009 was diluted to $5×10^6$ CFU/ml with 1×PBS with our standard dilution procedures. Each mouse was administered via the tail vein 0.2 ml of Salmonella ($1×10^6$ CFU/mouse) on day 12 according to Table 8, infra. In order to determine the actual number of injected bacteria, the $5×10^6$ CFU/ml bacterial suspensions were further diluted to $1×10^3$ CFU/ml and plated on MsBb plates. The colonies formed were counted the next day.

The cisplatin was administered to mice on day 14, two days post bacterial injection (Table 8, infra). The cisplatin was diluted to 0.5 mg/ml with normal saline prior to administration. The tumor volume was measured twice a week until the end of the experiment. The behavior, appearance and mortality of the animals was observed daily. The mice were kept in a clean, temperature constant laboratory. The bedding was changed twice a week and the mice were provided with enough food and drinking water.

TABLE 8

| Group | Number of Mice |
| --- | --- |
| Control (no treatment) | 9 |
| VNP20009, 1 × $10^6$/mouse i.v., on day 12 | 9 |
| 5 mpk cisplatin, i.p. qw × 2, on day 14, 19 | 9 |
| VNP20009, 1 × $10^6$/mouse i.v., on day 12 + 5 mpk cisplatin, i.p. qw × 2, on day 14, 19, 33 | 9 |

As shown in FIG. 41, the combination treatment with VNP20009+cisplatin inhibited the growth of the M27 lung carcinoma more than VNP20009 treatment alone or cisplatin treatment alone. These results suggest that the administration of attenuated tumor-targeted bacteria in combination with chemotherapeutic agent such as cisplatin may act synergistically or additively to inhibit the growth of solid tumors such as lung carcinoma.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. An attenuated tumor-targeted bacteria comprising a first nucleic acid molecule encoding a primary effector molecule operably linked to a eukaryotic promoter and a second nucleic acid molecule encoding a secondary effector molecule operably linked to a eukaryotic promoter, wherein said attenuated tumor-targeted bacteria is *Salmonella*, said primary effector molecule is endostatin, and said secondary effector molecules is bacteriocin release factor (BRP).

2. The attenuated tumor-targeted bacteria of claim 1, wherein the BRP is obtained from the cloacin DF13 plasmid.

3. The attenuated tumor-targeted bacteria of claim 1, wherein the *Salmonella* is an msbB *Salmonella* mutant.

4. A pharmaceutical composition comprising a pharmaceutically acceptable carrier and an attenuated tumor-targeted bacteria comprising a first nucleic acid molecule encoding a primary effector molecule operably linked to a eukaryotic promoter and a second nucleic acid molecule encoding a secondary effector molecule operably linked to a eukaryotic promoter, wherein said attenuated tumor-targeted bacteria is *Salmonella*, said primary effector molecule is endostatin, and said secondary effector molecule is bacteriocin release factor (BRP).

5. The pharmaceutical composition of claim 4, wherein the BRP is obtained from the cloacin DF13 plasmid.

6. The pharmaceutical composition of claim 4 wherein the *Salmonella* is an msbB *Salmonella* mutant.

7. A method for delivering a primary effector molecule to a subject to treat a solid tumor cancer, comprising administering to said subject a pharmaceutical composition comprising a pharmaceutically acceptable carrier and an attenuated tumor-targeted bacteria comprising a first nucleic acid molecule encoding a primary effector molecule operably linked to a eukaryotic promoter and a second nucleic acid molecule encoding a secondary effector molecule operably linked to a eukaryotic promoter, wherein said attenuated tumor-targeted bacteria is *Salmonella*, said primary effector molecules is endostatin, and said secondary effector molecule is bacteriocin release factor (BRP).

8. The method of claim 7, wherein the BRP is obtained from the cloacin DF13 plasmid.

9. The method of claim 7, wherein the *Salmonella* is an msbB *Salmonella* mutant.

* * * * *

UNITED STATES PATENT AND TRADEMARK OFFICE
CERTIFICATE OF CORRECTION

PATENT NO.        : 6,962,696 B1
APPLICATION NO. : 09/645415
DATED              : November 8, 2005
INVENTOR(S)      : Bermudes et al.

It is certified that error appears in the above-identified patent and that said Letters Patent is hereby corrected as shown below:

Sequence Listing 34, which begins on column 105, line 67, and extending to column 111, line 66, is missing its first column of letters and should read as follows:

```
cccgggcact tccggggcat gagtatgtga tatccggggc tgcaccccgg accccgccaa     60
cacatcacgg gccacaaaat tttttgtggc ccgctctgcg ttttctaagt gttatccctc    120
ctgatttcta aaaattttc  cacctgaact tgacagaaaa aacgatgacg agtacttttt    180
gatctgtaca taaacccagt ggttttatgt acagtattaa tcgtgtaatc aattgtttta    240
acgcttaaaa gagggaattt ttatgagcgg tggcgatgga cgcggccata acacgggcgc    300
gcatagcaca agtggtaaca ttaatggtgg cccgaccggg cttggtgtag gtggtggtgc    360
ttctgatggc tccggatgga gttcggaaaa taacccgtgg ggtggtggtt ccggtagcgg    420
cattcactgg ggtggtggtt ccggtcatgg taatggcggg gggaatggta attccggtgg    480
tggttcggga acaggcggta atctgtcagc agtagctgcg ccagtggcat ttggtttttcc   540
ggcactttcc actccaggag ctggcggtct ggcggtcagt atttcagcgg gagcattatc    600
ggcagctatt gctgatatta tggctgccct gaaaggaccg tttaaatttg gtctttgggg    660
ggtggcttta tatggtgtat tgccatcaca aatagcgaaa gatgacccca atatgatgtc    720
aaagattgtg acgtcattac ccgcagatga tattactgaa tcacctgtca gttcattacc    780
tctcgataag gcaacagtaa acgtaaatgt tcgtgttgtt gatgatgtaa aagacgagcg    840
acagaatatt tcggttgttt caggtgttcc gatgagtgtt ccggtggttg atgcaaaacc    900
taccgaacgt ccgggtgttt ttacggcatc aattccaggt gcacctgttc tgaatatttc    960
agttaataac agtacgccag cagtacagac attaagccca ggtgttacaa ataatactga   1020
taaggatgtt cgcccggcag gatttactca gggtggtaat accagggatg cagttattcg   1080
attcccgaag gacagcggtc ataatgccgt atatgtttca gtgagtgatg ttcttagccc   1140
tgaccaggta aaacaacgtc aagatgaaga aaatcgccgt cagcaggaat gggatgctac   1200
gcatccggtt gaagcggctg agcgaaatta tgaacgcgcg cgtgcagagc tgaatcaggc   1260
aaatgaagat gttgccagaa atcaggagcg acaggctaaa gctgttcagg tttataattc   1320
gcgtaaaagc gaacttgatg cagcgaataa aactcttgct gatgcaatag ctgaaataaa   1380
acaatttaat cgatttgccc atgacccaat ggctggcggt cacagaatgt ggcaaatggc   1440
cgggcttaaa gcccagcggg cgcagacgga tgtaaataat aagcaggctg catttgatgc   1500
tgctgcaaaa gagaagtcag atgctgatgc tgcattgagt tctgctatgg aaagcaggaa   1560
gaagaaagaa gataagaaaa ggagtgctga aaataattta aacgatgaaa agaataagcc   1620
cagaaaaggt tttaaagatt acgggcatga ttatcatcca gctccgaaaa ctgagaatat   1680
taaagggctt ggtgatctta agcctgggat accaaaaaca ccaaagcaga atggtggtgg   1740
aaaacgcaag cgctggactg gagataaagg gcgtaagatt tatgagtggg attctcagca   1800
tggtgagctt gaggggtatc gtgccagtga tggtcagcat cttggctcat ttgaccctaa   1860
```

UNITED STATES PATENT AND TRADEMARK OFFICE
CERTIFICATE OF CORRECTION

PATENT NO. : 6,962,696 B1  
APPLICATION NO. : 09/645415  
DATED : November 8, 2005  
INVENTOR(S) : Bermudes et al.

It is certified that error appears in the above-identified patent and that said Letters Patent is hereby corrected as shown below:

```
aacaggcaat cagttgaaag gtccagatcc gaaacgaaat atcaagaaat atctttgaga  1920
ggaagttatg ggacttaaat tggatttaac ttggtttgat aaaagtacag aagattttaa  1980
gggtgaggag tattcaaaag attttggaga tgacggttca gttatggaaa gtctaggtgt  2040
gcctttaag gataatgtta ataacggttg ctttgatgtt atagctgaat gggtaccttt   2100
gctacaacca tacttaatc atcaaattga tatttccgat aatgagtatt ttgtttcgtt   2160
tgattatcgt gatggtgatt ggtgatcaaa tattatcagg gatgagttga tatacgggct  2220
tctagtgttc atggatgaac gctggagcct ccaaatgtag aaatgttata tttttattg   2280
agttcttggt tataattgct ccgcaatgat ttaaataagc attatttaaa acattctcag  2340
gagaggtgaa ggtggagcta aaaaaaagta ttggtgatta cactgaaacc gaattcaaaa  2400
aatttattga agacatcatc aattgtgaag gtgatgaaaa aaaacaggat gataacctcg  2460
agtattttat aaatgttact gagcatccta gtggttctga tctgatttat tacccagaag  2520
gtaataatga tggtagccct gaaggtgtta ttaaagagat taaagaatgg cgagccgcta  2580
acggtaagtc aggatttaaa cagggctgaa atatgaatgc cggttgttta tggatgaatg  2640
gctggcattc tttcacaaca aggagtcgtt atgaaaaaaa taacagggat tattttattg  2700
cttcttgcag tcattattct gtctgcatgt caggcaaact atatccggga tgttcagggc  2760
gggaccgtat ctccgtcatc aacagctgaa gtgaccggat tagcaacgca gtaacccgaa  2820
atcctctttg acaaaaacaa agcgtgtcag gctgattctg atgcgctttt tttttgaaat  2880
gtcacaaaaa ttccatgtgg gagatgggat ctaaaatcct cgtgcagaac tttccatcca  2940
gggggagaaa acttgtcgtt ttgagccgtt cggtgttcag aacgcacgaa accgatcgcg  3000
cgcatcgctt tcgtgaatag ttatgcaggc ccctgaaaac gattctgacg cgttttttcg  3060
gttttgcctg gtgttttcct gtcttttttgc gttttttgcg tcagaacgcg tctgagggcg  3120
ttttaagggg tgcgtacaac gggagttatg gtaaatggat cggttttttcg ggaaggatcg  3180
acaggatttg ccgttgggtg tagtgtaagc gactgaaaaa caaacgcccc gtaaatcgtg  3240
ctctcaccgc caagattgat cacgaaatta cagggcgccg ggttccgcgt ttcccgatgg  3300
gaaagcgcgg ttagttaaac tgtgtaccga gagaaatcgt atcacatgag cgccgtactt  3360
caacgcttca gggaaaaatt accgcacaaa ccgtactgta cgaacgattt cgcgtacggc  3420
gttcgcattc tgccgaaaaa cattgccatt cttgcccgtt tcatccagca gaaccagcca  3480
catgcactgt actggcttcc ctttgacgtg gaccggacgg gggcatcaat cgactggagc  3540
gaccggaatt gtccggcccc gaacatcacc gtaaaaaatc cccgtaacgg gcacgcgcat  3600
ctgctctacg cgctcgccct tcctgtgaga actgcgccgg atgcatcggc ttcggcgctc  3660
agatacgctg ccgctattga gcgtgcgttg tgtgaaaaac tgggcgcgga tgtgaattac  3720
agcggcctga tctgcaaaaa tccgtgccac cctgaatggc aggaagtgga atggcgcgag  3780
```

UNITED STATES PATENT AND TRADEMARK OFFICE
CERTIFICATE OF CORRECTION

PATENT NO. : 6,962,696 B1  Page 3 of 4
APPLICATION NO. : 09/645415
DATED : November 8, 2005
INVENTOR(S) : Bermudes et al.

It is certified that error appears in the above-identified patent and that said Letters Patent is hereby corrected as shown below:

```
gaaccctaca ctctcgacga actggctgat tatctcgatt tgagcgcctc agcgcgccgt   3840
agcgtcgata aaaattacgg gctggggcga aactgctatc tgttcgaaaa gggccgtaaa   3900
tgggcttacc gggctattcg tcagggctgg ccggcattct cacaatggct tgatgcggtg   3960
attcagcgtg tcgaaatgta caacgcatcg ctccccgttc cgctttcacc tcctgaatgt   4020
cgggctattg gcaagagtat tgcgaaatac acgcacagga acttcacgcc ggaaactttc   4080
gcacagtatg tggctgatac gcacacgcca gaaattcagg ctacacgcgg tcgcaagggc   4140
ggttctaagt ctaagcgcgg cacagtagct acatcagcac gcacgctgaa accttgggag   4200
aaattaggga tcagtcgcgc ctggtattac caactgaaaa aacgaggtct cgtagagtag   4260
accaaataag cctatatcag ataacagcgc cttttggcg cctttttgag cagcttggtt    4320
tgttgctatt tccctcgttg aatcccgcaa tggcgcggct ttccgcatga ttgaggtggt   4380
agcgctcgcc gcagtctcat gaccgagcgt agcgagcgaa tgagcgagga agcgcaaagg   4440
cgtccggtgt tgcatgtggc acttacgcgc cggggcttag tggttctgcg gtttcgccgg   4500
tggtctgggt agcttctcca gctcgttaat cagcggttgt agtcggttca catccacctg   4560
tcttgtgact tcctttcgca gaaactggag caggaacgca cgcagttgcg cttcttccgg   4620
cctccgtacc cttgccagca tggctgcccc cacaatgact ttttgcgccg tgtccaggct   4680
tcggctcttc gccttcaggc gctgtaatct ggcctcagct tcggcaatct tctgttcgag   4740
tgttctgctc atttcgtgac tccgtgcgcg gtgaaaaatc gcattttagc gcgtcactgg   4800
tagtttaaaa actaaactgg cataatgcac ggcacatcac gaagtgcgca cttatacaat   4860
ctccacttcg tttcgattgt gtgcggtctg cgacgctaaa agaaaacggc aaaaaggcat   4920
tacggcagaa atggcgattt atcatctcag catgaaaatc atttcgcgaa aaaacggcta   4980
cagtgctgtt gcttctgctg cctaccgttc cggctctgtc atacccgatg accgtaccgg   5040
attaatccac gattacaccc gtaaacgcgg cgttgatgat gcggtcattc tcaccctgc    5100
gaatgcaccg tcctggtgtg ttgaccgttc cgttctttgg aatgcggtcg agaaagccga   5160
acagcgccgg aactcccagc tggcaaggga ggttgaactc gccattcccc gtgagatttc   5220
ccgcgaggcc gcacgggaga ccgttctcgc tttgtccggg aaaactttgt cagtcggggc   5280
atgattgccg atgtggcgtt ccatcacatg gaccggacca atccccatgc gcacatcatg   5340
ctgaccacga gagctgtcgg ggaaacggaa ttcgcaggaa aggtcaggga tggaacgacc   5400
gggcactcgc cgagacgtgg cgcgcatcat gggctgacca tgcgaacaga gcgcttgcga   5460
acgccggcta ccaggaagag atagaccatc gttcatacga gcgtcaggga ctggagaaag   5520
cgccggcctt cacctcggaa aggctgcctg tgcgatgaa aaacgggaa tggaaacaga     5580
acgcggtgag cagaaccgtc tgattaacag ccttaacctg gaaatacagg tttcccgcac   5640
gcagcttgct ctcaggacgg ttcaggaaac gcagcgtaag cgggaactca gcgatgctgc   5700
acgtcgtgca gtggaagccc ttaacctgac cattcccgct gcgaatgcct cagcggatac   5760
```

UNITED STATES PATENT AND TRADEMARK OFFICE
CERTIFICATE OF CORRECTION

PATENT NO.       : 6,962,696 B1
APPLICATION NO.  : 09/645415
DATED            : November 8, 2005
INVENTOR(S)      : Bermudes et al.

It is certified that error appears in the above-identified patent and that said Letters Patent is hereby corrected as shown below:

```
cctgcgggaa ttcattgcca cgctgccgca ggaatgcggg aacgcgtggg agatgacccc    5820
ggagttcctg gcgatgagcg ggaaggtgaa cgacatcgaa cgtgagggga atgcgctgct    5880
gaaagagcag gccattctcg aaaaggagat gaccggactc aaaaaagcac gccctgtcgc    5940
gtcccttctg tcagagattc ccctgatgac atgggctgaa ccggaatacc gcaaaagaca    6000
actccgtttc ttggaaactc gggaaacaga ttgaatctct tcgccgcacc tacagggccg    6060
tgaaagaacg ggacattccc gcccgtcgtc aggcctttga aacgcagtgg aatacgtgga    6120
ttgcgccgga atggcagagc tgaaagaaaa actgtcagca cgggaagcgg agcggcgcag    6180
ggaggagccc gaagcggaag cgcgccggaa ggaacaggag catgaggcgc ggctgaaacg    6240
tcatgataac caccgtctga gccgtgaaac ggcattagtc ggggttatta cggagctggg    6300
gcgtgccaga gagccgggaa cgggcaggat aacccgctac atgatgttga gtaacagagc    6360
cggagaattc acggtatggg gtgatgagct ggcgcattac ccccagagtg ttcatgaccc    6420
ggtgaatgtt tacctgtcgc caggcgggc tgtgatggtc tcggatatac gtgagggaat     6480
gccagaatct catgagacga tggcgcggcc tgagcgtgtg agaatgtatt ccggtgcgac    6540
ggtccggcat gtactggaac agatgcgcca ggggtggccc tcttacggtt ttccggcgct    6600
gccgcatcac tggccggata atttttattt cagcgacgac cgcaggcccg tagcctctcc    6660
gctgccgtct gcgcaccggg tggacgtcac cgcttatgcg gcaccggagc aactcatgcc    6720
cgttgtattt tcgacagagc gaaacagcag gacgctgaat ctgctgttgt gcaaagggcc    6780
ggaggaagtg cttgtcggat ttgtgcgcca ggaggacggg ctgcgtcccg ttcttgcgct    6840
tccgtcgccg gattacagtc atctgatggt cagcaccatc acggagaacg gggtatgcct    6900
ggcaggttac ggagaagcta taaaccatga tgcggatact ccgtacccac cggaaccgca    6960
cctgatgcag ttccggctca aaggccatca tgacaggctt ttggctgctg tccacaaacc    7020
ggaagagatg ccggattatc tcttccgtca actcggtttt aatcagacct ggcatgagtg    7080
gaagcgggac gaacagcaca ggcaacaaca acgccgc                             7117
```

Signed and Sealed this

Twenty-fourth Day of October, 2006

JON W. DUDAS
*Director of the United States Patent and Trademark Office*